US009233067B2

(12) United States Patent
Lammel et al.

(10) Patent No.: US 9,233,067 B2
(45) Date of Patent: Jan. 12, 2016

(54) SILK PARTICLES FOR CONTROLLED AND SUSTAINED DELIVERY OF COMPOUNDS

(75) Inventors: Andreas Lammel, Munich (DE); Thomas Scheibel, Bayreuth (DE); Martin Schwab, Munich (DE); Gerhard Winter, Penzberg (DE); Markus Hofer, Munich (DE); Julia Myschik, Munich (DE)

(73) Assignee: Amsilk GmbH, Planneg/Martinsried (DE)

( * ) Notice: Subject to any disclaimer, the term of this patent is extended or adjusted under 35 U.S.C. 154(b) by 0 days.

(21) Appl. No.: 13/512,789

(22) PCT Filed: Nov. 30, 2010

(86) PCT No.: PCT/EP2010/007266
§ 371 (c)(1),
(2), (4) Date: Dec. 7, 2012

(87) PCT Pub. No.: WO2011/063990
PCT Pub. Date: Jun. 3, 2011

(65) Prior Publication Data
US 2013/0109762 A1    May 2, 2013

Related U.S. Application Data

(60) Provisional application No. 61/265,344, filed on Nov. 30, 2009.

(51) Int. Cl.
*A61K 9/00*    (2006.01)
*A61K 31/137*    (2006.01)
*A61K 31/138*    (2006.01)
*A61K 31/245*    (2006.01)
*A61K 31/285*    (2006.01)
*A61K 31/40*    (2006.01)
*A61K 31/485*    (2006.01)
*C07K 14/435*    (2006.01)
*A61K 38/00*    (2006.01)

(52) U.S. Cl.
CPC .............. *A61K 9/0002* (2013.01); *A61K 31/137* (2013.01); *A61K 31/138* (2013.01); *A61K 31/245* (2013.01); *A61K 31/285* (2013.01); *A61K 31/40* (2013.01); *A61K 31/485* (2013.01); *C07K 14/43518* (2013.01); *A61K 38/00* (2013.01)

(58) Field of Classification Search
None
See application file for complete search history.

(56) References Cited

U.S. PATENT DOCUMENTS 8,288,512 B2    10/2012    Liebmann et al.

FOREIGN PATENT DOCUMENTS

| WO | 03/057727 A1 | 7/2003 |
| WO | 2006/008163 A2 | 1/2006 |
| WO | 2007/014755 A1 | 2/2007 |
| WO | WO 2007014755 A1 * | 2/2007 |
| WO | 2007/078239 A2 | 7/2007 |
| WO | 2007/082936 A1 | 7/2007 |

OTHER PUBLICATIONS

Liebmann, et al., "Formulation of poorly water-soluble substances using self-assembling spider silk protein," *Colloids and Surfaces A, Physicachemical and Engineering Aspects*, vol. 331, No. 1-2, pp. 126-132 (Dec. 10, 2008).
Wang, et al., "Silk microspheres for encapsulation and controlled release," *Journal of Controlled Release*, vol. 117, No. 3, pp. 360-370 (Feb. 10, 2007).
International Preliminary Report on Patentability and International Search Report for PCT/EP2010/007266, dated Feb. 9, 2012, 10 pages.

* cited by examiner

*Primary Examiner* — Amber D Steele
*Assistant Examiner* — Schuyler Milton
(74) *Attorney, Agent, or Firm* — Kilpatrick Townsend & Stockton LLP

(57) ABSTRACT

The present invention relates to a method of producing and loading silk particles, preferably spider silk particles, with a compound. In particular, the present invention provides a novel two step method for loading silk particles, preferably spider silk particles, with small and water-soluble compounds. Also disclosed are silk particles, preferably spider silk particles, loaded with at least one compound which are eminently suited as carriers for controlled and sustained delivery applications. Furthermore, the invention relates to pharmaceutical or cosmetic compositions comprising said silk particles, preferably spider silk particles, and a pharmaceutically active compound or cosmetic compound for controlled and sustained release. The present invention is also directed to silk particles, preferably spider silk particles, loaded with a compound obtainable by the method according to the invention.

26 Claims, 9 Drawing Sheets a)

b)

a)

b)

SILK PARTICLES FOR CONTROLLED AND
SUSTAINED DELIVERY OF COMPOUNDS

This application is a National Stage of International Application No. PCT/EP2010/007266, filed Nov. 30, 2010, and entitled SILK PARTICLES FOR CONTROLLED AND SUSTAINED DELIVERY OF COMPOUNDS, which is incorporated herein in its entirety.

FIELD OF THE INVENTION

The present invention relates to a method of producing and loading silk particles, preferably spider silk particles, with a compound. In particular, the present invention provides a novel two step method for loading silk particles, preferably spider silk particles, with small and water-soluble compounds. Also disclosed are silk particles, preferably spider silk particles, loaded with at least one compound which are eminently suited as carriers for controlled and sustained delivery applications. Furthermore, the invention relates to pharmaceutical or cosmetic compositions comprising said silk particles, preferably spider silk particles, and a pharmaceutically active compound or cosmetic compound for controlled and sustained release. The present invention is also directed to silk particles, preferably spider silk particles, loaded with a compound obtainable by the method according to the invention.

BACKGROUND

In the past years sophisticated drug depot systems for controlled delivery of substances have been developed, for example to achieve constant drug levels in plasma during therapy. These systems have the advantage of reducing toxic side effects so that the number of drug administrations can be decreased, while at the same time improving cellular uptake and bioavailability. Especially colloidal micro- and nanoparticulate carriers have been extensively investigated as a platform for controlled drug delivery. There is also an ongoing quest to design nano- or microparticles which facilitate controlled release of substances other than pharmaceutical compounds. In general, the material employed as carrier for controlled and sustained release of a substance should offer control of structure, morphology and function, while also exhibiting good mechanical stability.

For example, biodegradable and biocompatible polymers are preferred because of their ability to retain their properties for a limited period of time before gradually decomposing into soluble nontoxic degradation products which can be excreted from the body. Many synthetic (aliphatic polyesters, polyglycolic acid (PGA), polylactid acid (PLA), etc.) and natural (polysaccharides, chitin, chitosan, proteins) polymers have been employed to produce degradable vehicles for encapsulation, incorporation or binding of active compounds [Freiberg, S., Zhu, X. X. Polymer microspheres for controlled drug release. International Journal of Pharmaceutics 2004; 282(1-2):1-18].

While synthetic polymers potentially posses the feature of sustained release of the encapsulated therapeutic agent from a period of days up to several months, they typically demand organic solvents or relatively harsh formulation conditions during processing with potentially limited biocompatibility because of remaining toxic solvents and acidic degradation products.

A further advance in the art was to consider natural polymers which have the advantage of being biocompatible. However, most biopolymers known at present have a major drawback, namely that they resolubilize rapidly in aqueous environment due to their hydrophilic nature, thus resulting in fast drug release profiles. In order to circumvent this problem, chemical cross-linking procedures have been considered. Unfortunately, the presence of residual cross-linking agents can lead to toxic side effects. In addition, undesirable reactions between the drug and the cross-linker could result in the formation of either toxic or inactivated derivatives.

The use of hydrophobic biopolymers as carriers for sustained drug release has also been investigated in the art. For example, silk proteins have been considered as being suitable biopolymers. In particular, silk proteins from spiders and insects, especially *Bombyx mori* fibroin, have been tested for their ability to deliver drugs and other substances.

For example, silk microspheres consisting of silkworm fibroin for encapsulation and controlled release of a model protein drug has been described in the art. These silk fibroin microspheres with diameters of several microns are obtained by a method using lipid vesicles as a template [Wang, X., Silk microspheres for encapsulation and controlled release. Journal of Controlled Release 2007; 117(3): 360-370].

Larger silk fibroin particles with diameters ranging from 100 to 440 µm and improved loading efficiencies have also been described in the art. However, the preparation techniques for producing these particles are highly sophisticated and lack scalability [Wenk, E., Silk fibroin spheres as a platform for controlled drug delivery. Journal of controlled release 2008; 132(1):26-34].

WO 2007/014755 describes a method of producing nano- and microcapsules consisting of spider silk proteins. These capsules with sizes of several microns are composed of an outer spider silk protein shell and can generally be filled with substances such as proteins or chemical reactants. The microcapsules are formed by the encapsulation of emulsion droplets resulting in hollow spider silk protein shells.

WO 2007/0829223 relates to the use of protein microbeads in cosmetics. In particular, this international patent application describes protein microbeads composed of synthetic spider silk proteins for delivery of cosmetic substances [Hümerich, D., Primary structure elements of spider dragline silks and their contribution to protein solubility. Biochemistry 2004 Oct. 26; 43(42): 13604-13612]. Similarly, WO 2007/082923 describes the use of protein microbeads for formulating poorly water-soluble effect substances. In both patent applications, the water-insoluble effect substances can be either associated with or encapsulated in the protein microbeads. The association of the substances to these beads is mainly due to hydrophobic interactions. This encapsulation strategy has the basic disadvantage that the loaded substances are only released upon proteolysis of the protein microbeads by the activity of proteases which makes a constant and controlled release difficult. A further problem is that this system is only suitable for the formulation of mainly water-insoluble substances.

Hence, there is a strong need in the field to provide a novel method of producing micro- or submicroparticles with improved qualities. In particular, there is still an ongoing quest to produce nano-scaled particles which are biocompatible and biodegradable as well as being stable carriers for small and water soluble compounds. There is also a need to provide a suitable method of loading silk particles, e.g. spider silk particles, effectively with a compound of interest. The silk particles, e.g. spider silk particles, should also be capable of releasing the loaded compound controllably and sustainably.

Accordingly, it is an object of the present invention to provide a novel and simple drug delivery system which takes into account all of the above criteria. The present invention, therefore, provides a novel method of producing silk particles, preferably spider silk particles, loaded with a compound. More particularly, the method comprises the steps of providing silk particles, preferably spider silk particles, comprising one or more silk polypeptides, preferably spider silk polypeptides, comprising at least two identical repetitive units, and incubating said silk particles, preferably spider silk particles, with at least one compound, wherein the compound is water-soluble and has a molecular weight of between about 50 Da and about 20 kDa.

Surprisingly, one major advantage of the silk carrier system according to the invention is that these particles can be produced and loaded within an all-aqueous system and under ambient condition. This is particularly important with regard to the loading of labile compounds as well as to the overall biocompatibility of the product. The silk particles, e.g. spider silk particles, of the invention have revealed unexpected loading efficiencies for small and water-soluble compounds. Surprisingly, the silk particles, e.g. spider silk particles, obtained by the method according to the invention have further demonstrated a most favourable release profile, rendering them eminently suitable for controlled and sustained delivery of a compound. The produced silk particles, e.g. spider silk particles, are, therefore, very well suited for delivery of pharmaceutical and cosmetic compounds. Due to their colloidal stability and biocompatibility under physiological conditions, the loaded silk particles, e.g. spider silk particles, according to the invention are especially suitable for in vivo applications.

SUMMARY OF THE INVENTION

In a first aspect, the invention relates to a method of producing silk particles, preferably spider silk particles, loaded with a compound comprising the steps of
i) providing silk particles, preferably spider silk particles, comprising one or more silk polypeptides, preferably spider silk polypeptides, comprising at least two identical repetitive units, and
ii) incubating said silk particles, preferably spider silk particles, with at least one compound,
wherein the compound is water-soluble and has a molecular weight of between about 50 Da and about 20 kDa.

In a preferred embodiment of the invention, the compound has a molecular weight of 50 Da or about 50 Da to 10 kDa or about 10 kDa, preferably 50 Da or about 50 Da to 6 kDa or about 6 kDa, more preferably 50 Da or about 50 Da to 4 kDa or about 4 kDa and most preferably 50 Da or about 50 Da to 1 kDa or about 1 kDa.

In preferred embodiments of the invention, the silk particles, preferably spider silk particles, provided in step i) are produced by the steps of
a) providing an aqueous solution comprising one or more silk polypeptides, preferably spider silk polypeptides, comprising at least two identical repetitive units,
b) triggering aggregation of the silk polypeptides, preferably spider silk polypeptides, to form silk particles, preferably spider silk particles, and
c) separating the silk particles, preferably spider silk particles, by phase separation.

Preferably, the compound is able to permeate into the matrix of the silk particles, preferably spider silk particles.

In further preferred embodiments, at least 40%, preferably at least 50%, 60%, 70%, 80%, 90%, or 95% of the loaded compound is located within the matrix of the silk particles, preferably spider silk particles.

In further preferred embodiments, the silk particles, preferably spider silk particles, have a median size of between 0.1 µm and 500 µm, preferably of between 0.1 µm and 100 µm, more preferably of between 0.2 µm and 20 µm, even more preferably of between 0.2 to 1 µm, and most preferably of between 0.25 µm and 0.7 µm.

In preferred embodiments, the at least two identical repetitive units each comprise at least one consensus sequence selected from the group consisting of:
i) GPGXX (SEQ ID NO: 3), wherein X is any amino acid, preferably in each case independently selected from the group consisting of A, S, G, Y, P and Q;
ii) GGX, wherein X is any amino acid, preferably in each case independently selected from the group consisting of Y, P, R, S, A, T, N and Q; and
iii) $A_x$, wherein x is an integer from 5 to 10.

In further preferred embodiments, the repetitive unit(s) of the respective silk polypeptide, preferably spider silk polypeptide, is (are) independently selected from module A (SEQ ID NO: 20) or variants thereof, module C (SEQ ID NO: 21) or variants thereof, module Q (SEQ ID NO: 22) or variants thereof, module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34).

In further specific embodiments, the silk polypeptide, preferably spider silk polypeptide, further comprises at least one non-repetitive (NR) unit.

More preferably, the non-repetitive (NR) unit is independently selected from the group consisting of NR3 (SEQ ID NO: 41 and SEQ ID NO: 45) or variants thereof and NR4 (SEQ ID NO: 42 and SEQ ID NO: 46) or variants thereof.

In further specific embodiments, the silk polypeptide, preferably the spider silk polypeptide, is selected from the group consisting of ADF-3 (SEQ ID NO: 1 and SEQ ID NO: 47), ADF-4 (SEQ ID NO: 2 and SEQ ID NO: 48), MaSp I (SEQ ID NO: 43 and SEQ ID NOs: 53-64), MaSp II (SEQ ID NO: 44 and SEQ ID NOs: 65-78), $(C)_m NR_z$, $NR_z(C)_m$, $(AQ)_n NR_z$, $NR_z(AQ)_n$, $NR_z(QAQ)_o$, $(QAQ)_o NR_z$, $(C)_m$, $(AQ)_n$, and $(QAQ)_o$, wherein m is an integer of 8 to 48, n is an integer of 6 to 24, o is an integer of 8 to 16, z is an integer of 1 to 3.

More preferably, the silk polypeptide, preferably spider silk polypeptide, is $C_{16}$, $C_{32}$, $(AQ)_{12}$, $(AQ)_{24}$, $C_{16}NR4$, $C_{32}NR4$, $(AQ)_{12}NR3$, or $(AQ)_{24}NR3$.

In further preferred embodiments of the invention, the concentration of the silk polypeptide, preferably spider silk polypeptide, in the aqueous solution is of between 0.01 wt %/vol and 30 wt %/vol, more preferably between 0.1 wt %/vol and 30 wt %/vol, and most preferably between 1 wt %/vol and 20 wt %/vol.

In further specific embodiments, the aggregation is triggered by pH shift, ion exchange, shear forces, the addition of alcohol, or a lyotropic salt or by combinations thereof. More preferably the alcohol is methanol.

Also preferably, the lyotropic salt is selected from the group consisting of ammonium sulphate, sodium phosphate, and potassium phosphate.

More preferably, the concentration of the lyotropic salt is of between about 400 mM and about 3 M, preferably about 1 to about 2 M, most preferably about 2 M.

In preferred embodiments of the invention, the compound is a pharmaceutically active compound, a cosmetic substance, an agricultural substance, a chemoattractant, a chemorepellent, an anti-fungal substance, an anti-bacterial substance, a nutrient, a dietary supplement, a dye, a fragrance or an agent selected from the group consisting of hemostatic agents, growth stimulating agents, inflammatory agents, anti-fouling agents, antimicrobial agents and UV protecting agents.

In further specific embodiments, the compound has an overall positive net charge.

In further specific embodiments, the compound is able to permeate into the silk matrix, preferably spider silk matrix, by electrostatic interaction and/or diffusion. In preferred embodiments, the compound has a neutral or alkaline nature. In further specific embodiments, step ii) of the method is carried out at temperatures of between 4° C. and 40° C., preferably of between 10° C. and 30° C. and more preferably of between 20° C. and 25° C.

In further specific embodiments, step ii) of the method is carried out at a pH of between 1 and 9, preferably of between 4 and 9 and most preferably of between 6 and 8.

In a second aspect, the present invention relates to silk particles, preferably spider silk particles, comprising at least one silk polypeptide, preferably spider silk polypeptide, comprising at least two identical repetitive units loaded with at least one compound, which is water-soluble and has a molecular weight of between about 50 Da and about 20 kDa.

In a preferred embodiment of the invention, the compound has a molecular weight of 50 Da or about 50 Da to 10 kDa or about 10 kDa or about 50 Da to 6 kDa or about 6 kDa, more preferably 50 Da or about 50 Da to 4 kDa or about 4 kDa and most preferably 50 Da or about 50 Da to 1 kDa or about 1 kDa.

In further preferred embodiments, at least 40%, preferably 50%, 60%, 70%, 80%, 90%, or 95% of the loaded compound is located within the matrix of the silk particles, preferably spider silk particles.

In preferred embodiments of the invention, the median size of the particles is 0.1 μm to 500 μm, preferably 0.1 μm to 100 μm, more preferably 0.2 μm to 20 μm, even more preferably 0.2 μm to 1 μm and most preferably 0.25 μm to 0.7 μm.

In further specific embodiments, the at least two identical repetitive units each comprise at least one consensus sequence selected from the group consisting of:
  i) GPGXX (SEQ ID NO: 3), wherein X is any amino acid, preferably in each case independently selected from the group consisting of A, S, G, Y, P and Q;
  ii) GGX, wherein X is any amino acid, preferably in each case independently selected from the group consisting of Y, P, R, S, A, T, N and Q; and
  iii) $A_x$, wherein x is an integer from 5 to 10.

More preferably, the repetitive unit(s) of the silk polypeptide, preferably spider silk polypeptide, is (are) independently selected from module A (SEQ ID NO: 20) or variants thereof, module C (SEQ ID NO: 21) or variants thereof, module Q (SEQ ID NO: 22) or variants thereof, module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34).

In further specific embodiments, the silk polypeptide, preferably spider silk polypeptide, further comprises one or more non-repetitive (NR) units.

More preferably, the NR unit is independently selected from the group consisting of NR3 (SEQ ID NO: 41 and SEQ ID NO: 45) or variants thereof and NR4 (SEQ ID NO: 42 and SEQ ID NO: 46) or variants thereof.

In preferred embodiments of the invention, the silk polypeptide, preferably spider silk polypeptide, is selected from the group consisting of ADF-3 (SEQ ID NO: 1 and SEQ ID NO: 47), ADF-4 (SEQ ID NO: 2 and SEQ ID NO: 48), MaSp I (SEQ ID NO: 43 and SEQ ID NOs: 53-64), MaSp II (SEQ ID NO: 44 and SEQ ID NOs: 65-78), $(C)_m NR_z$, $NR_z(C)_m$, $(AQ)_n NR_z$, $NR_z(AQ)_n$, $NR_z(QAQ)_o$, $(QAQ)_o NR_z$, $(C)_m$, $(AQ)_n$, and $(QAQ)_o$, wherein m is an integer of 8 to 48, n is an integer of 6 to 24, o is an integer of 8 to 16, z is an integer of 1 to 3.

More preferably, the silk polypeptide, preferably spider silk polypeptide, is $C_{16}$, $C_{32}$, $(AQ)_{12}$, $(AQ)_{24}$, $C_{16}NR4$, $C_{32}NR4$, $(AQ)_{12}NR3$, or $(AQ)_{24}NR3$.

In further preferred embodiments of the invention, the compound is a pharmaceutically active compound, a cosmetic substance, an agricultural substance, a chemoattractant, a chemorepellent, an anti-fungal substance, an anti-bacterial substance, a nutrient, a dietary supplement, a dye, a fragrance or an agent selected from the group consisting of hemostatic agents, growth stimulating agents, inflammatory agents, anti-fouling agents, antimicrobial agents and UV protecting agents.

In further specific embodiments, the compound has an overall positive net charge.

In further specific embodiments, the compound is able to permeate into the silk matrix, preferably spider silk matrix, by electrostatic interaction and/or diffusion.

In further specific embodiments, the compound has a neutral or alkaline nature.

In preferred embodiments of the invention, the compound is released from the silk particles, preferably spider silk particles, by diffusion upon exposure to physiological conditions.

In further preferred embodiments, less than 20%, preferably less than 15%, and most preferably less than 10% of the compound is released within the first 24 hours.

In a third aspect, the invention relates to a pharmaceutical composition comprising the silk particles; preferably spider silk particles, according to the invention and additionally a pharmaceutically acceptable buffer, diluent and/or excipient for controlled and sustained delivery, wherein the compound is a pharmaceutically active compound.

In a fourth aspect, the invention relates to a cosmetic composition comprising the silk particles, preferably spider silk particles, according to the invention for controlled and sustained delivery, wherein the compound is a cosmetic compound.

In a fifth aspect, the invention relates to silk particles, preferably spider silk particles, loaded with a compound, wherein the compound is water soluble, has a molecular weight of about 50 Da to about 20 kDa and has an overall positive net charge and wherein the silk particles, preferably spider silk particles, comprise one or more silk polypeptides, preferably spider silk polypeptides, comprising at least two identical repetitive units, the particles being obtainable by a process according to the invention.

DETAILED DESCRIPTION OF THE INVENTION

Figure 1:
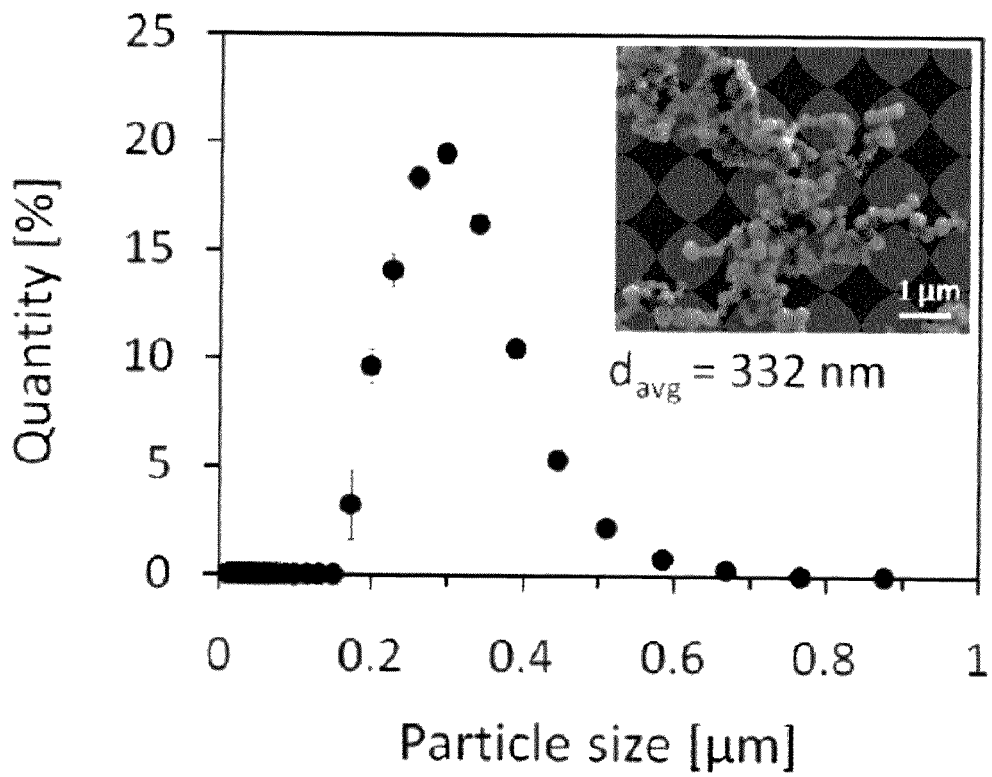
FIG. 1: eADF4(C16) particle characterization: *a*) Size distribution of obtained eADF4(C16) particles analyzed using laser diffraction spectrometry. The inset, shows an scanning electron micrograph of corresponding eADF4(C16) particles. The average diameter of the particle ensemble was $d_{avg}$=332±95 nm. *b*) Investigation of colloidal stability assessed by intensity of scattered light at 400 nm. $R^2$ is the correlation coefficient of the linear fit.
Figure 1:
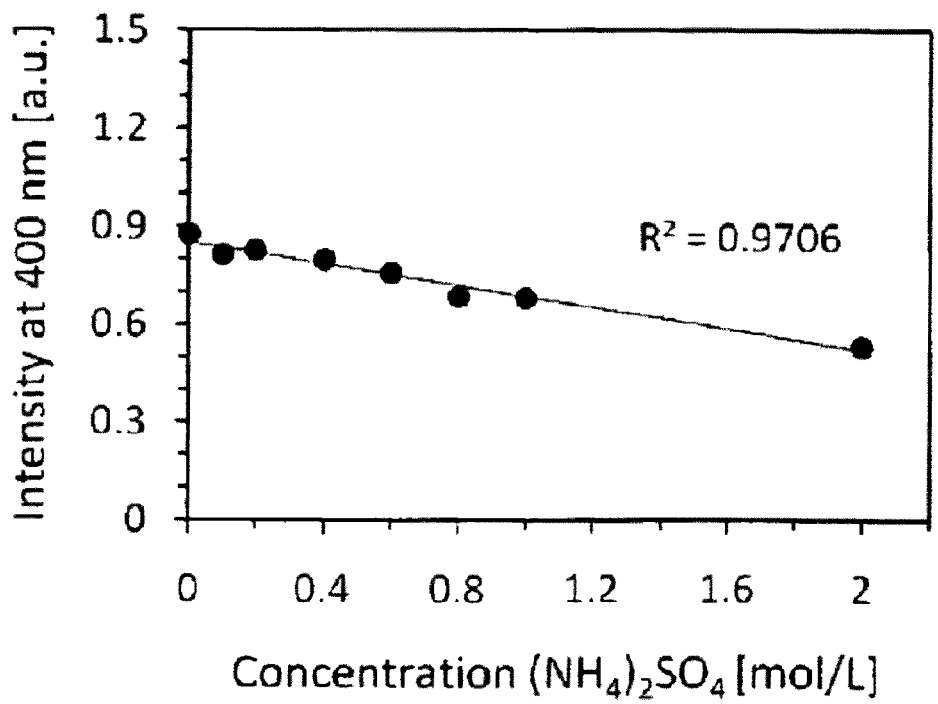

It is a primary object of the present invention to find a simple, mild and efficient way of producing silk particles, e.g. spider silk particles, with improved qualities for controlled and sustained delivery of a compound. It is another object to provide a novel and simple two step method for loading of silk particles, e.g. spider silk particles, with a compound of interest, thereby circumventing the disadvantages and drawbacks of the conventional methods of loading silk particles, e.g. spider silk particles, known from the art. In particular, it is yet another object to provide a method for loading of small and water-soluble compounds effectively. Another object of the invention is to provide silk particles, e.g. spider silk particles, having favourable carrier characteristics. One major advantage is that the particles produced by the method of the present invention are small in size, colloidally stable, biocompatible as well as biodegradable, and show an overall constant release profile. Other objects and advantages of the present invention will be apparent from the further reading of the specification and of the appended claims.

The present invention has solved the problems of the prior art by considering and making use of the intrinsic properties of the silk protein, e.g. spider silk protein, as well as of the compound to be loaded. Surprisingly, the inventors discovered that especially small and water-soluble compounds can be effectively loaded onto the silk particles, e.g. spider silk particles, under very mild conditions. It was further an unexpected finding that the method according to the invention can be conducted without using any organic solvents or toxic cross-linking chemicals, thereby avoiding relatively harsh formulation conditions. In particular, it was quite surprising that the method according to the invention can be carried out in an all-aqueous process. One major advantage of the method according to the present invention is that the particles are produced in a first step and are afterwards loaded with a compound of interest in a second step. Thus, contrary to the methods of the art, said two steps of the method according to the invention can be carried out separately, i.e. both spatially as well as at different times. Further, it was also surprising that the loaded compound can be continuously and controllably released once produced, which renders the silk particles, e.g. spider silk particles, according to the invention a very suitable carrier system, especially where sustained delivery of a compound is required. Because of their good biocompatibility as well as biodegradability, these silk particles, e.g. spider silk particles, are eminently suitable in pharmaceutical and cosmetic applications. It is however also evident that the silk particles, e.g. spider silk particles, according to the invention are not only limited to medical and cosmetic use. Depending on the nature of the loaded compound, the silk particles, e.g. spider silk particles, produced by the method according to the invention can also be employed as a carrier system for practically any kind of substances, e.g. nutrients, dietary supplements, dyes, fragrances, and a variety of other agents.

Some of the used terms will hereinafter be defined in greater detail below: Where the term "comprising" is used in the present description and the claims, it does not exclude other elements or steps. For the purposes of the present invention, the term "consisting of" is considered to be a preferred embodiment of the term "comprising". If hereinafter a group is defined as comprising at least a certain number of embodiments, this is also to be understood as disclosing a group which preferably consists only of these embodiments.

Where an indefinite or definite article is used when referring to a singular noun e.g. "a", "an" or "the", this includes a plural of that noun unless something else is specifically stated.

The term "about" in the context of the present invention denotes an interval of accuracy that the person skilled in the art will understand to still ensure the technical effect of the feature in question. The term typically indicates deviation from the indicated numerical value of ±10%, preferably 5%, most preferably 2%.

Residues in two or more polypeptides are said to "correspond" to each other if the residues occupy an analogous position in the polypeptide structures. It is well known in the art that analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS: needle, Matrix: Blosum62, Gap Open 10.0, Gap Extend 0.5.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted as including not only the explicitly recited values of about 1 to about 5, but also include individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the breadth of the range or the characteristic being described.

Within the context of the present invention, "median size" or "mean size" or "median particle size" or "mean particle size" can be used interchangeably and define the median silk particle size, preferably spider silk particle size, i.e., the silk particle, preferably spider silk particle diameter, where 50% of the silk particles, preferably spider silk particles, are smaller and 50% of the silk particles, preferably spider silk particles, are larger than the stated value. Usually, this corresponds to the maximum of a Gaussian size distribution.

The present invention will hereinafter be described with respect to particular embodiments and with reference to certain drawings, although the invention is not limited thereto, but only by the claims.

In a first aspect, the invention relates to a method of producing silk particles, preferably spider silk particles, loaded with a compound comprising, essentially consisting of, or consisting of the steps of:
  i) providing silk particles, preferably spider silk particles, comprising one or more silk polypeptides, preferably spider silk polypeptides, comprising at least two identical repetitive units, and
  ii) incubating said silk particles, preferably spider silk particles, with at least one compound,
    wherein preferably the compound is water-soluble and/or has a molecular weight of between about 50 Da and about 20 kDa.

It is to be understood that the method according to the invention is a process of two or more steps, wherein the particles are produced in a first step and are afterwards loaded with a compound of interest in a second step. Thus, contrary to the methods of the art, said at least two steps of the method according to the invention can be carried out separately, i.e. both spatially as well as at different times. According to preferred embodiments of the present invention, the steps i) and ii) of the method are carried out in separated processes, i.e. step ii) follows the provision of the silk particles, e.g. spider silk particles, in step i). Surprisingly, in contrast to the state of the art (e.g. in the form of WO 2007/082923), the second step in this invention is mainly based of diffusion of a compound into the matrix of the silk particle, e.g. spider silk particle, leading to a highly efficient permeation.

As used herein, "silks", e.g. "spider silks", are protein polymers that display extraordinary physical properties. Among the different types of silks, e.g. spider silks, draglines are most intensely studied. Dragline silks are generally utilized by orb weaving spiders to build frame and radii of their nets and as lifelines that are permanently dragged behind. For these purposes, high tensile strength and elasticity are required. The combination of such properties results in a toughness that is greater than that of most other known materials.

Dragline silks are generally composed of two major proteins whose primary structures share a common repetitive architecture. For example, the two major protein components of draglines from *Nephila clavipes* are termed MaSp1 and MaSp2 (Major ampullate Spidroins) and from *Araneus diadematus* ADF-3 and ADF-4 (*Araneus Diadematus* Fibroin). The dragline silk proteins have apparent molecular masses between 180 kDa and 720 kDa depending on the conditions of analysis.

Silk proteins, e.g. spider silk proteins, in comparison to common cellular proteins, show a quite aberrant amino acid composition. In particular, silk polypeptides, e.g. spider silk polypeptides, possess large quantities of hydrophobic amino acids such as glycine or alanine, but, for example, no (or only very little) tryptophan. Furthermore, silk polypeptides, e.g. spider silk polypeptides, contain highly repetitive amino acid sequences or repetitive units, especially in their large core domain.

Based on DNA analysis it was shown that all silk polypeptides, particularly spider silk polypeptides, are chains of repetitive units which further comprise a limited set of distinct shorter peptide motifs. The expressions "shorter peptide motif" and "consensus sequence" can be used interchangeably. Generally, the silk consensus sequences, particularly the spider silk consensus sequences, can be grouped into four major categories: GPGXX, GGX, $A_x$ or $(GA)_n$ and spacers. These categories of peptide motifs in silk polypeptides, particularly spider silk polypeptides, have been assigned structural roles. For example, it has been suggested that the GPGXX motif is involved in a β-turn spiral, probably providing elasticity. The GGX motif is known to be responsible for a glycine-rich $3_1$-helix. Both GPGXX and GGX motifs are thought to be involved in the formation of an amorphous matrix that connects crystalline regions, thereby providing elasticity of the fiber. Alanine-rich motifs typically contain 6-9 residues and have been found to form crystalline β-sheets. The spacers typically contain charged groups and separate the iterated peptide motifs into clusters.

A fifth category is represented by a non-repetitive (NR) region at the amino- and carboxyl termini of the proteins, often representing chains of about 100 amino acids. It is thought that the NR carboxy-termini might play a crucial role during assembly of the silk fiber.

The term "silk particles", e.g. "spider silk particles", as used herein refers to micro- or submicro-sized spherical structures which are formed by protein aggregation under certain conditions. Preferably, the silk particles, e.g. spider silk particles, have a smooth surface, are mechanical stable and/or are not water soluble. It is also preferred that the silk particles, e.g. spider silk particles, have a homogenous matrix, preferably without any clearly visible inclusions (e.g. determined via electron microscopy). In this respect, it should be noted that said inclusions may be air and polypeptides which are not related to silk polypeptides. In this respect, it should be noted that said inclusions do not encompass the at least one compound which is loaded into and/or onto the silk particles according to the present invention.

The silk particles, e.g. spider silk particles, according to the invention comprise one or more silk polypeptides, e.g. spider silk polypeptides, each comprising at least two identical repetitive units.

As used herein, the term "one or more silk polypeptides", e.g. "one or more spider silk polypeptides", preferably means that the silk particle, e.g. spider silk particle, does not additionally contain any other repetitive proteins, such as elastines, which do not relate, for example, to spider silk.

The silk polypeptide according to the invention may be any silk polypeptide known to one skilled in the art. The silk polypeptide, according to the invention may, for example, be any naturally occurring wild type polypeptide sequence, e.g. the polypeptide sequence of an arthropod silk polypeptide, such as a spider silk polypeptide or an insect silk polypeptide, or a mussel silk polypeptide.

The silk polypeptide, e.g. the spider silk polypeptide, according to the invention may also be a synthetic or recombinant silk polypeptide, e.g. a synthetic or recombinant spider silk polypeptide, which sequence may be derived from one or more authentic silk protein sequences, e.g. spider silk protein sequences.

Preferably, the silk polypeptide comprises a sequence derived from an arthropod silk polypeptide, such as a spider silk polypeptide or an insect silk polypeptide. The silk polypeptide may also comprise a sequence derived from a mussel silk polypeptide.

It is preferred that the spider silk polypeptide comprises a sequence derived from a major ampullate gland polypeptide (MaSp), such as a dragline spider silk polypeptide, a minor ampullate gland polypeptide (MiSp), a flagelliform polypeptide, an aggregate spider silk polypeptide, a tubuliform spider silk polypeptide, an aciniform spider silk polypeptide or a pyriform spider silk polypeptide.

It is further preferred that the insect silk polypeptide comprises a sequence derived from a silk polypeptide of Lepidoptera. More preferably, the insect silk polypeptide comprises a sequence derived from a silk polypeptide of Bombycidae, most preferably of *Bombyx mori*.

Useful spider silk polypeptides in the framework of the present invention are describdd in the literature, e.g. in the review article of R. V. Lewis (2006) Spider Silk: Ancient ideas for new biomaterials, Chem. Rev. 106:3762-3774. The amino acid sequences (and corresponding nucleic acid sequences) of spider silk polypeptides which can be used in the present invention can also be found in the databases known to the skilled person, e.g. the NCBI database. Some examples of such spider silk polypeptide sequences are given below in the sequence listing in SEQ ID NOs. 49 to 96. In detail, SEQ ID NOs: 49 to 52 represent spider silk polypeptide sequences of *araneus diadematus* fibroin 1 to 4, SEQ ID NOs: 53 to 64 represent spider silk polypeptide sequences of major ampullate spidroin I (MaSp I), SEQ ID NOs: 65 to 78 represent spider silk polypeptide sequences of major ampullate spidroin II (MaSp II), SEQ ID NOs: 79 to 81 represent sequences of minor ampullate silk polypeptides, SEQ ID NOs: 82 to 89 represent sequences of flagelliform silk polypeptides, SEQ ID NO: 90 represents the spider silk polypeptide sequence of aciniform spidroin, SEQ ID NO: 91 to 96 represent the spider silk polypeptide sequences of tubuliform spidroin.

It is particularly preferred that the spider silk polypeptide sequences are derived from spider silk dragline (major ampullate), flagelliform, piriform, tubuliform, minor ampullate, aggregate silk, or aciniform proteins. The spider silk sequences may be derived from orb-web spider such as Araneidae and Araneoids. More preferably, the spider silk sequence can be derived from the group consisting of the following spiders:

*Arachnura higginsi, Araneus circulissparsus, Araneus diadematus, Argiope picta*, Banded Garden Spider (*Argiope trifasciata*), Batik Golden Web Spider (*Nephila antipodiana*), Beccari's Tent Spider (*Cyrtophora beccarii*), Bird-dropping Spider (*Celaenia excavata*), Black-and-White Spiny Spider (*Gasteracantha kuhlii*), Black-and-yellow Garden Spider (*Argiope aurantia*), Bolas Spider (*Ordgarius furcatus*), Bolas Spiders—Magnificent Spider (*Ordgarius magnificus*), Brown Sailor Spider (*Neoscona nautica*), Brown-Legged Spider (*Neoscona rufofemorata*), Capped Black-Headed Spider (*Zygiella calyptrata*), Common Garden Spider (*Parawixia dehaani*), Common Orb Weaver (*Neoscona oxancensis*), Crab-like Spiny Orb Weaver (*Gasteracantha cancriformis* (elipsoides)), Curved Spiny Spider (*Gasteracantha arcuata*), *Cyrtophora moluccensis, Cyrtophora parnasia, Dolophones conifera, Dolophones turrigera*, Doria's Spiny Spider (*Gasteracantha doriae*), Double-Spotted Spiny Spider (*Gasteracantha mammosa*), Double-Tailed Tent Spider (*Cyrtophora exanthematica*), *Aculeperia ceropegia, Eriophora pustuloses*; Flat Anepsion (*Anepsion depressium*), Four-spined Jewel Spider (*Gasteracantha quadrispinosa*), Garden Orb Web Spider (*Eriophora transmarina*), Giant Lichen Orbweaver (*Araneus bicentenarius*), Golden Web Spider (*Nephila maculata*), Hasselt's Spiny Spider (*Gasteracantha hasseltii*), *Tegenaria atrica, Heurodes turrita*, Island Cyclosa Spider (*Cyclosa insulana*), Jewel or Spiny Spider (*Astracantha minax*), Kidney Garden Spider (*Araneus mitificus*), Laglaise's Garden Spider (*Eriovixia laglaisei*), Long-Bellied Cyclosa Spider (*Cyclosa bifida*), Malabar Spider (*Nephilengys malabarensis*), Multi-Coloured St Andrew's Cross Spider (*Argiope versicolor*), Ornamental Tree-Trunk Spider (*Herennia ornatissima*), Oval St. Andrew's Cross Spider (*Argiope aemula*), Red Tent Spider (*Cyrtophora unicolor*), Russian Tent Spider (*Cyrtophora hirta*), Saint Andrew's Cross Spider (*Argiope keyserlingi*), Scarlet Acusilas (*Acusilas coccineus*), Silver Argiope (*Argiope argentata*), Spinybacked Orbweaver (*Gasteracantha cancriformis*), Spotted Orbweaver (*Neoscona domiciliorum*), St. Andrews Cross (*Argiope aetheria*), St. Andrew's Cross Spider (*Argiope Keyserlingi*), Tree-Stump Spider (*Pols illepidus*), Triangular Spider (*Arkys clavatus*), Triangular Spider (*Arkys lancearius*), Two-spined Spider (*Poecilopachys australasia*), *Nephila* species, e.g. *Nephila clavipes, Nephila senegalensis*, and *Nephila madagascariensis*. The spider silk sequence may also be derived from widow spiders such as brown widow spiders (*Latrodectus geometricus*), black widow spiders or grey widow spiders.

As used herein "a recombinant silk polypeptide", e.g. "a recombinant spider silk polypeptide", may comprise
a) one or more synthetic repetitive silk protein, e.g. spider silk protein, sequences and/or
b) one or more authentic non-repetitive silk protein, e.g. spider silk protein, sequences.

It is also clear that a recombinant silk polypeptide, e.g. spider silk polypeptide, may comprise sequences derived from different species, e.g. spider species. For example, the synthetic repetitive silk protein sequences may be derived from one species, while the one or more non-repetitive silk protein sequences, e.g. spider silk protein sequences, may be derived from another species. It is also possible to design a recombinant silk polypeptide, e.g. spider silk polypeptide, comprising one or more repetitive sequences which are derived from different species, e.g. spider species.

The term "synthetic repetitive sequence" as used herein is to be understood as a recombinant protein sequence which is not a natural silk protein sequence, e.g. spider silk protein sequence, but may nevertheless be derived from the repetitive units comprising consensus sequences or motifs of authentic silk proteins, e.g. spider silk proteins. The recombinant silk polypeptide, e.g. spider silk polypeptide, according to the present invention comprises at least two identical repetitive units. A repetitive unit may further comprise either one or more monomeric sequence modules or one or more short peptide motifs.

A system for producing recombinant spider silk proteins has already been developed and described in WO 2007/025719. In this expressions system, single building blocks, so called modules, can be freely combined to yield synthetic spider silk polypeptides. Modules of this type are also described in Hümmerich et al. [Hümmerich, D. (2004): "Primary structure elements of dragline silks and their contribution to protein solubility and assembly," Biochemistry 43, 13604-13612.] Spider silk monomeric sequence modules are further described in WO 2007/025719 in detail. Suitable vectors and plasmids for the expression of silk polypeptide, e.g. spider silk polypeptide, sequences in a host cell are described in these references.

In brief, the recombinant silk proteins, preferably spider silk proteins, can be produced in a host by expression of suitable nucleic acids or vectors. The host may be for example a prokaryotic cell. Preferred prokaryotic organisms are *E. coli* or *Bacillus subtilis*.

The host may also be a eukaryotic cell. Preferred eukaryotic cells are mammalian cells, plant cells, yeast cells or insect cells. Preferred mammalian cells are, for instance, CHO, COS, HeLa, 293T, HEH or BHK cells. If yeast cells are used, preferred organisms are *Saccharomyces cerevisiae*, *Schizosaccharomyces pombe*, *Pichia pastoris*, *Candida albicans* or *Hansenula polymorpha*. Preferred insect cells are cells from Lepidoptera insects, more preferably cells from *Spodoptera frugiperda* and from *Trichoplusia ni*. Most preferably, the insect cell is a Sf0, Sf21 or high five cell. If the host is a plant cell, the cell is preferably derived from tobacco, potato, corn and tomato.

Preferably, the basis of the sequence modules are the genes ADF-3 and ADF-4 of the spider *Araneus diadematus* as well as the gene FLAG of the spider *Nephila clavipes*. The genes ADF-3 and ADF-4 encode for proteins which form the dragline thread of the spider. Both proteins, ADF-3 and ADF-4 belong to the class of MaSp II proteins (major ampullate spidroin II). The gene FLAG encodes for a flagelliform silk protein.

Modules suitable for the assembly of a synthetic silk protein construct, e.g. spider silk protein construct, are for example:

```
Modul A:
                                          (SEQ ID NO: 20)
GPYGPGASAA AAAAGGYGPG SGQQ, Modul C:
                                          (SEQ ID NO: 21)
GSSAAAAAAA ASGPGGYGPE NQGPSGPGGY GPGGP, Modul Q:
                                          (SEQ ID NO: 22)
GPGQQGPGQQ GPGQQGPGQQ, Modul K:
                                          (SEQ ID NO. 23)
GPGGAGGPYGPGGAGGPYGPGGAGGPY, Modul sp:
                                          (SEQ ID NO: 24)
GGTTIIEDLD ITIDGADGPITISEELTI, Modul X:
                                          (SEQ ID NO: 27)
GGAGGAGGAG GSGGAGGS,
and
```

```
-continued
Modul Y:
                                          (SEQ ID NO: 28)
GPGGAGPGGY GPGGSGPGGY GPGGSGPGGY.
```

Further suitable modules are for example:

```
Modul A^C:
                                          (SEQ ID NO: 29)
GPYGPGASAA AAAAGGYGPG CGQQ, Modul A^K:
                                          (SEQ ID NO: 30)
GPYGPGASAA AAAAGGYGPG KGQQ, Modul CC:
                                          (SEQ ID NO: 31)
GSSAAAAAAA ASGPGGYGPE NQGPCGPGGY GPGGP, Modul C^{K1}:
                                          (SEQ ID NO: 32)
GSSAAAAAAA ASGPGGYGPE NQGPKGPGG Y GPGGP, Modul C^{K2}:
                                          (SEQ ID NO: 33)
GSSAAAAAAA ASGPGGYGPK NQGPSGPGGY GPGGP,
and Modul C^{KC}:
                                          (SEQ ID NO: 34)
GSSAAAAAAA ASGPGGYGPK NQGPCGPGGY GPGGP.
```

Said modules may further comprise the following amino terminal and/or a carboxy terminal TAGs:

```
TAG^{CYS1}:
                                          (SEQ ID NO: 35)
GCGGGGGGSGGGG,

TAG^{CYS2}:
                                          (SEQ ID NO: 36)
GCGGGGGG,

TAG^{CYS3}:
                                          (SEQ ID NO: 37)
GCGGSGGGGSGGGG,

TAG^{LYS1}:
                                          (SEQ ID NO: 38)
GKGGGGGGSGGGG,
and TAG^{LYS2}:
                                          (SEQ ID NO: 39)
GKGGGGGG.
```

Still further modules which can be present in the silk polypeptides, e.g. spider silk polypeptides, of the invention are described in the prior art literature. In this context, it is referred to international patent application WO 2008/155304 A1 and herein in particular to SEQ ID NO: 2 (R16) and SEQ ID NO: 4 (S16) in the sequence listing of WO 2008/155304 A1.

The amino acid sequences of the above modules and TAGs comprise one or more lysine and/or cysteine residues. The modules and/or TAGs are, therefore, capable of producing modified silk proteins, particularly spider silk proteins. Modified silk proteins, particularly spider silk polypeptides, are described in detail in WO 2007/025719. It has to be understood that compounds may also be coupled to the modified silk proteins, particularly spider silk proteins, via their lysine and/or cysteine residues.

Further, the above described modules can be freely combined in order to yield a suitable silk polypeptide, e.g. spider silk polypeptide, according to the invention. The number of modules of a silk polypeptide, e.g. spider silk polypeptide, is generally not restricted. Preferably, the recombinant silk polypeptides, e.g. spider silk polypeptides, may comprise between 2 and 50 modules, more preferably between 10 and 40, and most preferably between 15 and 35 modules.

For example, a synthetic repetitive sequence may comprise at least two of the combinations (AQ) and/or (QAQ) as repetitive units.

If the synthetic repetitive sequence is derived from ADF-4, it may comprise at least two identical repetitive units, each comprising the amino acid sequence of module C (SEQ ID NO: 21) or a variant thereof. For example, the resulting sequence may be $C_{16}$ or $C_{32}$, i.e. comprising 16 or 32 repetitive units, respectively. In this respect it should be noted that the terms "eADF4(C16)" and "$C_{16}$" are interchangeable be used in the context of the present invention and have the same meaning.

A compound which is well-suited for efficient loading of the silk particles, e.g. spider silk particles, is preferably sufficiently small in size. In a preferred embodiment of the invention, the compound has a molecular weight of 50 Da or about 50 Da to 20 kDa or about 20 kDa; or 50 Da or about 50 Da to 10 kDa or about 10 kDa, preferably 50 Da or about 50 Da to 6 kDa or about 6 kDa, more preferably 50 Da or about 50 Da to 4 kDa or about 4 kDa and most preferably 50 Da or about 50 Da to 1 kDa or about 1 kDa, e.g. 50 Da, 100 Da, 150 Da, 200 Da, 250 Da, 300 Da, 350 Da, 400 Da, 450 Da, 500 Da, 550 Da, 600 Da, 650 Da, 700 Da, 750 Da, 800 Da, 850 Da, 900 Da, 950 Da, 1 kDa, 1.5 kDa, 2 kDa, 2.5 kDa, 3 kDa, 3.5 kDa, 4 kDa, 4.5 kDa, 5 kDa, 5.5 kDa, 6 kDa, 6.5 kDa, 7 kDa, 7.5 kDa, 8 kDa, 8.5 kDa, 9 kDa, 9.5 kDa, 10 kDa, 11 kDa, 12 kDa, 13 kDa, 14 kDa, 15 kDa, 16 kDa, 17 kDa, 18 kDa, 19 kDa, or 20 kDa.

Further, a compound which is well-suited for efficient loading of the silk particles, e.g. spider silk particles, is preferably water-soluble.

Furthermore, a preferred compound according to the invention may be any compound, which is a small and water-soluble compound, preferably having a molecular weight of between about 50 Da and 20 kDa, more preferably 50 Da to 10 kDa or 50 Da to 6 kDa and most preferably 50 Da to 4 kDa or 50 Da to 1 kDa (see above).

The term "soluble" as used herein means that a solid, liquid or gaseous chemical substance called solute is able to dissolve in a liquid solvent to form a homogeneous solution. Generally, the solubility of a substance strongly depends on the solvent that is used as well as on temperature and pressure. The extent of the solubility of a substance in a specific solvent is measured as the saturation concentration where adding more solute does not increase the concentration of the solution.

A "solvent" is a liquid which can dissolve gases, other liquids or solid materials without chemical reactions between dissolved matter and dissolving liquid taking place.

A "water-soluble" compound is usually any ionic compound (or salt) which is able to dissolve in water. Generally, the underlying solvation arises because of the attraction between positive and negative charges of the compound with the partially-negative and partially positive charges of the $H_2O$-molecules, respectively. Substances or compounds which dissolve in water are also termed "hydrophilic" ("water-loving"). Water solubility ($S_W$), also known as aqueous solubility, is the maximum amount of a substance that can dissolve in water at equilibrium at a given temperature and pressure. Generally, the limited amount is given by the solubility product.

Following the definition of solubility in the European Pharmacopoeia, "sparingly solube" means that the approximate volume of solvent in millilitres per gram of solute is from 30 to 1.00 (at a temperature between 15° C. and 25° C.); "soluble" means that the approximate volume of solvent in millilitres per gram of solute is from 10 to 30 (at a temperature between 15° C. and 25° C.), "freely soluble" means that the approximate volume of solvent in millilitres per gram of solute is from 1 to 10 (at a temperature between 15° C. and 25° C.), and "very soluble" means that the approximate volume of solvent in millilitres per gram of solute is less than 1 (at a temperature between 15° C. and 25° C.).

Accordingly, in the context of the present invention "water-soluble" means a water solubility of 10 g compound or more per 1 liter of water. Preferably, the water solubility is at least 20 g, at least 30 g, at least 40 g, and at least 50 g compound per 1 liter of water, more preferably at least 60 g, at least 70 g, at least 80 g, at least 90 and at least 100 g compound per 1 liter of water, and most preferably at least 200 g, at least 300 g, at least 400 g, at least 500 g, and at least 800 g compound per 1 liter of water. Very water-soluble compounds that can be used in the present invention even have a water solubility of 1 g/ml or more.

Compounds which are water soluble typically comprise the following chemical groups: cationic groups such as metallic cations, ammonium cations and/or anionic groups such as acetate, nitrate, chloride, bromide, iodide or sulphate.

Typical measures for water solubility used in organic chemistry and the pharmaceutical sciences are a partition—(P) or distribution coefficient (D), which give the ratio of concentrations of a compound in the two phases of a mixture of two immiscible solvents at equilibrium.

For example, the octanol-water partition coefficient ($\log P_{o/w}$) is typically used to estimate the water solubility of substances and is defined as the ratio of a compound's concentration in the octanol phase to its concentration in the aqueous phase of a two-phase octanol/water system. Thus, the octanol-water partition coefficient provides a measure of the lipophilic versus hydrophilic nature of a compound. In general, log P tends to be large for compounds with extended non-polar-structures and small for a compound of a hydrophilic nature. Methods for determining the log P value of a compound are for example the shake flask (or tube) method, HPLC or electrochemical methods such as ITIES (Interfaces between two immiscible electrolyte solutions).

There are many log P calculators or predictors available both commercially and for free on the internet, e.g. Chemistry Development Kit, JOELib, ACD/LogP-DB, ACD/Log P Freeware, Simulations Plus—S+logP, ALOGPS, Molecular Property Explorer, Free online log P calculations using ChemAxon's Marvin and Calculator Plugins, miLogP free log P, PreADMET, XLOGP3.

Preferably, the log P value can be predicted using ACD-logP-Software (available at Advanced Chemistry Development, ACD/labs, http://www.acdlabs.com).

In the context of the present invention, the compound preferably has an overall hydrophilic nature. Compounds suitable for loading of the silk particles, preferably spider silk particles, comprise also amphiphilic substances such as proteins or peptides. According to preferred embodiments, the log P value of the compound is less than 6, preferably less than 5.5, even more preferably less than 5, and most preferably less than 4.5, e.g. less than 6, 5.5, 5, 4.5, 4, 3.5, 3, 2.5, 2, 1.5, 1 or 0.5.

Further, the distribution between a hydrophobic and a hydrophilic phase of two different species of a specific compound, i.e. the native and the protonated form, can be described by its apparent distribution coefficient (log D), which can be calculated using the following equations:

for acids: $\log D = \log P - \log(1+10^{pH-pKa})$, and for bases: $\log D = \log P - \log(1+10^{pKa-pH})$.

In the context of the present invention, compounds are preferred which possess a distribution coefficient (log D) of more than −2, preferably of more than −1.5, more preferably of more than −1, even more preferably of more than −0.5 and most preferably of more than 0.

In preferred embodiments of the invention, the silk particles, preferably spider silk particles, provided in step i) are produced by the steps of
 a) providing an aqueous solution comprising one or more silk polypeptides, preferably spider silk polypeptides, comprising at least two identical repetitive units,
 b) triggering aggregation of the silk polypeptides, preferably spider silk polypeptides, to form silk particles, preferably spider silk particles, and
 c) separating the silk particles, preferably spider silk particles, by phase separation.

Generally, starting from an aqueous solution, aggregation of the silk polypeptides, preferably spider silk polypeptides, can be triggered under certain conditions to form silk particles, preferably spider silk particles.

"Aggregation" or "phase separation" as used herein means the particle formation due to a salting-out mechanism which in particular can be considered as a liquid-liquid phase separation. The "one-phase state" is the initial state displayed by a solution of monomeric and intrinsically unfolded protein molecules. For example, changing constraints such as the ionic strength by addition of kosmotropic ions alters the free energy of the system and leads to phase separation into protein-rich and solvent-rich phases. This phase-separated state is energetically favoured and the protein concentration in the "protein phase" increases to a critical level. Upon reaching the critical concentration for nucleation, several structured nuclei are formed simultaneously in the protein-rich phase. The nuclei start to grow in a spherical manner, interacting with additional monomers and thereby converting their structure. Spherical growth stops when the protein concentration in the protein-rich phase is below the equilibrium of solubility. Hence the sphere size does not increase further. Phase separation thus means that protein-rich and solvent-rich phases are separated. Without being bound to a theory, the sphere size is generally dependent on protein concentration and mixing conditions. There exist however various other methods in the art for triggering aggregation of proteins.

The process of microsphere assembly is typically monitored by light-scattering after initiation of aggregation. In particular, the colloidal stability of the resulting particles can be analysed by measuring the intensity of scattered light, at a certain wavelength. Also the mean particle size and particle size distribution can be determined by laser diffraction, also called static light scattering (SLS). Generally, laser diffraction utilizes the theories of Mie and Fraunhofer to determine particle size distribution from a light scattering pattern. These depend upon analysis of the "halo" of diffracted light produced when a laser beam passes through a dispersion of particles in air or in a liquid. The angle of diffraction increases as particle size decreases. The mass and the root mean square radius or a measure of geometric size can be determined using this technique on a mega Dalton scale. Thus, according to the Mie theory, the intensity of scattered light in forward direction increases with increasing particle size. The onset of aggregation in dilute dispersions can thus be detected by intensity of scattered light in forward direction.

The obtained silk particles, preferably spider silk particles, may also be analysed using methods such as scanning electron microscopy (SEM) and Fourier transform infrared spectroscopy (FTIR). A further description of these methods can be found in the description and in the examples below.

In order to analyze the morphology and structure of the silk particles, preferably spider silk particles, scanning electron microscopy (SEM) can typically be employed. The scanning electron microscope (SEM) is a type of electron microscope that images the sample surface by scanning it with a high-energy beam of electrons in a raster scan pattern. The electrons interact with the atoms that make up the sample producing signals that contain information about the sample's surface topography, composition and other properties such as electrical conductivity.

Further characteristics such as the secondary structure of the obtained silk particles, preferably spider silk particles, can for example be analyzed by Fourier transform infrared spectroscopy (FTIR). The technique is based on the fact that bonds and groups of bonds vibrate at characteristic frequencies. A molecule that is exposed to infrared rays absorbs infrared energy at frequencies which are characteristic for that molecule. During FTIR analysis, a spot on the specimen is subjected to a modulated IR beam. The specimen's transmittance and reflectance of the infrared rays at different frequencies is translated into an IR absorption plot consisting of reverse peaks. The resulting FTIR spectral pattern is then analyzed and matched with known signatures of identified materials in the FTIR library. For example, peaks at 1648-1660 cm$^{-1}$, 1625-1640 cm$^{-1}$ and 1660-1668 cm$^{-1}$, can be assigned to α-helical, β-sheets and β-turn structures of the silk polypeptides, e.g. spider silk polypeptides, respectively.

After phase separation, the produced particles can be separated by routine methods such as centrifugation. The prepared particles may subsequently be washed and incubated with a compound of interest. As will be mentioned below, the particles may also be stored, for example, in a dried or lyophilized form.

The particles according to the invention usually consist of a smooth surface and a solid matrix. In the context of the invention, the term "surface" defines the outer sphere of the particle, which includes those sphere sections that are directly exposed to the surrounding space, i.e. the surrounding medium. Although the particles appear rather smooth and uniform, their surfaces on the sub-microscopic level reveal a thin mantle with irregular and diffuse structures. A surface, thus, delineates the outermost layer of the particle which shares an interface with the surrounding medium and at which adhesion and bidirectional diffusion of the compound molecules may occur.

The term "matrix" as used herein defines the inner sphere of the silk particle, preferably spider silk particle, which is not the surface, i.e. which according to the above definition does not include any interface to the surrounding medium. The matrix is to be understood as a solid sphere having a radius and accordingly a volume usually smaller than that of the particle.

The volume of the matrix is usually more than 50% of the total volume, preferably more than 60%, 70%, 80%, 90%, most preferably more than 95%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%.

The term "loading" in the context of the present invention means the non-covalent binding of a compound to a silk particle, preferably spider silk particle, via adhesion to the surface and via diffusion and/or permeation and subsequent adhesion to the matrix of the silk particle, preferably spider silk particle, wherein preferably at least 40%, more preferably at least 50%, 60%, 70%, 80%, 90%, or 95% of the loaded compound is located within the matrix of the silk particle, preferably spider silk particle. The non-covalent binding mentioned herein is caused, for example, by electrostatic interactions, hydrophilic interactions (hydrogen-bonds) and/or hydrophobic interactions (van der Waals forces).

There are several ways to determine the "loading" of a silk particle, e.g. spider silk particle. For example, one way is to determine the residual concentration of the compound in the supernatant after a period of time of incubation with the silk particles, e.g. spider silk particles. As will be explained in more detail in the examples below, the residual concentrations of a compound may be measured using UV-Vis spectroscopy.

To determine the percentage of the loaded compound which is adhered to the matrix of the silk particle, preferably spider silk particle, the following model calculation can be used: For calculation of the theoretical maximal adhesion capacity of a silk particle, the closest/densest sphere packing of a compound on the silk particle is taken. By means of the medians of the silk particle and the compound, the surface of the silk particle and the compound can be determined. Corresponding to the surface, the maximum amount of compound which can be in direct contact to the particle surface can be determined. A monolayer of compound will be assumed as closest/densest sphere packing of a compound on the silk particle. More than one layer of compound loaded to the surface of a silk particle is unlikely, due to the electrostatic repulsion between, for example, two positively charged compounds. On the basis of ratio of totally loaded compound to compound loaded to the surface of a silk particle, the percentage of loaded compound into the matrix can be determined.

The non-covalent binding of a positively charged compound to the surface of a negatively charged particle via adhesion decreases the absolute value of zeta-potential in contrast to the non-covalent binding of a positively charged compound to the matrix of a negatively charged particle via diffusion and/or permeation and subsequent adhesion, which does not substantially alter the zeta-potential of the particle.

The high percentage of a particle-bound (adhered) compound compared to a free compound in solution results in a very high loading efficiency.

The adhered compound is protected in the matrix of the silk particle and can, therefore, safely be stored for several weeks for later use.

The adhered compound can also be efficiently and constantly released from the silk particle without the requirement of degradation of the silk particle—in contrast to an irreversible/sterically-trapped bound compound. The compound can be steadily released over a time period of days to weeks—in contrast to the burst release of compounds which are exclusively adhered at the surface of the silk particle, preferably spider silk particle.

In further preferred embodiments, the compound is able to permeate into the matrix of the silk particles, preferably spider silk particles. The term "permeate" in physics and engineering generally means the penetration of a permeate, which can be a liquid, gas or vapour, through a solid and is dependent on the material's intrinsic permeability. In particular, permeation of a compound according to the present invention occurs by molecular diffusion, which by definition is a net transport of molecules from a region of higher concentration to one of lower concentration by random molecular motion. It has to be understood that during the process of permeation the compound at first adheres to the surface of the silk particles, preferably spider silk particles, and then permeates the surface layer into the matrix of the silk particles, preferably spider silk particles, by molecular diffusion.

As used herein the term "is able to permeate into the silk particles", e.g. "is able to permeate into the spider silk particles" thus means that the compound is able to soak into the silk matrix, e.g. spider silk matrix, by molecular diffusion. Whether a compound is able to permeate into the matrix of the silk particles, e.g. spider silk particles, can be determined using several methods.

For example, one way is to determine the residual concentration of the compound in the supernatant after a period of time of incubation with the silk particles, e.g. spider silk particles. As will be explained in more detail in the examples below, the residual concentrations of a compound may be measured using UV-Vis spectroscopy.

Generally, Ultraviolet-visible spectroscopy or ultraviolet-visible spectrophotometry (UV-Vis or UV/Vis) involves the spectroscopy of photons in the UV-visible region. This technique thus uses light in the visible and adjacent (near ultraviolet (UV) and near infrared (NIR)) ranges. In this region of the electromagnetic spectrum, molecules in the measured sample undergo electronic transition. The UV-Vis-spectroscopy is, therefore, generally used in the quantitative determination of solution of organic compounds. Within the context of the present invention, the encapsulation efficiency and loading of the silk particles, preferably spider silk particles, can be determined using UV-Vis spectroscopy and calculated on basis of the following equations:

$$\text{encapsulation efficiency } (w/w\ \%) = \frac{\text{amount of compound in particles}}{\text{compound initially added}} \times 100$$

For example, the "encapsulation efficiency" is calculated to be 66% with the following data: amount of compound non-covalently bound to the surface and to the matrix of the silk particle: 0.1 g, amount of compound initially added: 0.15 g.

$$\text{encapsulation efficiency} = \frac{0,1\ g}{0,15\ g} 0,66 = 66\%$$

$$\text{loading } (w/w\ \%) = \frac{\text{amount compound in particles}}{\text{amount of particles}} \times 100$$

For example the "loading" is calculated to be 10% with the following data: amount of compound non-covalently bound to the surface and to the matrix of the silk particle: 0.1 g, amount of compound initially added: 1.0 g.

$$\text{loading} = \frac{0,1\ g}{1,0\ g} = 0,1 = 10\%$$

The terms "encapsulation efficiency" and "loading efficiency" are used interchangeable in the context of the present invention and have, therefore, the same meaning.

In a preferred embodiment, at least 10%, 20%, or 30%, more preferably at least 40%, 50%, or 60%, and most preferably at least 70%, 80%, 90%, or 95% of the compound is loaded to the silk particles (to the silk surface and to the matrix), preferably spider silk particles, e.g. at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%.

In another preferred embodiment, at least 40%, preferably at least 50%, 60%, 70%, 80%, 90%, or 95% of the loaded compound is located within the matrix of the silk particles, preferably spider silk particles, e.g. at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%.

In a more preferred embodiment, at least 10%, 20%, or 30%, more preferably at least 40%, 50%, or 60%, and most preferably at least 70%, 80%, 90%, or 95% of the compound is loaded to the silk particles (to the silk surface and to the matrix), preferably spider silk particles, e.g. at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%, wherein at least 40%, preferably at least 50%, 60%, 70%, 80%, 90%, or 95% of the loaded compound is located within the matrix of the silk particles, preferably spider silk particles, e.g. at least 40, 41, 42, 43, 44, 45, 46; 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%.

One further criterion which gives an indication whether a compound is able to permeate into the interior of the silk particles, e.g. spider silk particles, is the zeta-potential. As will be apparent from the examples, monitoring of the zeta-potential of the particles may particularly indicate whether a compound is merely bound at the particle surface or is able to diffuse into the interior. Zeta-potential measurements are especially applicable when the produced silk particles, e.g. spider silk particles, possess an overall net charge.

As used herein, "zeta potential" or "ζ-potential" is the electrical potential in the interfacial double layer (DL) at the location of the slipping plane versus a point in the bulk fluid away from the interface. In other words, zeta potential is the potential difference between the dispersion and the stationary layer of fluid attached to a dispersed particle.

In particular, the permeation process can be monitored on the basis of the observed changes of the zeta potential during loading. A change of the zeta potential is thus a measure for the permeation of a compound into the matrix of the silk particles, e.g. spider silk particles.

The mechanism of permeation according to the present invention is, thus, clearly distinguishable from mechanisms such as encapsulation of compounds as has been described in the art. For instance, the encapsulation as described in patent applications WO 2007/082936 and WO 2007/082923 are is in both cases based on the inclusion of poorly water-insoluble compounds. However, diffusion of the compound molecules into the interior of the particles was not described at all in these prior art references. Rather, the compounds are enveloped by the spider silk material during particle formation. For this reason, particle formation and loading of a compound according to the prior art must to be carried out in one single step.

In contrast, the method of the present invention allows that the incubation step, i.e. loading of a compound, can be carried out during, but preferably also after the step of preparing the silk particles, e.g. spider silk particles. However, this does not mean that these two steps must also be carried out consecutively in one continuous process. As mentioned above, one major advantage of the present invention is that the steps of producing and loading of the particles can be carried out separately, both spatially and at different times.

As mentioned above, the produced silk particles, e.g. spider silk particles, may be provided separately in a dry form, e.g. in the form of a powder. Suitable methods such as lyophilisation are known in the art. Lyophilisation may however also occur after the particles were loaded with a compound. Before use, the dried silk particles, e.g. spider silk particle's, have to be redispersed, i.e. hydrated with an aqueous liquid or suitable buffer.

Further, the silk particles, e.g. spider silk particles, produced by the method of the invention generally may have a median size ranging from several nanometers to several hundred micrometers. As mentioned above, particle size and size distribution can be determined using laser diffraction spectroscopy.

According to preferred embodiments, the silk particles, preferably spider silk particles, have a median size of between 0.1 μm and 500 μm, preferably of between 0.1 μm and 100 μm, more preferably of between 0.2 μm and 20 μm, even more preferably of between 0.2 μm and 1 μm and most preferably of between 0.25 μm and 0.7 μm, e.g. 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 μm.

As mentioned above, the silk polypeptide, preferably spider silk polypeptide, according to the invention can be either any naturally occurring wild type polypeptide sequence or any synthetic or recombinant silk polypeptide, preferably spider silk polypeptide, or also a mixture thereof. Preferably, the silk polypeptide, more preferably spider silk polypeptide, according to the invention is a synthetic or a recombinant silk polypeptide, more preferably spider silk polypeptide.

A "silk polypeptide", e.g. "spider silk polypeptide", as used in the context of the present invention may refer to a polypeptide with an amino acid sequence which comprises or consists of at least 20%, 30%, 40%, 50%, 60%, 65%, 70%, 75%, 80%, 85%, 90%, preferably at least 95% and most preferably 100% of multiple copies of one identical repetitive unit (e.g. $A_2$, $Q_6$, or $C_{16}$, wherein the items 2, 6, or 16 represent the number of repetitive units) or multiple copies of two or more different repetitive units (e.g. $(AQ)_{24}$, or $(AQ)_{12}C_{16}$).

The terms "repetitive unit" and "repeat unit" are interchangeable be used in the context of the present invention.

In the context of the present invention, a "repetitive unit" may refer to a region which corresponds in amino acid sequence to a region that comprises or consists of at least one peptide motif (e.g. AAAAAA (SEQ ID NO: 13) or GPGQQ (SEQ ID NO: 4)) that repetitively occurs within a naturally occurring silk polypeptide (e.g. MaSpI, ADF-3, ADF-4, or Flag) (i.e. identical amino acid sequence) or to an amino acid sequence substantially similar thereto (i.e. variational amino acid sequence). In this regard "substantially similar" may mean a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over the whole length of the respective reference naturally occurring amino acid sequence. A "repetitive unit" having an amino acid sequence which is "substantially similar" to a corresponding amino acid sequence within a naturally occurring silk polypeptide (i.e. wild-type repetitive unit) is also similar with respect to its functional properties, e.g. the silk particle comprising the silk polypeptide which comprises the "substantially similar repetitive unit" can still be loaded with a compound. Preferably, the silk particle comprising the silk polypeptide which comprises the "substantially similar repetitive unit" is capable of being loaded with a compound so that at least 20%, preferably at least 40%, more preferably at least 50%, 60%, 70%, 80%, 90%, or 95% of the loaded compound is located within the matrix of the silk particle. The skilled person can readily determine the "loading" of a silk particle (e.g. via UV-Vis-spectroscopy), in particular the percentage of the compound which is located within the matrix of silk particles (see, for example, experimental section).

A "repetitive unit" having an amino acid sequence which is "identical" to the amino acid sequence of a naturally occurring silk polypeptide, for example, can be a portion of a silk polypeptide corresponding to one or more peptid motifs of MaSp I (SEQ ID NO: 43) MaSp II (SEQ ID NO: 44), ADF-3 (SEQ ID NO: 1) and/or ADF-4 (SEQ ID NO: 2). A "repetitive unit" having an amino acid sequence which is "substantially similar" to the amino acid sequence of a naturally occurring silk polypeptide, for example, can be a portion of a silk polypeptide corresponding to one or more peptide motifs of MaSpI (SEQ ID NO: 43) MaSpII (SEQ ID NO: 44), ADF-3 (SEQ ID NO: 1) and/or ADF-4 (SEQ ID NO: 2), but having one or more amino acid substitution at specific amino acid positions.

The "repetitive unit" does not include the non-repetitive hydrophilic amino acid domain generally thought to be present at the carboxyl terminus of naturally occurring silk polypeptides.

A "repetitive unit" according to the present invention may further refer to an amino acid sequence with a length of 3 to 200 amino acids, or 5 to 150 amino acids, preferably with a length of 10 to 100 amino acids, or 15 to 80 amino acids and more preferably with a length of 18 to 60, or 20 to 40 amino acids. For example, the repetitive unit according to the present invention can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 amino acids. Most preferably, the repetitive unit according to the invention consists of 3, 4, 5, 6, 7, 8, 9, 10, 12, 15, 18, 20, 24, 27, 28, 30, 34, 35, or 39 amino acids.

The silk polypeptide according to the present invention may consist of between 6 to 1500 amino acids, or between 200 to 1300 amino acids and most preferably between 250 to 1200 amino acids, or between 500 to 1000 amino acids.

The silk polypeptide according to the present invention may comprise or consist of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units. For example, the silk polypeptide according to the present invention can comprise or consists of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units. Most preferably, the silk polypeptide comprises 4, 8, 12, 16, 24, 32 or 48 repetitive units. As mentioned above, at least two of the repetitive units comprised in the silk polypeptide according to the present invention are identical repetitive units. Thus, the silk polypeptide according to the present invention may comprise multiple copies of one identical repetitive unit (e.g. $A_2$ or $C_{16}$, wherein the items 2 or 6 represent the number of repetitive units) or multiple copies of two or more different repetitive units (e.g. $(AQ)_{24}$ or $(QAQ)_8$). For example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 of the 80 repetitive units comprised in the silk polypeptide according to the present invention may be identical repetitive units.

The term "consensus sequence" as used in the context of the present invention refers to an amino acid sequence which contains amino acids which frequently occur in a certain position (e.g. "G") and wherein, other amino acids which are not further determined are replaced by the place holder "X".

According to preferred embodiments, the silk polypeptide, preferably spider silk polypeptide, comprises, essentially consists of, or consists of at least two identical repetitive units each comprising at least one, preferably one, consensus sequence selected from the group consisting of
i) GPGXX (SEQ ID NO: 3), wherein X is any amino acid, preferably in each case independently selected from the group consisting of A, S, G, Y, P and Q;
ii) GGX, wherein X is any amino acid, preferably in each case independently selected from the group consisting of Y, P, R, S, A, T, N and Q; and
iii) $A_x$, wherein x is an integer from 5 to 10.

It is also preferred that the silk polypeptide comprises, essentially consists of, or consists of at least two identical repetitive units each comprising at least one, preferably one, amino acid sequence selected from the group consisting of: GGRPSDTYG (SEQ ID NO: 18) and GGRPSSSYG (SEQ ID NO: 19). The GGRPSDTYG (SEQ ID NO: 18) and GGRPSSSYG (SEQ ID NO: 19) (peptide) motifs have been selected from Resilin (WO 08/155304). Resilin is an elastomeric protein found in most arthropods (arthropoda). It is located in specialised regions of the cuticle, providing low stiffness and high strength (Elvin et al., Nature (473): 999-1002, 2005).

Thus, in a preferred embodiment of the present invention, the silk polypeptide comprises, essentially consists of, or consists of repetitive units each comprising at least one (e.g. 1, 2, 3, 4, 5, 6, 7, 8, or 9), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), and GPGGS (SEQ ID NO: 11). In another preferred embodiment of the present invention, the silk polypeptide comprises, essentially consists of, or consists of repetitive units each comprising at least one (e.g. 1, 2, 3, 4, 5, 8, 7, or 8), preferably one, amino acid sequence selected from the group consisting of GGY, GGP, GGA, GGR, GGS, GGT, GGN, and GGQ. In a further preferred embodiment of the present invention, the silk polypeptide comprises, essentially consists of, or consists of repetitive units each comprising at least one (e.g. 1, 2, 3, 4, 5, or 6), preferably one, amino acid sequence selected from the group consisting of AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), and AAAAAAAAAA (SEQ ID NO: 17).

In another preferred embodiment of the invention, the silk polypeptide comprises, essentially consists of, or consists of repetitive units each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40); GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

Most preferably, the silk polypeptide comprises, essentially consists of, or consists of repetitive units, which comprise or consist of
  (i) GPGAS (SEQ ID NO: 5), AAAAAA (SEQ ID NO: 13), GGY, and GPGSG (SEQ ID NO: 6) as amino acid sequence, preferably in this order,
  (ii) AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
  (iii) GPGQQ (SEQ ID NO: 4), GPGQQ (SEQ ID NO: 4), GPGQQ (SEQ ID NO: 4) and GPGQQ (SEQ ID NO: 4) as amino acid sequence,
  (iv) GPGGA (SEQ ID NO: 9), GGP, GPGGA (SEQ ID NO: 9), GGP, GPGGA (SEQ ID NO: 9), and GGP as amino acid sequence, preferably in this order,
  (v) AAAAAAAA (SEQ ID NO: 15), GPGQG (SEQ ID NO: 40), and GGR as amino acid sequence, preferably in this order,
  (vi) AAAAAAAA (SEQ ID NO: 15), GPGGG (SEQ ID NO: 10), GGR, GGN, and GGR as amino acid sequence, preferably in this order,
  (vii) GGA, GGA, GGA, GGS, GGA, and GGS as amino acid sequence, preferably in this order, and/or
  (viii) GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

It should be noted that at least two of the repetitive units comprised in the silk polypeptides mentioned above are identical repetitive units.

Preferably, the silk polypeptide comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, each comprising at least one, preferably one, consensus sequence selected from the group consisting of:
  i) GPGXX (SEQ ID NO: 3), wherein X is any amino acid, preferably in each case independently selected from A, S, G, Y, P, and Q;
  ii) GGX, wherein X is any amino acid, preferably in each case independently selected from Y, P, R, S, A, T, N and Q, more preferably in each case independently selected from Y, P and Q; and
  iii) $A_x$, wherein x is an integer from 5 to 10.

As mentioned above, at least two of the repetitive units comprised in the silk polypeptide according to the present invention are identical repetitive units.

It is also preferred that the silk polypeptide comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, each comprising at least one, preferably one, amino acid sequence selected from the group consisting of: GGRPSDTYG (SEQ ID NO: 18) and GGRPSSSYG (SEQ ID NO: 19).

Thus, the silk polypeptide preferably comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGQG (SEQ ID NO: 40), GPGGG (SEQ ID NO: 10), GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

Most preferably, the silk polypeptide comprises, essentially consists of, or consists of
  (i) repetitive units which comprise or consist of GPGAS (SEQ ID NO: 5), AAAAAA (SEQ ID NO: 13), GGY, and GPGSG (SEQ ID NO: 6) as amino acid sequence, preferably in this order,
  (ii) repetitive units which comprise or consist of AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
  (iii) repetitive units which comprise or consist of GPGQQ (SEQ ID NO: 4), GPGQQ (SEQ ID NO: 4), GPGQQ (SEQ ID NO: 4) and GPGQQ (SEQ ID NO: 4) as amino acid sequence,
  (iv) repetitive units which comprise or consist of GPGGA (SEQ ID NO: 9), GGP, GPGGA (SEQ ID NO: 9), GGP, GPGGA (SEQ ID NO: 9), and GGP, as amino acid sequence, preferably in this order,
  (v) repetitive units which comprise or consist of AAAAAAAA (SEQ ID NO: 15), GPGQG (SEQ ID NO: 40), and GGR as amino acid sequence, preferably in this order,
  (vi) repetitive units which comprise or consist of AAAAAAAA (SEQ ID NO: 15), GPGGG (SEQ ID NO: 10), GGR, GGN, and GGR as amino acid sequence, preferably in this order,
  (vii) repetitive units which comprise or consist of GGA, GGA, GGA, GGS, GGA, and GGS as amino acid sequence, preferably in this order, and/or
  (viii) repetitive units which comprise or consist of GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

It should be noted that at least two of the repetitive units comprised in the silk polypeptides mentioned above are identical repetitive units.

Preferably, the silk polypeptide comprises, essentially consists of, or consists of
- (i) (GPGXX)$_n$ (SEQ ID NO: 3) as a repetitive unit, wherein X is any amino acid, preferably in each case independently selected from A, S, G, Y, P, and Q and n is 2, 3, 4, 5, 6, 7, 8, or 9;
- ii) (GGX)$_n$ as a repetitive unit, wherein X is any amino acid, preferably in each case independently selected from Y, P, R, S, A, T, N and Q, more preferably in each case independently selected from Y, P and Q, and n is 2, 3, 4, 5, 6, 7, or 8; and/or
- iii) (A$_x$)$_n$ as a repetitive unit, wherein x is an integer from 5 to 10 and n is 2, 3, 4, 5, 6, 7, 8, 9, or 10.

As mentioned above, at least two of the repetitive units comprised in the silk polypeptide according to the present invention are identical repetitive units.

It is preferred that the repetitive units are independently selected from module A (SEQ ID NO: 20), module C (SEQ ID NO: 21), module Q (SEQ ID NO: 22), module K (SEQ ID NO: 23), module sp (SEQ ID NO: 24), module S (SEQ ID NO: 25), module R (SEQ ID NO: 26), module X (SEQ ID NO: 27), or module Y (SEQ ID NO: 28), or variants thereof (i.e. module A variants, module C variants, module Q variants, Module K variants, module sp variants, module S variants, module R variants, module X variants or module Y variants). The modules A (SEQ ID NO: 20) and Q (SEQ ID NO: 22) are based on the amino acid sequence of ADF-3 of the spider *Araneus diadematus*. Module C (SEQ ID NO: 21) is based on the amino acid sequence of ADF-4 of the spider *Araneus diadematus*. The modules K (SEQ ID NO: 23), sp (SEQ ID NO: 24), X (SEQ ID NO: 27) and Y (SEQ ID NO: 28) are based on the amino acid sequence of the flagelliform protein FLAG of the spider *Nephila clavipes* (WO 2006/008163). The modules S (SEQ ID NO: 25) and R (SEQ ID NO: 26) are based on Resilin (*Arthropoda*) (WO 2008/155304).

Preferably, the silk polypeptide according to the present invention comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module A (SEQ ID NO: 20), module C (SEQ ID NO: 21), module Q (SEQ ID NO: 22), module K (SEQ ID NO: 23), module sp (SEQ ID NO: 24), module S (SEQ ID NO: 25), module R (SEQ ID NO: 26), module X (SEQ ID NO: 27) or module Y (SEQ ID NO: 28), or variants thereof (i.e. module A variants, module C variants, module Q variants, module K variants, module sp variants, module S variants, module R variants, module X variants or module Y variants). It should be noted that at least two of the repetitive units comprised in the silk polypeptide according to the present invention are identical repetitive units (modules).

Thus, it is preferred that the silk polypeptide according to the present invention comprises, essentially consists of, or consists of (i) repetitive unit(s) consisting of module A and/or repetitive unit(s) consisting of module A variants, (ii) repetitive unit(s) consisting of module C and/or repetitive unit(s) consisting of module C variants, (iii) repetitive unit(s) consisting of module Q and/or repetitive unit(s) consisting of module Q variants, (iv) (a) repetitive unit(s) consisting of module A and repetitive unit(s) consisting of module Q, (b) repetitive unit(s) consisting of module A and repetitive unit(s) consisting of module Q variants, (c) repetitive unit(s) consisting of module A variants and repetitive unit(s) consisting of module Q, (d) repetitive unit(s) consisting of module A variants and repetitive unit(s) consisting of module Q variants, (v) (a) repetitive units) consisting of module A and repetitive unit(s) consisting of module C, (b) repetitive unit(s) consisting of module A and repetitive unit(s) consisting of module C variants, (c) repetitive unit(s) consisting of module A variants and repetitive unit(s) consisting of module C, (d) repetitive unit(s) consisting of module A variants and repetitive unit(s) consisting of module C variants, (vi) (a) repetitive unit(s) consisting of module C and repetitive unit(s) consisting of module Q, (b) repetitive unit(s) consisting of module C and repetitive unit(s) consisting of module Q variants, (c) repetitive unit(s) consisting of module C variants and repetitive unit(s) consisting of module Q, (d) repetitive unit(s) consisting of module C variants and repetitive unit(s) consisting of module Q variants, or (vii) (a) repetitive unit(s) consisting of module A, repetitive unit(s) consisting of module Q and repetitive unit(s) consisting of module C, (b) repetitive unit(s) consisting of module A, repetitive unit(s) consisting of module Q and repetitive unit(s) consisting of module C variants, (c) repetitive unit(s) consisting of module A, repetitive unit(s) consisting of module Q variants and repetitive unit(s) consisting of module C, (d) repetitive unit(s) consisting of module A variants, repetitive unit(s) consisting of module Q and repetitive unit(s) consisting of module C, (e) repetitive unit(s) consisting of module A, repetitive unit(s) consisting of module Q variants and repetitive unit(s) consisting of module C variants, (f) repetitive unit(s) consisting of module A variants, repetitive unit(s) consisting of module Q variants and repetitive unit(s) consisting of module C, (g) repetitive unit(s) consisting of module A variants, repetitive unit(s) consisting of module Q and repetitive unit(s) consisting of module C variants, (h) repetitive unit(s) consisting of module A variants, repetitive unit(s) consisting of module Q variants and repetitive unit(s) consisting of module C variants.

The modules A, C, Q, K, sp, S, R, X, or Y or variants thereof (i.e. module A variants, module C variants, module Q variants, module K variants, module sp variants, module S variants, module R variants, module X variants or module Y variants) can also be combined with each other in any combination and in any number of each, i.e. module (repetitive unit) A can be combined with module (repetitive unit) Q (i.e. combination AQ), module (repetitive unit) C can be combined with module (repetitive unit) Q (i.e. combination CQ), module (repetitive unit) Q can be combined with module (repetitive unit) A and with module (repetitive unit) Q (i.e. combination QAQ), module (repetitive unit) A can be combined with module (repetitive unit) A and with module (repetitive unit) Q (i.e. combination AAQ), etc., under the proviso that the silk polypeptide used in the method of the present invention comprises or consists of at least two repetitive units which are identical. For example, the silk polypeptide used in the method of the present invention can/comprise or consist of A$_n$, (AA)$_n$, (AQ)$_n$, (QA)$_n$, Q$_n$, (QQ)$_n$, (QAQ)$_n$, (AQA)$_n$, C$_n$, (CC)$_n$, (CCC)$_n$, (CQ)$_n$, (QC)$_n$, (QCQ)$_n$, (CQC)$_n$, (AA)$_n$Q$_n$, (QQ)$_n$A$_n$, (AAA)$_n$Q$_n$, (QQQ)$_n$A$_n$, (AQQ)$_n$, (QQA)$_n$, K$_n$, sp$_n$, S$_n$, R$_n$, X$_n$, Y$_n$, (Ksp)$_n$, (sPK)$_n$, (XY)$_n$, (YX)$_n$, (XX)$_n$, (YY)$_n$, (XXX)$_n$, (YYY)$_n$, (AX)$_n$, (XA)$_n$, (CX)$_n$, (XC)$_n$, (QX)$_n$, (XQ)$_n$, (YQ)$_n$, (QY)$_n$, (SS)$_n$, (SR)$_n$, (RS)$_n$, or (RR)$_n$, wherein n is at least 2, preferably 4, 8, 9, 10, 12, 16, 20, 24, or 32. In case that the silk polypeptide consists of (AQ)$_{12}$, it is noted that module (repetitive unit) A is 12 times present and module (repetitive unit) Q is also 12 times present in the silk polypeptide and that, thus, the silk polypeptide consists of 24 modules (repetitive units). The arrangement of the modules (repeat units) of a silk polypeptide consisting of $(AQ)_{12}$ is as follows: AQAQAQAQAQAQAQAQAQAQAQAQ. Further, in case that the silk polypeptide of the modules (repeat units) of a silk polypeptide consists of $(QAQ)_8$, it is noted that module (repeat unit) A is 8 times present and module (repetitive unit) Q is 16 times present in the silk polypeptide and that, thus, the silk polypeptide consists of 24 modules (repetitive units). The arrangement of the modules (repeat units) of a silk polypeptide consisting of $(QAQ)_8$ is as follows: QAQQAQQAQQAQQAQQAQQAQQAQ.

The silk polypeptide according to the present invention can also comprise or consist of $(A^*Q)_n$, $(AQ^*)_n$, $(A^*Q^*)_n$, $(Q^*A)_n$, $(QA^*)_n$, $(Q^*A^*)_n$, $(QAQ^*)_n$, $(QA^*Q)_n$, $(Q^*AQ)_n$, $(QA^*Q^*)_n$, $(Q^*A^*Q)_n$, $(Q^*AQ^*)_n$, $(Q^*A^*Q^*)_n$, $(AQA^*)_n$, $(AQ^*A)_n$, $(A^*QA)_n$, $(AQ^*A^*)_n$, $(A^*Q^*A)_n$, $(A^*QA^*)_n$, $(A^*Q^*A^*)_n$, wherein n is at least 2, preferably 4, 8, 9, 10, 12, 16, 20, 24, or 32 and wherein * indicates a module variant, i.e. module A or Q variant.

The terms "combined with each other" or "concatenated with each other" may mean in the context of the present invention that the modules (repetitive units) are directly combined or concatenated with each other or may mean in the context of the present invention that the modules (repetitive units) are combined or concatenated with each other via one or more spacer amino acids. In preferred embodiments, the modules (repetitive units) comprised in the silk polypeptide are directly combined or concatenated with each other. In other preferred embodiments, the modules (repetitive units) comprised in the silk polypeptide are combined or concatenated with each other via 1 to 25 or 1 to 20 spacer amino acids, more preferably via 1 to 15 or 1 to 10 spacer amino acids, and most preferably, via 1 to 5 spacer amino acids, i.e. via 1, 2, 3, 4, 5, 6, 7, 8, 9, 10, 11, 12, 13, 14, 15, 16, 17, 18, 19, 20, 21, 22, 23, 24, or 25 spacer amino acids. Said spacer amino acids may be any amino acids naturally occurring in proteins. Preferably, said spacer amino acid is not proline. It is preferred that the spacer amino acid(s) contain(s) charged groups. Preferably, the spacer amino acid(s) containing charged groups is (are) independently selected from the group consisting of aspartate, glutamate, histidine, and lysine. Said spacer amino acids should be amino acids which do not negatively affect the ability of a silk particle comprising a silk polypeptide to receive a compound. The ability of a silk particle to receive a compound can easily be tested (see above and experimental section). Further, said spacer amino acids should be amino acids which do not cause steric hindrance, e.g. amino acids having a small size such as lysine and cysteine.

It is further preferred that the repetitive units are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). The modules $A^C$ (SEQ ID NO: 29), $A^K$ (SEQ ID NO: 30), $C^C$ (SEQ ID NO: 31), $C^{K1}$ (SEQ ID NO: 32), $C^{K2}$ (SEQ ID NO: 33) and $C^{KC}$ (SEQ ID NO: 34) are variants of the module A which is based on the amino acid sequence of ADF-3 of the spider *Araneus diadematus* and of module C which is based on the amino acid sequence of ADF-4 of the spider *Araneus diadematus* (WO 2007/025719). In module $A^C$ (SEQ ID NO: 29) the amino acid S (serine) at position 21 has been replaced by the amino acid C (cysteine), in module $A^K$ (SEQ ID NO: 30) the amino acid S at position 21 has been replaced by the amino acid K (lysine), in module $C^C$ (SEQ ID NO: 31) the amino acid S at position 25 has been replaced by the amino acid 25 by C, in module $C^{K1}$ (SEQ ID NO: 32) the amino acid S at position 25 has been replaced by the amino acid K, in module $C^{K2}$ (SEQ ID NO: 33) the amino acid E (glutamate) at position 20 has been replaced by the amino acid K, and in module $C^{KC}$ (SEQ ID NO: 34) the amino acid E at position 20 has been replaced by the amino acid K and the amino acid S at position 25 has been replaced by the amino acid C (WO 2007/025719).

It is also preferred that the silk polypeptide according to the present invention comprises, essentially consists of, or consists of between 2 to 80 repetitive units, between 3 to 80 repetitive units, or between 4 to 60 repetitive units, preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). It should be noted that at least two of the repetitive units comprised in the silk polypeptide according to the present invention are identical repetitive units (modules).

For example, the silk polypeptide used in the method of the present invention can comprises or consists of the modules $C^C_4$, $C^C_8$, $C^C_{16}$, $C^C_{32}$, $A^C_5$, $A^C_8$, or $A^C_{10}$.

The modules $A^K$, $C^C$, $C^{K1}$, $C^{K2}$ and $C^{KC}$ can also be combined with each other, i.e. module (repetitive unit) $A^K$ can be combined with module (repetitive unit) $C^C$ (i.e. combination $A^K C^C$), module (repetitive unit) $C^{K1}$ can be combined with module (repetitive unit) $C^{K2}$ and with module (repetitive unit) $C^{KC}$ (i.e. combination $C^{K1} C^{K2} C^{KC}$), etc., under the proviso that the silk polypeptide used in the method of the present invention comprises or consists of at least two repetitive units which are identical. Thus, the silk polypeptide used in the method of the present invention can also comprise or consist of the modules $(A^K)_n$, $(C^C)_n$, $(C^{K1})_n$, $(C^{K2})_n$, $(C^{KC})_n$, $(A^K A^C)_n$, $(C^C C^C)_n$, $(C^{K1} C^{K2})_n$, $(C^{K2} C^{K1})_n$, $(C^{K1} C^{K2} C^{K1})_n$, $(C^{K2} C^{K1} C^{K2})_n$, $(C^{K1} C^{K2} C^{KC})_n$, $(C^{KC} C^{K2} C^{KC})_n$, or $(C^{KC} C^{K2} C^{K1})_n$, wherein n is at least 2, preferably 4, 5, 6, 7, 8, 10, 12, 16, or 20. The term "combined with each other" is defined above.

In further preferred embodiments, the repetitive units of the respective silk polypeptide, preferably spider silk polypeptide, are independently selected from module A (SEQ ID NO: 20) or variants thereof, module C (SEQ ID NO: 21) or variants thereof, module Q (SEQ ID NO: 22) or variants thereof, module K (SEQ ID NO: 23) or variants thereof, module sp (SEQ ID NO: 24) or variants thereof, module S (SEQ ID NO: 25) or variants thereof, module R (SEQ ID NO: 26) or variants thereof, module X (SEQ ID NO: 27) or variants thereof, module Y (SEQ ID NO: 28) or variants thereof, module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34).

In more preferred embodiments, the silk polypeptide according to the present invention comprises, essentially consists of, or consists of between 2 to 80, between 3 to 80 repetitive units, or between 4 to 60 repetitive units, preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module A (SEQ ID NO: 20) or variants thereof, module C (SEQ ID NO: 21) or variants thereof, module Q (SEQ ID NO: 22) or variants thereof, module K (SEQ ID NO: 23) or variants thereof, module sp (SEQ ID NO: 24) or variants thereof, module S (SEQ ID NO: 25) or variants thereof, module R (SEQ ID NO: 26) or variants thereof, module X (SEQ ID NO: 27) or variants thereof, module Y (SEQ ID NO: 28) or variants thereof, module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). Again, it should be noted that at least two of the repetitive units comprised in the silk polypeptide according to the present invention are identical repetitive units (modules).

The modules $A^K$, $C^C$, $C^{K1}$, $C^{K2}$ and $C^{KC}$ can also be combined with the modules A, C, Q, K, sp, S, R, X or Y, i.e. module (repetitive unit) $A^K$ can be combined with module (repetitive unit) C (i.e. combination $A^K C$), or module (repetitive unit) $C^C$ can be combined with module (repetitive unit) C (i.e. combination $C^C C$), etc., under the proviso that the silk polypeptide used in the method of the present invention comprises or consists of at least two repetitive units which are identical. Thus, the silk polypeptide used in the method of the present invention can also comprise or consist of the modules $(AQA^K)_n$, $(QA^K)_n$, $(QA^K Q)_n$, $(A^K QA)_n$, $(A^K QA^K)_n$, $(CC^C)_n$, $(CC^C C)_n$, $(C^C C^C C)_n$, $(CC^C C^C)_n$, $(C^C Q)_n$, $(QC^C)_n$, $(QC^C Q)_n$, $(C^C QC)_n$, $(CQC^C)_n$, $(C^C QC^C)_n$, $(CC^{K1})_n$, $(C^{K1} C)_n$, $(C^{K1} CC)_n$, $(CC^{K1} C)_n$, $(C^{KC} C^{KC} C)_n$, $(CC^{KC} C^{KC})_n$, $(C^{KC} Q)_n$, $(QC^{KC})_n$, $(QC^{KC} Q)_n$, $(A^K C^{K1} Q)_n$, $(QC^{K2} A^K)_n$, or $(C^{K1} C^{K2} C)_n$, wherein n is at least 2, preferably 4, 5, 6, 7, 8, 10, 12, 16, or 20. The term "combined with each other" is defined above.

For example, the silk polypeptide used in the method of the present invention comprises or consists of the modules $C_{16} C^C$, $C^C C_{16}$, $C_8 C^C C_8$, $C_8 C^C_8$, $C^C_8 C_8$, $C_4 C^C_8 C_4$, $C^C_4 C_8 C^C_4$, $C^C (AQ)_{24}$, or $(AQ)_{24} C^C$.

The term "independently selected" as used herein means that the silk polypeptide, e.g. spider silk polypeptide, may comprise one or more different repetitive units each comprising one or more of the above described modules. As mentioned above, the silk polypeptides, e.g. spider silk polypeptides, according to the invention comprise at least two identical repetitive units.

The term "variants thereof" as used herein means that suitable amino acid sequences are not necessarily restricted to the exact sequences as given in the SEQ ID NOs. Variants of the amino acid sequences indicated herein may also comprise sequences wherein one or more amino acid are inserted, deleted, modified and/or substituted.

Variants of the amino acid sequences as described herein are capable of producing polypeptides having the same properties, i.e. having the same or similar secondary structural elements. Preferably not more than 1%, 2%, 3%, 4%, 5%, 6%, 7%, 8%, 9%, 10%, 11%, 12%, 13%, 14%, 15%, 16%, 17%, 18%, 19%, or 20%, more preferably not more than 15%, even more preferably not more than 10%, most preferably not more than 5% or 2% of all amino acids of the polypeptide are altered (i.e. are deleted, inserted, modified and/or substituted).

Preferably, in all these embodiments the sequence identity is at least about 80%, 85% or 90%, more preferably at least about 91%, 92%, 93%, 94%, 95%, 96%, 97%, 98%, and most preferably at least about 99%. Sequence identity may be determined over the whole length of the respective sequences.

The determination of percent identity between two sequences is preferably accomplished using the mathematical algorithm of Karlin and Altschul (1993) *Proc. Natl. Acad. Sci USA* 90: 5873-5877. Such an algorithm is incorporated into the BLASTn and BLASTp programs of Altschul et al. (1990) *J. Mol. Biol.* 215: 403-410 available at NCBI (http://www.ncbi.nlm.nih.gov/blast/Blast.cge).

The determination of percent identity is performed with the standard parameters of the BLASTn and BLASTp programs.

BLAST polynucleotide searches are performed with the BLASTn program.

For the general parameters, the "Max Target Sequences" box may be set to 100, the "Short queries" box may be ticked, the "Expect threshold" box may be set to 10 and the "Word Size" box may be set to 28. For the scoring parameters the "Match/mismatch Scores" may be set to 1,−2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "Mask lower case letters" box may not be ticked.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

By "modification" it is meant that amino acids of the polypeptide may be chemically or biologically modified, e.g. by glycosylation, amidation, phosphorylation, ubiquitination, etc.

"Substitution" is the result of replacing one amino acid with another amino acid having similar structural and/or chemical properties, i.e. conservative amino acid replacements. Amino acid substitutions may be made on the basis of similarity in polarity, charge, solubility, hydrophobicity and/or hydrophilicity of certain residues of the amino acid sequence. Examples of preferred suitable amino acid substitutions are given in the table below:

| Original radical | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Insertions" or "deletions" typically can be in the range of about 1 to 5 amino acids, preferably about 1, 2 or 3 amino acids. Amino acid additions are typically not more than 100, preferably not more than 80, more preferably not more than 50, most preferably not more than 20 amino acids, which are added and/or inserted into the proteins. Further, only those additions are contemplated which do not negatively affect the desired characteristics of the proteins.

Particularly, a module A, C, Q, K, sp, S, R, X or Y variant differs from the reference (wild-type) module A, C, Q, K, sp, S, R, X or Y from which it is derived by up to 1, 2, 3, 4, 5, 6, 7, 8, 9, 10, 11, 12, 13, 14, or 15 amino acid changes in the amino acid sequence (i.e. substitutions, additions, insertions, deletions, N-terminal truncations and/or C-terminal truncations). Such a module variant can alternatively or additionally be characterized by a certain degree of sequence identity to the reference (wild-type) module from which it is derived. Thus, a module A, C, Q, K, sp, S, R, X or Y variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) module A, C, Q, K, sp, S, R, X or Y. Preferably, the sequence identity is over a continuous stretch of at least 10, 15, 18, 20, 24, 27, 28, 30, 34, 35, or more amino acids, preferably over the whole length of the respective reference (wild-type) module A, C, Q, K, sp, S, R, X or Y.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) module A, C, Q, K, sp, S, R, X or Y. It is further particularly preferred that the sequence identity is at least 80% over a continuous stretch of at least 10, 15, 18, 20, 24, 28, or 30 amino acids, is at least 85% over a continuous stretch of at least 10, 15, 18, 20, 24, 28, or 30 amino acids, is at least 90% over a continuous stretch of at least 10, 15, 18, 20, 24, 28, or 30 amino acids, is at least 95% over a continuous stretch of at least 10, 15, 18, 20, 24, 28, or 30 amino acids, is at least 98% over a continuous stretch of at least 10, 15, 18, 20, 24, 28, or 30 amino acids, or is at least 99% over a continuous stretch of at least 10, 15, 18, 20, 24, 28, or 30 amino acids of the respective reference (wild-type) module A, C, Q, K, sp, S, R, X or Y.

A fragment (or deletion variant) of module A, C, Q, K, sp, S, R, X or Y has preferably a deletion of up to 1, 2, 3, 4, 5, 6, 7, 8, 9, 10, 11, 12, 13, 14, or 15 amino acids at its N-terminus and/or at its C-terminus. The deletion can also be internally.

Additionally, the module A, C, Q, K, sp, S, R, X or Y variant or fragment is only regarded as a module A, C, Q, K, sp, S, R, X or Y variant or fragment within the context of the present invention, if the changes with respect to the amino acid sequence on which the variant or fragment is based do not negatively affect the ability of the silk particle comprising the silk polypeptide to be loaded with a compound. Preferably, the silk particle comprising the silk polypeptide which comprises the module A, C, Q, K, sp, S, R, X, or Y variant or fragment is capable of being loaded with a compound so that at least 20%, preferably at least 40%, more preferably at least 50%, 60%, 70%, 80%, 90%, or 95% of the loaded compound is located within the matrix of the silk particle. The skilled person can readily determine the "loading" of a silk particle (e.g. via UV-Vis-spectroscopy), in particular the percentage of the compound which is located within the matrix of silk particles (see, for example, experimental section).

As mentioned above, the silk polypeptide, e.g. spider silk polypeptide, may be an authentic polypeptide naturally occurring in nature or be synthetically or recombinantly produced. When recombinantly produced, the above described modules and sequences may be combined to yield the silk polypeptide, e.g. spider silk polypeptide, with favourable characteristics. Preferably, the modules may be combined such that the resulting polypeptide possesses at least two identical repetitive units.

In specific embodiments, the silk polypeptide, preferably spider silk polypeptide, further comprises at least one non-repetitive (NR) unit, i.e. 1, 2, 3, 4, 5, 6, or more NR units, preferably one NR unit. Preferably, the NR sequences are authentic sequences.

In the context of the present invention, the term "non-repetitive (NR) unit" refers to a region of amino acids present in a naturally occurring silk polypeptide that displays no obvious repetition pattern (non-repetitive unit or NR unit).

Preferably, the amino acid sequence of the non-repetitive unit corresponds to a non-repetitive amino acid sequence of naturally occurring dragline polypeptides, preferably of ADF-3 (SEQ ID NO: 1 or SEQ ID NO: 47) or ADF-4 (SEQ ID NO: 2 or SEQ ID NO: 48), or to an amino acid sequence substantially similar thereto.

It is particularly preferred that the amino acid sequence of the non-repetitive unit corresponds to a non-repetitive carboxy terminal amino acid sequence of naturally occurring dragline polypeptides, preferably of ADF-3 (SEQ ID NO: 1 or SEQ ID NO: 47) or ADF-4 (SEQ ID NO: 2 or SEQ ID NO: 48), or to an amino acid sequence substantially similar thereto. More preferably, the amino acid sequence of the non-repetitive unit corresponds to a non-repetitive carboxy terminal amino acid sequence of ADF-3 (SEQ ID NO: 1) which comprises amino acids 513 through 636, or of ADF-4 (SEQ ID NO: 2) which comprises amino acids 302 through 410, or to an amino acid sequence substantially similar thereto.

In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over 20, 30, 40, 50, 60, 70, 80 or more amino acids, more preferably over the whole length of the respective reference non-repetitive (carboxy terminal) amino acid sequence of naturally occurring dragline polypeptides, preferably of ADF-3 (SEQ ID NO: 1) or ADF-4 (SEQ ID NO: 2).

A "non-repetitive unit" having an amino acid sequence which is "substantially similar" to a corresponding non-repetitive (carboxy terminal) amino acid sequence within a naturally occurring dragline polypeptide (i.e. wild-type non-repetitive (carboxy terminal) unit), preferably within ADF-3 (SEQ ID NO: 1 or SEQ ID NO: 47) or ADF-4 (SEQ ID NO: 2 or SEQ ID NO: 48), is also similar with respect to its functional properties, e.g. the silk particle comprising the silk polypeptide which comprises the "substantially similar non-repetitive unit" can still be loaded with a compound. Preferably, the silk particle comprising the silk polypeptide which comprises the "substantially similar non-repetitive unit" is capable of being loaded with a compound so that at least 20%, preferably at least 40%, more preferably at least 50%, 60%, 70%, 80%, 90%, or 95% of the loaded compound is located within the matrix of the silk particle. The skilled person can readily determine the "loading" of a silk particle (e.g. via UV-Vis-spectroscopy), in particular the percentage of the compound which is located within the matrix of silk particles (see, for example, experimental section).

More preferably, the non-repetitive (NR) unit is independently selected from the group consisting of NR3 (SEQ ID NO: 41 and SEQ ID NO: 45) or variants thereof and NR4 (SEQ ID NO: 42 and SEQ ID NO: 46) or variants thereof. The NR3 (SEQ ID NO: 41) unit is based on the amino acid sequence of ADF-3 of the spider *Araneus diadematus* and the NR4 (SEQ ID NO: 42) unit is based on the amino acid sequence of ADF-4 of the spider *Araneus diadematus* (WO 2006/008163).

A NR3 or NR4 unit variant differs from the reference NR3 (SEQ ID NO: 41 or SEQ ID NO: 45) or NR4 (SEQ ID NO: 42 or SEQ ID NO: 46) unit from which it is derived by up to 1, 2, 3, 4, 5, 6, 7, 8, 9, 10, 11, 12, 13, 14, 15, 16, 17, 18, 19, 20, 25, or 30 amino acid changes in the amino acid sequence (i.e. exchanges, insertions, deletions, N-terminal truncations and/or C-terminal truncations). Such a NR3 or NR4 unit variant can alternatively or additionally be characterized by a certain degree of sequence identity to the reference NR3 or NR4 unit from which it is derived. Thus, a NR3 or NR4 unit variant has a sequence identity of at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference NR3 or NR4 unit. Preferably, the sequence identity is over a continuous stretch of at least 10, 20, 30, 40, 50, 60, 70, 80, 90, or more amino acids, preferably over the whole length of the respective reference NR3 or NR4 unit.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference NR3 or NR4 unit. It is further particularly preferred that the sequence identity is at least 80% over a continuous stretch of at least 20, 30, 40, 50, 60, 70, or 80 amino acids, is at least 85% over a continuous stretch of at least 20, 30, 40, 50, 60, 70, or 80 amino acids, is at least 90% over a continuous stretch of at least 20, 30, 40, 50, 60, 70, or 80 amino acids, is at least 95% over a continuous stretch of at least 20, 30, 40, 50, 60, 70, or 80 amino acids, is at least 98% over a continuous stretch of at least 20, 30, 40, 50, 60, 70, or 80 amino acids, or is at least 99% over a continuous stretch of at least 20, 30, 40, 50, 60, 70, or 80 amino acids of the respective reference NR3 or NR4 unit.

A fragment (or deletion variant) of a NR3 or NR4 unit has preferably a deletion of up to 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 amino acids at its N-terminus and/or at its C-terminus. The deletion can also be internally.

Additionally, the NR3 or NR4 unit variant or fragment is only regarded as a NR3 or NR4 unit variant or fragment within the context of the present invention, if the changes with respect to the amino acid sequence on which the variant or fragment is based do not negatively affect the ability of the silk particle comprising the silk polypeptide to be loaded with a compound. Preferably, the silk particle comprising the silk polypeptide which comprises the NR3 or NR4 unit variant or fragment is capable of being loaded with a compound so that at least 20%, preferably at least 40%, more preferably at least 50%, 60%, 70%, 80%, 90%, or 95% of the loaded compound is located within the matrix of the silk particle. The skilled person can readily determine the "loading" of a silk particle (e.g. via UV-Vis-spectroscopy), in particular the percentage of the compound which is located within the matrix of silk particles (see, for example, experimental section). Within the context of the present invention, the term "authentic" means that the respective nucleic acid sequences are isolated from their natural environment without substantial modifications being made to the sequence itself. However, this does not mean that the nucleic acid sequences may not be modified in order to adapt the sequence to the expression in a specific host without changing the resulting amino acid sequence encoded therefrom (codon usage adaption).

In further specific embodiments, the silk polypeptide, preferably spider silk polypeptide, is selected from the group consisting of ADF-3 (SEQ ID NO: 1 and SEQ ID NO: 47) or variants thereof, ADF-4 (SEQ ID NO: 2 and SEQ ID NO: 48) or variants thereof, MaSp I (SEQ ID NO: 43 and SEQ ID NOs: 53-64) or variants thereof, MaSp II (SEQ ID NO: 44 and SEQ ID NOs: 65-78) or variants thereof, $(C)_m NR_z$, $NR_z(C)_m$, $(AQ)_n NR_z$, $NR_z(AQ)_n$, $NR_z(QAQ)_o$, $(QAQ)_o NR_z$, $(C)_m$, $(AQ)_n$, $(QAQ)_o$, $Y_p$, $X_p$, and $IC_P$, wherein m is an integer of 8 to 48 (i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48), n is an integer of 6 to 24 (i.e. 6, 7, 8, 9, 10, 11, 12, 13, 14, 15, 16, 17, 18, 19, 20, 21, 22, 23, or 24), o is an integer of 8 to 16 (i.e. 8, 9, 10, 11, 12, 13, 14, 15, or 16), p is an integer of 8 to 16 (i.e. 8, 9, 10, 11, 12, 13, 14, 15, or 16), z is an integer of 1 to (i.e. 1, 2, or 3), and NR stands for a non-repetitive unit. The above mentioned formulas are defined by one of the following: In the formula (i) $(C)_m$, a "m" number of C modules, namely 8 to 48 C modules, represented by the amino acid sequence according to SEQ ID NO: 21, are combined with each other, (ii) $(C)_m NR_z$, a "m" number of C modules, namely 8 to 48 C modules, represented by the amino acid sequence according to SEQ ID NO: 21, are combined with each other, wherein said C modules are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, (iii) $NR_z(C)_m$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "m" number of C modules, namely 8 to 48 C modules, represented by the amino acid sequence according to SEQ ID NO: 21, (iv) $(AQ)_n$, a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, are combined with each other, (v) $(AQ)_n NR_z$, a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, are combined with each other, and wherein said A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, (vi) $NR_z(AQ)_n$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, (vii) $(QAQ)_o$, a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, are combined with each other, (viii) $(QAQ)_oNR_z$, a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, are combined with each other, and wherein said Q, A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, (ix) $NR_z(QAQ)_o$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, (x) $Y_p$, a "p" number of Y modules, namely 8 to 16 Y modules, represented by the amino acid sequence according to SEQ ID NO: 28, are combined with each other, (xi) $X_p$, a "p" number of X modules, namely 8 to 16 X modules, represented by the amino acid sequence according to SEQ ID NO: 27, are combined with each other, and (xii) $K_p$, a "p" number of K modules, namely 8 to 16 K modules, represented by the amino acid sequence according to SEQ ID NO: 23, are combined with each other.

More preferably, the silk polypeptide, preferably spider silk polypeptide, is $C_{16}$, $C_{32}$, $(AQ)_{12}$, $(AQ)_{24}$, $C_{16}NR4$, $C_{32}NR4$, $(AQ)_{12}NR3$, $(AQ)_{24}NR3$, $Y_8$, $Y_{16}$, $X_8$, $X_{16}$, $K_8$, or $K_{16}$.

An ADF-3, ADF-4, MaSp I or MaSp II variant differs from the reference (wild-type) ADF-3 (SEQ ID NO: 1 or SEQ ID NO: 47), ADF-4 (SEQ ID NO: 2 or SEQ ID NO: 48), MaSp I (SEQ ID NO: 43 and SEQ ID NOs: 53 to 64) or MaSp II (SEQ ID NO: 44 and SEQ ID NOs: 65 to 78) polypeptide from which it is derived by up to 150 (up to 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 150) amino acid changes in the amino acid sequence (i.e. substitutions, insertions, deletions, N-terminal truncations and/or C-terminal truncations). Such a variant can alternatively or additionally be characterized by a certain degree of sequence identity to the reference (wild-type) polypeptide from which it is derived. Thus, an ADF-3, ADF-4, MaSp I or MaSp II variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) ADF-3, ADF-4, MaSp I or MaSp II polypeptide. Preferably, the sequence identity is over a continuous stretch of at least 20, 25, 30, 35, 40, 50, 60, 70, 80, 90, 100, 120, 150, 180, 200, 250, 300, 350, 400, or more amino acids, preferably over the whole length of the respective reference (wild-type) ADF-3, ADF-4, MaSp I or MaSp II polypeptide.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) ADF-3, ADF-4, MaSp I or MaSp II polypeptide. It is further particularly preferred that the sequence identity is at least 80% over a continuous stretch of at least 20, 30, 50, 100, 150, 200, 250, or 300 amino acids, is at least 85% over a continuous stretch of at least 20, 30, 50, 100, 150, 200, 250, or 300 amino acids, is at least 90% over a continuous stretch of at least 20, 30, 50, 100, 150, 200, 250, or 300 amino acids, is at least 95% over a continuous stretch of at least 20, 30, 50, 100, 150, 200, 250, or 300 amino acids, is at least 98% over a continuous stretch of at least 20, 30, 50, 100, 150, 200, 250, or 300 amino acids, or is at least 99% over a continuous stretch of at least 20, 30, 50, 100, 150, 200, 250, or 300 amino acids of the respective reference (wild-type) ADF-3, ADF-4, MaSp I or MaSp II polypeptide.

A fragment (or deletion variant) of the ADF-3 (SEQ ID NO: 1) polypeptide has preferably a deletion of up to 1, 2, 3, 4; S, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 350, 370, 400, 420, 450, 470, 500, 520, 550, 570, 600, or 610 amino acids at its N-terminus and/or at its C-terminus. The deletion can also be internally.

A fragment (or deletion variant) of the ADF-4 (SEQ ID NO: 2) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 330, 340, 350, 360, 370, 380, or 390 amino acids at its N-terminus and/or at its C-terminus. The deletion can also be internally.

A fragment (or deletion variant) of the MaSp I (SEQ ID NO: 43) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 620, 640, 660, 670, 680, or 690 amino acids at its N-terminus and/or at its C-terminus. The deletion can also be internally.

A fragment (or deletion variant) of the MaSp II (SEQ ID NO: 44) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 520, 540, 560, or 570 amino acids at its N-terminus and/or at its C-terminus. The deletion can also be internally.

Additionally, the ADF-3, ADF-4, MaSp I or MaSp II variant or fragment is only regarded as an ADF-3, ADF-4, MaSp I or MaSp II variant or fragment within the context of the present invention, if the changes with respect to the amino acid sequence on which the variant or fragment is based do not negatively affect the ability of the silk particle comprising the silk polypeptide to be loaded with a compound. Preferably, the silk particle comprising the silk polypeptide which comprises the ADF-3, ADF-4, MaSp I or MaSp II variant or fragment is capable of being loaded with a compound so that at least 20%, preferably at least 40%, more preferably at least 50%, 60%, 70%, 80%, 90%, or 95% of the loaded compound is located within the matrix of the silk particle. The skilled person can readily determine the "loading" of a silk particle (e.g. via UV-Vis-spectroscopy), in particular the percentage of the compound which is located within the matrix of silk particles (see, for example, experimental section).

Preferably, the concentration of the silk polypeptide, more preferably spider silk polypeptide, in the aqueous solution is of between 0.01 wt %/vol and 30 wt %/vol, more preferably 0.1 wt %/vol and 30 wt %/vol, and most preferably between 1 wt %/vol and 20 wt %/vol, e.g. 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %/vol.

In preferred embodiments, aggregation is triggered by pH-shift, ion exchange, shear forces, the addition of an alcohol or a lyotropic salt or by a combination thereof. More preferably, the pH-shift is achieved by lowering the pH of the aqueous silk solution, preferably spider silk solution. Even more preferred is a pH of less than 4, less than 3, less than 2 and most preferred of about 1. Preferred alcohols for triggering aggregation are selected from the group consisting of methanol, ethanol, and isopropanol. In a preferred embodiment, the alcohol is methanol. Preferably, aggregation may be triggered by the addition of ions, which generally leads to the salting-out of proteins. In particular, structural formation of the unfolded proteins may thereby be induced. The salting out-properties of ions are generally described by the Hofmeister series. The "Hofmeister series" or "lyotropic series" is a classification of ions in order of their ability to change water structure. The effects of these changes were first worked out by Franz Hofmeister, who studied the effects of cations and anions on the solubility of proteins. Thereafter, anions appear to have a larger effect than cations, and are usually ordered $F^-=SO_4^{2-}>HPO_4^{2-}>acetate>Cl^->NO_3^->Br^->ClO_3^->I^->ClO_4^-$. The order of cations is usually given as $NH_4^+>K^+>Na^+>Li^+>Mg^{2+}>Ca^{2+}>$guanidinium. Generally any lyotropic salt can be used to trigger aggregation of silk polypeptides, e.g. spider silk polypeptides. Preferred lyotropic salts which can be used to trigger aggregation are selected from the group consisting of ammonium sulphate, sodium phosphate, potassium phosphate and carbonate salts such as ammonium carbonate, sodium carbonate or potassium carbonate. In further preferred embodiments the lyotropic salt is selected from the group consisting of ammonium sulphate, sodium phosphate, and potassium phosphate. Preferably, the concentration of the lyotropic salt is of between about 400 mM and about 3 M, preferably about 1 to about 2 M, most preferably about 2 M, e.g. 400 mM, 500 mM, 600 mM, 700 mM, 800 mM, 900 mM, 1 M, 1.5 M, 2 M, 2.5 M, or 3 M.

In preferred embodiments of the invention, the compound is a pharmaceutically active compound, a cosmetic substance, an agricultural substance, a chemoattractant, a chemorepellent, an anti-fungal substance, an anti-bacterial substance, a nutrient, a dietary supplement, a dye, a fragrance or an agent selected from the group consisting of hemostatic agents, growth stimulating agents, inflammatory agents, anti-fouling agents, antimicrobial agents and UV protecting agents.

Preferably, the compound has an overall positive net charge. The terms "positive charge" and "cationic" can be used interchangeably. As will be shown in detail in the examples, especially positively charged compounds are well-suited for the loading of silk particles, e.g. spider silk particles. As used herein, "positive charge" means that the compound possesses at least one elementary charge of a proton. The skilled person knows that the presence of at least one charge of a water-soluble compound is dependent on factors such as the $pK_a$-value of the compound and the pH of the aqueous solvent.

As used herein, the term "$pK_a$-value", (also known as acidity constant, or acid-ionization constant) is a quantitative measure of the strength of an acid in solution. It is derived from the dissociation constant $K_a$ which describes the equilibrium for a chemical reaction known as dissociation in the context of an acid-base reaction. Due to the many orders of magnitude spanned by $K_a$ values, a logarithmic measure of the acid dissociation constant is more commonly used in practice. The larger the value $pK_a$ the smaller the extent of dissociation and the less strong is an acid. Accordingly, the $pK_b$ value describes the strength of a base in solution.

In aqueous solutions the $pK_a$-value may give an indication whether a compound has a positive charge or not. Preferably the compound possesses a positive net charge at the pH used for the loading step.

Various other methods for determining or measuring the net charge of a compound are known to one of skill in the art. For example, the net charge can typically be measured using electrophoretic methods. The charge of a molecule in aqueous solution may also be predicted using suitable software such as ACD/ChemSketch (available at Advanced Chemistry Development, ACD/labs, http://www.acdlabs.com).

The person skilled in the art also knows how to determine which compounds are suitable for loading, i.e. whether a compound of interest possesses at least one positive charge at the pH of the aqueous solution used for loading the particles. As will be clear from the description below and in the examples, methods for assessing whether a compound is suitable for loading of the silk particles, e.g. spider silk particles, according to the invention include titration methods and the measurement of the zeta-potential during titration.

If the compound is a peptide or a protein or any other amphiphilic compound, the presence of an overall positive net charge is dependent on the isoelectric point (pI) value of the compound. The isoelectric point, sometimes abbreviated IEP, is the pH at which a particular molecule or surface carries no net electrical charge. For example, amphoteric molecules or zwitterions contain both positive and negative charges depending on the functional groups present in the molecule. The net charge on the molecule is affected by pH of their surrounding environment and can become more positively or negatively charged due to the loss or gain of protons. The pI the pH value at which the molecule carries no electrical charge or the negative and positive charge are equal.

Methods for determining whether a peptide at a certain pH has a predominant net charge are known in the art. For example, suitable tools for calculating the pI value of proteins or peptides are provided by ExPasyProteomic server (www.expasy.ch). The program "Compute pI/Mw" is a tool which allows the computation of the theoretical pI (isoelectric point) and Mw (molecular weight) for a list of database entries (UniProtKnowledgebase (Swiss-prot or TrEMBL)) or for user entered sequences. Prediction of pI values are also described in Bjellqvist et al. (1993) and Gasteider et al. (2005) [Bjellqvist, B., The focusing positions of polypeptides in immobilized pH gradients can be predicted from their amino acid sequences. Electrophoresis 1993, 14, 1023-1031. Gasteiger E., Protein Identification and Analysis Tools on the ExPASy Server, (In) John M. Walker (ed): *The Proteomics Protocols Handbook*, Humana Press (2005).]

In further specific embodiments, the compound is able to permeate into the silk matrix, preferably spider silk matrix, by electrostatic interaction and/or diffusion. It has to be understood that the charged compound is attracted by an overall negative net charge of the silk particles, e.g. spider silk particles. Due to the attraction based on the presence of opposite charges, the compound is capable of adhering to the surface of the silk particle, e.g. spider silk particle, and diffusing into the silk matrix, e.g. spider silk matrix. Generally the repulsion or attraction of charges in colloidal systems can be explained with the zeta potential. Within the context of the present invention, a positively charged compound is of permeating into the silk matrix, e.g. spider silk matrix, by electrostatic interaction when the zeta potential of the silk particles, e.g. spider silk particles, is essentially negative.

Naturally, the one or more silk polypeptides, e.g. spider silk polypeptides, of the silk particles, e.g. spider silk particles, possess at least one negative charge at the carboxyl terminus. As used herein, the terms "negatively charged" and "anionic" can be used interchangeably. The person skilled in the art also knows how to select appropriate amino acid sequences in order obtain a polypeptide having an overall negative net charge. For example, this can be achieved by selecting sequences comprising negatively charged amino acids. A suitable negatively charged silk polypeptide, particularly spider silk polypeptide, is for example $C_{16}$ which comprises 16 repeats of the sequence of module C (SEQ ID NO: 21) or variants thereof. In preferred embodiments, the compound has a neutral or alkaline nature.

As used herein, the terms "pharmaceutical active compound", "drug", "pharmaceutical agent", "therapeutic agent" or "bioactive compound/agent" may be used interchangeably and refer to any physical, chemical or biological substance which may be used in the treatment, cure, prophylaxis, prevention, or diagnosis of a pathological condition, e.g. a disease or disorder, or which may be used to otherwise enhance physical, psychical or mental well-being. Accordingly, pharmaceutically active compounds envisaged in the context of the present invention include any compound with therapeutic or prophylactic effects. For example, it can be a compound that affects or participates in tissue growth, cell growth, cell differentiation, a compound that is able to invoke a biological action such as an immune response, or a compound that can play any other role in one or more biological processes.

The therapeutic agent can be, but is not limited to, an antimicrobial agent, an antibiotic, an anti-viral agent, antifungal agent, an urinary tract antiseptic, an agent for treating anaerobic infections, an agent for treating tuberculosis, an agent for treating leprosy, an agent for treating amebiasis, an anti-malarial agent, an anti-helminthiasis agent, an anti-gout agent, a thrombin inhibitors, an antithrombogenic agent, a thrombolytic agent, fibrinolytic agent, a vasospasm inhibitor, a vasodilator, an antihypertensive agent, an antihypotensive agent, an inhibitors of surface glycoprotein receptor, antiplatelet agent, an antimitotic, an actin inhibitors, a microtubule inhibitor, an anti secretory agent, a remodeling inhibitor, an antimetabolite, an antiproliferative (including anti-angiogenesis agents), an immunosuppressive agents, a growth hormone antagonist, a growth factor, a dopamine agonist, a radiotherapic agent, a extracellular matrix component, an ACE inhibitor, a free radical scavenger, a chelator, an antioxidant, an antipolymerase, a photodynamic therapy agent, a centrally active muscle relaxant, an opioid agonist, a non-opioid analgesic, a non-steroid anti-inflammatory agent, an antimigraine agent, a Cox-II inhibitor, an antiemetic, a β-adrenergic blocker, a $Ca^{2+}$-channel blocker, an anticonvulsant, an antidepressant, an anticancer agent, an agent for treating or preventing urinary incontinence (UI), an agent for treating or preventing an ulcer, an agent for treating or preventing infectious bursal disease (IBD), an agent for treating or preventing irritable bowel syndrome (IBS), an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating amytrophic lateral sclerosis (ALS), an agent for treating a cognitive disorder, an agent for treating a migraine, an agent for treating vomiting, an agent for treating dyskinesia, or an agent for treating depression, an anorexic, an antacid, antiacne agents, an antiallergic, an antianginal agent, an antiarrythmic, an antiasthmatic, an antibaldness agent, anticholinergic agent, an anticoagulant and blood thinner, anticolitis agent, an anticystitis agent, an antidiabetic agent, an antidiarrheal, an antidiuretic, an antiflatulent, an antiglaucoma agent, an antihistaminic, an antipneumonia agent, an antiobesity agent, an antipsoriatics, antipsychotic, an antipyretic, antirheumatic, antitussive, a bone densifier, a carbonic anhydrase inhibitor, a cardiotonic, a contraceptive, a decongestant, a diuretic, a CNS stimulant, dopamine receptor antagonist, HMG CoA reductase inhibitor, a phosphodiesterase inhibitor, a hormone, a hormone antagonist, a hematopoietic agent, an immunomodulator, an immunosuppressant, a laxative, an agent for treating multiple sclerosis, a sedative, a serotonin uptake inhibitor, and mixtures thereof.

Examples of useful antimicrobial agents belong to, but are not limited to, the group of antibiotics comprising ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, icarcillin, mezlocillin, cephalosporins such as cefaclor, cephalothin, cefadroxil, cephapirin, cefamandole, cephradine, cefatrizine, cefsulodine, cefazolin, ceftazidim, cefloranide, ceftriaxon, cefoxitin, cefuroxime, cephacetrile, latamoxef, or cephalexin, aminoglycosides such as amikacin, neomycin, dibekacyn, kanamycin, gentamycin, netilmycin or tobramycin, macrolides such as amphotericin B, novobiocin, bacitracin, nystatin, clindamycin, polymyxins, colistin, rovamycin, erythromycin, spectinomycin, lincomycin or vancomycin, tetracyclines such as chlortetracycline, oxytetracycline, demeclocycline, rolitetracycline, doxycycline, tetracycline, minocycline, chloramphenicol, rifamycin, rifampicin and thiamphenicol.

Examples of useful antifungal agents belong to, but are not limited to, the group comprising amphotericin B, ketoconazole, clotrimazole, miconazole, econazole, natamycin, flucytosine, nystatine and griseofulvin.

Examples of useful antiviral agents belong to, but are not limited to, the group comprising aciclovir, idoxuridine, amantidine, methisazone, cytarabine, vidarabine and ganciclovir.

Examples of useful urinary tract antiseptics belong to, but are not limited to, the group comprising methanamine, quinolones such as norfloxacin or cinoxacin, nalidixic acid, and nitro-compounds such as nitrofurantoine, nifurtoinol or oxolinic acid.

An example of an agent for treating anaerobic infections belong to, but is not limited to, metronidazole.

Examples of useful therapeutic agents for treating tuberculosis belong to, but are not limited to, the group comprising aminosalicyclic acid, isoniazide, cycloserine, rifampicine, ethambutol, tiocarlide, ethionamide and viomycin.

Examples of useful therapeutic agents for treating leprosy belong to, but are not limited to, the group comprising amithiozone, rifampicine, clofazimine, sodium sulfoxone and diaminodiphenylsulfone (DDS, dapsone).

Examples of useful chemotherapeutics for treatment of amebiasis belong to, but are not limited to, the group comprising chloroquine, iodoquinol, clioquinol, metronidazole, dehydroemetine, paromomycin, diloxanide, furoatetinidazole and emetine.

Examples of useful anti-malarial agents belong to, but are not limited to, the group comprising chloroquine, pyrimethamine, hydroxychloroquine, quinine, mefloquine, sulfadoxine/pyrimethamine, pentamidine, sodium suramin, primaquine, trimethoprim and proguanil.

Examples of useful anti-helminthiasis agents belong to, but are not limited to, the group comprising antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole and niclosamide.

Examples of useful anti-gout agents belong to, but are not limited to, the group comprising colchicine and allopurinol.

Examples of useful local anesthetics belong to, but are not limited to, the group comprising articaine, mepivacaine, bupivacaine, prilocalne, etidocaine, procaine, lidocaine or tetracaine.

Examples of useful centrally active muscle relaxants belong to, but are not limited to, the group comprising baclofen, carisoprodol, chlormezanone, chlorzoxazone, cyclobenzaprine, dantrolene, diazepam, febarbamate, mefenoxalone, mephenesin, metoxalone, methocarbamol or tolperisone.

Examples of useful thyroid drugs in therapy belong to, but are not limited to, the group comprising levothyronine and liothyronine.

Examples of useful anti-thyroid drugs belong to, but are not limited to, the group comprising carbimazole, methimazole, methylthiouracil and propylthiouracil.

Examples of useful opioid agonists belong to, but are not limited to, the group comprising alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, and mixtures thereof.

Examples of useful non-opioid analgesics belong to, but are not limited to, the group comprising non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenarnic acid, diflurisal, flufenisal, piroxicam, sudoxicam, and isoxicam.

Examples of other suitable non-opioid analgesics belong to, but are not limited to, the group comprising analgesics, antipyretics, nonsteroidal anti-inflammatory drugs such as salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid, enolic acids, including oxicams (piroxicam, tenoxicam), and pyrazolidinediones (phenylbutazone, oxyphenthartazone), and alkanones, including nabumetone.

Examples of useful Cox-II inhibitors belong to, but are not limited to, the group comprising rofecoxib and celecoxib.

Examples of useful antimigraine agents belong to, but are not limited to, the group comprising alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful antiemetic agents belong to, but are not limited to, the group comprising metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Examples of useful β-adrenergic blockers belong to, but are not limited to, the group comprising acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants belong to, but are not limited to, the group comprising acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants belong to, but are not limited to, the group comprising binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful $Ca^{2+}$-channel blockers belong to, but are not limited to, the group comprising bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexyline.

Examples of useful anticancer agents belong to, but are not limited to, the group comprising acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs belong to, but are not limited to, the group comprising 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab;

decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor, interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor, multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor, protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor, urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI belong to, but are not limited to, the group comprising propantheline, imipramine, hyoscyamine, oxybutynin, and dicyclomine.

Examples of useful therapeutic agents for treating or preventing an ulcer belong to, but are not limited to, the group comprising antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD belong to, but are not limited to, the group comprising anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; and methotrexate.

Examples of useful therapeutic agents for treating or preventing IBS include belong to, but are not limited to, the group comprising propantheline; muscarine receptor antogonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder belong to, but are not limited to, the group comprising methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism belong to, but are not limited to, the group comprising carbidopa/levodopa, pergolide, bromocriptine, ropinirole, pramipexole, entacapone, tolcapone, selegiline, amantadine, diphenhydramine, apomorphine, ethopropazine, benztropine mesylate, lergotril, biperiden, lisuride, metixen, chlorphenoxamine, orphenadrine, cycrimine, procyclidine, dexetimide, trihexyphenidyl, and trihexyphenidyl hydrochloride.

Examples of useful therapeutic agents for treating or preventing anxiety belong to, but are not limited to, the group comprising benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsaprione, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy belong to, but are not limited to, the group comprising carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing stroke belong to, but are not limited to, the group comprising anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure belong to, but are not limited to, the group comprising carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing a pruritic condition belong to, but are not limited to, the group comprising naltrexone; nalmefene; danazol; tricyclics such as amitriptyline, imipramine, and doxepin; antidepressants such as those given below, menthol; camphor, phenol; pramoxine; capsaicin; tar; steroids; and antihistamines.

Examples of useful therapeutic agents for treating or preventing psychosis belong to, but are not limited to, the group comprising phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea belong to, but are not limited to, the group comprising haloperidol and pimozide.

Examples of useful therapeutic agents for treating or preventing ALS belong to, but are not limited to, the group comprising baclofen, neurotrophic factors, riluzole, tizanidine, benzodiazepines such as clonazepan and dantrolene.

Examples of useful therapeutic agents for treating or preventing cognitive disorders belong to, but are not limited to, the group comprising agents for treating or preventing dementia such as tacrine; donepezil; ibuprofen; antipsychotic drugs such as thioridazine and haloperidol; and antidepressant drugs such as those given above.

Examples of useful therapeutic agents for treating or preventing a migraine belong to, but are not limited to, the group comprising sumatriptan; methysergide; ergotamine; caffeine; and beta-blockers such as propranolol, verapamil, and divaiproex.

Examples of useful therapeutic agents for treating or preventing vomiting belong to, but are not limited to, the group comprising 5-HT$_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia belong to, but are not limited to, the group comprising reserpine and tetrabenazine.

Examples of useful therapeutic agents for treating or preventing depression belong to, but are not limited to, the group comprising tricyclic antidepressants such as amityrptyline, amoxapine, bupropion, clomipramine, desipramine, doxepin, imipramine, maprotilinr, nefazadone, nortriptyline, protriptyline, trazodone, trimipramine, and venlaflaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

Examples of other useful pharmaceutical compounds can belong to, but are not limited to, the group of corticosteroids comprising mineralocorticosteroids such as cortisol, desoxycorticosterone and fluorohydrocortisone, lucocorticosteroids such as beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone and triamcinolone (acetonide), androgens comprising androgenic steroids used in therapy such as danazole, fluoxymesterone, mesterolone, methyltestosterone, and testosterone and salts thereof, anabolic steroids used in therapy such as calusterone, nandrolone and salts thereof, dromostanolone, oxandrolone, ethylestrenol, oxymetholone, methandriol, stanozolol, methandrostenolone and testolactone, anti-androgens such as cyproterone acetate, estrogens comprising estrogenic steroids used in therapy such as diethylstilbestrol, estradiol, estriol, ethinylestradiol, mestranol or quinestrol, anti-estrogens such as chlorotrianisene, clomiphene, ethamoxytriphetol, nafoxidine and tamoxifen, progestins such as allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, and progesterone.

The pharmaceutical active compound can be also a peptide or protein, e.g. an enzyme such as lysozyme. The terms "peptide", "polypeptide" or "protein" may be used interchangeably. The methods to determine whether a peptide or a protein is suitable for loading, i.e. is water-soluble and/or carries a net charge at a given pH-value is known to one of skill in the art, e.g. described in F. Lottspeich/Z. Zorbas [*Lottspeich*, F.; Zorbas, H. (Hrsg.) *Bioanalytik* Spektrum Akademischer Verlag: Heidelberg, 1998]. Relatively small peptides may be referred to by the number of amino acids (e.g. di-, tri-, tetrapeptides). A peptide having a relatively small number of amide bonds may also be called an oligopeptide (up to 50 amino acids), whereas a peptide with a relatively high number (more than 50 amino acids) may be called a polypeptide or protein. In addition to being a polymer of amino acid residues, certain proteins may further be characterized by the so called quaternary structure, a conglomerate of a number of polypeptides that are not necessarily chemically linked by amide bonds but are bonded by forces generally known to the skilled person, such as electrostatic forces and van-der-Waals forces. The term peptides, proteins or mixtures thereof as used herein is to include all above mentioned possibilities. Usually, the protein and/or peptide are selected on the basis of its biological activity.

Other examples of peptides or proteins or entities comprising peptides or proteins, which may advantageously be loaded onto and/or into the silk particles, preferably spider silk particles, according to the invention belong to, but are not limited to, the group comprising immunogenic peptides or immunogenic proteins which comprise the following:

Examples of useful toxins belong to, but are not limited to, the group comprising diphtheria toxin and tetanus toxin.

Examples of useful viral surface antigens or parts of viruses belong to, but are not limited to, the group comprising adenoviruses, Epstein-Barr Virus, Hepatitis A Virus, Hepatitis B Virus, Herpes viruses, HIV-1, HIV-2, HTLV-III, Influenzaviruses, Japanese encephalitis virus, Measles virus, Papilloma viruses, Paramyxoviruses, Polio Virus, Rabies, Virus, Rubella Virus, Vaccinia (Smallpox) viruses and Yellow Fever Virus.

Examples of useful proteins belong to, but are not limited to, the group of bacterial surface antigens or parts of bacteria such as *Bordetella pertussis, Helicobacter pylori, Clostridium tetani, Corynebacterium diphtheria, Escherichia coli, Haemophilus influenza, Klebsiella* species, *Legionella pneumophila, Mycobacterium bovis, Mycobacterium leprae, Mycrobacterium tuberculosis, Neisseria gonorrhoeae, Neisseria meningitidis, Proteus* species, *Pseudomonas aeruginosa, Salmonella* species, *Shigella* species, *Staphylococcus aureus, Streptococcus pyogenes, Vibrio cholera* or *Yersinia pestis*.

Examples of useful proteins belong to, but are not limited to, the group of surface antigens of parasites causing disease or portions of parasites such as *Plasmodium vivax* (malaria), *Plasmodium falciparum* (malaria), *Plasmodium ovale* (malaria), *Plasmodium malariae* (malaria), *Leishmania tropica* (leishmaniasis), *Leishmania donovani*), leishmaniasis), *Leishmania branziliensis* (leishmaniasis), *Trypanosoma rhodescense* (sleeping sickness), *Trypanosoma gambiense* (sleeping sickness), *Trypanosoma cruzi* (Chagas' disease), *Schistosoma mansoni* (schistosomiasis), *Schistosomoma haematobium* (schistomiasis), *Schistosoma japonicum* (shichtomiasis), *Trichinella spiralis* (trichinosis), *Strongyloides duodenale* (hookworm), *Ancyclostoma duodenale* (hookworm), *Necator americanus* (hookworm), *Wucheria bancrofti* (filariasis), *Brugia malaya* (filariasis), *Loa loa* (filariasis), *Dipetalonema perstaris* (filariasis), *Dracuncula medinensis* (filariasis), or *Onchocerca volvulus* (filariasis).

Examples of useful proteins belong to, but are not limited to, the group of antitoxins such as Botulinum antitoxin, diphtheria antitoxin, gas gangrene antitoxin and tetanus antitoxin. Examples of useful proteins belong to, but are not limited to, the group of antigens which elicit an immune response against foot and mouth disease. Examples of useful proteins belong to, but are not limited to, the group of hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII or Antithrombin III.

Examples of other proteins or peptides belong to, but are not limited to, the group of albumin, atrial natriuretic factor, renin, superoxide dismutase, alpha 1-antitrypsin, lung surfactant proteins, bacitracin, bestatin, cydosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, des-enkephalin-alpha-endorphin, gonadotropin releasing hormone, leuprolide, alpha-MSH or metkephamid.

Preferred useful therapeutic agents are selected from the group consisting of tetracaine, procaine, papaverine, ephedrine, propanolol, and ecthacridine lactate.

As used herein, the terms "cosmetic substances" and "cosmetic compounds" may be used interchangeably and designate substances intended mainly for external use on the human body or in the oral cavity for cleaning and personal hygiene to alter the appearance or body odor or to convey scent. In particular, it is meant that cosmetic substances are molecules which show a certain predictable effect. Such effect molecules can be for example proteinaceous molecules such as enzymes or non-proteinaceous molecules such as dyes, pigments, photoprotective agents, vitamins, provitamins, antioxidants, conditioners or compounds comprising metal ions.

Among the proteinaceous molecules enzymes and antibodies are preferred. Examples for useful belong to, but are not limited to, the group comprising oxidases, peroxidases, proteases, glucanases, mutanase, tyrosinases, laccases, metal-binding enzymes, lactoperoxidase, lysozyme, aminoglycosidase, glucose oxidase, super oxide dismutase, photolyase, T4 endonuclease, catalase, thioredoxin or thioredoxin-reductase.

Also preferable are proteinaceous substances which do not possess an enzymatic function. Examples for non-enzymatic proteinaceous molecules belong to, but are not limited to, the group comprising antimicrobial peptides, hydrophobins, collagen, proteins binding carotenoid, proteins binding heavy metals, proteins binding odorants, proteins binding cellulose, proteins binding starch or proteins binding keratin.

Examples of useful proteinaceous molecules belong to, but are not limited to, the group comprising protein hydrolysates of plant or animal sources. For example, the protein hydrolysate can be of marine origin.

The cosmetic compound can further be a UV-protective filter. These are by definition organic substances which can absorb specific wavelengths in the range of UV-wavelengths. The absorbed energy can then emitted in form of longer wave radiation, e.g. heat.

Examples of suitable water-soluble UV-protective filters belong to, but are not limited to, the group comprising to, 2-phenyl-benzimidazole-5-sulfonic acid and the alkali metal, alkaline earth metal, ammonium, alkylammonium, alkanolammonium and glucammonium salts thereof, sulfonic acid derivatives of benzophones such as 2-hydroxxy-4-methoxy-benzophene-5-sulfonic acid and its salts, sulfonic acid derivatives of 3-benzylidenecamphor such as 4-(2-oxo-3-bornylidene-methyl)benzenesulfonic acid and 2-methyl-5-(2-oxo-3-bornylidene)-sulfonic acid and salts thereof, esters of cinnamic acid such as 2-ethylhexyl 4-methoxycinnamate, isopentyl 4-methoxycinnamate or 2-ethylhexyl 2-cyano-3-phenylcinnamate (octocrylene), derivatives of benzophene such as 2-hydroxy-4-methoxybenzophne, 2-hydroxy-4-methoxy-4'-methyl-benzophenone, 2,2'-dihydroxy-4-methoxybenzophenone or propane-1,3-diones such as 1-(4-tert-butylphenyl)-3-(4'-methoxyphenyl)propane-1,3-dione.

The cosmetic compound may also comprise a secondary protective agent of the antioxidant type which interrupts the photochemical reaction chain triggered by UV radiation when penetrating into the skin. Typical examples belong to, but are not limited to, the group comprising super oxide dismutase, catalase, tocopherols (vitamin E), coenzyme Q10, ubiquinanes, quiniones and ascorbic acid (vitamin C).

The cosmetic, compound can also be a vitamin, a provitamin or precursors thereof. Examples belong to, but are not limited to, the group comprising β-carotene (provitamin of vitamin A), ascorbic acid (vitamin C), tocopherols, the vitamins, provitamins or precursors of the vitamin B group or derivatives thereof such as vitamin $B_1$ (thiamine), vitamin $B_2$ (riboflavin) or the stereoisomer lyxoflavin, vitamin $B_3$ (nicotinic acid or nicotinamid), vitamin B5 (panthothenic acid and panthenol) and derivatives thereof such as esters, ethers and cationically derivatized panthenol, derivatives of 2-furanone such as dihydro-3-hydroxy-4,4-dimethyl-2(3H)-furanone (pantolactone), 4-hydroxymethyl-γ-butyrolactone, 3,3-dimethyl-2-hydroxy-γ-butyrolactone and 2,5-dihydro-5-methoxy-2-furanone and stereoisomers thereof, vitamin $B_6$ such as derivatives of 5-hydroxymethyl-2-methylpyridin-3-ol (also known as pyridoxine, pyridoasamine or pyridoxal) and vitamin $B_7$ (biotin).

Examples of useful cosmetic compounds belong to, but are not limited to, the group of antioxidants, comprising amino acids such as tyrosine and cysteine and derivatives thereof, and tannins.

Examples of useful cosmetic compounds belong to, but are not limited to, the group of peroxide decomposers comprising pyridine-2-thiol-3-carboxylic acid, 2-methoxypyrimidinolcarboxylic acids, and 2-dimethylaminopyridinecarboxylic acids.

The cosmetic compound can also comprise dyes such as food dyes, semi-permanent dyes, reactive or oxidation dyes. Examples of useful dyes are for example described in Rowe Colour Index, $3^{rd}$ edition, Society of Dyers and Colourists, Bradford, England, 1971.

As used herein, the terms "agricultural substance", "agricultural compound" and "agricultural active ingredient" can be used interchangeably and means chemicals (including veterinary medicines) used in the production of primary produce (farmed plants or animals). They are also used by home gardeners, and for the health of domestic animals such as cats and dogs. Agricultural compounds can be any natural or synthetic and include substances such as veterinary medicines, fertilisers and pesticides.

The agricultural active ingredient may be a pesticide, selected from the group such as insecticides, nematocides, fungicides and herbicides; and possibly molluscicides and rodenticides.

Examples of useful agricultural active ingredients belong to, but are not limited to, the group comprising organophosphates, carbamates, benzimidazoles dicarboxamides, bipyridols, pyrethroids and chlorinated hydrocarbons.

Examples of useful organophosphates belong to, but are not limited to, the group comprising azinphos methyl, dimethoate, ethyl parathion, trichlorfon, dibrom, dimecron, mevinphos, and monocrotophos.

Examples of useful carbamates belong to, but are not limited to, the group comprising methomyl, oxamyl, aldicarb, carbofuran, fenoxycarb, carbaryl, ethionocarb, and fenobucarb.

Examples of useful benzimidazole belong to, but are not limited to, the group comprising as benomyl, carbendaz or thiophanate-methyl.

Examples of useful dicarboxamides belong to, but are not limited to, the group comprising vinclozolin, iprodione, procymidone or captan.

Examples of useful bipyridols belong to, but are not limited to, the group comprising paraquat and diquat.

The agricultural compound may also be a pyrethroid. Examples of useful pyrethroids belong to, but are not limited to, the group comprising cypermethrin or a chlorinated hydrocarbon such as DDT, dicofol, heptachlor, endosulfan, chlordane, aldrin, dieldrin, endrin, mirex, and pentachlorphenol.

The agricultural compound may also be a synthetic organic fertilizer such as urea.

The term "chemoattractant" means organic or inorganic substances possessing chemotacis inducer effect in motile cells. Effects of chemoattractants are elicited via described or hypothetic chemotaxis receptors, the chemoattractant moiety of a ligand is target cell specific and concentration dependent. Most frequently investigated chemoattractants are formyl peptides and chemokines.

Chemokines are a family of small cytokines, or proteins secreted by cells. Proteins are classified as chemokines according to shared structural characteristics such as small size (8-10 kD in size); and the presence of four cysteine residues in conserved locations that are key to forming their 3-dimensional shape.

Examples of useful chemokines belong to, but are not limited to, the group of the chemokine family including CC-chemokines (or β-chemokines) such as I-309, MCP-1, MEP-1α, MIP-1β, RANTES, C10 (MRP-2), MARC (MCP-3), MCP-2, MRP-2, Eotaxin, MCP-5, MCP-4, HCC-1, Leukotactin-1, LEC (NCC-4), TARC, PARC, ELC, LARC, SLC, MDC, MPIF-1, Eotaxin-2, TECK, Eotaxin-3, CTACK or MEC, CXC chemokines (or α-chemokines) such as Gro-α, Gro-β, Gro-γ, PF-4, ENA-78, GCP-2, NAP-2, IL-8, MIG, IP-10, I-TAC, SDF-1, BCA-1, BRAK, Lungkine, SRPDOC or VCC-1, C-chemokines such as lymphoctactin α and lymphotactin β, and $CX_3C$-chemokines such as fractalkine.

As used herein, "chemorepellents" are substances expressing adverse migratory effect. These are typically compounds capable of repelling (or chemorepelling) a eukaryotic cell with migratory capacity, i.e. a cell that can move away from a repellant stimulus.

Examples of useful chemorepellents belong to, but are not limited to, the group comprising amino acids and chemokines such as IL-8 or SDF-1.

The terms "anti-fungal substance" or "fungizide" can be used interchangeably. By definition fungicides are chemical compounds which inhibit fungi or fungal spores. It is meant that fungicides are substances used both in agriculture and to fight fungal infectionsin animals (antifungal drug). Chemicals used to control oomycetes, which are not fungi, are also referred to as fungicides since oomycetes use the same mechanisms as fungi to infect plants.

Examples of used antifungal drugs belong to, but are not limited to, the group comprising polyene antifungals such as natamycin, rimocidin, filipin, nystatin, amphotericin B or candicin, imidazoles such as miconazole, ketoconazole, clotrimazole, econazole, bifonazole, butaoconazole, fenticonazole, isoconazole, oxiconazole, sertaconazole, sulconazole, tioconazole or gresofluin, thiazoles such as fluconazole, itraconazole, isavulconazole, ravuconazole, posaconazole, terconazole or voriconazole, thiazoles such as abafungin, allylamines such as terinafine, amorolfine, naftifine or bunafine, echinocandins such as anidulafungin, caspofungin or micafungin.

Examples of other anti-fungal drugs belong to, but are not limited to, the group comprising ciclopirox olamine, tolnaftate, flucytosine, griseofluvin or haloprogin.

As used herein, a "nutrient" is a chemical that an organism needs to live and grow or a substance used in an organism's metabolism which must be taken in from its environment. Organic nutrients include carbohydrates, fats, proteins (amino acids), and vitamins. Inorganic nutrients are dietary minerals, water, and oxygen. Preferred nutrients are macronutrients such as carbohydrates, amino acids or proteins and micronutrients such as vitamins.

Examples of useful carnohydrates belong to, but are not limited to, the group od monosaccharides such as, glyceraldehyde, erythrose, threose, ribose, arabinose, xylose, lyxose, allose, altrose, glucose, mannose, gulose, idose, galactose, talose, dihydroxacetone, erythrulose, ribulose, xylulose, psicose, fructose, sorbose, tagatose or stereoisomers thereof, amino sugars such as galactosamine, glucosamine, sialic acid, N-acetylglucosamine, sulfosugars such as sulfoquinovose, disaccharides such as sucrose, lactulose, lactose, maltose, trehalose or maltobiose, or oligosacharides such as Fructooligosaccharides (FOS), Galactooligosaccharides (GOS) or Mannan-oligosaccharides (MOS).

The terms "dietary supplement", "food supplement" or "nutritional supplement" as used herein, refer to a preparation intendended nutrients such as vitamins, minerals, fiber, fatty acids or amino acids, that are missing or are not consumed in sufficient quantitiy in a person's diet. Depending on the country dietary supplements are either definded as foods or as drugs.

Examples of other dietary supplements belong to, but are not limited to, the group comprising steroids such as dehydroepiandrosterone (DHEA), pregnenolone, or derivatives thereof, hormones such as melatonin, and other substances such as hydrrazine sulfate, caffeine (1,3,7-trimethylxanthine), catechins, soy isoflavones, glucosamine, coenzyme-Q10, ephedrine-type alkaloids such as ephedra or ephedrine, synephrine, norephedrine, or pseudodoephedrine.

The term "dye" as used herein refers to a coloured substance having affinity to a substrate to which it is being applied. Dyes are generally applied in aqueous solution. In contrast, pigments are typically insoluble and possess no affinity to the substrate. Both dyes and pigments appear to be coloured because of their ability to absorb specific wavelength of light. The dye can be a naturally occurring or synthetic organic dye or a food dye.

Examples of useful dyes belong to, but are not limited to, the group of a acridine dyes such as acridine orange or acridine yellow, anthrachinone dyes such as Alizarin, Anthrapurpurin, Carminic acid, Disperse Red 11, Disperse Red 9, Indathrene blue RS, Morindone, Oil blue 35, Oil blue A, Quinizarine Green SS, Solven violet 13 or Vat Yellow 4, diarylmethane dyes such as the diarylmethane dye auramine O or triarylmethanes such as Aluminon, Aniline Blue WS, Aurin, Brilliant Blue FCF, Brilliant Green, Bromocresol green, Bromocresol purple, Bromophenol blue, Bromothymol blue, Bromosulphtalein, Chlorophenol red, Chromoxane cyanin R, Coomassie, Cresol red, Crystal violet lactone, Ethyl Green, Fast Green FCF, Fluoran, Fuchsin, Fuchsin acid, Green S, Light Green SF yellowish, Malachite green, Methyl violet, Methyl blue, Methylrosaniline, New fuchsine, pararosaniline, Patent Blue V, Phenol red, Phenolphtalein, Rose bengal, Thymolphtalein, Victoria blue BO, Xylene cyanol or Xylenol orange, azo dyes such as Alizarine Yellow R, Allura Red AC, Amaranth, Amido black 10 B, Aniline Yellow, Azo rubine, Biebrich scarlet, Bismarck brown Y, Black 7984, Brilliant black BN, Brown FK, Brown HT, Chrysoine resorcinol, Citrus red 2, Congo red, D&C Red 33, Disperse Orange 1, Eriochrome Black T, Fast Yellow AB, Hydroxynaphtol blue, Janus Green B, Lithol Rubine BK, Lithiol Rubine BK, Methyl orange, Methyl Red, Methyl yellow, Mordant Red 19, Oil Red O, Oil Yellow DE, Orange B, Orange G, Orange GGN, Para Red, Ponceau 2R, Ponceau 4R, Ponceau 6R, Ponceau S, Prontosil, Red 2G, Scarlet GN, Solvent Red 164, Solvent Red 26, Solvent Yellow 124, Sudan Black B, Sudan I, Sudan II, Sudan III, Sudan IV, Sudan Red 7B, Sudan Red G, Sudan Yellow 3G, Sudan Yellow FCF, Tartrazine, Tropaeolin OO, Tropaeolin OOO or Trypan blue, cyanin dyes (or phtalocyanines) such as Alcian blue, Luxol fast blue, Direct blue 86, Direct blue 199, Phtalocyanine blue BN or Phtalocyanine green GN, azin dyes such as Neutral Red or Safranin, Nitro dyes such as picric acid and martius yellow, indolphenol dyes such as dichlorophenolindophenol, oxazin dyes such as nile blue, nile red, gallocyanin, gallamin blue or celestin blue, thiazin dyes such as methylene blue or new methylene blue or toluidine blue O, xanthene dyes or derivatives thereof including fluorescein, eosins such as Eosin Y and Eosin B and rhodamines such as Rhodamine B, Rhodamine 6G, Rhodamine 123, pyronin dyes such as Pyronin B and Pyronin Y, tetramethylrhodamine (TAMRA) and its isothiocyanate derivative (TRITC), sulforhodamine 101 and its sulfonyl chloride form Texas Red and Rhodamine Red or newer fluorophores such as Alexa dyes, e.g. Alexa 546, Alexa 555, Alexa 633, or Dylight dyes, e.g. DyLight 549, DyLight 633, or a mixture thereof.

The terms "fragrance", "odorant" "aroma", "aroma compound" or "flavour" can be used interchangeably and refer to a chemical compound that has a smell or odor. Typically, a chemical compound possess a smell or odor when the compound is essentially volatile, so it can be transported to the olfactory in the upper part of the nose in sufficiently high concentrations to be able to interact with one or more of the olfactory receptors.

Examples of useful aroma compounds belong to, but are not limited to, the group of esters such as methyl formate, methyl acetate, methyl butyrate, ethyl acetate, ethyl butyrate, isoamyl acetate, pentyl butyrate, pentyl pentanoate, octyl acetate, fructone, hexy acetate or ethyl methylphenylglycidate, terpenes such as myrcene, geraniol, nerol, citral, citronellal, citronellol, linalool or nerolidol, cyclic terpenes such as limonene, camphor, terpineol, alpha-ionone, terpineol, thujone, aromatic compounds such as benzaldehyde, eugenol, cinnamaldehyde, ethyl maltol, vanillin, anisole, anethole, estragole or thymol, amines such as trimethylamine, putrescine, cadaverine, pyridine, indole or skatole, alcohols such as furaneol, 1-hexanol, cis-3-hexen-1-ol or menthol, aldehydes such as acetaldehyde, hexanal, cis-3-hexenal, furfural, ketones such as dihydrojasmone, oct-1-en-3-one, 2-acetyl-1-pyrroline, 6-acetyl-2,3,4,5-tetrahydropyridine, lactones such as gamma-decalactone, gamma-nonalactone, delta-octalocatone, jasmine lactone, massoia lactone, wine lactone or sotolon, thiols such as ethanethiols, nerolin, tetrahydrothiophene, 2,4,6-trichloranisole or substituted pyrazines, and mixtures thereof.

The compound can be also any other agent such as a hemostatic agent such as sulmarin, carbazochrome, etamsylate, calcium dobesilate, esculamine, oxamarin, ornipressin, desmopressin, felypressin, octreotide, poliglusam or aprotinin.

Examples of useful other hemostatic compounds belong to, but are not limited to, the group comprising different, suitable hydrates such as potassium aluminum sulfate, aluminum sulfate, aluminum iron sulfate, aluminum ammonium sulfate, iron chloride, aluminum chloride, sodium chloride, zinc chloride, zinc phenol sulfate, tannic acids and adrenalin.

The other agent can also be a growth stimulating agent. The terms "growth stimulating agent", "growth factor" and "growth horomone" may be used interchangeably and refer to substances capable of stimulating cellular growth, proliferation and cellular differentiation. Typically these agents a proteins or steroids hormones. Growth factors are important for regulating a variety of cellular processes. Growth factors typically act as signaling molecules between cells. Examples are cytokines and hormones that bind to specific receptors on the surface of their target cells.

Examples of suitable growth stimulating belong to, but are not limited to, the group comprising bone morphogenetic proteins (BMPs), epidermal growth factors (EGF), erythropoietin (EPO), fibroblast growth factor (FG), granulocyte-colony stimulating factor (G-CSF), granulocyte-macrophage stimulating factor (GM-CSF), growth differentiation factor-9 (GDF9), hepatocyte growth factor (HGF), hepatoma derived growth factor (HDGF), insulin-like growth factor (HDGF), insulin-like growth factor (IGF), myostatin (GDF8), nerve-growth factor (NGF), platelet-dervived growth factor (PDGF), transforming growth factor alpha (TGF-α), transforming growth factor beta (TGF-β), and vascular ecdothelial growth factor (VEGF).

The other agent can be also an anti-fouling agent. The term "anti-fouling agent" as used herein refer to an agent that inhibits the growth of barnacles and other marine organisms on a ship's bottom (an antifouling paint or other coating).

Examples of useful anti-fouling agents belong to, but are not limited to, the group comprising irgarol 1051, copper- or zinc pyrithione, diuron and isothioazolinons such as Sea-nine 211.

The terms "proinflammatory agent" or "inflammatory agent" herein refer to any substance produced in an animal that is a direct or indirect mediator of inflammation, or is directly or indirectly involved in production of a mediator of inflammation. A variety of proinflammatory substances are known to those skilled in the art.

Examples of useful proinflammatory substances include belong to, but are not limited to, the group comprising eicosanoids such as prostaglandins, e.g., PGE2 and leukotrienes e.g., LTB4, enzymes such as phospholipases, inducible nitric oxide synthase (iNOS), COX-1 and COX-2 and cytokines such as interleukins (e.g., IL-1α, IL-1β, IL-2, IL-3, IL-4, IL-5, IL-6, IL-8, IL-10, IL-12 and IL-18), members of the tumor necrosis factor family, e.g. TNF-α, TNF-β and lymphotoxin β, interferons, e.g., IFN-β and IFN-γ, granulocyte/macrophage colony-stimulating factor (GM-CSF), transforming growth factors such as TGF-β1, TGF-β2 and TGF-β3, leukemia inhibitory factor (LIF), ciliary neurotrophic factor (CNTF), migration inhibitory factor (MIF), monocyte chemoattractant protein (MCP-1), macrophage inflammatory proteins (e.g., MIP-1α, MIP-1β and MIP-2), and RANTES.

Examples of other suitable substances having pro-inflammatory activity belong to, but are not limited to, the group comprising bacterial components such as lipopolysaccaride (LPS), teichoic and lipoteichoic acids, peptidoglycans, bacterials DNA such as fragments containing CpG-motifs, bacterial proteins such as entero- and exotoxins or hemolysins such as pneumoslysins, and yeast cell wall component such as zymosan.

In further specific embodiments, step ii) of the method is carried out at temperatures of between 4° C. and 40° C., preferably of between 10° C. and 30° C. and more preferably of between 20° C. and 25° C., e.g. 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C.

In further specific embodiments, step ii) of the method is carried out at a pH of between 1 and 9, preferably of between 4 and 9 and most preferably of between 6 and 8, e.g. pH 1, 2, 3, 4, 5, 6, 7, 8, or 9.

All features and characteristics according to the first aspect also apply to further aspects of the present invention as are described as follows.

In a second aspect, the present invention relates to silk particles, preferably spider silk particles, comprising at least one silk polypeptide, preferably spider silk polypeptide, comprising at least two identical repetitive units loaded with at least one compound, which is preferably water-soluble and/or has a molecular weight of between about 50 Da and about 20 kDa.

A compound which is well-suited for efficient loading of the silk particles, e.g. spider silk particles, is sufficiently small in size. In a preferred embodiment of the invention, the compound has a molecular weight of 50 Da or about 50 Da to 20 kDa or about 20 kDa; or 50 Da or about 50 Da to 10 kDa or about 10 kDa, preferably 50 Da or about 50 Da to 6 kDa or about 6 kDa, more preferably 50 Da or about 50 Da to 4 kDa or about 4 kDa and most preferably 50 Da or about 50 Da to 1 kDa or about 1 kDa, e.g. 50 Da, 100 Da, 150 Da, 200 Da, 250 Da, 300 Da, 350 Da, 400 Da, 450 Da, 500 Da, 550 Da, 600 Da, 650 Da, 700 Da, 750 Da, 800 Da, 850 Da, 900 Da, 950 Da, 1 kDa, 1.5 kDa, 2 kDa, 2.5 kDa, 3 kDa, 3.5 kDa, 4 kDa, 4.5 kDa, 5 kDa, 5.5 kDa, 6 kDa, 6.5 kDa, 7 kDa, 7.5 kDa, 8 kDa, 8.5 kDa, 9 kDa, 9.5 kDa, 10 kDa, 11 kDa, 12 kDa, 13 kDa, 14 kDa, 15 kDa, 16 kDa, 17 kDa, 18 kDa, 19 kDa, or 20 kDa.

Further, a compound which is well-suited for efficient loading of the silk particles, e.g. spider silk particles, is preferably water-soluble.

Furthermore, a preferred compound according to the invention may be any compound, which is a small and water-soluble compound, preferably having a molecular weight of between about 50 Da and 20 kDa, more preferably 50 Da to 10 kDa or 50 Da to 6 kDa and most preferably 50 Da to 4 kDa or 50 Da to 1 kDa (see above).

As mentioned above, the compound is able to permeate into the silk matrix, preferably spider silk matrix. Preferably, at least 40%, more preferably 50%, 60%, 70%, 80%, 90%, or 95% of the loaded compound is located within the matrix of the silk particles, preferably spider silk particles, e.g. at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%.

In preferred embodiments of the invention, the median size of the particles is 0.1 μm to 500 μm, preferably 0.1 μm to 100 μm, more preferably 0.2 μm to 20 μm, even more preferably 0.2 μm to 1 μm and most preferably 0.25 μm to 0.7 μm, e.g. 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500

In further specific embodiments, the silk polypeptide, preferably spider silk polypeptide, comprises, essentially consists of, or consists of at least two identical repetitive units each comprising at least one, preferably one, consensus sequence selected from the group consisting of:
  i) GPGXX (SEQ ID NO: 3), wherein X is any amino acid, preferably in each case independently selected from the group consisting of A, S, G, Y, P and Q;
  ii) GGX, wherein X is any amino acid, preferably in each case independently selected from the group consisting of Y, P, R, S, A, T, N and Q; and
  iii) $A_x$, wherein x is an integer from 5 to 10.

It is also preferred that the silk polypeptide comprises, essentially consists of, or consists of at least two identical repetitive units each comprising at least one, preferably one, amino acid sequence selected from the group consisting of: GGRPSDTYG (SEQ ID NO: 18) and GGRPSSSYG (SEQ ID NO: 19). The GGRPSDTYG (SEQ ID NO: 18) and GGRPSSSYG (SEQ ID NO: 19) (peptide) motifs have been selected from Resilin (WO 08/155304).

Preferably, the silk polypeptide comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, each comprising at least one, preferably one, consensus sequence selected from the group consisting of:
  i) GPGXX (SEQ ID NO: 3), wherein X is any amino acid, preferably in each case independently selected from A, S, G, Y, P, and Q;
  ii) GGX, wherein X is any amino acid, preferably in each case independently selected from Y, P, R, S, A, T, N and Q, more preferably in each case independently selected from Y, P and Q; and
  iii) $A_x$, wherein x is an integer from 5 to 10.

It is also preferred that the silk polypeptide comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, each comprising at least one, preferably one, amino acid sequence selected from the group consisting of: GGRPSDTYG (SEQ ID NO: 18) and GGRPSSSYG (SEQ ID NO: 19).

It should be noted that at least two of the repetitive units comprised in the silk polypeptides according to the present invention are identical repetitive units.

As to the silk polypeptide definitions, repetitive unit definitions, specific silk polypeptides, specific motifs and motif combinations, it is referred to the first aspect of the present invention.

It is preferred that the repetitive units are independently selected from module A (SEQ ID NO: 20), module C (SEQ ID NO: 21), module Q (SEQ ID NO: 22), module K (SEQ ID NO: 23), module sp (SEQ ID NO: 24), module S (SEQ ID NO: 25), module R (SEQ ID NO: 26), module X (SEQ ID NO: 27), or module Y (SEQ ID NO: 28), or variants thereof (i.e. module A variants, module C variants, module Q variants, module K variants, module sp variants, module S variants, module R variants, module X variants or module Y variants).

It is further preferred that the repetitive units are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34).

It is particularly preferred that the repetitive units of the silk polypeptide, preferably spider silk polypeptide, are independently selected from module A (SEQ ID NO: 20) or variants thereof, module C (SEQ ID NO: 21) or variants thereof, module Q (SEQ ID NO: 22) or variants thereof, module K (SEQ ID NO: 23) or variants thereof, module sp (SEQ ID NO: 24) or variants thereof, module S (SEQ ID NO: 25) or variants thereof, module R (SEQ ID NO: 26) or variants thereof, module X (SEQ ID NO: 27) or variants thereof, module Y (SEQ ID NO: 28) or variants thereof, module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34).

It should be noted that at least two of the repetitive units comprised in the silk polypeptides according to the present invention are identical repetitive units.

In more preferred embodiments, the silk polypeptide according to the present invention comprises, essentially consists of, or consists of between 2 to 80, between 3 to 80 repetitive units, or between 4 to 60 repetitive units, preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module A (SEQ ID NO: or variants thereof, module C (SEQ ID NO: 21) or variants thereof, module Q (SEQ ID NO: 22) or variants thereof, module K (SEQ ID NO: 23) or variants thereof, module sp (SEQ ID NO: 24) or variants thereof, module S (SEQ ID NO: 25) or variants thereof, module R (SEQ ID NO: 26) or variants thereof, module X (SEQ ID NO: 27) or variants thereof, module Y (SEQ ID NO: 28) or variants thereof, module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34).

Again, it should be noted that at least two of the repetitive units comprised in the silk polypeptides according to the present invention are identical repetitive units.

As to the specific module combinations and module variant or fragment definitions, it is referred to the first aspect of the present invention.

In further specific embodiments, the silk polypeptide, preferably spidersilk polypeptide, further comprises one or more non-repetitive (NR) units.

More preferably, the NR unit is independently selected from the group consisting of NR3 (SEQ ID NO: 41 and SEQ ID NO: 45) or variants thereof and NR4 (SEQ ID NO: 42 and SEQ ID NO: 46) or variants thereof.

In preferred embodiments of the invention, the silk polypeptide, preferably spider silk polypeptide, is selected from the group consisting of ADF-3 (SEQ ID NO: 1 and SEQ ID NO: 47) or variants thereof, ADF-4 (SEQ ID NO: 2 and SEQ ID NO: 48) or variants thereof, MaSp I (SEQ ID NO: 43 and SEQ ID NOs: 53-64) or variants thereof, MaSp II (SEQ ID NO: 44 and SEQ ID NOs: 65-78) or variants thereof, $(C)_m NR_z$, $NR_z(C)_m$, $(AQ)_n NR_z$, $NR_z(AQ)_n$, $NR_z(QAQ)_o$, $(QAQ)_o NR_z$, $(C)_m$, $(AQ)_n$, $(QAQ)_o$, $Y_p$, $X_p$, and $K_p$, wherein m is an integer of 8 to 48 (i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48), n is an integer of 6 to 24 (i.e. 6, 7, 8, 9, 10, 11, 12, 13, 14, 15, 16, 17, 18, 19, 20, 21, 22, 23, or 24), o is an integer of 8 to 16 (i.e. 8, 9, 10, 11, 12, 13, 14, 15, or 16), p is an integer of 8 to 16 (i.e. 8, 9, 10, 11, 12, 13, 14, 15, or 16), z is an integer of 1 to 3 (i.e. 1, 2, or 3), and NR stands for a non-repetitive unit.

More preferably, the silk polypeptide, preferably spider silk polypeptide, is $C_{16}$, $C_{32}$, $(AQ)_{12}$, $(AQ)_{24}$, $C_{16}NR4$, $C_{32}NR4$, $(AQ)_{12}NR3$, $(AQ)_{24}NR3$, $Y_8$, $Y_{16}$, $X_8$, $X_{16}$, $K_8$, or $K_{16}$.

As to the specific module combinations, NR3, NR4, ADF-3, ADF-4, MaSp I and MaSp II variant or fragment definitions, it is referred to the first aspect of the present invention.

In further preferred embodiments of the invention, the compound is a pharmaceutically active compound, a cosmetic substance, an agricultural substance, a chemoattractant, a chemorepellent, an anti-fungal substance, an anti-bacterial substance, a nutrient, a dietary supplement, a dye, a fragrance or an agent selected from the group consisting of hemostatic agents, growth stimulating agents, inflammatory agents, anti-fouling agents, antimicrobial agents and UV protecting agents.

In further specific embodiments, the compound has an overall positive net charge. In further specific embodiments, the compound is able to permeate into the silk matrix, preferably spider silk matrix, by electrostatic interaction and/or diffusion. Preferably, the compound has an overall positive net charge and is able to permeate into the silk matrix, preferably spider silk matrix, by electrostatic interaction and/or diffusion.

In further preferred embodiments, the compound has a neutral or alkaline nature. Preferably, the compound has an overall positive net charge, is able to permeate into the silk matrix, preferably spider silk matrix, by electrostatic interaction and/or diffusion and has a neutral or alkaline nature.

In preferred embodiments of the invention, the compound is released from the silk particles, preferably spider silk particles, by diffusion upon exposure to physiological conditions. The silk particles, preferably spider silk particles, according to present invention are, therefore, clearly distinguishable from the silk particles, e.g. spider silk particles, of the prior art, where release of the encapsulated compound is dependent on proteolysis. The compound is capable of being released upon exposure of the loaded silk particles, preferably spider silk particles, to physiological conditions, i.e. introducing the silk particles, preferably spider silk particles, into a buffer or an aqueous solution. Preferably the silk particles, more preferably spider silk particles, show a sustained and controlled release of the loaded compound. Sustained (or controlled) release refers to the gradual release of a compound from the silk matrix, preferably spider silk matrix, over a period of time. While there may be an initial burst phase, it is preferred that the release display relatively linear kinetics, thereby providing a constant supply of the compound over the release period. The release period may vary from several hours to several months, depending upon the properties of the compound and its intended use. For example, it can be desirable that the cumulative release of a pharmaceutically active compound from the silk matrix, preferably spider silk matrix, over a certain treatment period be relatively high to avoid the need for excessive loading of the matrix and consequent waste of unreleased pharmaceutically active agent.

Preferably, the release profile of the silk particles, preferably spider silk particles, has a small burst release within the first 24 hours. In further preferred embodiments, less than 20%, preferably less than 15%, and most preferably less than 10%, e.g. less than 20%, 19%, 18%, 17%, 16%, 15%, 14%, 13%, 12%, 11%, or 10%, of the compound is released, e.g. into the surrounding medium, within the first 24 hours. Said surrounding medium may be a buffered solution, a physiological buffered solution, blood, a body fluid, lymph, liquor, or water.

Preferably, up to 100% of the compound is released, e.g. into the surrounding medium, within 36 hours, 48 hours, or 72 hours, more preferably within 7 days, 14 days, 21 days, 31 days, or 35 days, most preferably within 5 weeks, 6 weeks, 7 weeks, or 8 weeks. As shown in example 8, almost 100% of the compound ethacridine lactate is released within 35 days.

In a third aspect, the invention relates to a pharmaceutical composition comprising the silk particles, preferably spider silk particles, according to the invention and additionally a pharmaceutically acceptable buffer, diluent and/or excipient, wherein the pharmaceutical composition is being useful for controlled and sustained delivery, and wherein the compound is a pharmaceutically active compound.

In a further aspect, the invention relates to a pharmaceutical composition comprising the silk particles, preferably spider silk particles, according to the invention and additionally one or more pharmaceutically acceptable buffer(s), diluent(s) and/or excipient(s). Preferably, the pharmaceutical composition is (useful) for controlled and sustained delivery of a compound. It is further preferred that the silk particle, preferably spider silk particle, of the invention comprises a compound which is a pharmaceutically active compound.

The compound mentioned above can be any pharmaceutically compound as mentioned above. In a preferred embodiment of the invention, the compound has a molecular weight of 50 Da or about 50 Da to 20 kDa or about 20 kDa; or 50 Da or about 50 Da to 10 kDa or about 10 kDa, preferably 50 Da or about 50 Da to 6 kDa or about 6 kDa, more preferably 50 Da or about 50 Da to 4 kDa or about 4 kDa and most preferably 50 Da or about 50 Da to 1 kDa or about 1 kDa, e.g. 50 Da, 100 Da, 150 Da, 200 Da, 250 Da, 300 Da, 350 Da, 400 Da, 450 Da, 500 Da, 550 Da, 600 Da, 650 Da, 700 Da, 750 Da, 800 Da, 850 Da, 900 Da, 950 Da, 1 kDa, 1.5 kDa, 2 kDa, 2.5 kDa, 3 kDa, 3.5 kDa, 4 kDa, 4.5 kDa, 5 kDa, 5.5 kDa, 6 kDa, 6.5 kDa, 7 kDa, 7.5 kDa, 8 kDa, 8.5 kDa, 9 kDa, 9.5 kDa, 10 kDa, 11 kDa, 12 kDa, 13 kDa, 14 kDa, 15 kDa, 16 kDa, 17 kDa, 18 kDa, 19 kDa, or 20 kDa.

As used herein, the terms "subject" or "patient" may be used interchangeably to refer to a mammal that may benefit from the administration of a composition or method as recited herein. Most often the subject or patient will be a human or other mammal such as for example horses, dogs or cats.

"Administration" refers to the manner in which an active agent or composition containing such is presented to a subject. The pharmaceutical composition according to the invention may be administered to a subject using several ways.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. Due the constant release profile of the silk particles, preferably spider silk particles, which are capable of releasing the loaded pharmaceutically over a period of weeks, the present pharmaceutical composition is in particular well-suited for parenteral administration. Since the silk particles, preferably spider silk particles, are also gastro-resistant the pharmaceutical composition are however also eminently suitable for oral forms of administration. It is also possible to formulate the silk particles, preferably spider silk particles, loaded with a pharmaceutically active compound in a depot system. For example, the particles may be embedded in films, lipids or gels.

The present pharmaceutical composition can optionally comprise a suitable amount of a pharmaceutically acceptable excipient so as to provide the form for proper administration to a subject. Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or can contain pH buffering agents. Further examples of suitable pharmaceutically acceptable excipients described herein may be found in the "Handbook of Pharmaceutical Excipients", 2nd Edition, (1994), Edited by A Wade and PJ Weller. Acceptable carrier or diluents for therapeutic use are well known in the pharmaceutical art, and are described, for example, in Remington's Pharmaceutical Sciences, Mack Publishing Co. (A. R Gennaro edit. 1985). Examples of suitable carriers include lactose, starch, glucose, methyl cellulose, magnesium stearate, mannitol, sorbitol and the like. Examples of suitable diluents include ethanol, glycerol and water.

In a fourth aspect, the invention relates to a cosmetic composition comprising the silk particles, preferably spider silk particles, according to the invention for controlled and sustained delivery, wherein the compound is a cosmetic compound.

In another further aspect, the invention relates to a cosmetic composition comprising the silk particles, preferably spider silk particles, according to the invention and additionally one or more cosmetically acceptable buffer(s), diluent(s) and/or excipient(s). Preferably, the cosmetic composition is (useful) for controlled and sustained delivery of a compound. It is further preferred that the silk particle, preferably spider silk particle, of the invention comprises a compound which is a cosmetic compound.

In a fifth aspect, the invention relates to silk particles, preferably spider silk particles, loaded with a compound, wherein the compound is water soluble, has a molecular weight of 50 Da to 20 kDa and/or has an overall positive net charge and wherein the silk particles, preferably spider silk particles, comprise one or more silk polypeptides, preferably spider silk polypeptides, comprising at least two identical repetitive units, the particles being obtainable by a process according to the invention.

Further embodiments will become obvious from the following examples which illustrate the invention in some of its major aspects, without limiting the scope thereof.

Free Text of the Sequence Listing

---

SEQ ID NOs: 3, 20-24, 27-34, 45-96:

SEQ ID NO: 3   GPGXX; X = A, S, G, Y, P, Q

SEQ ID NO: 20  Modul A:   GPYGPGASAA AAAAGGYGPG SGQQ

SEQ ID NO: 21  Modul C:   GSSAAAAAAA ASGPGGYGPE NQGPSGPGGY GPGGP

SEQ ID NO: 22  Modul Q:   GPGQQGPGQQ GPGQQGPGQQ

SEQ ID NO: 23  Modul K:   GPGGAGGPYGPGGAGGPYGPGGAGGPY

SEQ ID NO: 24  Modul sp:  GGTTIIEDLD ITIDGADGPITISEELTI

SEQ ID NO: 27  Modul X:   GGAGGAGGAG GSGGAGGS

SEQ ID NO: 28  Modul Y:   GPGGAGPGGY GPGGSGPGGY GPGGSGPGGY

SEQ ID NO: 29  Modul $A^C$:   GPYGPGASAA AAAAGGYGPG CGQQ

SEQ ID NO: 30  Modul $A^K$:   GPYGPGASAA AAAAGGYGPG KGQQ

SEQ ID NO: 31  Modul $C^C$:   GSSAAAAAAA ASGPGGYGPE NQGPCGPGGY GPGGP

SEQ ID NO: 32  Modul $C^{K1}$:  GSSAAAAAAA ASGPGGYGPE NQGPKGPGG Y GPGGP

SEQ ID NO: 33  Modul $C^{K2}$:  GSSAAAAAAA ASGPGGYGPK NQGPSGPGGY GPGGP

SEQ ID NO: 34  Modul $C^{KC}$:  GSSAAAAAAA ASGPGGYGPK NQGPCGPGGY GPGGP

---

SEQ ID NO: 45 - NR3 (ADF-3):
MASMTGGQQMGRGSMGAASAAVSVGGYGPQSSSAPVASAAASRLSSPAASSRVSSAV
SSLVSSGPTNQAALSNTISSVVSQVSASNPGLSGCDVLVQALLEVVSALVSILGSSSIGQIN
YGASAQYTQMVGQSVAQALAG

SEQ ID NO: 46 - NR4 (ADF-4):
MASMTGGQQMGRGSMGAYGPSPSASASVAASRLSSPAASSRVSSAVSSLVSSGPTNGA
AVSGALNSLVSQISASNPGLSGCDALVQALLELVSALVALLSSASIGQVNVSSVSQSTQM
ISQALSG

SEQ ID NO: 47 - ADF-3:
MASMTGGQQMGRDPNSARAGSGQQGPGQQGPGQQGPGQQGPYGPGASAAAAAAGG
YGPGSGQQGPSQQGPGQQGPGGQGPYGPGASAAAAAAGGYGPGSGQQGPGGQGPYG

SEQ ID NOs: 3, 20-24, 27-34, 45-96:

GSSAAAAAAGGNGPGSGQQGPGQQGPGQQGPGASAAAAAAGGYGPGSGQQGPGQQG
PGGQGPYGPGASAAAAAAGGYGPGSGQQGPGQQGPGGQGPYGPGASAAAAAAGGYG
PGSGQQGPGQQGPGQQGPGGQGPYGPGASAAAAAAGGYGPGSGQQGPGQQGPGGQG
PYGPGASAASAASGGYGPGSGQQGPGQQGPGGQGPYGPGASAAAAAAGGYGPGSGQQ
GPGQQGPGQQGPGQQGPGGQGPYGPGASAAAAAAGGYGPGSGQQGPGQQGPGQQGP
GQQGPGQQGPGQQGPGQQGPGQQGPGGQGAYGPGASAAAGAAGGYGPGSGQ
QGPGQQGPGQQGPGQQGPGQQGPGQQGPGQQGPYGPGASAAAAAAGGYGPG
SGQQGPGQQGPGQQGPVGQGPYGPGAASAAVSVGGYGPQSSSAPVASAAASRLSSPAA
SSRVSSAVSSLVSSGPTNQAALSNTISSVVSQVSASNPGLSGCDVLVQALLEVVSALVSIL
GSSSIGQINYGASAQYTQMVGQSVAQALA

SEQ ID NO: 48 - ADF-4:
MASMTGGQQMGRAARAGSSAAAAAAASGSGGYGPENQGPSGPVAYGPGGPVSSAAA
AAAAGSGPGGYGPENQGPSGPGGYGPGGSGSSAAAAAAAASGPGGYGPGSQGPSGPGG
SGGYGPGSQGPSGPGASSAAAAAAAASGPGGYGPGSQGPSGPGAYGPGGPGSSAAASG
PGGYGPGSQGPSGPGGSGGYGPGSQGPSGPGASAAAAAAAAASGPGGYGPGSQGP
SGPGAYGPGGPGSSAAAASGPGGYGPGSQGPSGPGAYGPGGPGSSAAAAAAAAGSGPGGY
GPGNQGPSGPGGYGPGGPGSSAAAAAAASGPGGYGPGSQGPSGPGVYGPGGPGSSAAA
AAAAAGSGPGGYGPGNQGPSGPGGYGPGGSGSSAAAAAAAASGPGGYGPGSQGPSGPG
GSGGYGPGSQGPSGPGASSAAAAAAAASGPGGYGPGSQGPSGPGAYGPGGPGSSAAAS
GPGGYGPGSQGPSGPGAYGPGGPGSSAAAAAAAAASGPGGYGPGSQGPSGPGGSRGYGPG
SQGPGGPGASAAAAAAAAASGPGGYGPGSQGPSGPGYQGPSGPGAYGPSPSASASVAA
SRLSSPAASSRVSSAVSSLVSSGPTNGAAVSGALNSLVSQISASNPGLSGCDALVQALLEL
VSALVAILSSASIGQVNVSSVSQSTQMISQALSG

Araneus diadematus fibroin
SEQ ID No 49:
>gi|1263283|gb|AAC47008.1| fibroin-1
HESSYAAAMAASTRNSDFIRNMSYQMGRLLSNAGAITESTASSAASSASSTVTESIRTYGPAAIFSGAGA
GAGVGVGGAGGYGQGYGAGAGAGAGAGAGAGGAGGYGQGYGAGAAAAAGAGAGAAGGYGGGSGAGAGGAG
GYGQGYGAGSGAGAGAAAAAGASAGAAGGYGGGAGVGAGAGAGAAGGYGQSYGSGAGAGAGAGAAAAAGA
GARAAGGYGGGYGAGAGAGAGAAASAGASGGYGGGYGGGAGAGAVAGASAGSYGGAVNRLSSAGAASRVS
SNVAAIASAGAAALPNVISNIYSGVLSSGVSSSEALIQALLEVISALIHVLGSASIGNVSSVGVNSALNA
VQNAVGAYAG SEQ ID No 50:
>gi|1263285|gb|AAC47009.1| fibroin-2
GSQGAGGAGQGGYGAGGGGAAAAAAAAVGAGGGGQGGLGSGGAGQGYGAGLGGQGGASAAAAAAGGQGGQ
GGQGGYGGLGSQGAGGAGQLGYGAGQESAAAAAAAAGGAGGGGQGGLGAGGAGQGYGAAGLGGQGGAGQG
GGSGAAAAAAGGQGGQGGYGGLGPQGAGGAGQGGYGGGSLQYGGQGQAQAAAASAAASRLSSPSAAARVSS
AVSLVSNGGPTSPAALSSSISNVVSQISASNPGLSGCDILVQALLEIISALVHILGSANIGPVNSSSAGQ
SASIVGQSVYRALS SEQ ID No 51:
>gi|1263287|gb|AAC47010.1| fibroin-3
ARAGSGQQGPGQQGPGQQGPGQQGPYGPGASAAAAAAGGYGPGSGQQGPSQQGPGQQGPGGQGPYGPGAS
AAAAAAGGYGPGSGQQGPGGQGPYGPGSSAAAAAAGGNGPGSGQQGAGQQGPGQQGPGASAAAAAAGGYG
PGSGQQGPGQQGPGGQGPYGPGASAAAAAAGGYGPGSGQQGPGQQGPGQQGPGGQGPYGPGASAAAAAAGGYGPGS
GQQGPGQQGPGQQGPGGQGPYGPGASAAAAAAGGYGPGSGQQGPGQQGPGGQGPYGPGASAASAASGGYG
PGSGQQGPGQQGPGGQGPYGPGASAAAAAAGGYGPGSGQQGPGQQGPGQQGPGQQGPGGQGPYGPGASAA
AAAAGGYGPGSGQQGPGQQGPGQQGPGQQGPGQQGPGQQGPGQQGPGQQGPGGQGAYGPGASAAA
GAAGGYGPGSGQQGPGQQGPGQQGPGQQGPGQQGPGQQGPGQQGPGQQGPYGPGASAAAAAAGGYGPGSG
QQGPGQQGPGQQGPGGQGPYGPGAASAAVSVGGYGPQSSSVPVASAVASRLSSPAASSRVSSAVSSLVSS
GPTKHAALSNTISSVVSQVSASNPGLSGCDVLVQALLEVVSALVSILGSSSIGQINYGASAQYTQMVGQS
VAQALA SEQ ID No 52:
>gi|1263289|gb|AAC47011.1| fibroin-4
AGSSAAAAAASGSGGYGPENQGPSGPVAYGPGGPVSSAAAAAAAGSGPGGYGPENQGPSGPGGYGPGGS
GSSAAAAAAAASGPGGYGPGSQGPSGPGGSGGYGPGSQGASGPGGPGASAAAAAAAAASGPGGYGPGSQ
GPSGPGAYGPGGPGSSAAAAAAAAASGPGGYGPGSQGPSGPGVYGPGGPAAAAAAAAASGPGGYGPENQ
GPSGPGGYGPGGSGSSAAAAAAAASGPGGYGPGSQGPSGPGPGGSGGYGPGSQGGSGPGASAAAAAAAASGP
GGYGPGSQGPSGPGYQGPSGPGAYGPSPSASASVAASVYLRLQPRLEVSSAVSSLVSSGPTNGAAVSGAL
NSLVSQISASNPGLSGCDALVQALLELVSALVAILSSASIGQVNVSSVSQSTQMISQALS major ampullate spidroin 1
SEQ ID No 53:
>gi|185179256|gb|ACC77633.1| major ampullate spidroin 1 [Nephila clavipes]
AGQGGLGGQGAGQGAGAAAAAGGAGQGGYGGLGSQGAGRGGLGGQGAGAAAAAGGAGQGGYGGLGGQG
AGQGAGQGGYGGLGSQGAGRGGQGAGAAAAAGGAGQGGYGGLGGQGVGRGGLGGQGAAAAGGAGQGGYG
GVGSGASAASAAASRLSSPQASSRVSSAVSNLVASGPTNSAALSSTISNVVSQIGASNPGLSGCDVLIQA
LLEVVSALIHILGSSSIGQVNYGSAGQATQIVGQSVYQALG SEQ ID No 54:
>gi|50363145|gb|AAT75312.1| major ampullate spidroin 1 [Nephila clavipes]
GGQGAGRGAGAAAAAGGAGQGGYGGLGGQGAGQGAGAAAAAGGAGQGGYGGLGSQGAGRGGYGGQGAE
AAAAAAGGAGQGGQGLGGQGAGAAAAGGAGQGGEGGLGGQGAGAAAAAGGAGQGGYGGLGSQGAGRGAG -continued SEQ ID NOs: 3, 20-24, 27-34, 45-96:

AAAAAAGGAGQGGYGGLGGQGAGRGAGAAAAAAGGAAQGGYGDLGSQGAGAAAAAAGSAGQGGYGGLGGQ
GAGQGAGAAAAAAGSAGQGGLGGRAGQGAGAASAAAGGAGQGGYGGLGGQGAGQGGYGGVGSGASAASSA
ASRLSSPEASSRVSSAVSNLVSSGPTNSAALSSTISNVVSQIGASNPGLSGCDVLVQALLEVVSALIHIL
GSSSIGQVNYGSAGQATQIVGQSIYQALG

SEQ ID No 55:
>gi|50363143|gb|AAT75311.1| major ampullate spidroin 1 [*Nephila clavipes*]
AGAAAAAGSAGQGGYGGQGAGQGGYGGLGSQGAGRGGLGGQGAGAAAAAAGGAGQGGLGGQGAGQGAGA
AAAAAGGAGQGGYGGLGNQGAGRGGQGAAAAAAGGAGQGGYGGLGSQGAGRGGLGGQGAGAAAAAAGGAG
QGGYGGLGGQGAGQGGYGGLGSQGSGRGGLGGQGAGAAAAAAGGAGQGGLGGQGAGQGAGAAAAAAGGVR
QGGYGGLGSQGAGRGGQGAGAAAAAAGGAGQGGYGGLGGQGVGRGGLGGQGAGAAAAAGGAGQGGYGGVGS
GASAASAAASRLSSPQASSRVSSAVSNLVASGPTNSAALSSTISNVVSQIGASNPGLSGCDVLIQALLEV
VSALIHILGSSSIGQVNYGSAGQATQIVGQSVYQALG SEQ ID No 56:
>gi|50363141|gb|AAT75310.1| major ampullate spidroin 1 [*Nephila clavipes*]
GGLGIQGSGRGGLGGQGAVAAAAAAAGGAVQVVLGGQGAGQGAGAAAAAAGGAGQGGYGGLGSQGAGRGG
QGAGARTAAAVGAGQGGYGGQGAGQGGYGGLGSQGAGRGGLGGQGAGAAAAAAGSAEQGLGGQGAGQGA
GAAAAAAGGAGQGGYGGLGSQGAGRGGLGGQGAGAAAAAAGGAGQGGYGGLGGQGAGQGGYGGLGSQGSG
RGGLGGQGAGAAAAAAGGAGQGGLGGQGAGQGAGAAAAAAGGAGQGGLGSQGAGRGGQGAGAAAAAA
GGAGQGGYGGLGGQGVGRGGLGGQGAGAAAAGGAGQGGYGGVGSGASAASAAASRLSSPQASSRVSSAVS
NLVASGPTNSAALSSTISNVVSQIGASNPGLSGCDVLIQALLEVVSALIHILGSSSIGQVNYGSAGQATQ
IVGQSVYQALG SEQ ID No. 57:
>gi|50363139|gb|AAT75309.1| major ampullate spidroin 1 [*Nephila clavipes*]
QGTDAAAAAAGGAGQGGYGGLGGQGAGQGGYGGLGSQGSGRGGLGGQGAGAAAAAAGGAGQGAGQGAGAA
AAAAGGVRQGGYGGLGSQGAGRGGQGAGAAAAAAGGAGQGGYGGLGGQGVGRGGLGGQGAGAAAAAGGAGQ
GGYGGVGSGASAASAAASRLSSPQASSRVSSAVSNLVASGPTNSAALSSTISNVVSQIGSSNPGLSGCDV
LIQALLEVVSALIQILGSSSIGQVNYGSAGQATQIVGQSVYQALG SEQ ID No. 58:
>gi|50363137|gb|AAT75308.1| major ampullate spidroin 1 [*Nephila clavipes*]
GQGAGQGAGAAAAAAGGAGQGGYGGLGNQGAGRGGQGAAAAAAGGAGQGGYGGLGSQGAGRGGLGGQGAG
AAAAAAGGAGQGGYGGLGGQGAGQGAGQGGYGGLGIQGSGRGGLGGQGAGAAAAAAGGAGQGGLGGQGAG
QGAGAAAAAAGGVRQGGYGGLGSQGAGRGGQGAGAAAAAAGGAGQGGYGGLGGQGVGRGGLGGQGoQGAGAAA
AGGAGQGGYGGVGSGASAASAAASRLSSPQASSRVSSAVSNLVASGPTNSAALSSTISNVVSQIGASNPG
LSGCDVLIQALLEVVSALIQILGSSSIGQVNYGSAGQATQIVGQSVYQALG SEQ ID No. 59:
>gi|13562006|gb|AAK30606.1|AF350277_1 major ampullate spidroin 1
[*Nephila madagascariensis*]
GLGGQGAGQGAGAAAAAAGGAGQGGYGGLGSQGAGRGGYGGQGAGAAAAAAAGGAGQGGYGGLGSWAGQ
GGYGGLGGQGAGQGAAAAAAGGAGQGGYGGLGSQGAGRGGYGGQGAGAAAATGGAGQGGYGGVGSGAS
AASAAASRLSSpQASSRVSSAVSNLVASGPTNSAALSSTISNAVSQIGASNPGLSGCDVLIQALLEVVSA
LIHILGSSSIGQVNYGSAGQATQ SEQ ID No. 60:
>gi|13562022|gb|AAK30614.1|AF350285_1 major ampullate spidroin 1
[*Tetragnatha kauaiensis*]
SGLGGAGQGAGQGASAAAAAAXGGLGGGQGAGQGGQQGAGQGGYGSLGGAGQGASAAAAAAAAGGLGG
GQGAGQGGQQGAGQGGYGSLGGAGQGASAAAAAAAGGLGGGQGAGQGGINGAGQGGYGSLGGAGQGA
GQGASAAAAAAGGLGGGQGGYGSLGGVGQGGQGALGGSRNSATNAISNSASNAVSLLSSPASNARISS
AVSALASGAASGPGYLSSVISNVVSQVSSNSGGLVGCDTLVQALLEAAAALVHVLASSGGQVNLNTAGY
TSQL SEQ ID No. 61:
>gi|13562010|gb|AAK30608.1|AF350279_1 major ampullate spidroin 1
[*Nephila senegalensis*]
GLGGQGAGRGAGAAAAAAGGAGQGGYGGLGGQGAGAAAAAAGGAGQGGQGLGGRGAAAAGGAGQGGYGGL
GGQGAGRGAGAAAAAAGGAGQGGYGGLGGQGAGAAAAAAGGAGQGGYGGLGSQGAGRGGYGGQGAGAA
VAAIGGVGQGGYGGVGSGASAASAAASRLSSPEASSRVSSAVSNLVSSGPTNSAALSSTISNVVSQIGAS
NPGLSGCDVLIQALLEVVSALVHILGSSSIGQVNYGSAGQATQ SEQ ID No. 62:
>gi|13582024|gb|AAK30615.1|AF350286_1 major ampullate spidroin 1
[*Tetragnaiha versicolor*]
SGQGASAAAAAAGGLGGGQGGYGSGIZGAGQGGQQGAGQGAAAAAASAAAGGLGGGQGGQQGAGRGGLQG
AGQGGQGALGGSRNSAANAVSRLSSPASNARISSAVSALASGGASSPGYLSSIISNVVSQVSSNNDGLSG
CDTVVQALLEVAAALVHVLASSNIGQVNLNTAGYTSQL SEQ ID No. 63:
>gi|13561998|gb|AAK30602.1|AF350273_1 major ampullate spidroin 1
[*Latrodectus geometricus*]
AGSGQGGYGQGYGEGGAGQGGAGAAAAAAAAGGAGQGGQGGYGQGYGQGGAGQGGAGAAAAAAGGAGQ
GGYGRGGAGQGAAAAAAGSGQGGQGGYGQGYGQGGAGQGGAGAAAAAAAAGGAGQGGYGRGGAGQGGA
AAAAAGGAGQGGQGGYGQGYGQGGAGQGGAGAAAAAAAGGAGQGGYGRGGAGQGGSAAAAAAGGAG

| SEQ ID NOs: 3, 20-24, 27-34, 45-96: |
|---|
| QGGYGRGGAGQGGAGSAAAAAAGGSGQGGQGGYGQGYGQGGAGQGGAAAAASALAAPATSARISSHAST<br>LLSNGPTNPASISNVISNAVSQISSSNPGASSCDVLVQALLELVTALLTIIGSSNVGNVNYDSSGQYAQV<br>VSQSVQNAFV |

SEQ ID No. 64:
>gi|13561984|gb|AAK30595.1|AF350266_1 major ampullate spidroin 1
[*Argiope trifasciata*]
AAAAAAAAAGGQGGQGGYDGLGSQGAGQGGYGQGGAAAAAAASGAGSAQRGGLGAGGAGQGYGAGSGGQ
GGAGQGGAAAATAAAAGGQGGQGGYGGLGSQGSQGGYGQGGAAAAAAAASGDGAGQEGLGAGGAGQGY
GAGLGGQGGAGQGGAAAAAAAAGGQGGQGGYGGLGSQGAGQGGYGQGGAAAAAAAASGAGGAGQGGLGA
AGAGQGYGAGSGGQGGAGQGGAAAAAAAGGQGGQGGYGQGGVAAAAAAASGAGGA
GRGGLGAGGAGQEYGAVSGGQGGAGQGGEAAAAAAAGGQGGQGGYGGLGSQGAGQGGYGQGGAAAAAAA
ASGAGGARRGGLGAGGAGQGYGAGLGGQGGAGQGSASAAAAAAAGGQGGQGGyGGLGSQGSGQGGYGQGG
AAAAAAAASGAGGAGRGSLGAGGAGQGYGAGLGGQGGAGQGGAAAAASAAAGGQGGQGGYGGLGSQGAGQ
GGYGQGGAAAAAASAGGQGGQGGYGGLGSQGAGQGGYGGGAFSGQQGGAASVATASAAASRLSSPGAASR
VSSAVTSLVSSGGPTNSAALSNTISNVVSQISSSNPGLSGCDVLVQALLEIVSALVHILGSANIGQVNSS
GVGRSASIVGQSINQAFS major ampullate spidroin 2
SEQ ID No. 65:
>gi|50363155|gb|AAT75317.1| major ampullate spidroin 2 [*Nephila clavipes*]
GGYGPGQQGPGGYGPGQQGPSGSGSAAAAAAAGPGQQGPGGYGPGQQGPGGYGPGQQGPSGPGSAAAAAA
AAAGPGGYGPAQQGPSGPGIAASAASAGPGGYGPAQQGPAGYGPGSAVAASAGAGSAGYGPGSQASAAAS
RLASPDSGARVASAVSNLVSSGPTSSAALSSVISNAVSQIGASNPGLSGCDVLIQALLEIVSACVTILSS
SSIGQVNYGAASQFAQVVGQSVLSAF SEQ ID No. 66:
>gi|50363153|gb|AAT75316.1| major ampullate spidroin 2 [*Nephila clavipes*]
PGGYGPGQQGPGSGAGSAAAAAAAGPGQQGLGGYGPGQQGPGGYGPGQQGPGGYGPGSASAAAAAAGPGQQ
GPGGYGPGQQGPSGPGSASAAAAAAAGPGGYGPGQQGPGGYAPGQQGPSGPGSAAAAAAAAAGPGGYGP
AQQGPSGPGIAASAASAGPGGYGPAQQGPAGYGPGSAVAASAGAGSAGYGPGSQASAAASRLASPDSGAR
VASAVSNLVSSGPTSSAALSSVISNAVSQIGASNPGLSGCDVLIQALLEIVSACVTILSSSSIGQVNYGA
ASQFAQVVGQSVLSAF SEQ ID No. 67:
>gi|50363147|gb|AAT75313.1| major ampullate spidroin 2 [*Nephila clavipes*]
GPGGYRPGQQGPSGPGSAAAAAAAAGPGGYGPGQQGPGGYGPGQQGPSGAGSAAAAAAAGPGQQGLGGY
GPGQQGPGGYGPGQQGPGGYGPGSASAAAAAAGPGQQGPGGYGPGQQGPSGPGSASAAAAAAAGPGGYGPG
QQGPGGYAPGQQGPSGPGSAAAAAAAARAGPGGYGPAQQGPSGPGIAASAASAGPGGYGPAQQGPAGYGP
GSAVAASAGAGSAGYGPGSQASAAASRLASPDSGARVASAVSNLVSSGPTSSAALSSVISNAVSQIGASN
PGLSGCDVLIQALLEIVSACVTILSSSSIGQVNYGAASQFAQVVGQSVLSAF SEQ ID No. 68:
>gi|50363151|gb|AAT75315.1| major ampullate spidroin 2 [*Nephila clavipes*]
GRGAGQQGPGGYGPGQQGPGGYGPGQQGPSGPGSAAAAAAAASGPGQQGPGGYGPGQQGPGGYGPGQQGSP
SGPGSAAAAAAAAGPGQQGPGGYGPGQQGPSGPGSASAAAAAAGPGGYGPGQQGPGGYAPGQQGPSGPG
SAAAAAAAARAGPGGYGPAQQGPSGPGIAASAASAGPGGYGPAQQGPAGYGPGSAVAASAGAGSAGYGPGS
QASAAASRLASPDSGARVASAVSNLVSSGPTSSAALSSVISNAVSQIGASNPGLSGCDVLIQALLEIVSA
CVTILSSSSIGQVNYGAASQFAQVVGQSVLSAF SEQ ID NQ. 69:
>gi|50363149|gb|AAT75314.1| major ampullate spidroin 2 [*Nephila clavipes*]
SAAAAAAAAAGPGGYGPGQQGPGGYGPGQQGPSGAGSAAAAAAGPGQQGLGGYGPGQQGPGGYGPGQQGPG
GYGPGSASAAAAAAGPGQQGPGGYGPGQQGPSGPGSASAAAAAAAGPGGYGPGQQGPGGYAPGQQGPSGPG
SAAAAAAAAAGPGGYGPAQQGPSGPGIAASAASAGPGGYGPAQQGPAGYGPGSAVAASAGAGSAGYGPGS
QASAAASRLASPDSGARVASAVSNLVSSGPTSSAALSSVISNAVSQIGASNPGLSGCDVLIQALLEIVSA
CVTILSSSSIGQVNYGAASQFAQVVGQSVLSAF SEQ ID No. 70:
>gi|13562012|gb|AAK30609.1|AF350280_1 major ampullate spidroin 2
[*Nephila senegalensis*]
QGPGGYGPSGPGSAAAASAAAGPGQQGPGAYGPSGPGSAAAAAGPGXYGPGQQGPSGPGAAAAAAGPGQQ
GPGGYGPGAAAAAAAAGPGQQGPVAYGPSGPGSAASAAGPGGYGPARYGPSGSAAAAAAAGAGSAGYGP
GPQASAAASRLASPDSGARVASAVSNLVSSGPTSSAALSSVIXNAVSQIGASNPGLSGCDVLIXALLEIV
SACVTILSSSSIGQVNYGAA SEQ ID No. 71:
>gi|13562008|gb|AAX30607.1|AF350278_1 major ampullate spidroin 2
[*Nephila madagascariensis*]
QGPSGPGSAAAAAAAGPGQQGPGGYGPGQQGPGGYGPGQQGPSGPGSAAAAAAAAAAGPGQQGPGGYGPG
PQGPGGYGPGQQGPSGYGPGQQGPSGPGSAASAAAAGSGQQGPGGYGPGQQGPGGYGPGQQGPSGPGSA
AAAAAAGPGQQGPGGYGPGQQGPGGYGPGQQGPSGPGSAAAAAAAAGPGQQGPGGYGPGQQGPGGYGPGQ
QGPSGPGSAAAAAAAGPGQQGPGGYGPGQQGPGGYGPSGPGSAAAAAAAAGPGQQGPGGYGPGQQ
QGPGQQGPSGPGSAAAAAAAGPGPQGPGGYGPGQQGPGGYGPSGPGSAAAAAAAAGPGQQGPGGYGPGQQ
RPSGYGPGQQGPSGPGSAAAAAAAGPGQQGPGAYGPSGPGSAAAAAGLGGYGPAQQGPSGAGSAAAAAAA
GPGGYGPVQQGPSGPGSAAGPGGYGPAQQGPARYGPGSAAAAAAAAGSAGYGPGPQASAAASRLASPDSG SEQ ID NOs: 3, 20-24, 27-34, 45-96:

ARVASAVSNLVSSGPTSSAALSSVISNAVSQIGASNPGLSGCDVLIQALLEIVSACVTILSSSSIGQVNY
GAA

SEQ ID No. 72:
>gi|13562062|gb|AAK30604.1|AF350275_1 major ampullate spidroin 2
[*Latrodectus geometricus*]
AGPGSYGPSGPGGSGAAAAAAAASGPGGQQGYGPGGPGASAAAAAAAGGSGPGGYGQGPSGYGPSGPGAQ
QGYGPGGQGGSGAAAAAAAAAGSGPGGYGPGAAGPGNYGPSGPGGSGAAASAAAASGPGGQQGYGPGGSG
AAAAAASGGAGPGRQQGYGPGGSGAAAAAAAAAXGGSGPGGYGQGPXGYGPGGQGGSGGAAAAAAAASSGP
XGYGPGAAGPGNYGPSGPGGSGAAAAAAAAASGPGGQQGYGPGGSGASAAAAAGGAGXGRQQAYGPGGSGA
AAAAAASGSGGYGPAQYGXSSVASSAASAASALSSPTTHARISSHASTLLSSGPTNSAAISNVISNAVSQV
SASNPGSSSCDVLVQALLELITALISIVDSSNIGQVNYGSSGQYAQMVG SEQ ID No. 73:
>gi|13561986|gb|AAK30596.1|AF350267_1 major ampullate spidroin 2
[*Argiope trifasciata*]
AGPGYGPGAGQQGPGSQGPGSGGQQGPGGQGPYGPSAAAAAAAAGPGYGPGAGQQGPGSGGQQGPGQGSGQ
QGPGGAGQGGPRGQGPYGPGAAAAAAAAGGYGPGAGQQGPGSQGPGSGGQQGPGSQGPYGPSAAAAAAAA
GPGYGPGAGQQGPGSQGPGSGGQQGPGGQGPYGPSDAAAAAAAGPGYGPGAGQQGPGSGGQQGGQGSGQQ
GPGGAGQGGPRGQGPYGPGAAAAAAAAGGYGPGAGQQGPGSQGPGSGGQQGPGSQGPYGPSAAAAAAAAG
PGYGPGAGQQGPGSQGPGSGGQQGPGSQGPYGPSAAAAAAAAGPGYGPGAGQQGPGSQAPVASAAASRLS
SPQASSRVSSAVSTLVSSGPTNPASLSNAISSVVSQVSSSNPGLSGCDVLVQALLEIVSALVHILGSSSI
GQINYAASSQYAQLVGQSLTQALG SEQ ID No. 74:
>gi|13561978|gb|AAX30592.1|AF350263_1 major ampullate spidroin 2
[*Argiope aurantia*]
PGGAGQQGPGGQGPYGPGAAAAAAAAGGYGPGAGQQGPXGAGQQGPGSQGPGGAGQQGPGGQGPYGPGAA
AAAAAVGGYGPGAGQQGPGSQGPGSGGQQGPGGQGPYGPSAAAAAAAAGGYGPGAGQQGPGSQGPGSGGQ
QGPGGLGPYGPSAAAAAAAAGGYGPGAGQQGPGSQGPGSGGQQRPGGLGPYGPSAAAAAAAAGGYGPGAG
QQGPGSQGPGSGGQQRPGGLGPYGPSAAAAAAAAGGYGPGAGQQGPGSQAPVASAAASRLSSPQASSRVS
SAVSTLVSSGPTNPAALSNAISSVVSQVSASNPGLSGCDVLVQALLELVSALVHILGSSSIGQINYAAS SEQ ID No. 75:
>gi|70913274|gb|AAZ15372.1| major ampullate spidroin 2 [*Argiope trifasciata*]
GQGSGQQRPGGAGQGGLGPYGPGAAAAAAAAAGGYGPGAGQQGPGSQGPGSGGQQGPGSRGPYGPSAAAA
AAAAGPGYGPGAGQRGPRSQGPGSGGQQGPGGQGPYGPSAAAAAAAAGPGYGPGAGQQGPGSQAPVASAA
ASRLSSPQASSRVSSAVSTLVSSGPTNPASLSNAISSVVSQVSASNPGLSGCDVLVQALLEIVSALVHIL
GSSSIGQINYAASSQYAQMVG SEQ ID No. 76:
>gi|70913273|gb|AAZ15371.1| major ampullate spidroin 2 [*Argiope trifasciata*]
MNWSIRLALLGPVVLSTQTVFSAGQGATPWENSQLAESFISRFLRFIGQSGAFSPNQLDDMSSIGDTLKT
AIEKMAQSRKSSKSKLQALNMAFASSMAEIAVAEQGGLSLEAKTNAIASALSAAFLETTGYVNQQFVNEI
KTLIFMIAQASSNEISGSAAAAGGSSGGGGGSGQGGYGQGAYASASAAAAYGSAPQGTGGPASQGPSQQG
PVSQPSYGPSATVAVTAVGGRPQGPSAPRQQGPSQQGPGQQGPGGRGPYGPSAAAAAAAAGGYGPGAGQQ
GQGAGQGGSGQQGPGGAGQGGPRGQGPYGPGAATAAAAAAGPGYGPGAGQQGPGSQGPGSGGQQGPGSQGP
YGPSAAAAAAAAGPGYGPGAGQQGPGSQGPRSGGQQGPGGQGPYGPSAAAAAAAAGPGYGPGAGQQGPGS
GGQQGPGSGQQGPGGAGQGGPRGQGPYGPGAAAAAAAAAGGYGPGAGQQGPGSQGPGSGGQQGPGSQGP
YGPSAAAAAAAGPGYGPGAGQQGPGSQGPGSGGQQGPGGQGPYGPSAAAAAAAAGPGYGPGAGQQGPGS
GGQQGGGSGQQGPGGAGQGGPRGQGPYGPGAAAAAAAAGGYGPGAGQQGPGSQGPGSGGQQGPGSQGP
YGPSAAAAAAAGPGYGPGAGQQGPGSGGQQ SEQ ID No. 77:
>gi|164709224|gb|ABY67417.1| major ampullate spidroin 2
[*Latrodectus geometricus*]
LRWSSKDNADRFINAFLQAASNSGAFSSDQVDDMSVIGNTLMTAMDNMGGRITPSKLQALDMAFASSVAE
IAVALGQNVGGATNAISNALRSAFYQTTGVVNNQFISEISNLNINMFAQVSANEVSYASGGSSAAASAAA
SAGPAAQQVYAPSAGAPAAATASSGPGAYGPSAPGGPSAAAAAAASGGAGPGRQQSYGPGGSGAAAAAAA
TGGSGPGGYGQGPASYAPSGPGGQQGYGPGGSGAASAAAAAASSGPGGYGPGASGPGSYGPSGPGGSGAA
AAAAASAPGGQQGYGPGGSGAAAAAAAGGAGPGSQQAYGPGGSGAAAAAAGPGSGQQGYGPGGSAAA
AAAAAGGSGPGGYGQGPAGYGPSGPGAQQGYGPGGPG SEQ ID No. 78:
>gi|13561996|gb|AAK30601.1|AF350272_1 major ampullate spidroin 2
[*Gasteracantha mammosa*]
GQQGPGSQGPYGPAAAAAAAAGGYRPVSGQQGPGQQGPGSGGQQGPGGQRPYGPAAAAAAAAGGYGP
GSGQQGPGQQGPGSGGQQGPGGQGPYGPAAAAAAAAGGYGPGSGQGGQQGPGSQGPGSGGQ0GPGGQG
PYGPSAAAAAAAVGGYGPGAGQQGPGQQGPGSGGQRPGGQGPYGPAAAAAAAAGGYPASGQQGPGQ
QGPGSGGQRGPGGQGPYGPAAAAASAGGYGPGSGGSPASGAASRLSSPQAGARVSSAVSALVASGPTSP
AAVSSAISNVASQISASNPGLSGCDVLVQALLEIVSALVSILSSASIGQINYGASGQYAAMI minor ampullate silk protein
SEQ ID No. 79:
>gi|2605800|gb|AAC14590.1| minor ampullate silk protein [*Nephila clavipes*]
GAGGYGRGAGAGAAAVAGADAGGYGRNYGAGTTAYAGARAGGAGGYYGQGGYSSGAGAAAASGAGADITS
GYGRGVGAGAGAETIGAGGYGGGAGSGARAASASGAGTGYGSSGGYNVGTGISTSSGAASSYSVSAGGYA SEQ ID NOs: 3, 20-24, 27-34, 45-96:

STGVGIGSTVTSTTSRLSSAEACSRISAAASTLVSGSLNTAALPSVISDLFAQVSASSPGVSGNEVLIQV
LLEIVSSLIHILSSSSVGQVDFSSVGSSAAAVGQSMQVVMG

SEQ ID No. 80:
>gi|2605802|gb|AAC14591.1| minor ampullate silk protein MiSp2 [Nephila clavipes]
SYGPSVMPTSAGSYGAGAGGFGAGASAGVGAGAGTVAGYGGQGGYGAGSAGGYGRGTGAGAAAGAGAG
ATAGAGAGAAAGAGAGAGAGNSGGYSAGVGVGAAAAAAGGGAGTVGGYGRGAGVGAGAAAGFAAGAGGAGGY
RRDGGYGAGAGAGAAAA SEQ ID No. 81:
>gi|2605798|gb|AAC14589.1| minor ampullate silk protein MiSp1 [Nephila clavipes]
RGAASGAGAAAGAGAGAGGAGYGGQIGYGAGAGAGAAAAAGAGAGGAAGYGRGAGAGSGAAAGAGSGAGA
GGYGGQAGYGAGAGAGSSAGNAFAQSLSSNLLSSGDFVQMISSTTSTDHAVSVATSVAQNVGSQLGLDAN
AMNNLLGAVSGYVSTLGNAISDASAYANALSSAIGNVLANSGSISESTASSAASSAASSVTTTLTSYGPA
VFYAPSASSGGYGAGAGAVAAAGAAGAGGYGRGAGGYGGQGGYGAGAGAGAAAAAGAGAGGAGGYGRGAG
AGAGAAAGAGAGGAGYGGQGGYGAGAGAGAAAAAGAGAGGAGGYGRGAGAGAGAAAGAGAGGYGGQGGG
YGAGAGAGAAAAAGAGSGGAGGYGRGAGAGAGAAAGAGAGSYGGQGGYGAGAGAGAAAAAGAGAGAG
GYGRGAGAGAGAAARAGAGAGGAGYGGQGGYGAGAGAGAAAAAGAGAGGAGGYGRGAGAGAGAAAG
AGAGAGGYGGQSGYGAGAGAAAAAGAGAGGAGGYGRGAGAGAGAAAGAGAGAAAGAGAGGYGGQGGYGAG
AGAGAAAAAGAGAGGAGGYGRGAGAGAGVAAGAGAGGYGGQGGYGTGAGAGGYGRGA
GAGAGAAAGAGAGTGGAGYGGQGGYGAGAGAGAAAAAGAGAGGAGYGRGAGAGAGAAAGAGAGAAAGAGA
GAGGYGGQGGYGAGAGAGAAAAAGAGAGGAAGYSRGGRAGAAGAGAGAAAGAGAGAGGYGGQGGYGAGAG
AGAAAAAGAGSGGAGGYGRGAGAGAAAAGAGAAAGAGAGAGGYGGQGGYGAGAGAAAAAGAGAGRGGYGRG
AGAGGYGGQGGYGAGAGAGAAAAAGAGAGGYGDKEIACWSRCRYTVASTTSRLSSAEASSRISSAASTLV
SGGYLNTAALPSVISDLFAQVGASSPGVSDSEVLIQVLLEIVSSLIHILSSSSVGQVDFSSVGSSAAAVG
QSMQVVMG flagelliform silk protein
SEQ ID No. 82:
>gi|2833649|gb|AAC38847.1| flagelliform silk-protein [Nephila clavipes]
GPGGVGPGGSGPGGYGPGGAGPGGYGPGGSGPGGYGPGGSGPGGYGPGGSGPGGYGPGGSGPGGYGPGGS
GPGGYGPGGYGPGGSGPGGYGPGGTGPGGSGPGGYGPGGSGPGGYGPGGSGPGGSGPGPGGSGPGGY
GPGGSGPGGAGPGGVGPGGFGPGGAGPGGAGPGGAGPGGAGPGGAGPGGAGPGGAGPGGAGPGGAGpGGA
GPGGAGGAGGAGGAGGSGGAGGSGGTTIIEDLDITIDGADGPITISEELTISGAGGSGPGGAGPGGVGPG
GSGPGGVGPGGSGPGGVGPGGSGPGGVGPGGAGGPYGPGGSGPGGAGGAGGPGGAYGPGGSYGPGGSGGP
GGAGGPYGPGGEGPGGAGGPYGPGGAGGPYGPGGAGGPYGPGGEGGPYGPGGSYGPGGAGGPYGPGGPYG
PGGEGPGGAGGPYGPGGVGPGGSGPGGYGPGGSGPGGYGPGGAGPGGYGPGGSGPGGYGPGGSGPGGYGP
GGSGPGGYGPGGSGPGGYGSGGAGPGGYGPGGSGPGGYGPGGSGPGGYGPGGTGPGGTGPGGSGPGGYGP
GGSGPGGSGPGGSGPGGYGPSGSGPGGYGPSGSGPGGYGPGGSGPGGYGPGGSGAGGTGPGGAGGAGGAG
GSGGAGGSGGAGGSGGAGGSGGVGGSGGTTIITEDLDITIDGADGPITISEELTISGAGGSGPGGAGPGGV
GPGGSGPGGVGPGVSGPGGVGPGGSGPGGVGSGGSGPGGVGPGGYGPGGSGGVGPGGYGPGGSGGFYG
PGGSEGPYGPSGTYGSGGGYGPGGAGGPYGPGSPGGAYGPGSPGGAYYPSSRVPDMVNGIMSAMQGSGFN
YQMFGNMLSQYSSGSGTCNPNNVNVLMDALLAALHCLSNHGSSSFAPSPTPAAMSAYSNSVGRMFAY SEQ ID No. 83:
>gi|2833647|gb|AAC38846.1| flagelliform silk protein [Nephila clavipes]
MGKGRHDTKAKAKAMQVALASSIAELVIAESSGGDVQRKTNVISNALRNALMSTTGSPNEEFVHEVQDLI
QMLSQEQINEVDTSGPGQYYRSSSSGGGGGGGQGGPVVTETLTVTVGGSGGGQPSGAGPSGTGGYAPTGYA
PSGSGAGGVRPSASGPSGSGPSGGSRPSSSGPSGTRPSPNGASGSSPGGIAPGGSNSGGAGVSGATGGYA
SSGSYGPGSTGGTYGPSGGSEPFGPGVAGGPYSPGGAGPGGAGGAYGPGGAVGPGGAVTGGAGPGGYGPGGAGPGG
YGPGGAGPGGYGPGGAGPdGYGPGGAGPGGYGPGGAGPGGYGPGGAGPGGYGPGGTGPGGYGPGGTGPGG
VGPGGAGPGGYGPGGAGPGGAGPGGAGPGGAGPGGAGPGGYGPGGSGPGGAGPSGAGLGGAGPGG
AGLGGAGPGGAGTSGAGPGGAGPGGAGQGDAGPGGAGRGGAGRGGVGRGGAGRGGAGRGGARGAGGAGGA
GGAGGSGGTTIVEDLDITIDGADGPITISEELTIGGAGAGGSGPGGAGPGNVGPGRSGPGGVGPGGSGPG
GVGPGSFGPGGVGPGGSGPGGVGSGGSGQGGVRPSGSGPGGVGTGGVGPGGAGGPYGPGGSGPGGSAGSAG
GTYGPGGFGGPGGFGGPGGAGGPYGPGGAGGPYGPGGAGGPYGPGGAGGPYGPGGAGGPYGPGGAGGSYG
LGGAGGSGGVGPGGSGPGGYGPGGAGPGGYGPGGSGPGGYGPGGSGGSGGYGPGGSGPGGSGPGGYGPGGT
GPGGSESGGYGPGGSGPGGSGPGGSGPGGSGPGGYGPGGSGPSSFVPGGSGPGGSGPGGAGPGGAGPGGV
GLGGAGRGGAGRGGAGSVGAGRGGAGRGGTG SEQ ID No. 84:
>gi|13561982|gb|AAK30594.1|AF350265_1 flagelliform silk protein
[Argiope trifasciata]
GAPGGGPGGAGPGGAGFGPGGGAGFGPGGGAGFGPGGAAGGPGGPGGPGGPGGAGGYGPGGAGGYGPGGV
GPGGAGGYGPGGAGGYGPGGSGPGGAGPGGAGGEGPVTVDVDVTVGPEGVGGPGGAGPGGAGFGPGGGA
GFGPGGAGPAGPGGPGGPGGPGGPGGVGPGGAGGYGPGGAGGVGPAGTGGFGPGGAGGFGPGGAGGFG
PGGAGGFGPGGAGGYGPGGVGPGGAGGFGPGGVGPGGSGPGGAGGEGPVTVDVDVSVGGAPGGGPGGAGP
GGAGFGPGGGAGFGPGGGAGFGPGGAAGGPGGPGGPGGAGGYGPGGAGGYGPGGVGPGGAGGYGPGG
AGGYGPGGSGPGGAGPGGAGGEGPVTVDVDVTVGPEGVGGPGGAGPGGAGFGPGGGAGFGPGGAPGAPG
GPGPGGPGGPGGPGGVGPGGAGGYGPGGAGGVGPAGTGGFGPGGAGGFGPGGAGGFGPAGA
GGYGPGGVGPGGAGGFGPGGVGPGGSGPGGAGGEGPVTVDVDVSVGGAPGGGPGGAGPGGAGFGPGGGAG
FGPGGGAGFGPGGAAGGPGGPGGPGGAGGYGPGGAGGYGPGGVGPGGAGGYGPGGAGGYGPGGSGPG
GAGPGGAGGEGPVTVDVDVTVGPEGVGGPGGAGPGGAGFGPGGGAGFGPGGAPGAPGGPGPGGPGG
GPGGVGPGGAGGYGPGGAGGFGPGGTGGFGPGGAGGFGPGGAGGFGPGGAGGFGPGGAGGYGPGGVGPGG
AGGFGPGGVGPGGSGPGGAGGEGPVTVDVDVSVGGAPGGGPGGAGPGGAGFGPGGGAGFGPGGGAGFGPG
GAAGGPSGPGGPGGPGGAGGYGPGGAGGYGPGGVGPGGAGGYGPGGAGGYGPGGSGPGGAGPGGAGGEGP SEQ ID NOs: 3, 20-24, 27-34, 45-96:

VTVDVDVTVGPEGVGGGPGGAGPGGAGFGPGGGAGFGPGGAPGAPGGPGGPGGPGGPGGVGPGGAGG
YGPGGAGGVGPAGTGGFGPGGA

SEQ ID No. 85:
>gi|7106229|gb|AAF36092.1| flagelliform silk protein [*Nephila madagascariensis*]
SGGSGGTTVIEDLDITIDGADGPITISEELTISGAGAGGSGPGGAGPGGVGPGGSGPGGVGPGGSGPGGV
GPGGAGGPYGPGGSGPGGAGGAGGPGGAYGPGGSGGPGGAGGPYGPGGEGPGGAGGPYGPGGEGPGGAGG
PYGPGGAGGPYGPGGAGGPYGPGGAGGPYGPGGVGPGGTGPGGYGPGGAGPGGYGPGGSGP
GGYGPGGSGPGGYGPGGSGPGGFGPGGSGPGGSGPGGSGPGGYGPGGSGPGGYGPGGSGPGGYGPGGSGP
GGYGPGGSGPGGSGPGGYGPGGSGPGGYGPGGSGPGGAGPGGAGPGGVGPGGAGPGGAGPGGVGPGGAGP
GGAGPGGAGPGGAGRGGAGPGGAGGAGGAGGSGGAGGSGGTTVIEDLDITIEGADGPITISEELTIGGAG
GSGPGGAGGSGPGGAGPGGVGPGGSGPGGLGSGSGPGGVGPGGSGPGGVGPGGYGPGGSGGLYGPGSYG
PGGSGVPYGSSGTYGSGGGYGPGGAGGAYGPGSPGGAYGPGSGGSYYPSSRVPDMVNGIMSAMQGSGFNY
QMFGNMLSQYSSGSGSCNPNNVNVLMDALLAALHCLSNHGSSSFAPSPTPAAMSAYSNSVGRMFAY SEQ ID No. 86:
>gi|13561980|gb|AAK30593.1|AF350264_1 flagelliform silk protein
[*Argiope trifasciata*]
AGGPGAGGAGAGGVGPGGFGGPGGFGGAGGPGGPGGPGGAGGGAGGAGGLYGPGGAGGLYGPGGLYGPGG
AGVPGAPGASGRAGGIGGAAGGAGAGGVGPGGVSGGAGGAGGSGVTVVESVSVGGAGGPGAGGVGPGGVG
PGGVGPGGIYGPGGAGGLYGPGGAGGAFGPGGGAGAPGGPGGPGGPGGLGGGVGGAGTGGGVGPGAGG
VGPSGGAGGTGPVSVSSTVSVGGAGGPGAGGPGAGGAGAGGVGPGGFGGPGGFGGAGGPGGPGGPGAGG
GAGGAGGLYGPGGAGGLYGPGGLYGPGGAGVPGAPGASGRAGGIGGAAGAGGVGPGGVSGGAGGSGVSVT
ESVTVGGAGGAGAGGIGGPSGLGGAGATGGFGGRGGPGGPGGPGRFGGAAGGAGAGGVGPGGVSGGA
GGAGGSGVTVVESVSVGGAGGPGAGGVGPGGVGPGGVGPGGIYGPGGAGGLYGPGGAGGAFGSGGGAGAPG
GPGGPGGPGGPGGLGGGVGGAGTGGGVGPGVGGVGPSGGAGGTGPVSVSSTITVGGGQSSGGVLPSTSYA
PTTSGYERLPNLINGIKSSMQGGGFNYQNFGNILSQYATGSGTCNYYDINLLMDALLAALHTLNYQGASY
VPSYPSPSEMLSYTENVRRYF SEQ ID No. 87:
>gi|7106228|gb|AAF36091.1| flagelliform silk protein [*Nephila madagascariensis*]
MGKGRHDTKAKAKAMQVALASSIAELVIAESSGGDVQRKTNVISNALRNALMSTTGGSPNEEFVHEVQDLI
QMLSQEQINEVDTSGPGQYYRSSSSGGGGGGGGPVITETLTVVGGSGAGOPSGAGPSGTGYAPTGYA
PSGSGPGGVRPSASGPSGSGPSGSRPSSSGSSGTRPSANAAGGSSPGGIAPGGSSPGGAGVSGATGGPAS
SGSYGSGTTGGAYGPGGGSEPFGPGAAGGQYGPGGAGPGGAGAYGPGGVGPGGAGPGGYGPGGAGPGGYG
PGGAGPGGYGPGGAGPGGYGPGGAGPGGYGPGGAGPGGYGPGGAGPGGYGPGGSGTGGAGPGGYTPGGAG
PGGYGPGGYGPGGSGPGGAGSGGVGPGGYGPGGAGPGGAGPGGAGPGGAGPSGAGPGGAGTGGAGTGGAG
PGGAGPGGAGPGGAGPGGAGRGGAGRGGAGARGGAGRGGAGRGGAGRGGAGGAGGAGGAGGAGGAGGAGGS
GSTTIIEDLDITIDGADGPITISEELTIGGAGAGGSGPGGAGPGGVGPGRSGPGGVGPGGSGPGSVGPGG
SGQGGLGIGRSGPGGVGPGGSGPGSIGPGGSGQGGLGPGGSGQGGLGPGGSGPGGVGSGGVGGPYGPGGS
GPGGVGGAGGPYGPGGSGGPGGAGGPYGPGGYGPGGAGGPYGPGGAGGPYGPGGPYGPGGAGGPGGGGP
GGAGGPYGPGGPGGAGPGGYGPGGYGPGGAGPGGAGPGGYGPGGAGPGGYGPGGAGPGGSGPGGIGPGGS
GPGGYGPGGIGPGGTGPGGAGPGGAGPGGAGPSGAGPGGAGPGGYGPGGRGSVGRGGAGPGGAGAGGA
GGAGGSGGAGGSGGAGGSGGTTIIEDLDITVDGANGPITISEELTIGGAGAGGVGPGGSGPGGVGPGGSG
PGGVGPGGSGPGGVGSGGSGPGGVGPGGSGPGGVGSGGFGPGGIGPGGSGPGGVGPGGVGGPYGPGGSGP
GGAGGAGGSYGPGGPYGPGGSGPGGAGGPYGPGGAGGPYGPGGPYGPGGAGGPGGEGPGGAGGPYGPGG
PGGAGPGGYGPGGAGPGGYGPGGAGPGGYGPGGAGSGGYGPGGAGPGGYGPGGPGPGGYGPGGAGPGGYG
PGGTGPGGSAPGGAGPGGAGPGGYGPGGSGPGGYGPGGGPGGYGPGGAGPGGAGPGGAGPGGAGPGGAGP
GGAGPGGAGPGGAGPGGVGTGGLGRGGAGRGGAGRGGAGRGGAGRGGAGRGTTGGVGGAGGAGGA
GGVGGAGGSGGTTVIEDLDITIDGADGPITISEELTISGAGAGGSGPGGAGPGGVGPGGSGPGGVGPGGS
GPGGVGPGGAGGPYRPGGSGPGGAGGAGGPGGAYGPGGSGGPGGAGGPYGPGGEGPGGSGGPYGPGGEGP
GGAGGPYGPGGAGGPYGPGGAGGPYGPGGAGGPYGPGGAGGPYGPGGAGGPYGPGGEGPGG
AGGPYGPGGVGPGGTGPGGYGPGGAGPGGYGPGGSGPGGYGPGGSGPGGFGPGGSGPGGYGPGGSGPGGY
GPGGSGPGGAGPGGYGPGGTGPGGSGPGGYGPGGSGPGGYGPGGSGPGGYGPGGSGPGGAGPGGA
GPGGAGPGGVGPGGAGPGGSGPGGAGPGGAGRGGAGRGGAGXGGAGPGGAGGAGGAGGSGGAGGSGGTTV
IEDLDITIDGADGPITISEELTINGAGAGGSGPGGAGPGGVGPGGSGPGGVGPGGSGPGGVGPGGAGGPY
GPGGSGPGGAGGAGGPGGAYGPGGSGGPGGAGGPYGPGGEGPGGAGGPYGPGGEGPGGAGGPYGPGGAGG
PYGPGGAGGPYGPGGAGGPYGPGGAGGPYGPGGAGGPYGPGGAGGPYGPGGEGPGGAGGPYGPG SEQ ID No. 88:
>gi|7106224|gb|AAF36090.1| flagelliform silk protein [*Nephila clavipes*]
AGPSGTGGYAPTGYAPSGSGAGGVRPSASGPSGSGPSGGSRPSSSGPSGTRPSPNGASGSSPGGIAPGGS
NSGGAGVSGATGGPASSGSYGPGSTGGTYGPSGGSEPFGPGVAGGPYSPGGAGPGGAGGAYGPGGVGTGG
AGPGGYGPGGAGPGGYGPGGAGPGGYGPGGAGPGGYGPGGAGPGGYGPGGAGPGGYGPGGAGPGGYGPGG
TGPGGYGPGGTGPGGVGPGGAGPGGYGPGGAGPGGAGPGGAGPGGAGPGGAGPGGYGPGGSGPGGAGPSG
AGLGGAGPGGAGLGGAGPGGAGTSGAGPGGAGPGGAGQGGAGPGGAGRGGAGRGGVGRGGAGRGGAGRGG
ARGAGGAGGAGGAGGSGGTTIVEDLDITIDGADGPITISEELTIGGAGAGGSGPGGAGPGNVGPGRSGPG
GVGPGGSGPGGVGPGSFGPGGVGSGGSGPGGVRPSGSGPGGVGTGGVGPGGAGGPYGPGGSGPGGAGSAG
GTYGPGGFGGPGGFGGPGGAGGPYGPGGAGGPYGPGGAGGPYGPGGAGGPYGPGGAGGPYGPGGAGGSYG
LGGAGGSGGVGPGGSGPGGYGPGGAGPGGYGPGGSGPGGYGPGGSGSGGYGPGGSGPGGSGPGGYGPGGT
GPGGSESGGYGPGGSGPGGSGPGGSGPGGSGPGGYGPGGSGPSSFVPGGSGPGGSGPGGAGPGGAGPGGA
GPGGAGPGGVLGGAGRGGAGRGGAGSVGAGRGGAGRGGAGRGGAGRGGAGRGGAGGAGGAGGAGGPGGA
GGSGGTTVIEDLDITIDGADGPITISEELTISGAGGSGPGGAGTGGVGPGGSGPGGVGPGGFGPGGVGPG
GSGPGGVGPGGAGRPYGPGGSGPGGAGGAGGTGGAYGPGGAYGPGGSGGPGGAGGPGGEGPGGAGGPYGP
GGAGGPYGPGGAGGPYGPGGEGGPYGPGVSYGPGGAGGPYGPGGPYGPGGEGPGGAGGPYGPGGVGPGGS SEQ ID NOs: 3, 20-24, 27-34, 45-96:

GPGGYGPGGAGPGGYGPGGSGPGGYGPGGSGPGGYGPGGSGPGGYGPGGSGPGGYGPGGYGPGGSGPGGS
GPGGSGPGGYGPGGTGPGGSGPGGYGPGGSGPGGSGPGGYGPGGSGPGGFGPGGSGPGGYGPGGSGPGGA
GPGGVGPGGFGPGGAGPGGAAPGGAGPGGAGPGGAGPGGAGPGGAGGAGGAGGSGGAGGS
GGTTIIEDLDIT/DGADGPITISEELPISGAGGSGPGGAGPGGVGPGGSGPGGVGPGGSGPGGVGPGGSG
PGGVGPGGAGGPYGPGGSGPGGAGGAGGPGGAYGPGGSYGPGGSGGPGGAGGPYGPGGEGPGGAGGPYGP
GGAGGPYGPGGAGGPYGPGGEGGPYGPGGSYGPGGAGGPYGPGGPYGPGGEGPGGAGGPYGPGGVGPGGG
GPGGYGPGGAGPGGYGPGGSGPGGYGPGGSGPGGYGPGGSGPGGYGPGGSGPGGYGPGGSGPGGSGPGGY
GPGGSGPGGSGPGGYGPGGSGPGGYGPGGSGPGGYGPGGSGPGGSGPGGYGPGGSGPGGFGPGGF
GPGGSGPGGYGPGGSGPGGAGPGGVGPGGFGPGGAGPGGAGPGGAGPGGAGPGGAGPGGAGPGGAGPGGA
GPGGAGGAGGAGGAGGSGGAGGSGGTTIIEDLDITIDGADGPITISEELTISGAGGSGPGGAGPGGVGPG
GSGPGGVGPGGSGPGGVGPGGSGPGGVGPGGAGGPYGPGGSGPGGAGGAGGPGGAYGPGGSYGPGGAGGP
GGAGGPYGPGGEGPGGAGGPYGPGGAGGPYGPGGAGGPYGPGGEGGPYGPGGSYGPGGAGGPYGPGGPYG
PGGEGPGGAGGPYGPGGVGPGGGPGGYGPGGAGPGGYGPGGSGPGGYGPGGSGPGGYGPGGSGPGGYGP
GGSGPGGYGPGGSGPGGSGPGGYGPGGSGPGGYGPGGSGPGGSGPGGYGPGGSGPGGFGPGGFGPGGSGP
GGYGPGGSGPGGAGPGGVGPGGFGPGGAGPGGAGPGGAGPGGAGPGGAGPGGAGPGGAGPGGAGPGGAGG
AGGAGGAGGSGGAGGSGGTTIIEDLDITIDGADGPITISEELTISGAGGSGPGGAGPGGVGPGGSGPGGV
GPGGSGPGGVGPGGSGAGGVGPGGAGGPYGPGGSGPGGAGGAGGPGGAYGPGGSYGPGGSGGPGGAGGPY
GPGGEGPGGAGGPYGPGGAGGPYGPGGAGGPYGPGGEGGPYGPGGSYGPGGAGGPYGPGGPYGPGGEGPG
GAGGPYGPG

SEQ ID No. 89:
>gi|7106223|gb|AAF36089.1| flagelliform silk protein [Nephila clavipes]
VGPGGSGPGGYGPGGSGPGGYGPGGAGPGGYGPGGSGPGGYGPGGSGPGGYGPGGSGPGGYGPGGSGPGG
YGSGGAGPGGYGPGGSGPGGYGPGGSGPGGYGPGGTGPGGTGPGGSGPGGYGPGGSGPGGSGPGGSGPGG
YGPSGSGPGGYGPSGSGPGGYGPGGSGPGGYGPGGSGAGGTGPGGAGGAGGAGGSGGAGGSGGAGGSGGA
GGSGGVGGSGGTTITEDLDITIDGADGPITISEELTISGAGGSGPGGAGPGGVGPGGSGPGGVGPGVSGP
GGVGPGGSGPGGVGSGGSGPGGVGPGGYGPGGSGSGGVGPGGYGPGGSGGGFYGPGGSEGPYGPSGPYGSG
GGYGPGGAGGPYGPGSPGGAYGPGSPGGAYYPSSRVPDMVNGIMSAMQGSGFNYQMFGNMLSQYSSGSGT
CNPNNVNVLMDALLAALHCLSNHGSSSFAPSPTPAAMSAYSN aciniform spidroin
SEQ ID No. 90:
>gi|49871101|gb|AAR83925.1| aciniform spidroin 1 [Argiope trifasciata]
SSALFNAGVLNASNIDTLGSRVLSALLNGVSSAAQGLGINVDSGSVQSDISSSSSFLSTSSSSASYSQAS
ASSTSGAGYTGPSGPSTGPSGYPGPLGGGAPFGQSGFGGSDGPQGGFGATGGASAGLISRVANALANTST
LRTVLRTGVSQQIASSVVQRAAQSLASTLGVDGNNLARFAVQAVSRLPAGSDTSAYAQAFSSALFNAGVL
NASNIDTLGSRVLSALLNGVSSAAQGLGINVDSGSVQSDISSSSSFLSTSSSSASYSQASASSTSGAGYT
GPSGPSTGPSGYPGLLGGGAPFGQSGFGGSDGPQGGFGATGGASAGLISRVANALANTSTLRTVLRTGVS
QQIASSVVQRAAQSLASTLGVDGNNLARFAVQAVSRLPAGSDTSAYAQAFSSALFNAGVLNASNIDTLGS
RVLSALLNGVSSAAQGLGINVDSGSVQSDISSSSSFLSTSSSSASYSQASASSTSGAGYTGPSGPSTGPS
GYPGPLGGGAPFGQSGFGGSDGPQGGFGATGGASAGLISRVANALANTSTLRTVLRTGVSQQIASSVVQR
AAQSLASTLGVDGNNLARFAVQAVSRLPAGSDTSAYAQAFSSALFNAGVLNASNIDTLGSRVLSALLNGV
SSAAQGLGINVDSGSVQSDISSSSSFLSTSSSSASYSQASASSTSGAGYTGPSGPSTGPSGYPGPLGGGA
PFGQSGFGGSAGPQGGFGATGGASAGLISRVANALANTSTLRTVLRTGVSQQIASSVVQRAAQSLASTLG
VDGNNLARFAVQAVSRLPAGSDTSAYAQAFSSALFNAGVLNASNIDTLGSRVLSALLNGVSSAAQGLGIN
VDSGSVQSDISSSSSFLSTSSSSASYSQASASSTSGAGYTGPSGPSTGPSGYPGPLGGGAPFGQSGFGGS
AGPQGGFGATGGASAGLISRVANALANTSTLRTVLRTGVSQQIASSVVQRAAQSLASTLGVDGNNLARFA
VQAVSRLPAGSDTSAYAQAFSSALFNAGVLNASNIDTLGSRVLSALLNGVSSAAQGLGINVDSGSVQSDI
SSSSSFLSTSSSSASYSQASASSTSGAGYTGYTGPSGPSTGPSGYPGPLGGGAPFGQSGFGGSAGPQGGFGAT
GGASAGLISRVANALANTSTLRTVLRTGVSQQIASSVVQRAAQSLASTLGVDGNNLARFAVQAVSRLPAG
SDTSAYAQAFSSALFNAGVLNASNIDTLGSRVLSALLNGVSSAAQGLGINVDSGSVQSDISSSSSFLSTS
SSSASYSQASASSTSGAGYTGPSGPSTGPSGYPGPLGGGAPFGQSGFGGSAGPQGGFGATGGASAGLISR
VANALANTSTLRTVLRTGVSQQIASSVVQRAAQSLASTLGVDGNNLARFAVQAVSRLPAGSDTSAYAQAF
SSALFNAGVLNASNIDTLGSRVLSALLNGVSSAAQGLGINVDSGSVQSDISSSSSFLSTSSSSASYSQAS
ASSTSGAGYTGPSGPSTGPSGYPGPLGGGAPFGQSGFGGSDGPQGGFGATGGASAGLISRVANALANTST
LRTVLRTGVSQQIASSVVQRAAQSLASTLGVDGNNLARFAVQAVSRLPAGSDTSAYAQAFSSALFNAGVL
NASNIDTLGSRVLSALLNGVSSAAQGLGINVDSGSVQSDISSSSSFLSTSSSSASYSQASASSTSGAGYT
GPSGPSTGPSGYPGPLGGGAPFGQSGFGGSAGPQGGFGATGGASAGLISRVANALANTSTLRTVLRTGVS
QQIASSVVQRAAQSLASTLGVDGNNLARFAVQAVSRLPAGSDTSAYAQAFSSALFNAGVLNASNIDTLGS
RVLSALLNGVSSAAQGLGINVDSGSVQSDISSSSSFLSTSSSSASYSQASASSTSGAGYTGPSGPSTGPS
GYPGPLGGGAPFGQSGFGGSAGPQGGFGATGGASAGLISRVANALANTSTLRTVLRTGVSQQIASSVVQR
AAQSLASTLGVDGNNLARFAVQAVSRLPAGSDTSAYAQAFSSALFNAGVLNASNIDTLGSRVLSALLNGV
SSAAQGLGINVDSGSVQSDISSSSSFLSTSSSSASYSQASASSTSGAGYTGPSGPSTGPSGYPGPLGGGA
PFGQSGFGGSAGPQGGFGATGGASAGLISRVANALANTSTLRTVLRTGVSQQIASSVVQRAAQSLASTLG
VDGNNLARFAVQAVSRLPAGSDTSAYAQAFSSALFNAGVLNASNIDTLGSRVLSALLNGVSSAAQGLGIN
VDSGSVQSDISSSSSFLSTSSSSASYSQASASSTSGAGYTGPSGPSTGPSGYPGPLGGGAPFGQSGFGGS
AGPQGGFGATGGASAGLISRVANALANTSTLRTVLRTGVSQQIASSVVQRAAQSLASTLGVDGNNLARFA
VQAVSRLPAGSDTSAYAQAFSSALFNAGVLNASNIDTLGSRVLSALLNGVSSAAQGLGINVDSGSVQSDI
SSSSFLSTSSSSASYSQALASSTSGAGYTGPSGPSTGPSGYPGPLGGGAPFGQSGFGGSAGPQGGFGAT
GGASAGLISRVANALANTSTLRTVLRTGVSQQIASSVVQRAAQSLASTLGVDGNNLARFAVQAVSRLPAG
SDTSAYAQAFSSALFNAGVLNASNIDTLGSRVLSALLNGVSSAAQGLGINVDSGSVQSDISSSSSFLSTS
SSSASYSQASASSTSGAGYTGPSGPSTGPSGYPGPLGGASFGSGQSSFGQTSAFSASGAGQSAGVSVIS
SLNSPVGLRSASAASRLSQLTSSITNAVGANGVDANSLARSLQSSFSALRSSGMSSSDAKIEVLLETIVG
LLQLLSNTQVRGVNPATASSVANSAARSFELVLA SEQ ID NOs: 3, 20-24, 27-34, 45-96:

tubuliform spidroin
SEQ ID No. 91:
>gi|63054371|gb|AAY28953.1| tubuliform spidroin 1 [Argiope aurantia]
GNAAGLGNALSQAVSSVGVGASSSTYANAVSNAVGQFLAGQGILNXANAGSLASSFASALSASAASVASS
AAAQXASQSQAAASAFSRAASQSASQSAARSGAQSSSXTTTTSTSGSQAASQSASSAASQA SEQ ID No. 92:
>gi|61387231|gb|AAX45291.1| tubuliform spidroin [Argiope aurantia]
TTTSTAGSQAASQFASSAASQASASSFARASSASLAASSSFSSAFSSANSLSALGNVGYQLGFNVANNLG
IGNAAGLGNALSQAVSSVGVGASSSSYANAVSNAVGQLLAGQGILNAANAGSLASSFASALSASAASVAS
SAAAQAASQSQAAASAFSRAASQSASQSAARSGAQSISTTTTTSTAGSQAASQSASSAASQASASSFARA
SSASLAASSSFSSAFSSANSLSALGNVGYQLGFNVANNLGIGNAAGLGNALSQAVSSVGVGASSSTYANA
VSNAVGQFLAGQGILNAANAGSLASSFASALSASAASVASSAAAQAASQSQAAASAFSRAASQSASQSAA
RSGAQSSSTTTTTSTAGSQAASQFASSAASQASASSFARASSASLAASSSFSSAFSSANSLSALGNVGYQ
LGFNVANNLGISNAAGLGNALSQAVSSVGVGASSSSYANAVSNAVGQFLAGQGILNAANAGSLASSFASA
LSASAASVASSAAAQAASQSQAAASAFSRAASQSASQSAARSGAQSSSTTTTTST SEQ ID No. 93:
>gi|61387234|gb|AAX45292.1| tubuliform spidroin [Argiope aurantia]
STYANAVSNAVGQFLAGQGILNAANAGSLASSFASALSASAASVASSAAAQAASQSQAAASAFSRAASQS
ASQSAARSGAQSFSTTTTTSTAGSQAASQSASSAASQASASSFARASSASLAASSAFSSAFSSANSLSAL
GNVAYQLGFNVANTLGIGNAAGLGNALSQAVSSVGVGASSSTYANAVSNAVGQFLAGQGVLNAGNAGSLA
SSFANALSNSALSVGSRVSSPSYGALSPIAAGPNFISTGLNVGGPFTTLSQSLPTSLQTALAPIVSSSGL
GSSAATARVRSLANSIASAISSSGGSLSVPAFLNLLSSVGAQVSSSSSLNSSEVTNEVLLEAIAALLQVI
NGGSITSVDLRNVPNAQQDLVNALSG SEQ ID No. 94:
>gi|61387237|gb|AAX45293.1| tubuliform spidroin [Araneus gemmoides]
ASQSQAASQSQAAASAFRQAASQSASQSASRAGSQSSTKTTSTSTSGSQADSRSASSSASQASASAFAQQ
SSASLSSSSSFSSAFSSATSISAVGNVGYQLGLKVANSLGLGNAQALASSLSQAVSAVGVGASSNAYANA
VSNAVGQVLAGQGILNAANAGSLASSFASALSSSAASVASQSASQSQAASQSQAAASAFRQAASQSASQS
ASRAGSQSSTKTTSTSTSGSQADSRSASSSASQASASAFAQQSSASLSSSSSFSSAFSSATSISAVGNVG
YQLGLKVANSLGLGNAQALASSLSQAVSAVGVGASSNAYANAVSNAVGQVLAGQGILNAANAGSLASSFA
SALSSSAASVASQSASQSQAASQSQAAASAFRQAASQSASQSDSRAGSQSSTKTTSTSTSGSQADSRSAS
SSASQASASAFAQQSSASLSSSSSFSSAFSSATSISAVGNVGYQLGLKVANSLGLGNAQALASSLSQAVS
AVGVGASSNAYANAVSNAVGQVLAGQGILNAANAGSLASSFASALSSSAASVASQSASQSQAASQSQAAA
SAFRQAASQSASQSASRAGSQSSTKTTSTSTSGSQADSRSASSSASQASASAFAQQSSASLSSSSSFSSA
FSSATSISAVGNVGYQLGLKVANS SEQ ID No. 95:
gi|61387241|gb|AAX45294.1| tubuliform spidroin [Araneus gemmoides]
SASQSQAAASAFRQAASQSASQSASRAGSQSSSKTTSTSTSGSQADSRSASSSASQASASAIAQQSSASL
SSSSSFSSAFSSATSLSAVGNVGYQLGLKVANSLGLGNAQALASQGILNAANAGSLASSFASALSASAGS
VGNRSSAGPSAVGLGGVSAVPGFISATPVVGGPVTVNGQVLPAALQTALAPVVTSSGLASSAASARVSSL
AQSIASAISSSGGTLSVPIFLNLLSSAGAQATASSSLSSSQVTSQVLLEGIAALLQVINGAQIRSVNLAN
VPNVQQALVSALSG SEQ ID No. 96:
>gi|61387244|gb|AAX45295.1| tubuliform spidroin +Nephila clavipes+
ASAASSLAYSIGISAARSLGIADAAGLAGALARAAGALGQGDTAASYGNALSTAAGQFFATAGLLNAGNA
SALASSFARAFSASAESQSFAQSQAFQQASAFQQAASRSASQSAAEADSTSSSTTTTTSAARSQAASQSA
SSSYSSAFAQAASSSFAISSALSRAFSSVSSASAASSLAYSIGLSAARSLGIADATGLAGALARAVGALG
QGATAASYGNALSTAAAQFFATAGLLNAGNASALASSFARAFSASAESQSFAQSQAFQQASAFQQAASRS
ASQSAAEAGSTSSSTTTTTSAARSQAASQSASSSYSSAFAQAASSSLATSSALSRAFSSVSSASAASSLA
YSIGLSAARSLGIADAAGLAGVLARAAGALGQGATAASYGNALSTAAGQFFAAQGLLNAGNVSSLASALA
NALSYSAANSAASGNYIGVSQNFGSIAPVAGTAGISVGVPGLLPTSAGTVLAPANAQIIAPGLQTTLAPV
FSSSGLSSASANARVSSLAQSFASALSASRGTLSVSTFLTLLSPISSQIRANTSLDGTQATVQVLLEALA
ALLQVINAAQITEVNVSNVSSANAALVSALAG

EXAMPLES

Example 1

Engineering of Recombinant Spider Silk Protein eADF4(C16)

The amino acid sequence of eADF4 (C16) was adapted from the natural sequence of ADF4 from *Araneus diadematus*. eADF4(C16) protein was engineered by the combination and multimerization of single motifs. The resulting eADF4 (C16) comprises 16 repeats of Modul C with the amino acid sequence GSSAAAAAAA ASGPGGYGPE NQGPSG-PGGY GPGGP (SEQ ID NO: 21). The resulting protein has a molecular mass of 48 kDa. The protein was purified as described previously (Hümmerich et al., 2004) having a purity higher than 98%. Due to its amino acid composition, eADF4(C16) has a theoretical isoelectric point of 3.48 indicating a net negative charge at a physiological pH of 7.4.

Example 2

Preparation of Small Molecular Model Drugs

All drugs were dissolved in water at a concentration of 0.21 µmol/ml. Drug substances and their featured properties are depicted in Table 1. The main selection criteria were solubility in aqueous media (expressed by the octanol/water partition coefficient (log P)), the acidic dissociation constant (pKa for protonated bases (BH+) or for acids (HA)) and the resulting net-charge in aqueous media (predominant or permanent charge).

TABLE 1

List of small molecular weight model drugs used for eADF4(C16) sphere loading. Values for molecular weight, dissociations constants (pKa) and partition coefficients (logP) are taken from literature. The partition coefficient (logP) accounts for the individual unprotonated forms. The absorption wavelength λAbs was determined experimentally for each substance. All substances were purchased from Sigma-Aldrich (Deisenhofen, Germany).

| Model drug | Molecular weight [Da] | $\lambda_{Abs}$ (nm) | Dissociation constant of $BH^+$(pKa) | Dissociation constant of HA (pKa) | log P | Predominant charge at pH7 | Permanently charged |
|---|---|---|---|---|---|---|---|
| Phenol red | 354 | 510 | — | 1.7; 7.7 | 3.00 | negative | yes |
| Tetracaine*HCl | 301 | 310 | 8.20 | — | 4.00 | positive | no |
| Procaine*HCl | 272 | 290 | 8.05 | — | 2.40 | positive | no |
| Papaverine*HCl | 376 | 248 | 8.07 | — | 3.50 | positive | no |
| Ephedrine*HCl | 202 | 256 | 9.60 | — | 1.30 | positive | no |
| Propranolol*HCl | 295 | 290 | 9.10 | — | 3.18 | positive | no |
| Ethacridine lactate | 343 | 365 | 11.00 | — | 2.50 | positive | no |
| Methyl violet | 407 | 590 | — | — | 3.20 | positive | yes |

Example 3

Preparation of eADF4(C16) Particles

Lyophilized protein eADF4(C16) was dissolved in 6 M guanidiniumthiocyanate. Dialysis was performed against 10 mM tris(hydroxymethyl)aminomethane-(Tris)/HCl, pH 8, at 4° C. using membranes with a molecular weight cut-off at 6000-8000 Da (Spectrum Laboratories, Rancho Dominguez, USA). The concentration of eADF4(C16) solution was determined by UV-Vis-spectrometry at 20° C. using a Cary100 spectrophotometer (Varian Medical Systems, Palo Alto, USA) and the molar extinction coefficient of eADF4(C16) at 276 nm ($\epsilon$=46400 M-1 cm-1). eADF4 (C16) particles were prepared using a phase separation procedure as described previously in Slotta et al. (2008). An aqueous eADF4(C16) (c=1.0 mg/ml) solution was mixed with potassium phosphate (2 M, pH 8) in volumetric ratios of 1:10 using a pipette. The resulting particles were centrifuged for 10 min at 10.000×g and washed three times with purified water. The obtained particles were redispersed in water, and particle concentrations (particles in mg/ml) were determined gravimetrically. A stock dispersion of known protein particle concentration was used for all experiments.

Example 4

Colloidal Stability of eADF4(C16) Particles

The colloidal stability of eADF4(C16) particles in suspension was studied by adding 1.0 mg of particles to 1.0 ml of $(NH_4)_2SO_4$ solutions of varying concentration (0-2.0 M) and measuring the intensity of scattered light at a wavelength of 400 nm after 15 min. Based on the Mie theory, the intensity of scattered light in forward direction increases with increasing particle sizes. Therefore, the onset of electrolyte-induced flocculation in dilute dispersions can be detected by an increase in intensity of scattered light in forward direction.

Example 5

Characterization of eADF4(C16) Particles

The following methods of the state of art can be used to characterize the spider silk particles according to the invention:

a) Scanning Electron Microscopy

The eADF4(C16) particles were immobilized on Thermanox plastic cover slips (Nagle Nunc, USA), dried at room temperature, gold sputtered under vacuum, and analyzed with a JSM 5900 LV scanning electron microscope (JEOL Ltd., Japan, at 20 kV).

b) Laser Diffraction Spectrometry

Particle sizes and size distributions were determined in triplicate using laser diffraction spectrometry (Horiba, Partica LA-950, Japan). Refractive indices of 1.33 for water and 1.60 for protein were taken for computation of particle sizes. In order to eliminate concentration effects, all samples were measured at equal concentrations resulting in a transmittance of 82%. In addition, a dry specimen of each preparation was analyzed by scanning electron microscopy (SEM) to confirm spherical shape and sphere sizes.

c) Fourier Transform Infrared Spectroscopy (FTIR)

Fourier transform infrared (FTIR) spectra were collected using a Bruker Equinox 55 FTIR spectrometer. The samples were prepared by putting a droplet of eADF4(C16) particle suspension on CaF2 disks and subsequent air-drying. Absorbance spectra were recorded between 400 and 4000 cm-1 with unpolarized light at a resolution of 4 $cm^{-1}$. The measurements were carried out at 25° C. and 30% relative humidity and each spectrum was accumulated 32 times. The secondary structure of eADF4(C16) particles was analyzed using the amide I band (1600-1700 cm-1). Peaks at 1648-1660 $cm^{-1}$, 1625-1640 $cm^{-1}$ and 1660-1668 $cm^{-1}$ can be assigned to α-helical, β-sheet and β-turn structures, respectively d) UV-Vis-spectroscopy Ultraviolet-visible spectrometry, using a Cary100 spectrophotometer (Varian Medical Systems, Palo Alto, USA), has been employed for determination of the drug concentration in supernatants as a basis for the calculation of loading efficiencies and release behaviour. Calibration curves for all model drugs have been obtained by using five different concentrations of all stock solutions.

e) Zetapotential Analysis

In order to elucidate and characterize the loading mechanism of eADF4(C16) particles with model drugs, zeta potential measurements were conducted as a function of amount of model drug added. The zeta potential was determined using a Nanoseries Malvern Zetasizer (Malvern, Worcestershire, UK). Automatic titration was conducted with a Malvern Multipurpose Titrator MPT-2. Experiments were performed in distilled water (pH 7) at 25° C. Each measurement was performed in triplicate.

To characterize the morphology and determine the sizes of obtained eADF4(C16) particles, the prepared stock dispersion was examined using SEM and laser diffraction spectrometry. As shown in FIG. 1a), particles of spherical shape with diameters from 170 nm to 700 nm were obtained. The determined average diameter of particles was $d_{avg}=332\pm95$ nm. The yield of particle formation by salting-out was higher than 99% with remaining soluble protein below the detection limit. It could be observed that eADF4(C16) particles are colloidally stable within the complete studied concentration range from 0 to 2.0 M $(NH_4)_2SO_4$ (FIG. 1b). The slight linear decrease of intensity with increasing concentration of $(NH_4)_2SO_4$ can be explained by the linear increase in ion concentration yielding a decrease of number of particles per volume.

Example 6

Drug Loading of eADF4(C16) Particles

Drug loading of spider silk particles was conducted as follows: 100 μl of spider silk particle suspension containing 21 nmol silk protein were mixed with 1.0 ml of model drug solution containing 0.21 μmol model drug. After 10 min of incubation at room temperature samples were centrifuged for 10 min at 10.000 g, and the supernatant was analyzed for residual drug concentration using UV-Vis spectrometry. Standard calibration curves for model drugs were used for drug quantification. A control group of samples containing only 100 μl water mixed with 1.0 ml of model drug solution was prepared for each experiment. Drug concentrations from control and sample supernatants were used to calculate the amount of drug incorporated in the spider silk particles. All experiments were performed in triplicate. Encapsulation efficiency and loading were determined by using equation (1) and (2), respectively:

$$\text{encapsulation efficiency } (w/w\ \%) = \frac{\text{amount of model drug in particles}}{\text{model drug initially added}} \times 100 \quad (1)$$

$$\text{loading } (w/w\ \%) = \frac{\text{amount of model drug in particles}}{\text{amount of particles}} \times 100 \quad (2)$$

Example 7

Loading Efficiencies and Loading Procedure

Due to its negative charge at pH 7, eADF4(C16) can form complexes with positively charged molecules based on electrostatic interactions. In order to elucidate if small molecules attach to the particle surface or are able to permeate into the interior, loading efficiencies of glass beads were compared with that of eADF4(C16) particles assuming that permeation processes of drug molecules into the dense glass matrix cannot occur. Due to the high negative zeta potential ($\approx -50$ mV) of glass beads, the loading efficiency of glass beads should be higher than that of spider silk particles (zeta potential$\approx -22$ mV) if no diffusion into the protein matrix occurs.

Figure 2:
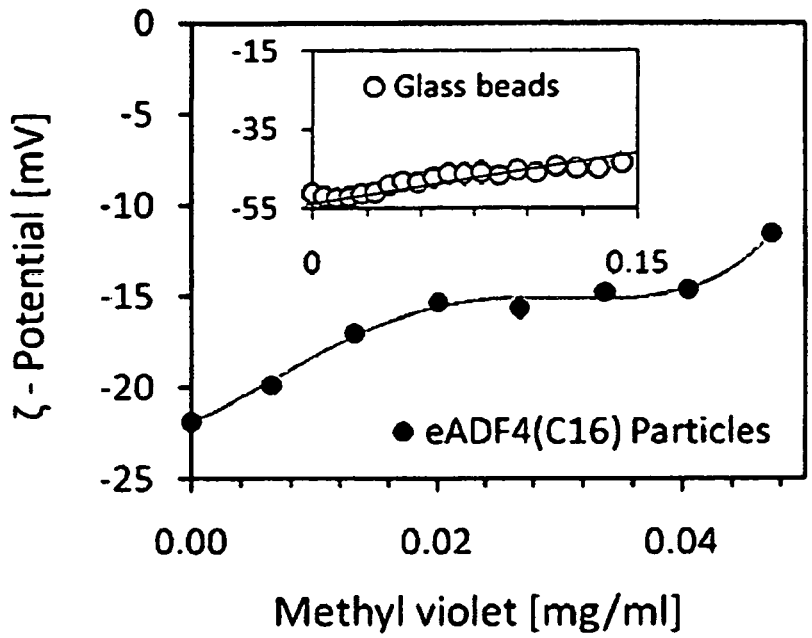
FIG. 2: Characterization of loading procedure: *a*) Zeta-Potential of eADF4(C16) particles as a function of added methyl violet. For comparison, the inlay shows the Zeta-potential of glass beads with methyl violet. *b*) Loading and loading efficiency of methyl violet on eADF4(C16) particles as a function of molar ratio.
Figure 2:
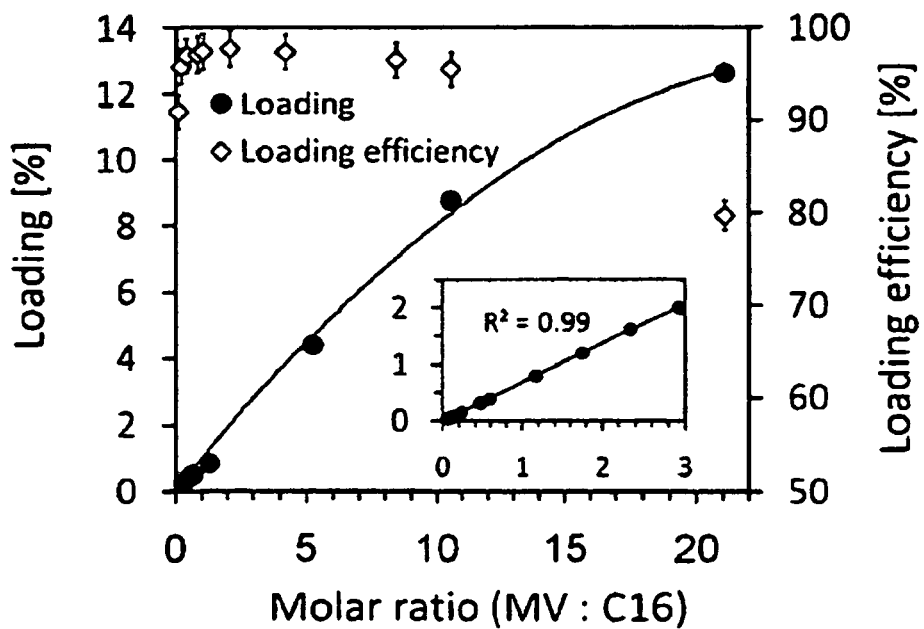

For this experiment methyl violet (MV) was employed with loading efficiencies above 95% at molar ratios of MV:eADF4(C16) of 10:1. Online zeta potential measurements during methyl violet loading revealed that the change of zeta potential during eADF4(C16) particle loading is a triphasic process (FIG. 2a). First, the potential changes gradually after addition of methyl violet solution. After an initial constant slope, the zeta potential curve exhibits a plateau phase, indicating no further change of surface loading upon increasing methyl violet concentration. Finally the zeta potential decreases further. The reduction of the zeta potential, as seen in the titration curve, is a direct consequence of the interaction of the silk particles with molecules of opposite charge. The initial lowering of surface charge can be explained by the charge compensation due to the addition of opposite charged methyl violet molecules. The plateau region indicates an equilibrium state of drug (compound) adsorbed at the solid-liquid particle interface and a diffusion of molecules into the hydrophobic core of the protein sphere. Said second phase is mainly characterized by the diffusion of the drug (compound) into the matrix of the particle, whereas the first phase is mainly characterized by the adsorption of the drug (compound) to the surface of the particle. After the core matrix is saturated, the influx of methyl violet molecules is reduced and eventually terminated. At that point the zeta potential starts to decrease again, as can be seen by the second slope in FIG. 2a, due to further loading of the particle surface. The decrease occurs at a methyl violet concentration corresponding to the molar ratio of MV:eADF4(C16) of 10:1 which was identified to be the molar ratio at which the loading efficiency decreases. FIG. 2b shows the obtained loading and loading efficiencies employing eADF4(C16) particles as a function of molar ratio. Up to a molar ratio of MV:eADF4(C16)$\approx 10$ the loading increases linearly with the amount of methyl violet added. Above a molar ratio of 10 the loading reaches a plateau leading to a decrease of loading efficiency.

In contrast, the zeta potential of glass microparticles during methyl violet addition showed no distinctive changes (inset FIG. 2a). The initial assumption that methyl violet cannot permeate the glass particle matrix was confirmed by analyzing the supernatant after completing the titration experiment. While the surface charge of glass particles is approximately two times higher compared to silk particles, the determined loading efficiency was only 0.03%. Furthermore, the loaded methyl violet could be easily washed off the surface of glass particles by three washing steps using Millipore water.

In order to investigate the influence of molecular parameters on the loading efficiency, twelve different small molecular drugs were used in this study (see Table 1). Since an individual eADF4(C16) molecule is amphiphilic with a dominating hydrophobic character (hydropathicity index=−0.46) exhibiting 17 negative charges (one at each C module and one at the carboxy terminus) and one positive charge at the amino terminus, it can be concluded that loading of eADF4(C16) particles with drugs is mainly driven by three parameters: (i) the charge of the drug molecule determined by its proton dissociation constant Ka (accounted for BH+ or HA), (ii) the octanol water partition coefficient (log $P_{o/w}$), as an indicator of solubility of the model drug, and (iii) the molecular weight (MW) which plays an important role in diffusion driven mass transport processes.

Further, the distribution between a hydrophobic and a hydrophilic phase of two different species of a specific drug, i.e. the native and the protonated form, can be described by its apparent distribution coefficient (log D), which can be calculated with equations (3) and (4) respectively.

$$\text{for acids: } \log D = \log P - \log(1 + 10^{pH-pKa}) \quad (3)$$

$$\text{for bases: } \log D = \log P - \log(1 + 10^{pKa-pH}) \quad (4)$$

The log P and pKa values of individual species used for calculation of log D are listed in Table 1. Table 2 summarizes the determined loading efficiencies, maximal (calculated by employing loading efficiencies of 100%) and experimental amount of entrapped drug, as well as the calculated distribution coefficient (log D) at pH 7.

TABLE 2

List of employed model drugs classified according to their chemical nature. The table provides an overview of theoretical and experimental model drug content of loaded spider silk particles (expressed as percentage of wt drug/wt spider silk protein particles), corresponding encapsulation efficiencies and calculated distribution coefficients (logD).

| Model drug | Chemical nature | Maximal drug content [w/w %] | Experimental drug content [w/w %] | Encapsulation efficiency [%] | log D |
|---|---|---|---|---|---|
| Ephedrin•HCl | base | 4.23 | 0.88 | 20.7 | −1.321 |
| Frocain•HCl | base | 5.71 | 2.16 | 38.0 | 0.396 |
| Propranolol•HCl | base | 6.19 | 2.78 | 45.0 | 1.197 |
| Papaverine•HCl | base | 7.89 | 3.71 | 47.0 | 2.395 |
| Tetracaine•HCl | base | 6.30 | 3.34 | 53.0 | 2.773 |
| Ethacridine lactat | strong base | 7.20 | 7.07 | 98.2 | 2.899 |
| Phenol red | strong acid | 7.12 | 0.00 | 0.0 | — |
| Methyl violet | — | 8.54 | 8.37 | 98.1 | — |

Figure 3:
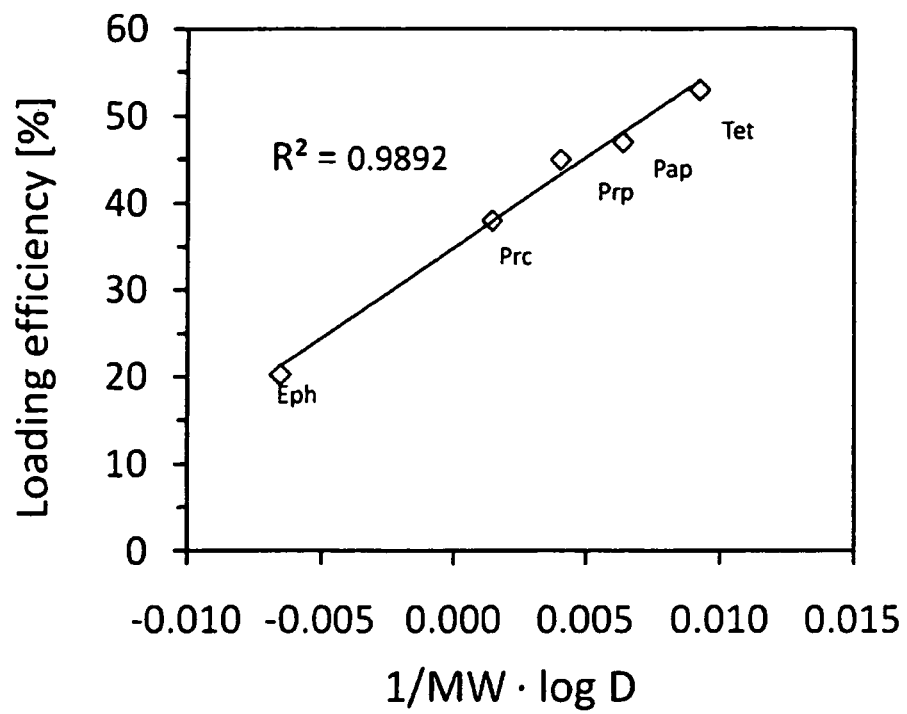
FIG. 3: Loading efficiencies for model drugs of weak alkaline nature such as Ephedrin (Eph), Procain (Prc), Propranolol (Prp), Papaverine (Pap) and Tetracaine (Tet) plotted over log D $MW^{-1}$.

Protonated weak organic bases were able to be loaded onto eADF4(C16) particles with efficiencies ranging between 20.7% and 53.0%. For this class of small molecular model drugs the quotient of calculated log D divided by the molecular mass of the individual molecule correlates linearly with the obtained loading efficiencies (see FIG. 3). This linear relationship clearly indicates that the combination of charge and solubility (expressed by the apparent distribution coefficient log D) and diffusion coefficient (expressed by the inverse proportionality of molecular weight) are the dominating factors responsible for effective loading of small weakly alkaline molecules onto eADF4(C16) particles.

Investigation of molecules with permanent charge revealed that positively charged molecules such as methyl violet were most successfully incorporated, whereas negatively charged molecules such as phenol red could not be incorporated using eADF4(C16), and slightly acidic molecules exhibited relatively low loading efficiencies from 0.2 to 17.3%. Strongly alkaline molecules such as ethacridine lactate showed a loading efficiency of more than 98%.

Example 8

In vitro Release Studies

Drug loaded eADF4(C16) particles were washed with distilled water and suspended in 1 ml PBS (pH 7.4) before incubation at 37° C. with constant shaking. Each vial contained 2 mg of drug loaded particles containing 4.2 μmol spider silk protein. The solvent was periodically removed from each sample and replaced with fresh PBS (pH 7.4). The drug content in the medium was then analyzed using UV-Vis-spectrometry. The percentage of cumulative model drug release (% w/w) was investigated as a function of incubation time. Each experiment was performed in triplicate. To study the effect of different pH values on the release behaviour of drug loaded eADF4(C16) particles, 1 mg drug loaded silk particles were incubated in 1.0 ml PBS at 5 different pH values (pH 2, 4, 6, 7.4 and 8.8) for 5 days. The solvent was withdrawn daily and the particles were redispersed in fresh media. Supernatants of drawn samples were analyzed for drug content determination with UV-Vis-spectrometry.

Figure 4:
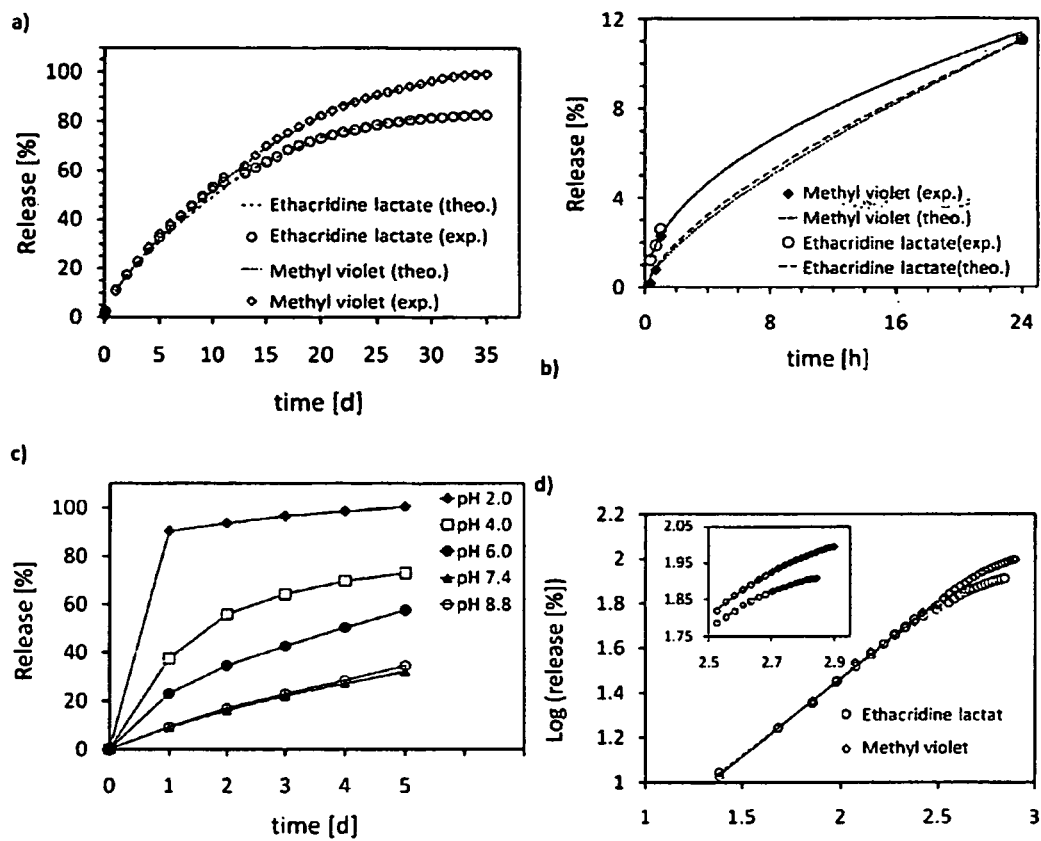
FIG. 4: Release studies of ethacridine lactate and methyl violet: a) Experimental and theoretical release kinetics of both model drugs over a period of 35 days. b) Experimental and theoretical release kinetics in the initial burst region (release <11%). c) Release of ethacridine lactate as a function of pH as indicated. (Buffer capacity PBS: pH 5.8-pH 8; non buffered conditions for pH 2.0, pH 4.0 and pH 8.8) d) Experimental release data of ethacridine lactate and methyl violet based on the power law model. A linear fit with a correlation parameter ($r^2$) above 0.99 was determined for three distinct time intervals. The linear fit for the interval from day 1 to day 13 is depicted in the main plot, whereas the inset shows the data and linear fits for the time intervals from day 14 to day 20 (open symbols) and day 21 to day 35 (filled symbols) respectively.

The in vitro release behavior of model drugs from eADF4 (C16) particles was exemplarily studied with methyl violet and ethacridine lactate. Cumulative release profiles showed that both molecules were released over a period of 30 days (FIG. 4a). Most interestingly, only a very small drug burst could be detected, i.e. an initial higher drug release within the first 24 hours of incubation. The release of ethacridine lactate and methyl violet within the first 24 hours was 11% of the total amount encapsulated. Subsequently, eADF4(C16) particles released approximately 5% of the entrapped molecules per day within the first week (FIG. 4a,b). To characterize the release behavior, the semi empirical power law equation was used (equation (5)), $$\frac{M_t}{M_\infty} = kt^n \tag{5}$$

where $M_t/M_\infty$ is the fractional amount of the drug released at time t, k is a characteristic constant of the system, and exponent n is related to the geometrical shape of the formulation and is indicative of the mechanism of drug release. The semi-empirical power law can be seen as a generalization of two independent mechanisms of drug transport, Fickian diffusion and Case II transport, reflecting the influence of polymer relaxation on molecules' movement in the matrix. For spherical systems the limiting value of n, when pure Fickian diffusion or pure Case II transport is operating, were determined to be equal to 0.43 and 0.85, respectively [42]. When n is between 0.43 and 0.85, a superposition of both transport processes occurs which is known as anomalous transport. In order to obtain a linear fit for the drug release data, equation (5) was modified leading to equation (6), $$\log\left(\frac{M_t}{M_\infty}\right) = \log(k) + n\log(t) \tag{6}$$

where n can be calculated from the slope of the log-log plot of release $M_t/M_\infty$ versus time t by linear fitting (FIG. 4d). Therefrom, three time intervals with different dominating release mechanisms could be identified excluding the initial burst region (<24 h). To distinguish between different time intervals, the criterion that the coefficient r2 had to be above 0.99 for the individual linear fits was employed. The values of release exponent (n), correlation coefficient (r2), and characteristic constant (k) are summarized in Table 3. For validation of the determined release parameters, the experimental release data were compared with theoretical data obtained by the semi-empirical power law employing the determined values for k and n. A very good agreement from post-initial burst stage (>24 hours) up to 100% release was obtained (FIG. 4 a). Since only release data after 24 hours were considered for calculation of release parameters (k and n), the initial burst is underestimated by theoretical data (FIG. 4 b).

TABLE 3

Drug release parameters (n: release exponent; $r^2$: correlation coefficient; k: characteristic constant) for methyl violet and ethacridine lactate for defined release intervals.

| Model drug | time [d] | Release [%] | n | $r^2$ | k |
|---|---|---|---|---|---|
| Methyl violet | 0-13 | ≤60 | 0.692 | 0.998 | 1.17 |
| | 14-20 | 60-82 | 0.6079 | 0.994 | 1.92 |
| | >20 | ≥82 | 0.3537 | 0.993 | 9.20 |

TABLE 3-continued

Drug release parameters (n: release exponent; $r^2$: correlation coefficient; k: characteristic constant) for methyl violet and ethacridine lactate for defined release intervals.

| Model drug | time [d] | Release [%] | n | $r^2$ | k |
|---|---|---|---|---|---|
| Ethacridine lactate | 0-13 | ≤60 | 00.6754 | 0.998 | 1.25 |
| | 14-20 | 60-73 | 0.5083 | 0.994 | 3.18 |
| | >20 | ≥73 | 0.2641 | 0.992 | 14.4 |

Within the first two weeks of release, the exponents n for ethacridine lactate (EL) and methyl (MV) violet are almost identical (nEL=0.6754, nMV=0.692), indicating an anomalous diffusional release. In the second time interval between day 14 and day 20, release profiles diverge from each other with the release exponent of ethacridine lactate dropping to 0.51 and that of methyl violet to n=0.61. In this second time interval, fickian transport begins to dominate for ethacridine lactate. After 20 days, release exponent n values for methyl violet and ethacridine lactate fall below the limiting value of n=0.43 indicating a fickian release behaviour for both (Table 3).

Next, the influence of pH on drug release was evaluated. Release experiments with ethacridine lactate loaded eADF4 (C16) particles incubated in PBS at 37° C. and different pH values showed a strong pH influence on the release rates (FIG. 4c) with an acidic environment accelerating drug release. Almost 80% of the loaded drug was released after 24 hours from silk spheres incubated at pH 2 (non buffered conditions). For silk particles incubated at pH 4 (non-buffered conditions) an initial release rate of almost 40% was obtained after the first day of incubation. Particles incubated at pH 6 showed double the release with a similar release profile as seen at pH 7.4 or 8.8, which were indistinguishable. The observed results confirm the predicted importance of electrostatic interactions between eADF4(C16) and drug molecules. Presumably an influx of protons into the biopolymer leads to a displacement of drug molecules from the matrix. In addition, the decreased pH influences the distribution of charged drug species by shifting the equilibrium towards the charged species. As these species are driven towards the negatively charged surface of the protein, they can easily be washed away by the solvent.

Example 9

In vitro Degradation of eADF4(C16) Particles

In order to analyze, the degradability of eADF4(C16) silk particles, a mixture of elastase and trypsin (both naturally occurring proteases in vertebrates) were used. 1.0 mg of silk particles was incubated in 1.0 ml PBS in the presence of 0.8 µg elastase and 12.5 µg trypsin. Over two weeks samples were drawn on a daily basis and centrifuged. The pellets containing eADF4(C16) particles were redispersed in distilled water and washed three times for further analysis of size and morphology using laser diffraction spectrometry and scanning electron microscopy. Elastase and trypsin from hog pancreas were supplied by Sigma Aldrich (St. Louis, USA).

Degradability of drug depot systems is a highly desirable property, since the risk of inflammation and intoxication is dramatically lower than for non-degradable systems. As most biopolymers feature the ability of enzymatic degradation, degradation studies were conducted using proteases (trypsin and elastase) naturally occurring in vertebrates to simulate a native-like degradation of eADF4(C16) drug carriers. Elastase and trypsin, i.e. serine proteases, can cleave peptide bonds on the carboxy side of small, hydrophobic amino acids such as glycine, alanine, and valine. Due to the relative high content of glycine and alanine in eADF4(C16) (≈50% of the total amino acid composition) such proteases may cleave peptide bonds at several sites in the amino acid backbone of eADF4(C16).

Figure 5:
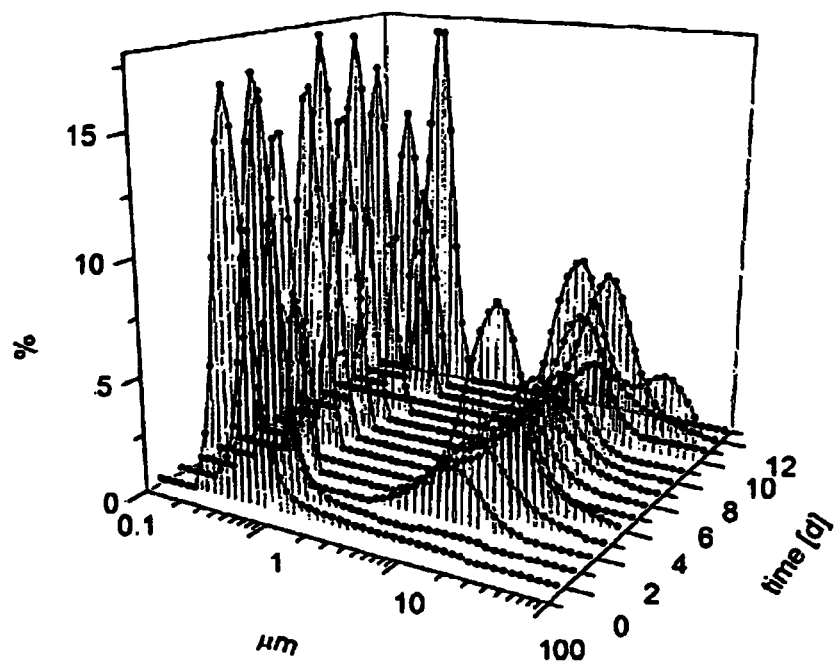
FIG. 5: Characterization of eADF4(C16) particles upon enzymatic degradation: a) Size distribution of eADF4(C16) particles upon enzymatic degradation at time points as indicated. b) Mean and mode of eADF4(C16) particles distribution over time. c) Percentage of particles and agglomerations of eADF4(C16) particles after degradation with elastase (c=4 µg/ml) and trypsin (c=50 µg/ml) at timepoints as indicated. d) Second derivative of FTIR spectra of eADF4(C16) particles upon degradation at time points as indicated.
Figure 5:
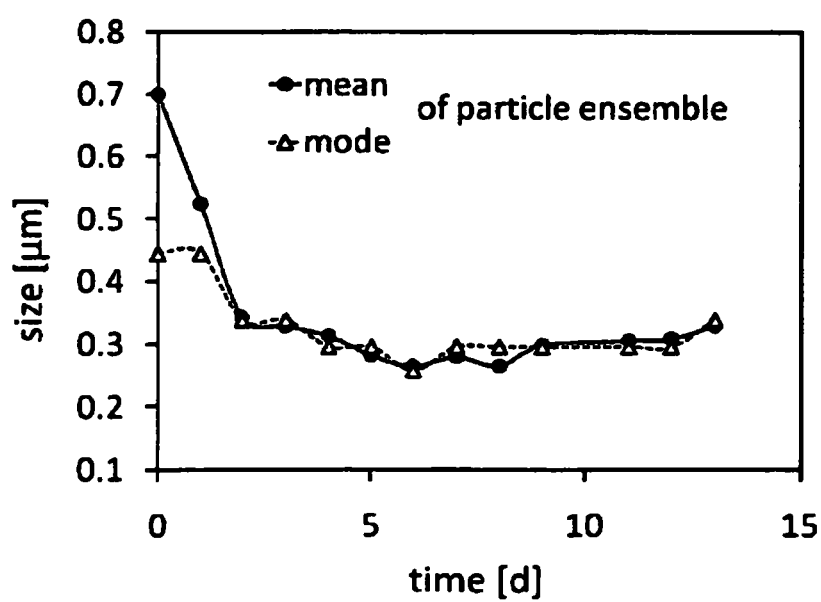
Figure 5:
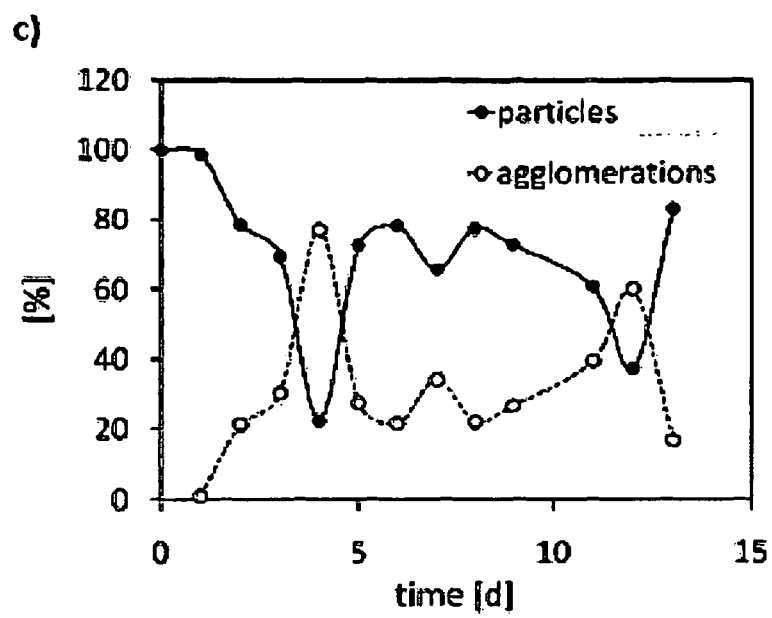
Figure 5:
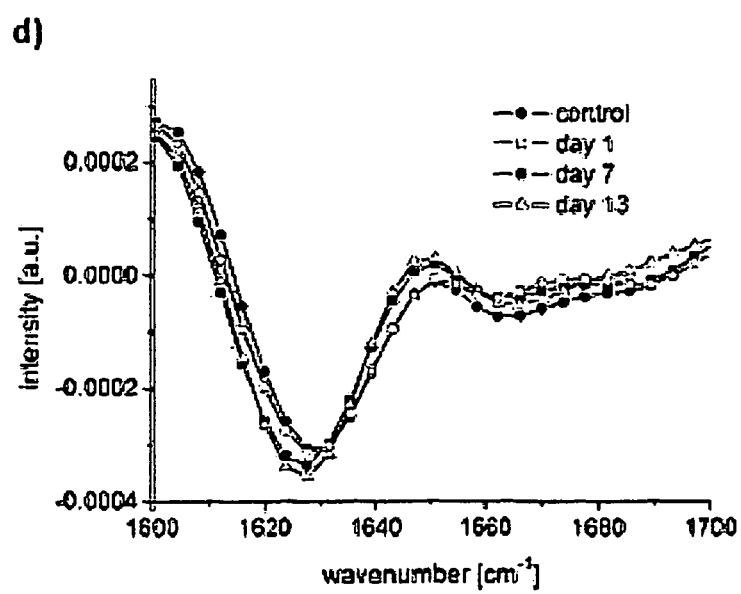

Size and morphology analysis of particle ensembles drawn from degradation experiments using LDS and SEM showed that after two days of degradation particles form clusters (FIG. 5a). By comparing the mode value, which represents the particle size most commonly found in the distribution, with the mean size of the particles leads to the conclusion that bigger particles of the ensemble are degraded preferentially (FIG. 5b).

At t=0 the mean is larger than the mode, indicating an asymmetric size distribution towards larger particles. Upon enzymatic degradation for two days mean and mode approach each other, indicating that larger particles disappear and the particle distribution becomes symmetric. The particle distribution remains symmetrical up to day 8 at which timepoint the mean falls below the mode, indicating an asymmetric size distribution towards smaller particles.

Analysis of the relative relation of single particles to agglomerations indicates a oscillatory agglomerative behaviour (FIG. 5a, c).

Changes of secondary structure of eADF(C16) particles can be most effectively detected by 2nd derivative changes of FTIR spectra at the wave numbers 1648-1660 cm-1 and 1625-1640 cm-1. The results indicate (FIG. 5d) that only minor changes in percental β-sheet and α-helical content occur. The overall structure of eADF4(C16) particles is conserved. This is an important result regarding the long term stability and release behaviour of eADF4(C16) particles at physiological conditions, since structural changes would significantly alter the release properties.

Example 10

Protein Loading and in vitro Degradation of $C_{16}$ Spider Silk Particles

The following protein compounds were chosen for loading experiments:
(a) Lysozyme, a protein compound with an isoelectric point of 11.35. The protein exhibits an overall positive net charge at the investigated pH of 7.0 and has a molecular weight of 14.3 kDa.
(b) Nerve growth factor (NGF) has an isoelectric point of 9.5 and a molecular weight of 13 kDa. NGF it is also positively charged at the investigated pH of 7.0.

Loading with lysozyme was conducted in buffer (10 mM phosphate, pH 7.0) at different ionic strengths of 30 mM, 60 mM and 100 mM (adjusted with sodium chloride). The loading procedure as applied in example 6 was modulated and implemented as follows: A stock dispersion of spider silk particles was centrifuged and redispersed in the desired buffer media before loading. A second stock solution comprising lysozyme was prepared by dissolving lyophilized lysozyme in an identical buffer solution. Spider silk particle suspension and lysozyme stock solution were mixed to achieve a final spider silk particle concentration of 0.5 mg/ml. After 30 minutes of incubation at room temperature under gentle agitation, 20 µl of the resulting particle suspension were used for dynamic light scattering measurements. Simultaneously, samples were centrifuged and the supernatant was analyzed for residual protein content using the Micro BCA Protein Assay Kit (Thermo Scientific). Encapsulation efficiencies and loading were determined according to example 6 by using equation (1) and (2), respectively.

Figure 6:
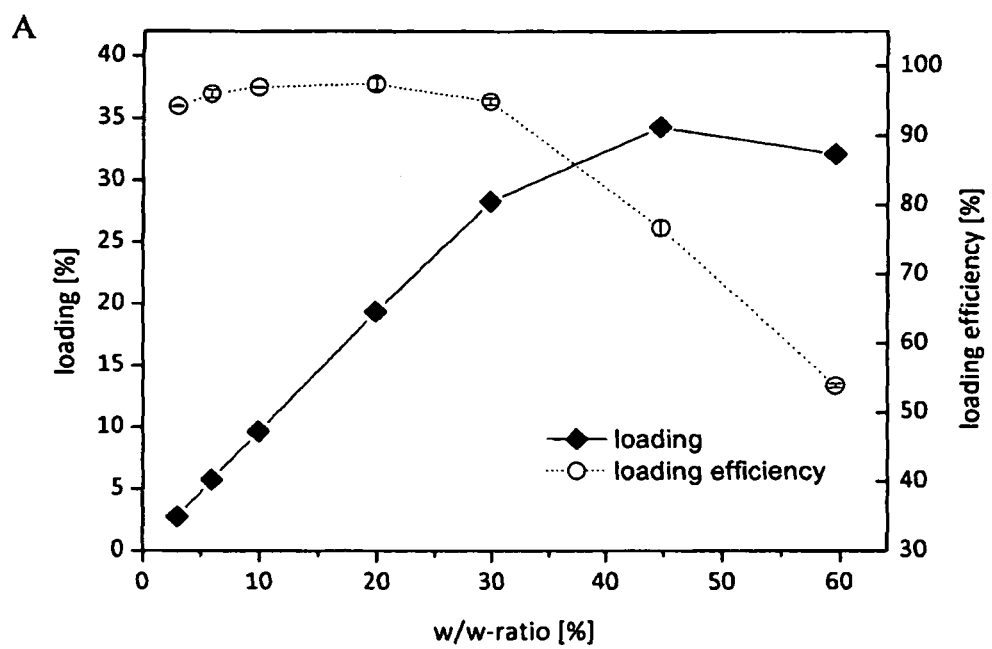
FIG. 6: A) Loading and loading efficiencies of lysozyme on $C_{16}$ spider silk particles as a function of w/w-ratio at pH 7.0/30 mM. The loading efficiency ranges above 90% for w/w ratios up to 30%, representing a very effective loading process (more than 90% of the overall added lysozyme is bound to/permeated into the particle). At w/w rations above 30% the loading efficiency slowly decreases, resulting in higher amounts of unloaded lysozyme in solution. B) Zeta-potential of spider silk particles after loading with different amounts of lysozyme at pH 7.0/30 mM.
Figure 6:
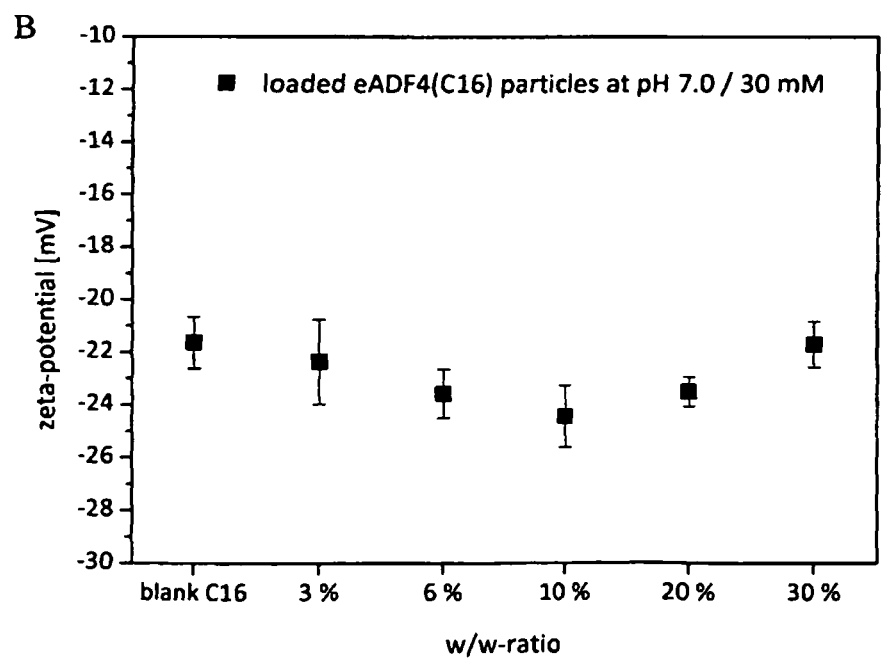

Lysozyme was loaded onto $C_{16}$ spider (eADF4 (C16)) silk particles in high amounts (see FIG. 6A). At an ionic strength of 30 mM it was possible to load more than 30% [w/w] lysozyme onto the spider silk particles. The associated loading efficiencies remain >90% up to 30% w/w-ratios ranging from 6 to 20%, representing a very effective loading of lysozyme. It could be shown that loading of particles with lysozyme did not show a significant change in the zeta-potential of particles up to loading of 30% (see FIG. 6B). This argues that lysozyme diffuses into the matrix and is not mainly adsorbed to the particles' surface.

The loading of a particle with lysozyme does not result in a significant increase of the zeta potential, which corresponds to no detectable increase of the median of the spider silk particle. Therefore, it can be concluded that the compound (lysozyme) permeates/diffuses into the spider silk particle.

According to a model calculation with 250 μg of almost 10% [w/w] loaded spider silk particles, a maximum of only 12.5% of the totally loaded compound (lysozyme with a hydrodynamic diameter of 4.1 nm) could be theoretically located as a monolayer on the surface of the particle.

Figure 8:
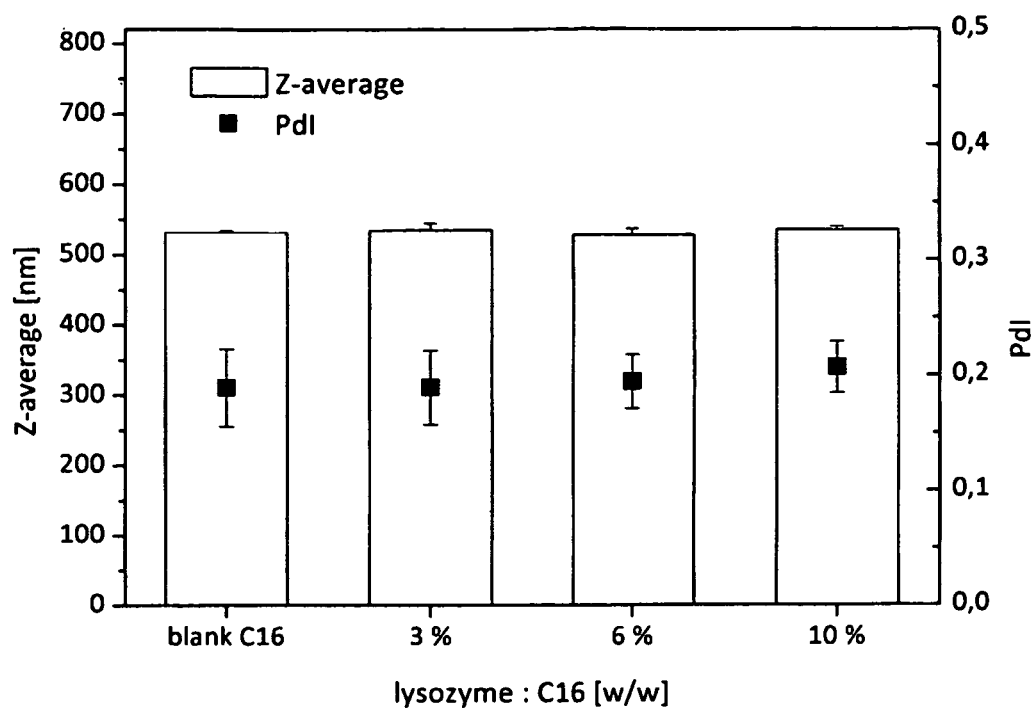
FIG. 8: Particle size of $C_{16}$ spider silk particles loaded with different w/w ratios of lysozyme to spider silk particles. The size of the spider silk particles loaded with approximately 10% [w/w] lysozyme did not differ from unloaded spider silk particles. "Pdi" means polydispersity index.

For calculation the closest/densest sphere packing of lysozyme on the spider silk particle is taken. In contrast to permeation into the spider silk particle the adsorption of lysozyme molecules at the surface would increase the diameter of the particle for about 80 nm. Surprisingly, no increase of z-average and thus no increase of particle-size could be detected. This further argues for the permeation/diffusion of lysozyme molecules into the matrix of the particle. FIG. 8 shows no increase in size of the (eADF4) $C_{16}$ spider silk particles loaded with approximately 10% [w/w] lysozyme compared to unloaded (eADF4) $C_{16}$ spider silk particles.

The loading efficiency ranges above 90% for w/w ratios up to 30%, representing a very effective loading process (more than 90% of the overall added lysozyme is bound to/permeated into the particle). At w/w rations above 30% the loading efficiency slowly decreases, resulting in higher amounts of unloaded lysozyme in solution.

Figure 7:
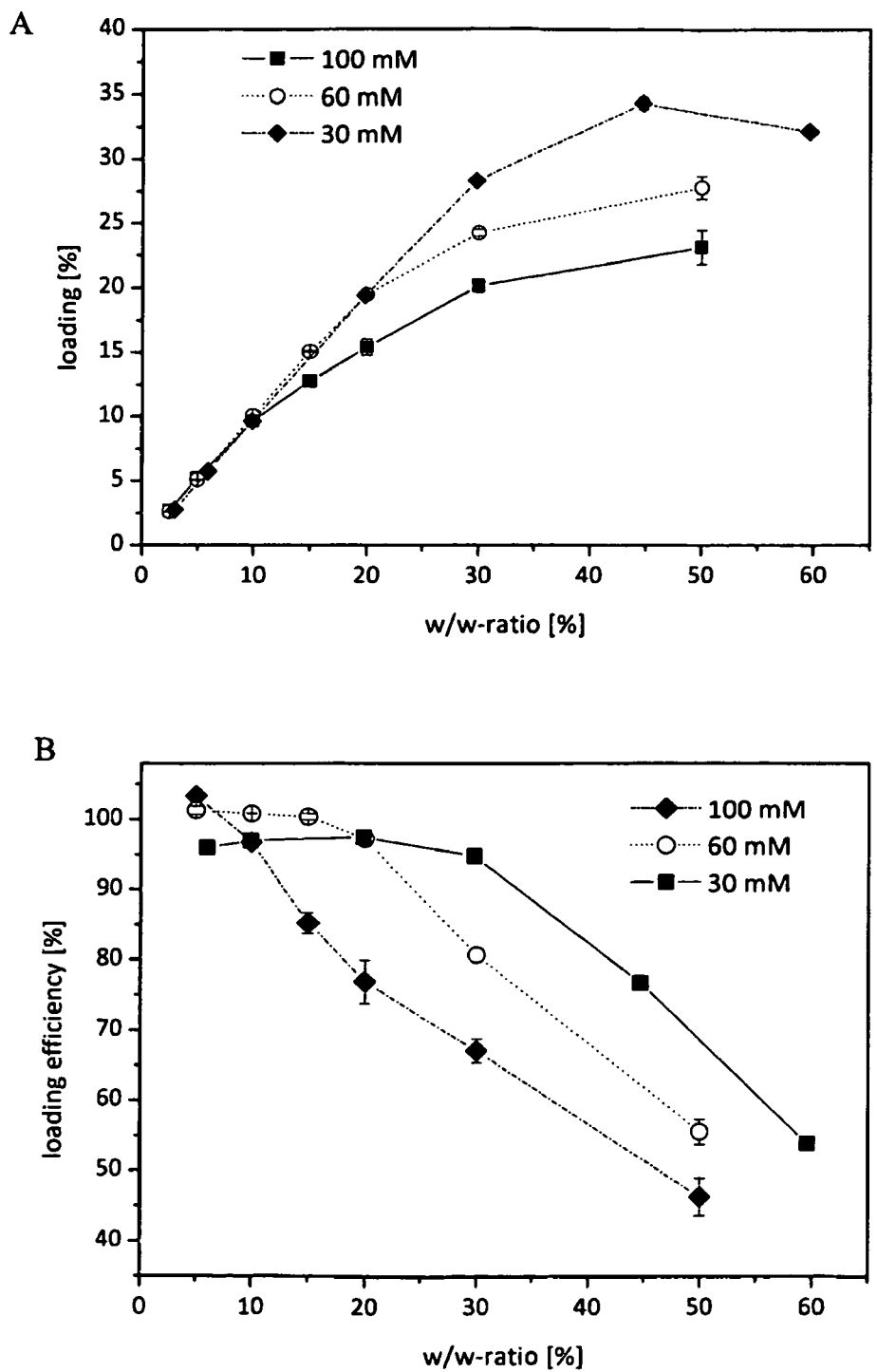
FIG. 7: Loading of lysozyme onto $C_{16}$ spider silk particles at different ionic strength at pH 7.0. A) Loading of lysozyme as a function of w/w-ratio lysozyme to spider silk particles. B) Loading efficiencies of lysozyme as a function of w/w-ratio lysozyme to spider silk particles.

FIG. 7 displays the influence of ionic strength on the loading of lysozyme into spider silk particles. An increase of ionic strength from 30 to 100 mM leads to a distinct decrease in loading and loading efficiencies. For example, loading at 30% w/w-ratio is reduced from 28% at 30 mM to 24% at 60 mM and 20% at 100 mM.

The invention claimed is:

1. A method of producing spider silk particles loaded with a compound comprising the steps of:
   i) providing spider silk particles that consist of an inner solid matrix with an outer surface, both the inner solid matrix and the outer surface homogenously comprising one or more spider silk polypeptides, wherein the one or more spider silk polypeptides comprise at least two identical repetitive units, and wherein the spider silk particles are produced by protein aggregation, and
   ii) incubating said spider silk particles with at least one compound.

2. The method of claim 1, wherein the spider silk particles provided in step i) are produced by the steps of:
   a) providing an aqueous solution comprising one or more spider silk polypeptides comprising at least two identical repetitive units,
   b) triggering aggregation of the spider silk polypeptides to form spider silk particles, and
   c) separating the spider silk particles by phase separation.

3. The method of claim 1, wherein the compound is able to permeate into the spider silk particles.

4. The method of claim 1, wherein at least 40%, 50%, 60%, 70%, 80%, 90%, or 95% of the loaded compound is located within the spider silk particles.

5. The method of claim 1, wherein the at least two identical repetitive units each comprise at least one consensus sequence selected from the group consisting of:
   i) GPGXX (SEQ ID NO:3), wherein X is any amino acid, preferably in each case independently selected from the group consisting of A, S, G, Y, P and Q;
   ii) GGX, wherein X is any amino acid, preferably in each case independently selected from the group consisting of Y, P, R, S, A, T, N and Q; and
   iii) $A_x$, wherein x is an integer from 5 to 10.

6. The method of claim 5, wherein the repetitive unit of the respective spider silk polypeptide is independently selected from module A (SEQ ID NO:20) or variants thereof, module C (SEQ ID NO:21) or variants thereof, module Q (SEQ ID NO:22) or variants thereof, module $A^C$ (SEQ ID NO:29), module $A^K$ (SEQ ID NO:30), module $C^C$ (SEQ ID NO:31), module $C^{K1}$ (SEQ ID NO:32), module $C^{K2}$ (SEQ ID NO:33) or module $C^{KC}$ (SEQ ID NO:34).

7. The method of claim 6, wherein the spider silk polypeptide further comprises at least one non-repetitive (NR) unit.

8. The method of claim 7, wherein the non-repetitive (NR) unit is independently selected from the group consisting of NR3 (SEQ ID NO:41 and SEQ ID NO:45) or variants thereof and NR4 (SEQ ID NO:42 and SEQ ID NO:46) or variants thereof.

9. The method of claim 1, wherein the compound is a pharmaceutically active compound, a cosmetic substance, an agricultural substance, a chemoattractant, a chemorepellent, an anti-fungal substance, an anti-bacterial substance, a nutrient, a dietary supplement, a dye, a fragrance or an agent selected from the group consisting of hemostatic agents, growth stimulating agents, inflammatory agents, anti-fouling agents, antimicrobial agents and UV protecting agents.

10. The method of claim 1, wherein the compound has an overall positive net charge.

11. The method of claim 1, wherein the compound is able to permeate into the spider silk particles by electrostatic interaction and/or diffusion.

12. The method of claim 1, wherein the compound has a neutral or alkaline nature.

13. Spider silk particles produced from the method of claim 1, which consist of an inner solid matrix with an outer surface, both the inner solid matrix and the outer surface homogenously comprising at least one spider silk polypeptide comprising at least two identical repetitive units, wherein the spider silk particles are loaded with at least one compound.

14. The spider silk particles of claim 13, wherein, at least 40%, 50%, 60%, 70%, 80%, 90%, or 95% of the loaded compound is located within the spider silk particles.

15. The spider silk particles of claim 13, wherein the spider silk polypeptide comprises at least two identical repetitive units each comprise at least one consensus sequence selected from the group consisting of:
  i) GPGXX (SEQ ID NO:3), wherein X is any amino acid, preferably in each case independently selected from the group consisting of A, S, G, Y, P and Q;
  ii) GGX, wherein X is any amino acid, preferably in each case independently selected from the group consisting of Y, P, R, S, A, T, N and Q; and
  iii) $A_x$, wherein x is an integer from 5 to 10.

16. The spider silk particles of claim 15, wherein the repetitive unit of the spider silk polypeptide is independently selected from module A (SEQ ID NO:20) or variants thereof, module C (SEQ ID NO:21) or variants thereof, module Q (SEQ ID NO:22) or variants thereof, module $A^C$ (SEQ ID NO:29), module $A^K$ (SEQ ID NO:30), module $C^C$ (SEQ ID NO:31), module $C^{K1}$ (SEQ ID NO:32), module $C^{K2}$ (SEQ ID NO:33) or module $C^{KC}$ (SEQ ID NO:34).

17. The spider silk particles of claim 16, wherein the spider silk polypeptide further comprises one or more non-repetitive (NR) units.

18. The spider silk particles of claim 17, wherein the NR unit is independently selected from the group consisting of NR3 (SEQ ID NO:41 and SEQ ID NO:45) or variants thereof and NR4 (SEQ ID NO:42 and SEQ ID NO:46) or variants thereof.

19. The spider silk particles of claim 13, wherein the compound is a pharmaceutically active compound, a cosmetic substance, an agricultural substance, a chemoattractant, a chemorepellent, an anti-fungal substance, an anti-bacterial substance, a nutrient, a dietary supplement, a dye, a fragrance or an agent selected from the group consisting of hemostatic agents, growth stimulating agents, inflammatory agents, antifouling agents, antimicrobial agents and UV protecting agents.

20. The spider silk particles of claim 13, wherein the compound has an overall positive net charge.

21. The spider silk particles of claim 13, wherein the compound is able to permeate into the spider silk particles by electrostatic interaction and/or diffusion.

22. The spider silk particles of claim 13, wherein the compound has a neutral or alkaline nature.

23. The spider silk particles of claim 13, wherein the compound is released from the spider silk particles by diffusion upon exposure to physiological conditions.

24. The spider silk particles of claim 23, wherein less than 20%, preferably less than 15%, and most preferably less than 10% of the compound is released within the first 24 hours.

25. A pharmaceutical composition comprising the spider silk particles according to claim 19, and additionally a pharmaceutically acceptable buffer, diluent and/or excipient, the pharmaceutical composition being useful for controlled and sustained delivery, wherein the compound is a pharmaceutically active compound.

26. A cosmetic composition comprising the spider silk particles according to claim 19 for controlled and sustained delivery, wherein the compound is a cosmetic compound.

* * * * *

SEQUENCE LISTING

```
<160> NUMBER OF SEQ ID NOS: 96

<210> SEQ ID NO 1
<211> LENGTH: 636
<212> TYPE: PRT
<213> ORGANISM: Araneus diadematus
<220> FEATURE:
<221> NAME/KEY: PEPTIDE
<222> LOCATION: (1)..(636)
<223> OTHER INFORMATION: ADF-3

<400> SEQUENCE: 1

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
            20                  25                  30

Ala Ala Ala Ala Ala Gly Gly Tyr Gly Pro Gly Ser Gly Gln Gln Gly
        35                  40                  45

Pro Ser Gln Gln Gly Pro Gly Gln Gln Gly Pro Gly Gly Gln Gly Pro
    50                  55                  60

Tyr Gly Pro Gly Ala Ser Ala Ala Ala Ala Ala Ala Gly Gly Tyr Gly
65                  70                  75                  80

Pro Gly Ser Gly Gln Gln Gly Pro Gly Gly Gln Gly Pro Tyr Gly Pro
                85                  90                  95

Gly Ser Ser Ala Ala Ala Ala Ala Ala Gly Gly Asn Gly Pro Gly Ser
            100                 105                 110

Gly Gln Gln Gly Ala Gly Gln Gln Gly Pro Gly Gln Gln Gly Pro Gly
        115                 120                 125

Ala Ser Ala Ala Ala Ala Ala Ala Gly Gly Tyr Gly Pro Gly Ser Gly
    130                 135                 140

Gln Gln Gly Pro Gly Gln Gln Gly Pro Gly Gly Gln Gly Pro Tyr Gly
145                 150                 155                 160

Pro Gly Ala Ser Ala Ala Ala Ala Ala Ala Gly Gly Tyr Gly Pro Gly
                165                 170                 175

Ser Gly Gln Gly Pro Gly Gln Gln Gly Pro Gly Gly Gln Gly Pro Tyr
            180                 185                 190
```

```
Gly Pro Gly Ala Ser Ala Ala Ala Ala Ala Gly Gly Tyr Gly Pro
            195                 200                 205
Gly Ser Gly Gln Gln Gly Pro Gly Gln Gln Gly Pro Gly Gln Gln Gly
    210                 215                 220
Pro Gly Gly Gln Gly Pro Tyr Gly Pro Gly Ala Ser Ala Ala Ala
225                 230                 235                 240
Ala Ala Gly Gly Tyr Gly Pro Gly Tyr Gly Gln Gln Gly Pro Gly Gln
                245                 250                 255
Gln Gly Pro Gly Gly Gln Gly Pro Tyr Gly Pro Gly Ala Ser Ala Ala
            260                 265                 270
Ser Ala Ala Ser Gly Gly Tyr Gly Pro Gly Ser Gly Gln Gln Gly Pro
            275                 280                 285
Gly Gln Gln Gly Pro Gly Gly Gln Gly Pro Tyr Gly Pro Gly Ala Ser
        290                 295                 300
Ala Ala Ala Ala Ala Ala Gly Gly Tyr Gly Pro Gly Ser Gly Gln Gln
305                 310                 315                 320
Gly Pro Gly Gln Gln Gly Pro Gly Gln Gln Gly Pro Gly Gln Gln Gly
                325                 330                 335
Pro Gly Gly Gln Gly Pro Tyr Gly Pro Gly Ala Ser Ala Ala Ala Ala
            340                 345                 350
Ala Ala Gly Gly Tyr Gly Pro Gly Ser Gly Gln Gln Gly Pro Gly Gln
            355                 360                 365
Gln Gly Pro Gly Gln Gln Gly Pro Gly Gln Gln Gly Pro Gly Gln Gln
        370                 375                 380
Gly Pro Gly Gln Gln Gly Pro Gly Gln Gln Gly Pro Gly Gln Gln Gly
385                 390                 395                 400
Pro Gly Gln Gln Gly Pro Gly Gln Gly Ala Tyr Gly Pro Gly Ala
            405                 410                 415
Ser Ala Ala Ala Gly Ala Ala Gly Gly Tyr Gly Pro Gly Ser Gly Gln
            420                 425                 430
Gln Gly Pro Gly Gln Gln Gly Pro Gly Gln Gln Gly Pro Gly Gln Gln
        435                 440                 445
Gly Pro Gly Gln Gln Gly Pro Gly Gln Gln Gly Pro Gly Gln Gln Gly
    450                 455                 460
Pro Gly Gln Gln Gly Pro Tyr Gly Pro Gly Ala Ser Ala Ala Ala Ala
465                 470                 475                 480
Ala Ala Gly Gly Tyr Gly Pro Gly Ser Gly Gln Gln Gly Pro Gly Gln
            485                 490                 495
Gln Gly Pro Gly Gln Gln Gly Pro Gly Gln Gln Gly Pro Tyr Gly Pro
        500                 505                 510
Gly Ala Ala Ser Ala Ala Val Ser Val Gly Gly Tyr Gly Pro Gln Ser
    515                 520                 525
Ser Ser Val Pro Val Ala Ser Ala Val Ala Ser Arg Leu Ser Ser Pro
    530                 535                 540
Ala Ala Ser Ser Arg Val Ser Ser Ala Val Ser Ser Leu Val Ser Ser
545                 550                 555                 560
Gly Pro Thr Lys His Ala Ala Leu Ser Asn Thr Ile Ser Ser Val Val
            565                 570                 575
Ser Gln Val Ser Ala Ser Asn Pro Gly Leu Ser Gly Cys Asp Val Leu
        580                 585                 590
Val Gln Ala Leu Leu Glu Val Val Ser Ala Leu Val Ser Ile Leu Gly
    595                 600                 605
```

```
Ser Ser Ser Ile Gly Gln Ile Asn Tyr Gly Ala Ser Ala Gln Tyr Thr
610                 615                 620

Gln Met Val Gly Gln Ser Val Ala Gln Ala Leu Ala
625                 630                 635

<210> SEQ ID NO 2
<211> LENGTH: 410
<212> TYPE: PRT
<213> ORGANISM: Araneus diadematus
<220> FEATURE:
<221> NAME/KEY: PEPTIDE
<222> LOCATION: (1)..(410)
<223> OTHER INFORMATION: ADF-4

<400> SEQUENCE: 2

Ala Gly Ser Ser Ala Ala Ala Ala Ala Ser Gly Ser Gly Gly
1               5                   10                  15

Tyr Gly Pro Glu Asn Gln Gly Pro Ser Gly Pro Val Ala Tyr Gly Pro
                20                  25                  30

Gly Gly Pro Val Ser Ser Ala Ala Ala Ala Ala Gly Ser Gly
                35                  40                  45

Pro Gly Gly Tyr Gly Pro Glu Asn Gln Gly Pro Ser Gly Pro Gly Gly
50                  55                  60

Tyr Gly Pro Gly Gly Ser Gly Ser Ser Ala Ala Ala Ala Ala
65                  70                  75                  80

Ala Ser Gly Pro Gly Gly Tyr Gly Pro Gly Ser Gln Gly Pro Ser Gly
                85                  90                  95

Pro Gly Gly Ser Gly Gly Tyr Gly Pro Gly Ser Gln Gly Ala Ser Gly
                100                 105                 110

Pro Gly Gly Pro Gly Ala Ser Ala Ala Ala Ala Ala Ala Ala
                115                 120                 125

Ala Ser Gly Pro Gly Gly Tyr Gly Pro Gly Ser Gln Gly Pro Ser Gly
                130                 135                 140

Pro Gly Ala Tyr Gly Pro Gly Gly Pro Gly Ser Ser Ala Ala Ala
145                 150                 155                 160

Ala Ala Ala Ala Ser Gly Pro Gly Gly Tyr Gly Pro Gly Ser Gln Gly
                165                 170                 175

Pro Ser Gly Pro Gly Val Tyr Gly Pro Gly Gly Pro Gly Ser Ser Ala
                180                 185                 190

Ala Ala Ala Ala Ala Gly Ser Gly Pro Gly Gly Tyr Gly Pro Glu
                195                 200                 205

Asn Gln Gly Pro Ser Gly Pro Gly Gly Tyr Gly Pro Gly Gly Ser Gly
                210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Gly Ser Gly Gly Tyr
                245                 250                 255

Gly Pro Gly Ser Gln Gly Gly Pro Gly Ala Ser Ala Ala Ala
                260                 265                 270

Ala Ala Ala Ala Ser Gly Pro Gly Gly Tyr Gly Pro Gly Ser Gln
                275                 280                 285

Gly Pro Ser Gly Pro Gly Tyr Gln Gly Pro Ser Gly Pro Gly Ala Tyr
                290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
```

```
                    325                 330                 335
Ser Ser Gly Pro Thr Asn Gly Ala Ala Val Ser Gly Ala Leu Asn Ser
                340                 345                 350

Leu Val Ser Gln Ile Ser Ala Ser Asn Pro Gly Leu Ser Gly Cys Asp
            355                 360                 365

Ala Leu Val Gln Ala Leu Leu Glu Leu Val Ser Ala Leu Val Ala Ile
    370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
                405                 410

<210> SEQ ID NO 3
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
<223> OTHER INFORMATION: consensus peptide motif
<220> FEATURE:
<221> NAME/KEY: VARIANT
<222> LOCATION: (4)..(4)
<223> OTHER INFORMATION: Xaa at position 4 may also be alanine, serine,
      glycine, tyrosine, proline, or glutamine
<220> FEATURE:
<221> NAME/KEY: VARIANT
<222> LOCATION: (5)..(5)
<223> OTHER INFORMATION: Xaa at position 5 may also be alanine, serine,
      glycine, tyrosine, proline, or glutamine

<400> SEQUENCE: 3

Gly Pro Gly Xaa Xaa
1               5

<210> SEQ ID NO 4
<211> LENGTH: 5
<212> TYPE: PRT
<213> ORGANISM: Araneus diadematus
<220> FEATURE:
<221> NAME/KEY: VARIANT
<222> LOCATION: (4)..(4)
<223> OTHER INFORMATION: Xaa at position 4 may also be alanine, serine,
      glycine, tyrosine, proline, or glutamine
<220> FEATURE:
<221> NAME/KEY: VARIANT
<222> LOCATION: (5)..(5)
<223> OTHER INFORMATION: Xaa at position 5 may also be alanine, serine,
      glycine, tyrosine, proline, or glutamine

<400> SEQUENCE: 4

Gly Pro Gly Xaa Xaa
1               5

<210> SEQ ID NO 5
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-3)

<400> SEQUENCE: 5

Gly Pro Gly Ala Ser
1               5
```

-continued

```
<210> SEQ ID NO 6
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-3)

<400> SEQUENCE: 6

Gly Pro Gly Ser Gly
1               5

<210> SEQ ID NO 7
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)

<400> SEQUENCE: 7

Gly Pro Gly Gly Tyr
1               5

<210> SEQ ID NO 8
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)

<400> SEQUENCE: 8

Gly Pro Gly Gly Pro
1               5

<210> SEQ ID NO 9
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 9

Gly Pro Gly Gly Ala
1               5

<210> SEQ ID NO 10
<211> LENGTH: 5
<212> TYPE: PRT
<213> ORGANISM: Unknown
<220> FEATURE:
<223> OTHER INFORMATION: Arthropoda
<220> FEATURE:
<221> NAME/KEY: REPEAT
<222> LOCATION: (1)..(5)
<223> OTHER INFORMATION: peptide motif (resilin)

<400> SEQUENCE: 10

Gly Pro Gly Gly Gly
1               5
```

```
<210> SEQ ID NO 11
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 11

Gly Pro Gly Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
<223> OTHER INFORMATION: Ax peptide motif

<400> SEQUENCE: 12

Ala Ala Ala Ala Ala
1               5

<210> SEQ ID NO 13
<211> LENGTH: 6
<212> TYPE: PRT
<213> ORGANISM: Araneus diadematus
<220> FEATURE:
<221> NAME/KEY: REPEAT
<222> LOCATION: (1)..(6)
<223> OTHER INFORMATION: Ax peptide motif (ADF 3)

<400> SEQUENCE: 13

Ala Ala Ala Ala Ala Ala
1               5

<210> SEQ ID NO 14
<211> LENGTH: 7
<212> TYPE: PRT
<213> ORGANISM: Araneus diadematus
<220> FEATURE:
<221> NAME/KEY: REPEAT
<222> LOCATION: (1)..(7)
<223> OTHER INFORMATION: Ax peptide motif (ADF-4)

<400> SEQUENCE: 14

Ala Ala Ala Ala Ala Ala Ala
1               5

<210> SEQ ID NO 15
<211> LENGTH: 8
<212> TYPE: PRT
<213> ORGANISM: Araneus diadematus
<220> FEATURE:
<221> NAME/KEY: REPEAT
<222> LOCATION: (1)..(8)
<223> OTHER INFORMATION: Ax peptide motif (ADF-4)

<400> SEQUENCE: 15

Ala Ala Ala Ala Ala Ala Ala Ala
1               5

<210> SEQ ID NO 16
<211> LENGTH: 9
```

<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(9)
<223> OTHER INFORMATION: Ax peptide motif

<400> SEQUENCE: 16

Ala Ala Ala Ala Ala Ala Ala Ala Ala
1               5

<210> SEQ ID NO 17
<211> LENGTH: 10
<212> TYPE: PRT
<213> ORGANISM: Araneus diadematus
<220> FEATURE:
<221> NAME/KEY: REPEAT
<222> LOCATION: (1)..(10)
<223> OTHER INFORMATION: Ax peptide motif (ADF-4)

<400> SEQUENCE: 17

Ala Ala Ala Ala Ala Ala Ala Ala Ala Ala
1               5                  10

<210> SEQ ID NO 18
<211> LENGTH: 9
<212> TYPE: PRT
<213> ORGANISM: Unknown
<220> FEATURE:
<223> OTHER INFORMATION: Anthropoda
<220> FEATURE:
<221> NAME/KEY: REPEAT
<222> LOCATION: (1)..(9)
<223> OTHER INFORMATION: peptide motif (based on resilin)

<400> SEQUENCE: 18

Gly Gly Arg Pro Ser Asp Thr Tyr Gly
1               5

<210> SEQ ID NO 19
<211> LENGTH: 9
<212> TYPE: PRT
<213> ORGANISM: Unknown
<220> FEATURE:
<223> OTHER INFORMATION: Anthropoda
<220> FEATURE:
<221> NAME/KEY: REPEAT
<222> LOCATION: (1)..(9)
<223> OTHER INFORMATION: peptide motif (based on resilin)

<400> SEQUENCE: 19

Gly Gly Arg Pro Ser Ser Ser Tyr Gly
1               5

<210> SEQ ID NO 20
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module A (ADF-3)

<400> SEQUENCE: 20

Gly Pro Tyr Gly Pro Gly Ala Ser Ala Ala Ala Ala Ala Ala Gly Gly
1               5                  10                  15

Tyr Gly Pro Gly Ser Gly Gln Gln
            20

<210> SEQ ID NO 21
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module C (ADF-4)

<400> SEQUENCE: 21

Gly Ser Ser Ala Ala Ala Ala Ala Ala Ala Ser Gly Pro Gly Gly
1               5                   10                  15

Tyr Gly Pro Glu Asn Gln Gly Pro Ser Gly Pro Gly Gly Tyr Gly Pro
            20                  25                  30

Gly Gly Pro
        35

<210> SEQ ID NO 22
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(20)
<223> OTHER INFORMATION: Module Q (ADF-3)

<400> SEQUENCE: 22

Gly Pro Gly Gln Gln Gly Pro Gly Gln Gln Gly Pro Gly Gln Gln Gly
1               5                   10                  15

Pro Gly Gln Gln
        20

<210> SEQ ID NO 23
<211> LENGTH: 27
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(27)
<223> OTHER INFORMATION: Module K (flagelliform protein)

<400> SEQUENCE: 23

Gly Pro Gly Gly Ala Gly Gly Pro Tyr Gly Pro Gly Gly Ala Gly Gly
1               5                   10                  15

Pro Tyr Gly Pro Gly Gly Ala Gly Gly Pro Tyr
            20                  25

<210> SEQ ID NO 24
<211> LENGTH: 28
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(28)
<223> OTHER INFORMATION: Module sp (flagelliform protein)

<400> SEQUENCE: 24

Gly Gly Thr Thr Ile Ile Glu Asp Leu Asp Ile Thr Ile Asp Gly Ala
1               5                   10                  15

Asp Gly Pro Ile Thr Ile Ser Glu Glu Leu Thr Ile
            20                  25

<210> SEQ ID NO 25
<211> LENGTH: 34
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(34)
<223> OTHER INFORMATION: Module S (Resilin)

<400> SEQUENCE: 25

Pro Gly Ser Ser Ala Ala Ala Ala Ala Ala Ala Ser Gly Pro Gly
1               5                   10                  15

Gln Gly Gln Gly Gln Gly Gln Gly Gln Gly Gly Arg Pro Ser Asp Thr
            20                  25                  30

Tyr Gly

<210> SEQ ID NO 26
<211> LENGTH: 39
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(39)
<223> OTHER INFORMATION: Module R (Resilin)

<400> SEQUENCE: 26

Ser Ala Ala Ala Ala Ala Ala Ala Gly Pro Gly Gly Gly Asn Gly
1               5                   10                  15

Gly Arg Pro Ser Asp Thr Tyr Gly Ala Pro Gly Gly Gly Asn Gly Gly
            20                  25                  30

Arg Pro Ser Ser Ser Tyr Gly
            35

<210> SEQ ID NO 27
<211> LENGTH: 18
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(18)
<223> OTHER INFORMATION: Module X (flagelliform protein)

<400> SEQUENCE: 27

Gly Gly Ala Gly Gly Ala Gly Gly Ala Gly Gly Ser Gly Gly Ala Gly
1               5                   10                  15

Gly Ser

<210> SEQ ID NO 28
<211> LENGTH: 30
<212> TYPE: PRT
<213> ORGANISM: Artificial Sequence
<220> FEATURE:
<223> OTHER INFORMATION: synthetic

```
<220> FEATURE:
<221> NAME/KEY: DOMAIN
<222> LOCATION: (1)..(30)
<223> OTHER INFORMATION: Module Y (flagelliform protein)

<400> SEQUENCE: 28

Gly Pro Gly Gly Ala Gly Pro Gly Gly Tyr Gly Pro Gly Gly Ser Gly
1               5                   10                  15

Pro Gly Gly Tyr Gly Pro Gly Gly Ser Gly Pro Gly Gly Tyr
            20                  25                  30

<210> SEQ ID NO 29
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module Ac

<400> SEQUENCE: 29

Gly Pro Tyr Gly Pro Gly Ala Ser Ala Ala Ala Ala Ala Gly Gly
1               5                   10                  15

Tyr Gly Pro Gly Cys Gly Gln Gln
            20

<210> SEQ ID NO 30
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module Ak

<400> SEQUENCE: 30

Gly Pro Tyr Gly Pro Gly Ala Ser Ala Ala Ala Ala Ala Gly Gly
1               5                   10                  15

Tyr Gly Pro Gly Lys Gly Gln Gln
            20

<210> SEQ ID NO 31
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Cc

<400> SEQUENCE: 31

Gly Ser Ser Ala Ala Ala Ala Ala Ala Ala Ser Gly Pro Gly Gly
1               5                   10                  15

Tyr Gly Pro Glu Asn Gln Gly Pro Cys Gly Pro Gly Tyr Gly Pro
            20                  25                  30

Gly Gly Pro
        35

<210> SEQ ID NO 32
<211> LENGTH: 35
```

```
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ck1

<400> SEQUENCE: 32

Gly Ser Ser Ala Ala Ala Ala Ala Ala Ala Ser Gly Pro Gly Gly
1               5                   10                  15

Tyr Gly Pro Glu Asn Gln Gly Pro Lys Gly Pro Gly Gly Tyr Gly Pro
                20                  25                  30

Gly Gly Pro
        35

<210> SEQ ID NO 33
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ck2

<400> SEQUENCE: 33

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Gly Tyr Gly Pro
                20                  25                  30

Gly Gly Pro
        35

<210> SEQ ID NO 34
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ckc

<400> SEQUENCE: 34

Gly Ser Ser Ala Ala Ala Ala Ala Ala Ala Ser Gly Pro Gly Gly
1               5                   10                  15

Tyr Gly Pro Lys Asn Gln Gly Pro Cys Gly Pro Gly Gly Tyr Gly Pro
                20                  25                  30

Gly Gly Pro
        35

<210> SEQ ID NO 35
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG cys1

<400> SEQUENCE: 35
```

```
Gly Cys Gly Gly Gly Gly Gly Ser Gly Gly Gly
1               5                   10
```

<210> SEQ ID NO 36
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG cys2

<400> SEQUENCE: 36

```
Gly Cys Gly Gly Gly Gly Gly Gly
1               5
```

<210> SEQ ID NO 37
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(14)
<223> OTHER INFORMATION: TAG cys3

<400> SEQUENCE: 37

```
Gly Cys Gly Gly Ser Gly Gly Gly Ser Gly Gly Gly Gly
1               5                   10
```

<210> SEQ ID NO 38
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG lys1

<400> SEQUENCE: 38

```
Gly Lys Gly Gly Gly Gly Gly Gly Ser Gly Gly Gly Gly
1               5                   10
```

<210> SEQ ID NO 39
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG lys2

<400> SEQUENCE: 39

```
Gly Lys Gly Gly Gly Gly Gly Gly
1               5
```

<210> SEQ ID NO 40
<211> LENGTH: 5
<212> TYPE: PRT
<213> ORGANISM: Unknown
<220> FEATURE:
<223> OTHER INFORMATION: Anthropoda

```
<220> FEATURE:
<221> NAME/KEY: REPEAT
<222> LOCATION: (1)..(5)
<223> OTHER INFORMATION: peptide motif (resilin)

<400> SEQUENCE: 40

Gly Pro Gly Gln Gly
1               5

<210> SEQ ID NO 41
<211> LENGTH: 124
<212> TYPE: PRT
<213> ORGANISM: Artificial Sequence
<220> FEATURE:
<223> OTHER INFORMATION: based on ADF-3
<220> FEATURE:
<221> NAME/KEY: DOMAIN
<222> LOCATION: (1)..(124)
<223> OTHER INFORMATION: NR3 (ADF-3)

<400> SEQUENCE: 41

Gly Ala Ala Ser Ala Ala Val Ser Val Gly Gly Tyr Gly Pro Gln Ser
1               5                   10                  15

Ser Ser Ala Pro Val Ala Ser Ala Ala Ala Ser Arg Leu Ser Ser Pro
            20                  25                  30

Ala Ala Ser Ser Arg Val Ser Ser Ala Val Ser Ser Leu Val Ser Ser
        35                  40                  45

Gly Pro Thr Asn Gln Ala Ala Leu Ser Asn Thr Ile Ser Ser Val Val
    50                  55                  60

Ser Gln Val Ser Ala Ser Asn Pro Gly Leu Ser Gly Cys Asp Val Leu
65                  70                  75                  80

Val Gln Ala Leu Leu Glu Val Val Ser Ala Leu Val Ser Ile Leu Gly
                85                  90                  95

Ser Ser Ser Ile Gly Gln Ile Asn Tyr Gly Ala Ser Ala Gln Tyr Thr
            100                 105                 110

Gln Met Val Gly Gln Ser Val Ala Gln Ala Leu Ala
        115                 120

<210> SEQ ID NO 42
<211> LENGTH: 109
<212> TYPE: PRT
<213> ORGANISM: Artificial Sequence
<220> FEATURE:
<223> OTHER INFORMATION: based on ADF-4
<220> FEATURE:
<221> NAME/KEY: DOMAIN
<222> LOCATION: (1)..(109)
<223> OTHER INFORMATION: NR4 (ADF-4)

<400> SEQUENCE: 42

Gly Ala Tyr Gly Pro Ser Pro Ser Ala Ser Ala Ser Val Ala Ala Ser
1               5                   10                  15

Arg Leu Ser Ser Pro Ala Ala Ser Ser Arg Val Ser Ser Ala Val Ser
            20                  25                  30

Ser Leu Val Ser Ser Gly Pro Thr Asn Gly Ala Ala Val Ser Gly Ala
        35                  40                  45

Leu Asn Ser Leu Val Ser Gln Ile Ser Ala Ser Asn Pro Gly Leu Ser
    50                  55                  60

Gly Cys Asp Ala Leu Val Gln Ala Leu Leu Glu Leu Val Ser Ala Leu
65                  70                  75                  80

Val Ala Ile Leu Ser Ser Ala Ser Ile Gly Gln Val Asn Val Ser Ser
                85                  90                  95
```

```
Val Ser Gln Ser Thr Gln Met Ile Ser Gln Ala Leu Ser
            100                 105
```

<210> SEQ ID NO 43
<211> LENGTH: 747
<212> TYPE: PRT
<213> ORGANISM: Araneus diadematus
<220> FEATURE:
<221> NAME/KEY: PEPTIDE
<222> LOCATION: (1)..(747)
<223> OTHER INFORMATION: MaSp I

<400> SEQUENCE: 43

```
Gln Gly Ala Gly Ala Ala Ala Ala Ala Gly Gly Ala Gly Gln Gly
1               5                   10                  15

Gly Tyr Gly Gly Leu Gly Gly Gln Gly Ala Gln Gly Gly Tyr Gly
            20                  25                  30

Gly Leu Gly Gly Gln Gly Ala Gly Gln Gly Ala Gly Ala Ala Ala
            35                  40                  45

Ala Ala Ala Gly Gly Ala Gly Gln Gly Gly Tyr Gly Gly Leu Gly Ser
        50                  55                  60

Gln Gly Ala Gly Arg Gly Gly Gln Gly Ala Gly Ala Ala Ala Ala
65                  70                  75                  80

Ala Gly Gly Ala Gly Gln Gly Gly Tyr Gly Gly Leu Gly Ser Gln Gly
            85                  90                  95

Ala Gly Arg Gly Gly Leu Gly Gly Gln Gly Ala Gly Ala Ala Ala
            100                 105                 110

Ala Ala Ala Gly Gly Ala Gly Gln Gly Gly Tyr Gly Gly Leu Gly Asn
            115                 120                 125

Gln Gly Ala Gly Arg Gly Gly Gln Gly Ala Ala Ala Ala Ala Gly
            130                 135                 140

Gly Ala Gly Gln Gly Gly Tyr Gly Gly Leu Gly Ser Gln Gly Ala Gly
145                 150                 155                 160

Arg Gly Gly Leu Gly Gly Gln Gly Ala Gly Ala Ala Ala Ala Ala
            165                 170                 175

Gly Gly Ala Gly Gln Gly Gly Tyr Gly Gly Leu Gly Gly Gln Gly Ala
            180                 185                 190

Gly Gln Gly Gly Tyr Gly Gly Leu Gly Ser Gln Gly Ala Gly Arg Gly
            195                 200                 205

Gly Leu Gly Gly Gln Gly Ala Gly Ala Ala Ala Ala Ala Ala Gly
            210                 215                 220

Gly Ala Gly Gln Gly Gly Leu Gly Gly Gln Gly Ala Gly Gln Gly Ala
225                 230                 235                 240

Gly Ala Ser Ala Ala Ala Gly Gly Ala Gly Gln Gly Gly Tyr Gly
            245                 250                 255

Gly Leu Gly Ser Gln Gly Ala Gly Arg Gly Gly Glu Gly Ala Gly Ala
            260                 265                 270

Ala Ala Ala Ala Ala Gly Gly Ala Gly Gln Gly Gly Tyr Gly Gly Leu
            275                 280                 285

Gly Gly Gln Gly Ala Gly Gln Gly Gly Tyr Gly Gly Leu Gly Ser Gln
            290                 295                 300

Gly Ala Gly Arg Gly Gly Leu Gly Gly Gln Gly Ala Gly Ala Ala Ala
305                 310                 315                 320

Ala Gly Gly Ala Gly Gln Gly Gly Leu Gly Gln Gly Ala Gly Gln
            325                 330                 335
```

Gly Ala Gly Ala Ala Ala Ala Gly Gly Ala Gly Gln Gly Gly
            340                 345                 350

Tyr Gly Gly Leu Gly Ser Gln Gly Ala Gly Arg Gly Gly Leu Gly Gly
                355                 360                 365

Gln Gly Ala Gly Ala Val Ala Ala Ala Ala Gly Gly Ala Gly Gln
            370                 375                 380

Gly Gly Tyr Gly Gly Leu Gly Ser Gln Gly Ala Gly Arg Gly Gly Gln
385                 390                 395                 400

Gly Ala Gly Ala Ala Ala Ala Ala Gly Ala Gly Gln Arg Gly
            405                 410                 415

Tyr Gly Gly Leu Gly Asn Gln Gly Ala Gly Arg Gly Gly Leu Gly Gly
            420                 425                 430

Gln Gly Ala Gly Ala Ala Ala Ala Ala Gly Gly Ala Gly Gln
            435                 440                 445

Gly Gly Tyr Gly Gly Leu Gly Asn Gln Gly Ala Gly Arg Gly Gly Gln
450                 455                 460

Gly Ala Ala Ala Ala Gly Gly Ala Gly Gln Gly Gly Tyr Gly Gly
465                 470                 475                 480

Leu Gly Ser Gln Gly Ala Gly Arg Gly Gly Gln Gly Ala Gly Ala Ala
                485                 490                 495

Ala Ala Ala Ala Val Gly Ala Gly Gln Glu Gly Ile Arg Gly Gln Gly
            500                 505                 510

Ala Gly Gln Gly Gly Tyr Gly Gly Leu Gly Ser Gln Gly Ser Gly Arg
            515                 520                 525

Gly Gly Leu Gly Gly Gln Gly Ala Gly Ala Ala Ala Ala Ala Gly
            530                 535                 540

Gly Ala Gly Gln Gly Gly Leu Gly Gly Gln Gly Ala Gly Gln Gly Ala
545                 550                 555                 560

Gly Ala Ala Ala Ala Ala Gly Gly Val Arg Gln Gly Gly Tyr Gly
            565                 570                 575

Gly Leu Gly Ser Gln Gly Ala Gly Arg Gly Gly Gln Gly Ala Gly Ala
            580                 585                 590

Ala Ala Ala Ala Ala Gly Gly Ala Gly Gln Gly Gly Tyr Gly Gly Leu
            595                 600                 605

Gly Gly Gln Gly Val Gly Arg Gly Gly Leu Gly Gly Gln Gly Ala Gly
            610                 615                 620

Ala Ala Ala Ala Gly Gly Ala Gly Gln Gly Gly Tyr Gly Gly Val Gly
625                 630                 635                 640

Ser Gly Ala Ser Ala Ala Ser Ala Ala Ala Ser Arg Leu Ser Ser Pro
                645                 650                 655

Gln Ala Ser Ser Arg Val Ser Ser Ala Val Ser Asn Leu Val Ala Ser
            660                 665                 670

Gly Pro Thr Asn Ser Ala Ala Leu Ser Ser Thr Ile Ser Asn Val Val
            675                 680                 685

Ser Gln Ile Gly Ala Ser Asn Pro Gly Leu Ser Gly Cys Asp Val Leu
            690                 695                 700

Ile Gln Ala Leu Leu Glu Val Val Ser Ala Leu Ile Gln Ile Leu Gly
705                 710                 715                 720

Ser Ser Ser Ile Gly Gln Val Asn Tyr Gly Ser Ala Gly Gln Ala Thr
                725                 730                 735

Gln Ile Val Gly Gln Ser Val Tyr Gln Ala Leu
            740                 745

<210> SEQ ID NO 44
<211> LENGTH: 627
<212> TYPE: PRT
<213> ORGANISM: Araneus diadematus
<220> FEATURE:
<221> NAME/KEY: PEPTIDE
<222> LOCATION: (1)..(627)
<223> OTHER INFORMATION: MaSp II

<400> SEQUENCE: 44

```
Pro Gly Gly Tyr Gly Pro Gly Gln Gln Gly Pro Gly Gly Tyr Gly Pro
1               5                   10                  15

Gly Gln Gln Gly Pro Ser Gly Pro Gly Ser Ala Ala Ala Ala Ala Ala
            20                  25                  30

Ala Ala Ala Gly Pro Gly Gly Tyr Gly Pro Gly Gln Gln Gly Pro
        35                  40                  45

Gly Gly Tyr Gly Pro Gly Gln Gln Gly Pro Gly Arg Tyr Gly Pro Gly
    50                  55                  60

Gln Gln Gly Pro Ser Gly Pro Gly Ser Ala Ala Ala Ala Ala Gly
65                  70                  75                  80

Ser Gly Gln Gln Gly Pro Gly Tyr Gly Pro Arg Gln Gln Gly Pro
            85                  90                  95

Gly Gly Tyr Gly Gln Gly Gln Gln Gly Pro Ser Gly Pro Gly Ser Ala
            100                 105                 110

Ala Ala Ser Ala Ala Ala Ser Ala Glu Ser Gly Gln Gln Gly Pro
        115                 120                 125

Gly Gly Tyr Gly Pro Gly Gln Gln Gly Pro Gly Gly Tyr Gly Pro Gly
    130                 135                 140

Gln Gln Gly Pro Gly Gly Tyr Gly Pro Gly Gln Gln Gly Pro Ser Gly
145                 150                 155                 160

Pro Gly Ser Ala Ala Ala Ala Ala Ala Ser Gly Pro Gly Gln
            165                 170                 175

Gln Gly Pro Gly Gly Tyr Gly Pro Gly Gln Gln Gly Pro Gly Gly Tyr
        180                 185                 190

Gly Pro Gly Gln Gln Gly Pro Ser Gly Pro Gly Ser Ala Ala Ala Ala
    195                 200                 205

Ala Ala Ala Ser Gly Pro Gly Gln Gln Gly Pro Gly Gly Tyr Gly
        210                 215                 220

Pro Gly Gln Gln Gly Pro Gly Tyr Gly Pro Gly Gln Gln Gly Leu
225                 230                 235                 240

Ser Gly Pro Gly Ser Ala Ala Ala Ala Ala Ala Gly Pro Gly Gln
            245                 250                 255

Gln Gly Pro Gly Gly Tyr Gly Pro Gly Gln Gln Gly Pro Ser Gly Pro
            260                 265                 270

Gly Ser Ala Ala Ala Ala Ala Ala Ala Gly Pro Gly Gly Tyr
        275                 280                 285

Gly Pro Gly Gln Gln Gly Pro Gly Gly Tyr Gly Pro Gly Gln Gln Gly
    290                 295                 300

Pro Ser Gly Ala Gly Ser Ala Ala Ala Ala Ala Gly Pro Gly
305                 310                 315                 320

Gln Gln Gly Leu Gly Gly Tyr Gly Pro Gly Gln Gln Gly Pro Gly Gly
            325                 330                 335

Tyr Gly Pro Gly Gln Gln Gly Pro Gly Gly Tyr Gly Pro Gly Ser Ala
        340                 345                 350

Ser Ala Ala Ala Ala Ala Ala Gly Pro Gly Gln Gln Gly Pro Gly Gly
    355                 360                 365
```

```
Tyr Gly Pro Gly Gln Gln Gly Pro Ser Gly Pro Ser Ala Ser Ala
        370                 375                 380

Ala Ala Ala Ala Ala Ala Gly Pro Gly Gly Tyr Gly Pro Gly Gln
385                 390                 395                 400

Gln Gly Pro Gly Gly Tyr Ala Pro Gly Gln Gln Gly Pro Ser Gly Pro
            405                 410                 415

Gly Ser Ala Ser Ala Ala Ala Ala Ala Ala Gly Pro Gly Gly
            420                 425                 430

Tyr Gly Pro Gly Gln Gln Gly Pro Gly Gly Tyr Ala Pro Gly Gln Gln
            435                 440                 445

Gly Pro Ser Gly Pro Gly Ser Ala Ala Ala Ala Ala Ala Ala
        450                 455                 460

Gly Pro Gly Gly Tyr Gly Pro Ala Gln Gln Gly Pro Ser Gly Pro Gly
465                 470                 475                 480

Ile Ala Ala Ser Ala Ala Ser Ala Gly Pro Gly Gly Tyr Gly Pro Ala
            485                 490                 495

Gln Gln Gly Pro Ala Gly Tyr Gly Pro Gly Ser Ala Val Ala Ala Ser
            500                 505                 510

Ala Gly Ala Gly Ser Ala Gly Tyr Gly Pro Gly Ser Gln Ala Ser Ala
        515                 520                 525

Ala Ala Ser Arg Leu Ala Ser Pro Asp Ser Gly Ala Arg Val Ala Ser
530                 535                 540

Ala Val Ser Asn Leu Val Ser Ser Gly Pro Thr Ser Ser Ala Ala Leu
545                 550                 555                 560

Ser Ser Val Ile Ser Asn Ala Val Ser Gln Ile Gly Ala Ser Asn Pro
            565                 570                 575

Gly Leu Ser Gly Cys Asp Val Leu Ile Gln Ala Leu Leu Glu Ile Val
            580                 585                 590

Ser Ala Cys Val Thr Ile Leu Ser Ser Ser Ile Gly Gln Val Asn
        595                 600                 605

Tyr Gly Ala Ala Ser Gln Phe Ala Gln Val Val Gly Gln Ser Val Leu
        610                 615                 620

Ser Ala Phe
625

<210> SEQ ID NO 45
<211> LENGTH: 140
<212> TYPE: PRT
<213> ORGANISM: Araneus diadematus (NR3 from ADF-3)

<400> SEQUENCE: 45

Met Ala Ser Met Thr Gly Gly Gln Gln Met Gly Arg Gly Ser Met Gly
1               5                   10                  15

Ala Ala Ser Ala Ala Val Ser Val Gly Gly Tyr Gly Pro Gln Ser Ser
            20                  25                  30

Ser Ala Pro Val Ala Ser Ala Ala Ser Arg Leu Ser Ser Pro Ala
        35                  40                  45

Ala Ser Ser Arg Val Ser Ser Ala Val Ser Ser Leu Val Ser Ser Gly
    50                  55                  60

Pro Thr Asn Gln Ala Ala Leu Ser Asn Thr Ile Ser Ser Val Val Ser
65                  70                  75                  80

Gln Val Ser Ala Ser Asn Pro Gly Leu Ser Gly Cys Asp Val Leu Val
            85                  90                  95

Gln Ala Leu Leu Glu Val Val Ser Ala Leu Val Ser Ile Leu Gly Ser
```

```
                100                 105                 110
Ser Ser Ile Gly Gln Ile Asn Tyr Gly Ala Ser Ala Gln Tyr Thr Gln
            115                 120                 125
Met Val Gly Gln Ser Val Ala Gln Ala Leu Ala Gly
        130                 135                 140

<210> SEQ ID NO 46
<211> LENGTH: 125
<212> TYPE: PRT
<213> ORGANISM: Araneus diadematus (NR4 from ADF-4)

<400> SEQUENCE: 46

Met Ala Ser Met Thr Gly Gly Gln Gln Met Gly Arg Gly Ser Met Gly
1               5                   10                  15
Ala Tyr Gly Pro Ser Pro Ser Ala Ser Ala Ser Val Ala Ala Ser Arg
            20                  25                  30
Leu Ser Ser Pro Ala Ala Ser Ser Arg Val Ser Ser Ala Val Ser Ser
        35                  40                  45
Leu Val Ser Ser Gly Pro Thr Asn Gly Ala Ala Val Ser Gly Ala Leu
    50                  55                  60
Asn Ser Leu Val Ser Gln Ile Ser Ala Ser Asn Pro Gly Leu Ser Gly
65                  70                  75                  80
Cys Asp Ala Leu Val Gln Ala Leu Leu Glu Leu Val Ser Ala Leu Val
                85                  90                  95
Ala Leu Leu Ser Ser Ala Ser Ile Gly Gln Val Asn Val Ser Ser Val
            100                 105                 110
Ser Gln Ser Thr Gln Met Ile Ser Gln Ala Leu Ser Gly
        115                 120                 125

<210> SEQ ID NO 47
<211> LENGTH: 652
<212> TYPE: PRT
<213> ORGANISM: Araneus diadematus (ADF-3)

<400> SEQUENCE: 47

Met Ala Ser Met Thr Gly Gly Gln Gln Met Gly Arg Asp Pro Asn Ser
1               5                   10                  15
Ala Arg Ala Gly Ser Gly Gln Gln Gly Pro Gly Gln Gln Gly Pro Gly
            20                  25                  30
Gln Gln Gly Pro Gly Gln Gln Gly Pro Tyr Gly Pro Gly Ala Ser Ala
        35                  40                  45
Ala Ala Ala Ala Ala Gly Gly Tyr Gly Pro Gly Ser Gly Gln Gln Gly
    50                  55                  60
Pro Ser Gln Gln Gly Pro Gly Gln Gln Gly Pro Gly Gly Gln Gly Pro
65                  70                  75                  80
Tyr Gly Pro Gly Ala Ser Ala Ala Ala Ala Ala Gly Gly Tyr Gly Pro
                85                  90                  95
Pro Gly Ser Gly Gln Gln Gly Pro Gly Gln Gly Pro Tyr Gly Gly
            100                 105                 110
Ser Ser Ala Ala Ala Ala Ala Gly Gly Asn Gly Pro Gly Ser Gly
        115                 120                 125
Gln Gln Gly Pro Gly Gln Gln Gly Pro Gly Gln Gln Gly Pro Gly Ala
    130                 135                 140
Ser Ala Ala Ala Ala Ala Gly Gly Tyr Gly Pro Gly Ser Gly Gln
145                 150                 155                 160
Gln Gly Pro Gly Gln Gln Gly Pro Gly Gly Gln Gly Pro Tyr Gly Pro
```

-continued

```
            165                 170                 175
Gly Ala Ser Ala Ala Ala Ala Ala Gly Gly Tyr Gly Pro Gly Ser
            180                 185                 190
Gly Gln Gln Gly Pro Gly Gln Gln Gly Pro Gly Gln Gln Gly Pro Tyr
            195                 200                 205
Gly Pro Gly Ala Ser Ala Ala Ala Ala Ala Gly Gly Tyr Gly Pro
        210                 215                 220
Gly Ser Gly Gln Gln Gly Pro Gly Gln Gln Gly Pro Gly Gln Gln Gly
225                 230                 235                 240
Pro Gly Gln Gly Pro Tyr Gly Pro Gly Ala Ser Ala Ala Ala Ala
                245                 250                 255
Ala Ala Gly Gly Tyr Gly Pro Gly Tyr Gly Gln Gln Gly Pro Gly Gln
                260                 265                 270
Gln Gly Pro Gly Gln Gly Pro Tyr Gly Pro Gly Ala Ser Ala Ala
                275                 280                 285
Ser Ala Ala Ser Gly Gly Tyr Gly Pro Gly Ser Gly Gln Gln Gly Pro
            290                 295                 300
Gly Gln Gln Gly Pro Gly Gln Gly Pro Tyr Gly Pro Gly Ala Ser
305                 310                 315                 320
Ala Ala Ala Ala Ala Ala Gly Gly Tyr Gly Pro Gly Ser Gly Gln Gln
                325                 330                 335
Gly Pro Gly Gln Gln Gly Pro Gln Gln Gly Pro Gly Gln Gln Gly
        340                 345                 350
Pro Gly Gln Gly Pro Tyr Gly Pro Gly Ala Ser Ala Ala Ala Ala
            355                 360                 365
Ala Ala Gly Gly Tyr Gly Pro Gly Ser Gly Gln Gln Gly Pro Gly Gln
            370                 375                 380
Gln Gly Pro Gly Gln Gln Gly Pro Gly Gln Gln Gly Pro Gly Gln Gln
385                 390                 395                 400
Gly Pro Gly Gln Gln Gly Pro Gly Gln Gln Gly Pro Gly Gln Gln Gly
                405                 410                 415
Pro Gly Gln Gln Gly Pro Gly Gly Gln Gly Ala Tyr Gly Pro Gly Ala
            420                 425                 430
Ser Ala Ala Ala Gly Ala Ala Gly Gly Tyr Gly Pro Gly Ser Gly Gln
            435                 440                 445
Gln Gly Pro Gly Gln Gln Gly Pro Gly Gln Gln Gly Pro Gly Gln Gln
            450                 455                 460
Gly Pro Gly Gln Gln Gly Pro Gly Gln Gln Gly Pro Gly Gln Gln Gly
465                 470                 475                 480
Pro Gly Gln Gln Gly Pro Tyr Gly Pro Gly Ala Ser Ala Ala Ala
                485                 490                 495
Ala Ala Gly Gly Tyr Gly Pro Gly Ser Gly Gln Gln Gly Pro Gly Gln
                500                 505                 510
Gln Gly Pro Gly Gln Gln Gly Pro Val Gly Gln Gly Pro Tyr Gly Pro
            515                 520                 525
Gly Ala Ala Ser Ala Ala Val Ser Val Gly Gly Tyr Gly Pro Gln Ser
            530                 535                 540
Ser Ser Ala Pro Val Ala Ser Ala Ala Ser Arg Leu Ser Ser Pro
545                 550                 555                 560
Ala Ala Ser Ser Arg Val Ser Ser Ala Val Ser Ser Leu Val Ser Ser
                565                 570                 575
Gly Pro Thr Asn Gln Ala Ala Leu Ser Asn Thr Ile Ser Ser Val Val
                580                 585                 590
```

```
Ser Gln Val Ser Ala Ser Asn Pro Gly Leu Ser Gly Cys Asp Val Leu
            595                 600                 605

Val Gln Ala Leu Leu Glu Val Val Ser Ala Leu Val Ser Ile Leu Gly
        610                 615                 620

Ser Ser Ile Gly Gln Ile Asn Tyr Gly Ala Ser Ala Gln Tyr Thr
625                 630                 635                 640

Gln Met Val Gly Gln Ser Val Ala Gln Ala Leu Ala
            645                 650

<210> SEQ ID NO 48
<211> LENGTH: 672
<212> TYPE: PRT
<213> ORGANISM: Araneus diadematus (ADF-4)

<400> SEQUENCE: 48

Met Ala Ser Met Thr Gly Gly Gln Gln Met Gly Arg Ala Ala Arg Ala
1               5                   10                  15

Gly Ser Ser Ala Ala Ala Ala Ala Ala Ser Gly Ser Gly Gly Tyr
            20                  25                  30

Gly Pro Glu Asn Gln Gly Pro Ser Gly Pro Val Ala Tyr Gly Pro Gly
        35                  40                  45

Gly Pro Val Ser Ser Ala Ala Ala Ala Ala Ala Gly Ser Gly Pro
50                  55                  60

Gly Gly Tyr Gly Pro Glu Asn Gln Gly Pro Ser Gly Pro Gly Gly Tyr
65                  70                  75                  80

Gly Pro Gly Gly Ser Gly Ser Ser Ala Ala Ala Ala Ala Ala Ala
                85                  90                  95

Ser Gly Pro Gly Gly Tyr Gly Pro Gly Ser Gln Gly Pro Ser Gly Pro
            100                 105                 110

Gly Gly Ser Gly Gly Tyr Gly Pro Gly Ser Gln Gly Pro Ser Gly Pro
        115                 120                 125

Gly Ala Ser Ala Ala Ala Ala Ala Ala Ala Ser Gly Pro Gly
    130                 135                 140

Gly Tyr Gly Pro Gly Ser Gln Gly Pro Ser Gly Pro Gly Ala Tyr Gly
145                 150                 155                 160

Pro Gly Gly Pro Gly Ser Ser Ala Ala Ala Ser Gly Pro Gly Gly Tyr
                165                 170                 175

Gly Pro Gly Ser Gln Gly Pro Ser Gly Pro Gly Gly Ser Gly Gly Tyr
            180                 185                 190

Gly Pro Gly Ser Gln Gly Pro Ser Gly Pro Gly Gly Pro Gly Ala Ser
        195                 200                 205

Ala Ala Ala Ala Ala Ala Ala Ala Ser Gly Pro Gly Gly Tyr Gly
    210                 215                 220

Pro Gly Ser Gln Gly Pro Ser Gly Pro Gly Ala Tyr Gly Pro Gly Gly
225                 230                 235                 240

Pro Gly Ser Ser Ala Ala Ala Ser Gly Pro Gly Gly Tyr Gly Pro Gly
                245                 250                 255

Ser Gln Gly Pro Ser Gly Pro Gly Ala Tyr Gly Pro Gly Gly Pro Gly
            260                 265                 270

Ser Ser Ala Ala Ala Ala Ala Ala Gly Ser Gly Pro Gly Gly Tyr
        275                 280                 285

Gly Pro Gly Asn Gln Gly Pro Ser Gly Pro Gly Gly Tyr Gly Pro Gly
    290                 295                 300

Gly Pro Gly Ser Ser Ala Ala Ala Ala Ala Ala Ala Ser Gly Pro Gly
```

```
                305                 310                 315                 320
Gly Tyr Gly Pro Gly Ser Gln Gly Pro Ser Gly Pro Gly Val Tyr Gly
                325                 330                 335

Pro Gly Gly Pro Gly Ser Ser Ala Ala Ala Ala Ala Ala Ala Gly Ser
                340                 345                 350

Gly Pro Gly Gly Tyr Gly Pro Gly Asn Gln Gly Pro Ser Gly Pro Gly
                355                 360                 365

Gly Tyr Gly Pro Gly Gly Ser Gly Ser Ser Ala Ala Ala Ala Ala Ala
                370                 375                 380

Ala Ala Ser Gly Pro Gly Gly Tyr Gly Pro Gly Ser Gln Gly Pro Ser
385                 390                 395                 400

Gly Pro Gly Gly Ser Gly Gly Tyr Gly Pro Gly Ser Gln Gly Pro Ser
                405                 410                 415

Gly Pro Gly Ala Ser Ser Ala Ala Ala Ala Ala Ala Ala Ala Ser Gly
                420                 425                 430

Pro Gly Gly Tyr Gly Pro Gly Ser Gln Gly Pro Ser Gly Pro Gly Ala
                435                 440                 445

Tyr Gly Pro Gly Gly Pro Gly Ser Ser Ala Ala Ala Ser Gly Pro Gly
                450                 455                 460

Gly Tyr Gly Pro Gly Ser Gln Gly Pro Ser Gly Pro Gly Ala Tyr Gly
465                 470                 475                 480

Pro Gly Gly Pro Gly Ser Ser Ala Ala Ala Ala Ala Ala Ser Gly
                485                 490                 495

Pro Gly Gly Tyr Gly Pro Gly Ser Gln Gly Pro Ser Gly Pro Gly Gly
                500                 505                 510

Ser Arg Gly Tyr Gly Pro Gly Ser Gln Gly Pro Gly Gly Pro Gly Ala
                515                 520                 525

Ser Ala Ala Ala Ala Ala Ala Ala Ser Gly Pro Gly Gly Tyr
                530                 535                 540

Gly Pro Gly Ser Gln Gly Pro Ser Gly Pro Gly Tyr Gln Gly Pro Ser
545                 550                 555                 560

Gly Pro Gly Ala Tyr Gly Pro Ser Pro Ser Ala Ser Ala Ser Val Ala
                565                 570                 575

Ala Ser Arg Leu Ser Ser Pro Ala Ala Ser Ser Arg Val Ser Ser Ala
                580                 585                 590

Val Ser Ser Leu Val Ser Gly Pro Thr Asn Gly Ala Ala Val Ser
                595                 600                 605

Gly Ala Leu Asn Ser Leu Val Ser Gln Ile Ser Ala Ser Asn Pro Gly
                610                 615                 620

Leu Ser Gly Cys Asp Ala Leu Val Gln Ala Leu Leu Glu Leu Val Ser
625                 630                 635                 640

Ala Leu Val Ala Ile Leu Ser Ser Ala Ser Ile Gly Gln Val Asn Val
                645                 650                 655

Ser Ser Val Ser Gln Ser Thr Gln Met Ile Ser Gln Ala Leu Ser Gly
                660                 665                 670

<210> SEQ ID NO 49
<211> LENGTH: 360
<212> TYPE: PRT
<213> ORGANISM: Araneus diadematus (Fibroin 1)

<400> SEQUENCE: 49

His Glu Ser Ser Tyr Ala Ala Met Ala Ala Ser Thr Arg Asn Ser
1               5                   10                  15
```

```
Asp Phe Ile Arg Asn Met Ser Tyr Gln Met Gly Arg Leu Leu Ser Asn
                20                  25                  30

Ala Gly Ala Ile Thr Glu Ser Thr Ala Ser Ser Ala Ala Ser Ser Ala
            35                  40                  45

Ser Ser Thr Val Thr Glu Ser Ile Arg Thr Tyr Gly Pro Ala Ala Ile
50                  55                  60

Phe Ser Gly Ala Gly Ala Gly Ala Gly Val Gly Val Gly Gly Ala Gly
65                  70                  75                  80

Gly Tyr Gly Gln Gly Tyr Gly Ala Gly Ala Gly Ala Gly Ala Gly Ala
                85                  90                  95

Gly Ala Gly Ala Gly Gly Ala Gly Tyr Gly Gln Gly Tyr Gly Ala
            100                 105                 110

Gly Ala Ala Ala Ala Gly Ala Gly Ala Gly Ala Ala Gly Gly Tyr
            115                 120                 125

Gly Gly Gly Ser Gly Ala Gly Ala Gly Ala Gly Gly Tyr Gly Gln
            130                 135                 140

Gly Tyr Gly Ala Gly Ser Gly Ala Gly Ala Gly Ala Ala Ala Ala
145                 150                 155                 160

Gly Ala Ser Ala Gly Ala Ala Gly Gly Tyr Gly Gly Gly Ala Gly Val
            165                 170                 175

Gly Ala Gly Ala Gly Ala Gly Ala Ala Gly Gly Tyr Gly Gln Ser Tyr
            180                 185                 190

Gly Ser Gly Ala Gly Ala Gly Ala Gly Ala Gly Ala Ala Ala Ala
            195                 200                 205

Gly Ala Gly Ala Arg Ala Ala Gly Gly Tyr Gly Gly Tyr Gly Ala
210                 215                 220

Gly Ala Gly Ala Gly Ala Gly Ala Ala Ala Ser Ala Gly Ala Ser Gly
225                 230                 235                 240

Gly Tyr Gly Gly Gly Tyr Gly Gly Ala Gly Ala Gly Ala Val Ala
            245                 250                 255

Gly Ala Ser Ala Gly Ser Tyr Gly Gly Ala Val Asn Arg Leu Ser Ser
            260                 265                 270

Ala Gly Ala Ala Ser Arg Val Ser Ser Asn Val Ala Ala Ile Ala Ser
            275                 280                 285

Ala Gly Ala Ala Ala Leu Pro Asn Val Ile Ser Asn Ile Tyr Ser Gly
            290                 295                 300

Val Leu Ser Ser Gly Val Ser Ser Ser Glu Ala Leu Ile Gln Ala Leu
305                 310                 315                 320

Leu Glu Val Ile Ser Ala Leu Ile His Val Leu Gly Ser Ala Ser Ile
                325                 330                 335

Gly Asn Val Ser Ser Val Gly Val Asn Ser Ala Leu Asn Ala Val Gln
            340                 345                 350

Asn Ala Val Gly Ala Tyr Ala Gly
            355                 360

<210> SEQ ID NO 50
<211> LENGTH: 294
<212> TYPE: PRT
<213> ORGANISM: Araneus diadematus (Fibroin 2)

<400> SEQUENCE: 50

Gly Ser Gln Gly Ala Gly Gly Ala Gly Gln Gly Gly Tyr Gly Ala Gly
1               5                   10                  15

Gly Gly Gly Ala Ala Ala Ala Ala Ala Ala Ala Val Gly Ala Gly Gly
            20                  25                  30
```

Gly Gly Gln Gly Gly Leu Gly Ser Gly Gly Ala Gly Gln Gly Tyr Gly
            35                  40                  45

Ala Gly Leu Gly Gly Gln Gly Ala Ser Ala Ala Ala Ala Ala
    50                  55                  60

Gly Gly Gln Gly Gly Gln Gly Gly Gln Gly Gly Tyr Gly Gly Leu Gly
65                  70                  75                  80

Ser Gln Gly Ala Gly Ala Gly Gln Leu Gly Tyr Gly Ala Gly Gln
                85                  90                  95

Glu Ser Ala Ala Ala Ala Ala Ala Gly Ala Gly Gly
            100                 105                 110

Gly Gln Gly Gly Leu Gly Ala Gly Ala Gly Gln Gly Tyr Gly Ala
            115                 120                 125

Ala Gly Leu Gly Gly Gln Gly Gly Ala Gly Gln Gly Gly Ser Gly
            130                 135                 140

Ala Ala Ala Ala Ala Gly Gly Gln Gly Gly Gln Gly Gly Tyr Gly Gly
145                 150                 155                 160

Leu Gly Pro Gln Gly Ala Gly Ala Gly Gln Gly Gly Tyr Gly Gly
                165                 170                 175

Gly Ser Leu Gln Tyr Gly Gly Gln Gly Gln Ala Gln Ala Ala Ala
            180                 185                 190

Ser Ala Ala Ala Ser Arg Leu Ser Ser Pro Ser Ala Ala Arg Val
            195                 200                 205

Ser Ser Ala Val Ser Leu Val Ser Asn Gly Gly Pro Thr Ser Pro Ala
            210                 215                 220

Ala Leu Ser Ser Ser Ile Ser Asn Val Val Ser Gln Ile Ser Ala Ser
225                 230                 235                 240

Asn Pro Gly Leu Ser Gly Cys Asp Ile Leu Val Gln Ala Leu Leu Glu
                245                 250                 255

Ile Ile Ser Ala Leu Val His Ile Leu Gly Ser Ala Asn Ile Gly Pro
            260                 265                 270

Val Asn Ser Ser Ser Ala Gly Gln Ser Ala Ser Ile Val Gly Gln Ser
            275                 280                 285

Val Tyr Arg Ala Leu Ser
    290

<210> SEQ ID NO 51
<211> LENGTH: 636
<212> TYPE: PRT
<213> ORGANISM: Araneus diadematus (Fibroin 3)

<400> SEQUENCE: 51

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
            20                  25                  30

Ala Ala Ala Ala Ala Gly Gly Tyr Gly Pro Gly Ser Gly Gln Gln Gly
            35                  40                  45

Pro Ser Gln Gln Gly Pro Gly Gln Gln Gly Gly Gln Gly Pro
    50                  55                  60

Tyr Gly Pro Gly Ala Ser Ala Ala Ala Ala Ala Gly Gly Tyr Gly
65                  70                  75                  80

Pro Gly Ser Gly Gln Gln Gly Pro Gly Gln Gly Pro Tyr Gly Pro
                85                  90                  95

Gly Ser Ser Ala Ala Ala Ala Ala Ala Gly Gly Asn Gly Pro Gly Ser

```
                100                 105                 110
Gly Gln Gln Gly Ala Gly Gln Gln Gly Pro Gly Gln Gln Gly Pro Gly
            115                 120                 125

Ala Ser Ala Ala Ala Ala Ala Gly Gly Tyr Gly Pro Gly Ser Gly
130                 135                 140

Gln Gln Gly Pro Gly Gln Gln Gly Pro Gly Gln Gly Pro Tyr Gly
145                 150                 155                 160

Pro Gly Ala Ser Ala Ala Ala Ala Ala Gly Gly Tyr Gly Pro Gly
                165                 170                 175

Ser Gly Gln Gly Pro Gly Gln Gly Pro Gly Gln Gly Pro Tyr
            180                 185                 190

Gly Pro Gly Ala Ser Ala Ala Ala Ala Ala Gly Gly Tyr Gly Pro
            195                 200                 205

Gly Ser Gly Gln Gln Gly Pro Gly Gln Gln Gly Pro Gly Gln Gln Gly
            210                 215                 220

Pro Gly Gln Gly Pro Tyr Gly Pro Gly Ala Ser Ala Ala Ala Ala
225                 230                 235                 240

Ala Ala Gly Gly Tyr Gly Pro Gly Tyr Gly Gln Gln Gly Pro Gly Gln
                245                 250                 255

Gln Gly Pro Gly Gly Gln Gly Pro Tyr Gly Pro Gly Ala Ser Ala Ala
            260                 265                 270

Ser Ala Ala Ser Gly Gly Tyr Gly Pro Gly Ser Gly Gln Gln Gly Pro
            275                 280                 285

Gly Gln Gln Gly Pro Gly Gln Gly Pro Tyr Gly Pro Gly Ala Ser
            290                 295                 300

Ala Ala Ala Ala Ala Gly Gly Tyr Gly Pro Gly Ser Gly Gln Gln
305                 310                 315                 320

Gly Pro Gly Gln Gln Gly Pro Gly Gln Gln Gly Pro Gly Gln Gln Gly
                325                 330                 335

Pro Gly Gly Gln Gly Pro Tyr Gly Pro Gly Ala Ser Ala Ala Ala Ala
            340                 345                 350

Ala Ala Gly Gly Tyr Gly Pro Gly Ser Gly Gln Gln Gly Pro Gly Gln
            355                 360                 365

Gln Gly Pro Gly Gln Gln Gly Pro Gly Gln Gln Gly Pro Gly Gln Gln
            370                 375                 380

Gly Pro Gly Gln Gln Gly Pro Gly Gln Gln Gly Pro Gly Gln Gln Gly
385                 390                 395                 400

Pro Gly Gln Gln Gly Pro Gly Gly Gln Gly Ala Tyr Gly Pro Gly Ala
                405                 410                 415

Ser Ala Ala Ala Gly Ala Ala Gly Gly Tyr Gly Pro Gly Ser Gly Gln
            420                 425                 430

Gln Gly Pro Gly Gln Gln Gly Pro Gly Gln Gln Gly Pro Gly Gln Gln
            435                 440                 445

Gly Pro Gly Gln Gln Gly Pro Gly Gln Gln Gly Pro Gly Gln Gln Gly
            450                 455                 460

Pro Gly Gln Gln Gly Pro Tyr Gly Pro Gly Ala Ser Ala Ala Ala Ala
465                 470                 475                 480

Ala Ala Gly Gly Tyr Gly Pro Gly Ser Gly Gln Gln Gly Pro Gly Gln
                485                 490                 495

Gln Gly Pro Gly Gln Gln Gly Pro Gly Gly Gln Gly Pro Tyr Gly Pro
            500                 505                 510

Gly Ala Ala Ser Ala Ala Val Ser Val Gly Gly Tyr Gly Pro Gln Ser
            515                 520                 525
```

```
Ser Ser Val Pro Val Ala Ser Val Ala Ser Arg Leu Ser Ser Pro
    530                 535                 540
Ala Ala Ser Ser Arg Val Ser Ser Ala Val Ser Ser Leu Val Ser Ser
545                 550                 555                 560
Gly Pro Thr Lys His Ala Ala Leu Ser Asn Thr Ile Ser Ser Val Val
                565                 570                 575
Ser Gln Val Ser Ala Ser Asn Pro Gly Leu Ser Gly Cys Asp Val Leu
                580                 585                 590
Val Gln Ala Leu Leu Glu Val Val Ser Ala Leu Val Ser Ile Leu Gly
            595                 600                 605
Ser Ser Ser Ile Gly Gln Ile Asn Tyr Gly Ala Ser Ala Gln Tyr Thr
    610                 615                 620
Gln Met Val Gly Gln Ser Val Ala Gln Ala Leu Ala
625                 630                 635

<210> SEQ ID NO 52
<211> LENGTH: 410
<212> TYPE: PRT
<213> ORGANISM: Araneus diadematus (Fibroin 4)

<400> SEQUENCE: 52

Ala Gly Ser Ser Ala Ala Ala Ala Ala Ala Ser Gly Ser Gly Gly
1               5                   10                  15
Tyr Gly Pro Glu Asn Gln Gly Pro Ser Gly Pro Val Ala Tyr Gly Pro
                20                  25                  30
Gly Gly Pro Val Ser Ser Ala Ala Ala Ala Ala Gly Ser Gly
            35                  40                  45
Pro Gly Gly Tyr Gly Pro Glu Asn Gln Gly Pro Ser Gly Pro Gly Gly
    50                  55                  60
Tyr Gly Pro Gly Gly Ser Gly Ser Ser Ala Ala Ala Ala Ala Ala
65                  70                  75                  80
Ala Ser Gly Pro Gly Gly Tyr Gly Pro Gly Ser Gln Gly Pro Ser Gly
                85                  90                  95
Pro Gly Gly Ser Gly Gly Tyr Gly Pro Gly Ser Gln Gly Ala Ser Gly
            100                 105                 110
Pro Gly Gly Pro Gly Ala Ser Ala Ala Ala Ala Ala Ala Ala
        115                 120                 125
Ala Ser Gly Pro Gly Gly Tyr Gly Pro Gly Ser Gln Gly Pro Ser Gly
    130                 135                 140
Pro Gly Ala Tyr Gly Pro Gly Gly Pro Gly Ser Ser Ala Ala Ala Ala
145                 150                 155                 160
Ala Ala Ala Ala Ser Gly Pro Gly Gly Tyr Gly Pro Gly Ser Gln Gly
                165                 170                 175
Pro Ser Gly Pro Gly Val Tyr Gly Pro Gly Gly Pro Gly Ser Ser Ala
            180                 185                 190
Ala Ala Ala Ala Ala Gly Ser Gly Pro Gly Gly Tyr Gly Pro Glu
        195                 200                 205
Asn Gln Gly Pro Ser Gly Pro Gly Gly Tyr Gly Pro Gly Gly Ser Gly
    210                 215                 220
Ser Ser Ala Ala Ala Ala Ala Ala Ala Gly Pro Gly Gly Tyr
225                 230                 235                 240
Gly Pro Gly Ser Gln Gly Pro Ser Gly Pro Gly Gly Ser Gly Gly Tyr
                245                 250                 255
Gly Pro Gly Ser Gln Gly Gly Ser Gly Pro Gly Ala Ser Ala Ala Ala
```

```
                        260                 265                 270
Ala Ala Ala Ala Ala Ser Gly Pro Gly Gly Tyr Gly Pro Gly Ser Gln
            275                 280                 285

Gly Pro Ser Gly Pro Gly Tyr Gln Gly Pro Ser Gly Pro Gly Ala Tyr
            290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
                325                 330                 335

Ser Ser Gly Pro Thr Asn Gly Ala Ala Val Ser Gly Ala Leu Asn Ser
            340                 345                 350

Leu Val Ser Gln Ile Ser Ala Ser Asn Pro Gly Leu Ser Gly Cys Asp
        355                 360                 365

Ala Leu Val Gln Ala Leu Leu Glu Leu Val Ser Ala Leu Val Ala Ile
    370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
                405                 410

<210> SEQ ID NO 53
<211> LENGTH: 251
<212> TYPE: PRT
<213> ORGANISM: Nephila clavipes (MaSp I)

<400> SEQUENCE: 53

Ala Gly Gln Gly Gly Leu Gly Gly Gln Gly Ala Gly Gln Gly Ala Gly
1               5                   10                  15

Ala Ala Ala Ala Ala Ala Gly Gly Ala Gly Gln Gly Gly Tyr Gly Gly
            20                  25                  30

Leu Gly Ser Gln Gly Ala Gly Arg Gly Gly Leu Gly Gly Gln Gly Ala
        35                  40                  45

Gly Ala Ala Ala Ala Ala Gly Gly Ala Gly Gln Gly Gly Tyr Gly Gly
    50                  55                  60

Gly Leu Gly Gly Gln Gly Ala Gly Gln Gly Ala Gly Gln Gly Gly Tyr
65                  70                  75                  80

Gly Gly Leu Gly Ser Gln Gly Ala Gly Arg Gly Gly Gln Gly Ala Gly
            85                  90                  95

Ala Ala Ala Ala Ala Gly Gly Ala Gly Gln Gly Gly Tyr Gly Gly
            100                 105                 110

Leu Gly Gly Gln Gly Val Gly Arg Gly Gly Leu Gly Gly Gln Gly Ala
        115                 120                 125

Ala Ala Ala Gly Gly Ala Gly Gln Gly Gly Tyr Gly Gly Val Gly Ser
    130                 135                 140

Gly Ala Ser Ala Ala Ser Ala Ala Ala Ser Arg Leu Ser Ser Pro Gln
145                 150                 155                 160

Ala Ser Ser Arg Val Ser Ser Ala Val Ser Asn Leu Val Ala Ser Gly
                165                 170                 175

Pro Thr Asn Ser Ala Ala Leu Ser Ser Thr Ile Ser Asn Val Val Ser
            180                 185                 190

Gln Ile Gly Ala Ser Asn Pro Gly Leu Ser Gly Cys Asp Val Leu Ile
        195                 200                 205

Gln Ala Leu Leu Glu Val Val Ser Ala Leu Ile His Ile Leu Gly Ser
    210                 215                 220
```

```
Ser Ser Ile Gly Gln Val Asn Tyr Gly Ser Ala Gly Gln Ala Thr Gln
225                 230                 235                 240

Ile Val Gly Gln Ser Val Tyr Gln Ala Leu Gly
            245                 250
```

<210> SEQ ID NO 54
<211> LENGTH: 379
<212> TYPE: PRT
<213> ORGANISM: Nephila clavipes (MaSp I)

<400> SEQUENCE: 54

```
Gly Gly Gln Gly Ala Gly Arg Gly Ala Gly Ala Ala Ala Ala Ala Ala
1               5                   10                  15

Gly Gly Ala Gly Gln Gly Gly Tyr Gly Gly Leu Gly Gly Gln Gly Ala
                20                  25                  30

Gly Gln Gly Ala Gly Ala Ala Ala Ala Ala Ala Gly Gly Ala Gly Gln
            35                  40                  45

Gly Gly Tyr Gly Gly Leu Gly Ser Gln Gly Ala Gly Arg Gly Gly Tyr
        50                  55                  60

Gly Gly Gln Gly Ala Glu Ala Ala Ala Ala Ala Ala Gly Ala
65                  70                  75                  80

Ala Gln Gly Gly Gln Gly Leu Gly Gly Gln Gly Ala Ala Ala Ala Ala
                85                  90                  95

Gly Gly Ala Gly Gln Gly Gly Phe Gly Gly Leu Gly Gly Gln Gly Ala
            100                 105                 110

Gly Ala Ala Ala Ala Ala Gly Gly Ala Gly Gln Gly Gly Tyr Gly
        115                 120                 125

Gly Leu Gly Ser Gln Gly Ala Gly Arg Gly Gly Ala Ala Ala Ala
    130                 135                 140

Ala Ala Gly Gly Ala Gly Gln Gly Gly Tyr Gly Gly Leu Gly Gly Gln
145                 150                 155                 160

Gly Ala Gly Arg Gly Ala Gly Ala Ala Ala Ala Ala Gly Gly Ala
            165                 170                 175

Ala Gln Gly Gly Tyr Gly Asp Leu Gly Ser Gln Gly Ala Gly Ala Ala
        180                 185                 190

Ala Ala Ala Ala Gly Ser Ala Gly Gln Gly Gly Tyr Gly Gly Leu Gly
    195                 200                 205

Gly Gln Gly Ala Gly Gln Gly Ala Gly Ala Ala Ala Ala Ala Gly
210                 215                 220

Ser Ala Gly Gln Gly Gly Leu Gly Gly Arg Ala Gly Gln Gly Ala Gly
225                 230                 235                 240

Ala Ala Ser Ala Ala Ala Gly Gly Ala Gly Gln Gly Gly Tyr Gly Gly
            245                 250                 255

Leu Gly Gly Gln Gly Ala Gly Gln Gly Gly Tyr Gly Gly Val Gly Ser
        260                 265                 270

Gly Ala Ser Ala Ala Ser Ser Ala Ala Ser Arg Leu Ser Ser Pro Glu
    275                 280                 285

Ala Ser Ser Arg Val Ser Ser Ala Val Ser Asn Leu Val Ser Ser Gly
290                 295                 300

Pro Thr Asn Ser Ala Ala Leu Ser Ser Thr Ile Ser Asn Val Val Ser
305                 310                 315                 320

Gln Ile Gly Ala Ser Asn Pro Gly Leu Ser Gly Cys Asp Val Leu Val
            325                 330                 335

Gln Ala Leu Leu Glu Val Val Ser Ala Leu Ile His Ile Leu Gly Ser
        340                 345                 350
```

```
Ser Ser Ile Gly Gln Val Asn Tyr Gly Ser Ala Gly Gln Ala Thr Gln
        355                 360                 365

Ile Val Gly Gln Ser Ile Tyr Gln Ala Leu Gly
    370                 375

<210> SEQ ID NO 55
<211> LENGTH: 387
<212> TYPE: PRT
<213> ORGANISM: Nephila clavipes (MaSp I)

<400> SEQUENCE: 55

Ala Gly Ala Ala Ala Ala Gly Ser Ala Gly Gln Gly Gly Tyr Gly
1               5                   10                  15

Gly Gln Gly Ala Gly Gln Gly Gly Tyr Gly Gly Leu Gly Ser Gln Gly
            20                  25                  30

Ala Gly Arg Gly Gly Leu Gly Gly Gln Gly Ala Gly Ala Ala Ala
        35                  40                  45

Ala Ala Ala Gly Gly Ala Gly Gln Gly Gly Leu Gly Gly Gln Gly Ala
50                  55                  60

Gly Gln Gly Ala Gly Ala Ala Ala Ala Ala Gly Gly Ala Gly Gln
65                  70                  75                  80

Gly Gly Tyr Gly Gly Leu Gly Asn Gln Gly Ala Gly Arg Gly Gly Gln
                85                  90                  95

Gly Ala Ala Ala Ala Ala Gly Gly Ala Gly Gln Gly Gly Tyr Gly
            100                 105                 110

Gly Leu Gly Ser Gln Gly Ala Gly Arg Gly Gly Leu Gly Gly Gln Gly
            115                 120                 125

Ala Gly Ala Ala Ala Ala Ala Gly Gly Ala Gly Gln Gly Gly Tyr
        130                 135                 140

Gly Gly Leu Gly Gly Gln Gly Ala Gly Gln Gly Gly Tyr Gly Gly Leu
145                 150                 155                 160

Gly Ser Gln Gly Ser Gly Arg Gly Gly Leu Gly Gly Gln Gly Ala Gly
                165                 170                 175

Ala Ala Ala Ala Ala Ala Gly Gly Ala Gly Gln Gly Gly Leu Gly Gly
            180                 185                 190

Gln Gly Ala Gly Gln Gly Ala Gly Ala Ala Ala Ala Ala Gly Gly
        195                 200                 205

Val Arg Gln Gly Gly Tyr Gly Gly Leu Gly Ser Gln Gly Ala Gly Arg
210                 215                 220

Gly Gly Gln Gly Ala Gly Ala Ala Ala Ala Ala Gly Gly Ala Gly
225                 230                 235                 240

Gln Gly Gly Tyr Gly Gly Leu Gly Gly Gln Gly Val Gly Arg Gly Gly
                245                 250                 255

Leu Gly Gly Gln Gly Ala Gly Ala Ala Ala Gly Gly Ala Gly Gln
            260                 265                 270

Gly Gly Tyr Gly Gly Val Gly Ser Gly Ala Ser Ala Ala Ser Ala Ala
            275                 280                 285

Ala Ser Arg Leu Ser Ser Pro Gln Ala Ser Ser Arg Val Ser Ser Ala
        290                 295                 300

Val Ser Asn Leu Val Ala Ser Gly Pro Thr Asn Ser Ala Ala Leu Ser
305                 310                 315                 320

Ser Thr Ile Ser Asn Val Val Ser Gln Ile Gly Ala Ser Asn Pro Gly
                325                 330                 335

Leu Ser Gly Cys Asp Val Leu Ile Gln Ala Leu Leu Glu Val Val Ser
```

```
            340                 345                 350
Ala Leu Ile His Ile Leu Gly Ser Ser Ile Gly Gln Val Asn Tyr
            355                 360                 365
Gly Ser Ala Gly Gln Ala Thr Gln Ile Val Gly Gln Ser Val Tyr Gln
    370                 375                 380
Ala Leu Gly
385

<210> SEQ ID NO 56
<211> LENGTH: 431
<212> TYPE: PRT
<213> ORGANISM: Nephila clavipes (MaSp I)

<400> SEQUENCE: 56

Gly Gly Leu Gly Ile Gln Gly Ser Gly Arg Gly Gly Leu Gly Gly Gln
1               5                   10                  15
Gly Ala Val Ala Ala Ala Ala Ala Ala Gly Gly Ala Val Gln Val
            20                  25                  30
Val Leu Gly Gly Gln Gly Ala Gly Gln Gly Ala Gly Ala Ala Ala
        35                  40                  45
Ala Ala Gly Gly Ala Gly Gln Gly Gly Tyr Gly Gly Leu Gly Ser Gln
    50                  55                  60
Gly Ala Gly Arg Gly Gly Gln Gly Ala Gly Ala Arg Thr Ala Ala Ala
65                  70                  75                  80
Val Gly Ala Gly Gln Gly Gly Tyr Gly Gly Gln Gly Ala Gly Gln Gly
                85                  90                  95
Gly Tyr Gly Gly Leu Gly Ser Gln Gly Ala Gly Arg Gly Gly Leu Gly
            100                 105                 110
Gly Gln Gly Ala Gly Ala Ala Ala Ala Ala Ala Gly Ser Ala Glu
        115                 120                 125
Gln Gly Leu Gly Gly Gln Gly Ala Gly Gln Gly Ala Gly Ala Ala Ala
    130                 135                 140
Ala Ala Ala Gly Gly Ala Gly Gln Gly Gly Tyr Gly Gly Leu Gly Ser
145                 150                 155                 160
Gln Gly Ala Gly Arg Gly Gly Leu Gly Gly Gln Gly Ala Gly Ala Ala
                165                 170                 175
Ala Ala Ala Ala Gly Gly Ala Gly Gln Gly Gly Tyr Gly Gly Leu Gly
            180                 185                 190
Gly Gln Gly Ala Gly Gln Gly Gly Tyr Gly Gly Leu Gly Ser Gln Gly
        195                 200                 205
Ser Gly Arg Gly Gly Leu Gly Gly Gln Gly Ala Gly Ala Ala Ala Ala
    210                 215                 220
Ala Ala Gly Gly Ala Gly Gln Gly Gly Leu Gly Gly Gln Gly Ala Gly
225                 230                 235                 240
Gln Gly Ala Gly Ala Ala Ala Ala Ala Gly Gly Val Arg Gln Gly
                245                 250                 255
Gly Tyr Gly Gly Leu Gly Ser Gln Gly Ala Gly Arg Gly Gly Gln Gly
            260                 265                 270
Ala Gly Ala Ala Ala Ala Ala Gly Gly Ala Gly Gln Gly Gly Tyr
        275                 280                 285
Gly Gly Leu Gly Gly Gln Gly Val Gly Arg Gly Gly Leu Gly Gly Gln
    290                 295                 300
Gly Ala Gly Ala Ala Ala Ala Gly Gly Ala Gly Gln Gly Gly Tyr Gly
305                 310                 315                 320
```

```
Gly Val Gly Ser Gly Ala Ser Ala Ala Ser Ala Ala Ser Arg Leu
                325                 330                 335

Ser Ser Pro Gln Ala Ser Ser Arg Val Ser Ser Ala Val Ser Asn Leu
            340                 345                 350

Val Ala Ser Gly Pro Thr Asn Ser Ala Ala Leu Ser Ser Thr Ile Ser
                355                 360                 365

Asn Val Ser Gln Ile Gly Ala Ser Asn Pro Gly Leu Ser Gly Cys
            370                 375                 380

Asp Val Leu Ile Gln Ala Leu Leu Glu Val Val Ser Ala Leu Ile His
385                 390                 395                 400

Ile Leu Gly Ser Ser Ile Gly Gln Val Asn Tyr Gly Ser Ala Gly
                405                 410                 415

Gln Ala Thr Gln Ile Val Gly Gln Ser Val Tyr Gln Ala Leu Gly
            420                 425                 430

<210> SEQ ID NO 57
<211> LENGTH: 255
<212> TYPE: PRT
<213> ORGANISM: Nephila clavipes (MaSp I)

<400> SEQUENCE: 57

Gln Gly Thr Asp Ala Ala Ala Ala Ala Gly Gly Ala Gly Gln Gly
1               5                   10                  15

Gly Tyr Gly Gly Leu Gly Gly Gln Gly Ala Gly Gln Gly Tyr Gly
                20                  25                  30

Gly Leu Gly Ser Gln Gly Ser Gly Arg Gly Gly Leu Gly Gly Gln Gly
            35                  40                  45

Ala Gly Ala Ala Ala Ala Ala Gly Gly Ala Gly Gln Gly Ala Gly
    50                  55                  60

Gln Gly Ala Gly Ala Ala Ala Ala Ala Gly Val Arg Gln Gly
65                  70                  75                  80

Gly Tyr Gly Gly Leu Gly Ser Gln Gly Ala Gly Arg Gly Gly Gln Gly
                85                  90                  95

Ala Gly Ala Ala Ala Ala Ala Gly Gly Ala Gly Gln Gly Gly Tyr
            100                 105                 110

Gly Gly Leu Gly Gly Gln Gly Val Gly Arg Gly Gly Leu Gly Gly Gln
            115                 120                 125

Gly Ala Gly Ala Ala Ala Ala Gly Gly Ala Gly Gln Gly Gly Tyr Gly
            130                 135                 140

Gly Val Gly Ser Gly Ala Ser Ala Ala Ser Ala Ala Ala Ser Arg Leu
145                 150                 155                 160

Ser Ser Pro Gln Ala Ser Ser Arg Val Ser Ser Ala Val Ser Asn Leu
                165                 170                 175

Val Ala Ser Gly Pro Thr Asn Ser Ala Ala Leu Ser Ser Thr Ile Ser
            180                 185                 190

Asn Val Ser Gln Ile Gly Ser Ser Asn Pro Gly Leu Ser Gly Cys
                195                 200                 205

Asp Val Leu Ile Gln Ala Leu Leu Glu Val Val Ser Ala Leu Ile Gln
210                 215                 220

Ile Leu Gly Ser Ser Ser Ile Gly Gln Val Asn Tyr Gly Ser Ala Gly
225                 230                 235                 240

Gln Ala Thr Gln Ile Val Gly Gln Ser Val Tyr Gln Ala Leu Gly
            245                 250                 255

<210> SEQ ID NO 58
```

```
<211> LENGTH: 331
<212> TYPE: PRT
<213> ORGANISM: Nephila clavipes (MaSp I)

<400> SEQUENCE: 58
```

Gly Gln Gly Ala Gly Gln Gly Ala Gly Ala Ala Ala Ala Ala Gly
1               5                   10                  15

Gly Ala Gly Gln Gly Gly Tyr Gly Gly Leu Gly Asn Gln Gly Ala Gly
            20                  25                  30

Arg Gly Gly Gln Gly Ala Ala Ala Ala Ala Ala Gly Gly Ala Gly Gln
            35                  40                  45

Gly Gly Tyr Gly Gly Leu Gly Ser Gln Gly Ala Gly Arg Gly Gly Leu
        50                  55                  60

Gly Gly Gln Gly Ala Gly Ala Ala Ala Ala Ala Gly Gly Ala Gly
65                  70                  75                  80

Gln Gly Gly Tyr Gly Gly Leu Gly Gly Gln Gly Ala Gly Gln Gly Ala
                85                  90                  95

Gly Gln Gly Gly Tyr Gly Gly Leu Gly Ile Gln Gly Ser Gly Arg Gly
            100                 105                 110

Gly Leu Gly Gly Gln Gly Ala Gly Ala Ala Ala Ala Ala Gly Gly
        115                 120                 125

Ala Gly Gln Gly Gly Leu Gly Gly Gln Gly Ala Gly Gln Ala Gly
130                 135                 140

Ala Ala Ala Ala Ala Gly Gly Val Arg Gln Gly Gly Tyr Gly Gly
145                 150                 155                 160

Leu Gly Ser Gln Gly Ala Gly Arg Gly Gly Gln Gly Ala Gly Ala Ala
                165                 170                 175

Ala Ala Ala Gly Gly Ala Gly Gln Gly Gly Tyr Gly Gly Leu Gly
            180                 185                 190

Gly Gln Gly Val Gly Arg Gly Gly Leu Gly Gly Gln Gly Ala Gly Ala
                195                 200                 205

Ala Ala Ala Gly Gly Ala Gly Gln Gly Gly Tyr Gly Gly Val Gly Ser
            210                 215                 220

Gly Ala Ser Ala Ala Ser Ala Ala Ser Arg Leu Ser Ser Pro Gln
225                 230                 235                 240

Ala Ser Ser Arg Val Ser Ser Ala Val Ser Asn Leu Val Ala Ser Gly
                245                 250                 255

Pro Thr Asn Ser Ala Ala Leu Ser Ser Thr Ile Ser Asn Val Val Ser
            260                 265                 270

Gln Ile Gly Ala Ser Asn Pro Gly Leu Ser Gly Cys Asp Val Leu Ile
            275                 280                 285

Gln Ala Leu Leu Glu Val Val Ser Ala Leu Ile Gln Ile Leu Gly Ser
            290                 295                 300

Ser Ser Ile Gly Gln Val Asn Tyr Gly Ser Ala Gly Gln Ala Thr Gln
305                 310                 315                 320

Ile Val Gly Gln Ser Val Tyr Gln Ala Leu Gly
                325                 330

```
<210> SEQ ID NO 59
<211> LENGTH: 233
<212> TYPE: PRT
<213> ORGANISM: Nephila madagascariensis (MaSp I)

<400> SEQUENCE: 59
```

Gly Leu Gly Gly Gln Gly Ala Gly Gln Gly Ala Gly Ala Ala Ala Ala
1               5                   10                  15

```
Ala Ala Gly Gly Ala Gly Gln Gly Gly Tyr Gly Gly Leu Gly Ser Gln
            20                  25                  30

Gly Ala Gly Arg Gly Gly Tyr Gly Gly Gln Gly Ala Gly Ala Ala Ala
        35                  40                  45

Ala Ala Ala Ala Gly Gly Ala Gly Gln Gly Gly Tyr Gly Gly Leu Gly
    50                  55                  60

Ser Gln Gly Ala Gly Gln Gly Gly Tyr Gly Gly Leu Gly Gly Gln Gly
65                  70                  75                  80

Ala Gly Gln Gly Ala Ala Ala Ala Ala Ala Gly Gly Ala Gly Gln
            85                  90                  95

Gly Gly Tyr Gly Gly Leu Gly Ser Gln Gly Ala Gly Arg Gly Gly Tyr
            100                 105                 110

Gly Gly Gln Gly Ala Gly Ala Ala Ala Ala Thr Gly Gly Ala Gly
            115                 120                 125

Gln Gly Gly Tyr Gly Gly Val Gly Ser Gly Ala Ser Ala Ala Ser Ala
    130                 135                 140

Ala Ala Ser Arg Leu Ser Ser Pro Gln Ala Ser Ser Arg Val Ser Ser
145                 150                 155                 160

Ala Val Ser Asn Leu Val Ala Ser Gly Pro Thr Asn Ser Ala Ala Leu
                165                 170                 175

Ser Ser Thr Ile Ser Asn Ala Val Ser Gln Ile Gly Ala Ser Asn Pro
            180                 185                 190

Gly Leu Ser Gly Cys Asp Val Leu Ile Gln Ala Leu Leu Glu Val Val
            195                 200                 205

Ser Ala Leu Ile His Ile Leu Gly Ser Ser Ser Ile Gly Gln Val Asn
    210                 215                 220

Tyr Gly Ser Ala Gly Gln Ala Thr Gln
225                 230

<210> SEQ ID NO 60
<211> LENGTH: 284
<212> TYPE: PRT
<213> ORGANISM: Tetragnatha kauaiensis (MaSp I)
<220> FEATURE:
<221> NAME/KEY: misc_feature
<222> LOCATION: (23)..(23)
<223> OTHER INFORMATION: Xaa can be any naturally occurring amino acid

<400> SEQUENCE: 60

Ser Gly Leu Gly Gly Ala Gly Gln Gly Ala Gly Gln Gly Ala Ser Ala
1               5                   10                  15

Ala Ala Ala Ala Ala Xaa Gly Gly Leu Gly Gly Gly Gln Gly Ala
            20                  25                  30

Gly Gln Gly Gly Gln Gln Gly Ala Gly Gln Gly Gly Tyr Gly Ser Gly
        35                  40                  45

Leu Gly Gly Ala Gly Gln Gly Ala Ser Ala Ala Ala Ala Ala Ala
    50                  55                  60

Ala Gly Gly Leu Gly Gly Gln Gly Ala Gly Gln Gly Gly Gln Gln
65                  70                  75                  80

Gly Ala Gly Gln Gly Gly Tyr Gly Ser Gly Leu Gly Gly Ala Gly Gln
            85                  90                  95

Gly Ala Ser Ala Ala Ala Ala Ala Ala Ala Gly Gly Leu Gly Gly
            100                 105                 110

Gly Gln Gly Ala Gly Gln Gly Gly Gln Gln Gly Ala Gly Gln Gly Gly
    115                 120                 125
```

```
Tyr Gly Ser Gly Leu Gly Gly Ala Gly Gln Gly Ala Gly Gln Gly Ala
    130                 135                 140

Ser Ala Ala Ala Ala Ala Ala Gly Gly Leu Gly Gly Gly Gln Gly
145                 150                 155                 160

Gly Tyr Gly Ser Gly Leu Gly Gly Val Gly Gln Gly Gly Gln Gly Ala
                165                 170                 175

Leu Gly Gly Ser Arg Asn Ser Ala Thr Asn Ala Ile Ser Asn Ser Ala
            180                 185                 190

Ser Asn Ala Val Ser Leu Leu Ser Ser Pro Ala Ser Asn Ala Arg Ile
        195                 200                 205

Ser Ser Ala Val Ser Ala Leu Ala Ser Gly Ala Ala Ser Gly Pro Gly
    210                 215                 220

Tyr Leu Ser Ser Val Ile Ser Asn Val Val Ser Gln Val Ser Ser Asn
225                 230                 235                 240

Ser Gly Gly Leu Val Gly Cys Asp Thr Leu Val Gln Ala Leu Leu Glu
                245                 250                 255

Ala Ala Ala Ala Leu Val His Val Leu Ala Ser Ser Ser Gly Gly Gln
            260                 265                 270

Val Asn Leu Asn Thr Ala Gly Tyr Thr Ser Gln Leu
        275                 280

<210> SEQ ID NO 61
<211> LENGTH: 253
<212> TYPE: PRT
<213> ORGANISM: Nephila senegalensis (MaSp I)

<400> SEQUENCE: 61

Gly Leu Gly Gly Gln Gly Ala Gly Arg Gly Ala Gly Ala Ala Ala Ala
1               5                   10                  15

Ala Ala Gly Gly Ala Gly Gln Gly Gly Tyr Gly Gly Leu Gly Gly Gln
            20                  25                  30

Gly Ala Gly Ala Ala Ala Ala Ala Gly Gly Ala Gly Gln Gly Gly
        35                  40                  45

Gln Gly Leu Gly Gly Arg Gly Ala Ala Ala Gly Gly Ala Gly Gln
    50                  55                  60

Gly Gly Tyr Gly Gly Leu Gly Gly Gln Gly Ala Gly Arg Gly Ala Gly
65                  70                  75                  80

Ala Ala Ala Ala Ala Gly Gly Ala Gly Gln Gly Gly Tyr Gly Gly
            85                  90                  95

Leu Gly Gly Gln Gly Ala Gly Ala Ala Ala Ala Ala Ala Ala Gly
            100                 105                 110

Gly Ala Gly Gln Gly Gly Tyr Gly Gly Leu Gly Ser Gln Gly Ala Gly
        115                 120                 125

Arg Gly Gly Tyr Gly Gly Gln Gly Ala Gly Ala Val Ala Ala Ile
    130                 135                 140

Gly Gly Val Gly Gln Gly Gly Tyr Gly Gly Val Gly Ser Gly Ala Ser
145                 150                 155                 160

Ala Ala Ser Ala Ala Ala Ser Arg Leu Ser Ser Pro Glu Ala Ser Ser
                165                 170                 175

Arg Val Ser Ser Ala Val Ser Asn Leu Val Ser Ser Gly Pro Thr Asn
            180                 185                 190

Ser Ala Ala Leu Ser Ser Thr Ile Ser Asn Val Val Ser Gln Ile Gly
        195                 200                 205

Ala Ser Asn Pro Gly Leu Ser Gly Cys Asp Val Leu Ile Gln Ala Leu
    210                 215                 220
```

```
Leu Glu Val Val Ser Ala Leu Val His Ile Leu Gly Ser Ser Ile
225                 230                 235                 240

Gly Gln Val Asn Tyr Gly Ser Ala Gly Gln Ala Thr Gln
            245                 250
```

<210> SEQ ID NO 62
<211> LENGTH: 178
<212> TYPE: PRT
<213> ORGANISM: Tetragnatha versicolor (MaSp I)

<400> SEQUENCE: 62

```
Ser Gly Gln Gly Ala Ser Ala Ala Ala Ala Ala Gly Gly Leu Gly
1               5                   10                  15

Gly Gly Gln Gly Gly Tyr Gly Ser Gly Leu Gly Gly Ala Gly Gln Gly
            20                  25                  30

Gly Gln Gln Gly Ala Gly Gln Gly Ala Ala Ala Ala Ala Ala Ser Ala
            35                  40                  45

Ala Ala Gly Gly Leu Gly Gly Gln Gly Gly Gln Gln Gly Ala Gly
50                  55                  60

Arg Gly Gly Leu Gln Gly Ala Gly Gln Gly Gly Gln Gly Ala Leu Gly
65                  70                  75                  80

Gly Ser Arg Asn Ser Ala Ala Asn Ala Val Ser Arg Leu Ser Ser Pro
            85                  90                  95

Ala Ser Asn Ala Arg Ile Ser Ser Ala Val Ser Ala Leu Ala Ser Gly
            100                 105                 110

Gly Ala Ser Ser Pro Gly Tyr Leu Ser Ser Ile Ile Ser Asn Val Val
            115                 120                 125

Ser Gln Val Ser Ser Asn Asn Asp Gly Leu Ser Gly Cys Asp Thr Val
130                 135                 140

Val Gln Ala Leu Leu Glu Val Ala Ala Ala Leu Val His Val Leu Ala
145                 150                 155                 160

Ser Ser Asn Ile Gly Gln Val Asn Leu Asn Thr Ala Gly Tyr Thr Ser
            165                 170                 175

Gln Leu
```

<210> SEQ ID NO 63
<211> LENGTH: 360
<212> TYPE: PRT
<213> ORGANISM: Latrodectus geometricus (MaSp I)

<400> SEQUENCE: 63

```
Ala Gly Ser Gly Gln Gly Gly Tyr Gly Gln Gly Tyr Gly Glu Gly Gly
1               5                   10                  15

Ala Gly Gln Gly Gly Ala Gly Ala Ala Ala Ala Ala Ala Ala Ala
            20                  25                  30

Gly Gly Ala Gly Gln Gly Gly Gln Gly Gly Tyr Gly Gln Gly Tyr Gly
        35                  40                  45

Gln Gly Gly Ala Gly Gln Gly Gly Ala Gly Ala Ala Ala Ala Ala
    50                  55                  60

Ala Gly Gly Ala Gly Gln Gly Gly Tyr Gly Arg Gly Gly Ala Gly Gln
65                  70                  75                  80

Gly Ala Ala Ala Ala Ala Ala Ala Gly Ser Gly Gln Gly Gly Gln
            85                  90                  95

Gly Gly Tyr Gly Gln Gly Tyr Gly Gln Gly Gly Ala Gly Gln Gly Gly
            100                 105                 110
```

Ala Gly Ala Ala Ala Ala Ala Ala Gly Gly Ala Gly Gln Gly
        115                 120                 125

Gly Tyr Gly Arg Gly Gly Ala Gly Gln Gly Gly Ala Ala Ala Ala
        130                 135                 140

Ala Ala Ala Gly Gly Ala Gly Gln Gly Gly Gln Gly Gly Tyr Gly Gln
145                 150                 155                 160

Gly Tyr Gly Gln Gly Gly Ala Gly Gln Gly Gly Ala Gly Ala Ala Ala
            165                 170                 175

Ala Ala Ala Ala Ala Gly Gly Ala Gly Gln Gly Gly Tyr Gly Arg Gly
        180                 185                 190

Gly Ala Gly Gln Gly Gly Ser Ala Ala Ala Ala Ala Gly Gly
        195                 200                 205

Ala Gly Gln Gly Gly Tyr Gly Arg Gly Gly Ala Gly Gln Gly Gly Ala
        210                 215                 220

Gly Ser Ala Ala Ala Ala Ala Ala Gly Gly Ser Gly Gln Gly Gly
225                 230                 235                 240

Gln Gly Gly Tyr Gly Gln Gly Tyr Gly Gln Gly Gly Ala Gly Gln Gly
            245                 250                 255

Gly Ala Ala Ala Ala Ala Ser Ala Leu Ala Pro Ala Thr Ser Ala
        260                 265                 270

Arg Ile Ser Ser His Ala Ser Thr Leu Leu Ser Asn Gly Pro Thr Asn
275                 280                 285

Pro Ala Ser Ile Ser Asn Val Ile Ser Asn Ala Val Ser Gln Ile Ser
        290                 295                 300

Ser Ser Asn Pro Gly Ala Ser Ser Cys Asp Val Leu Val Gln Ala Leu
305                 310                 315                 320

Leu Glu Leu Val Thr Ala Leu Leu Thr Ile Ile Gly Ser Ser Asn Val
            325                 330                 335

Gly Asn Val Asn Tyr Asp Ser Ser Gly Gln Tyr Ala Gln Val Val Ser
        340                 345                 350

Gln Ser Val Gln Asn Ala Phe Val
        355                 360

<210> SEQ ID NO 64
<211> LENGTH: 648
<212> TYPE: PRT
<213> ORGANISM: Argiope trifasciata (MaSp I)

<400> SEQUENCE: 64

Ala Ala Ala Ala Ala Ala Ala Ala Gly Gly Gln Gly Gly Gln Gly
1               5                   10                  15

Gly Tyr Asp Gly Leu Gly Ser Gln Gly Ala Gly Gln Gly Gly Tyr Gly
            20                  25                  30

Gln Gly Gly Ala Ala Ala Ala Ala Ala Ala Ser Gly Ala Gly Ser
        35                  40                  45

Ala Gln Arg Gly Gly Leu Gly Ala Gly Gly Ala Gly Gln Gly Tyr Gly
    50                  55                  60

Ala Gly Ser Gly Gly Gln Gly Gly Ala Gly Gln Gly Gly Ala Ala Ala
65                  70                  75                  80

Ala Thr Ala Ala Ala Gly Gly Gln Gly Gly Gln Gly Gly Tyr Gly
            85                  90                  95

Gly Leu Gly Ser Gln Gly Ser Gly Gln Gly Gly Tyr Gly Gln Gly Gly
        100                 105                 110

Ala Ala Ala Ala Ala Ala Ala Ser Gly Asp Gly Gly Ala Gly Gln
        115                 120                 125

```
Glu Gly Leu Gly Ala Gly Ala Gly Gln Gly Tyr Gly Ala Gly Leu
    130                 135                 140
Gly Gly Gln Gly Gly Ala Gln Gly Gly Ala Ala Ala Ala Ala Ala
145                 150                 155                 160
Ala Ala Ala Gly Gly Gln Gly Gly Gln Gly Gly Tyr Gly Gly Leu Gly
            165                 170                 175
Ser Gln Gly Ala Gly Gln Gly Gly Tyr Gly Gln Gly Gly Ala Ala Ala
            180                 185                 190
Ala Ala Ala Ala Ala Ser Gly Ala Gly Gly Ala Gly Gln Gly Gly Leu
            195                 200                 205
Gly Ala Ala Gly Ala Gly Gln Gly Tyr Gly Ala Gly Ser Gly Gly Gln
    210                 215                 220
Gly Gly Ala Gly Gln Gly Gly Ala Ala Ala Ala Ala Ala Ala Ala
225                 230                 235                 240
Gly Gly Gln Gly Gly Gln Gly Gly Tyr Gly Gly Leu Gly Ser Gln Gly
                    245                 250                 255
Ala Gly Gln Gly Gly Tyr Gly Gln Gly Gly Val Ala Ala Ala Ala
    260                 265                 270
Ala Ala Ser Gly Ala Gly Gly Ala Gly Arg Gly Gly Leu Gly Ala Gly
        275                 280                 285
Gly Ala Gly Gln Glu Tyr Gly Ala Val Ser Gly Gly Gln Gly Gly Ala
    290                 295                 300
Gly Gln Gly Gly Glu Ala Ala Ala Ala Ala Ala Ala Gly Gly Gln
305                 310                 315                 320
Gly Gly Gln Gly Gly Tyr Gly Gly Leu Gly Ser Gln Gly Ala Gly Gln
                    325                 330                 335
Gly Gly Tyr Gly Gln Gly Gly Ala Ala Ala Ala Ala Ala Ala Ser
            340                 345                 350
Gly Ala Gly Gly Ala Arg Arg Gly Gly Leu Gly Ala Gly Gly Ala Gly
        355                 360                 365
Gln Gly Tyr Gly Ala Gly Leu Gly Gly Gln Gly Gly Ala Gly Gln Gly
    370                 375                 380
Ser Ala Ser Ala Ala Ala Ala Ala Ala Ala Gly Gly Gln Gly Gly Gln
385                 390                 395                 400
Gly Gly Tyr Gly Gly Leu Gly Ser Gln Gly Ser Gly Gln Gly Gly Tyr
                    405                 410                 415
Gly Gln Gly Gly Ala Ala Ala Ala Ala Ala Ala Ser Gly Ala Gly
            420                 425                 430
Gly Ala Gly Arg Gly Ser Leu Gly Ala Gly Ala Gly Gln Gly Tyr
        435                 440                 445
Gly Ala Gly Leu Gly Gly Gln Gly Gly Ala Gly Gln Gly Gly Ala Ala
    450                 455                 460
Ala Ala Ala Ser Ala Ala Ala Gly Gly Gln Gly Gly Gln Gly Gly Tyr
465                 470                 475                 480
Gly Gly Leu Gly Ser Gln Gly Ala Gly Gln Gly Gly Tyr Gly Gln Gly
            485                 490                 495
Gly Ala Ala Ala Ala Ala Ala Ser Ala Gly Gly Gln Gly Gly Gln Gly
            500                 505                 510
Gly Tyr Gly Gly Leu Gly Ser Gln Gly Ala Gly Gln Gly Gly Tyr Gly
        515                 520                 525
Gly Gly Ala Phe Ser Gly Gln Gln Gly Gly Ala Ala Ser Val Ala Thr
    530                 535                 540
```

Ala Ser Ala Ala Ala Ser Arg Leu Ser Ser Pro Gly Ala Ser Arg
545                 550                 555                 560

Val Ser Ser Ala Val Thr Ser Leu Val Ser Ser Gly Gly Pro Thr Asn
            565                 570                 575

Ser Ala Ala Leu Ser Asn Thr Ile Ser Asn Val Val Ser Gln Ile Ser
            580                 585                 590

Ser Ser Asn Pro Gly Leu Ser Gly Cys Asp Val Leu Val Gln Ala Leu
        595                 600                 605

Leu Glu Ile Val Ser Ala Leu Val His Ile Leu Gly Ser Ala Asn Ile
    610                 615                 620

Gly Gln Val Asn Ser Ser Gly Val Gly Arg Ser Ala Ser Ile Val Gly
625                 630                 635                 640

Gln Ser Ile Asn Gln Ala Phe Ser
                645

<210> SEQ ID NO 65
<211> LENGTH: 236
<212> TYPE: PRT
<213> ORGANISM: Nephila clavipes (MaSp II)

<400> SEQUENCE: 65

Gly Gly Tyr Gly Pro Gly Gln Gln Gly Pro Gly Gly Tyr Gly Pro Gly
1               5                   10                  15

Gln Gln Gly Pro Ser Gly Ser Gly Ser Ala Ala Ala Ala Ala Ala Ala
            20                  25                  30

Gly Pro Gly Gln Gln Gly Pro Gly Gly Tyr Gly Pro Gly Gln Gln Gly
        35                  40                  45

Pro Gly Gly Tyr Gly Pro Gly Gln Gln Gly Pro Ser Gly Pro Gly Ser
    50                  55                  60

Ala Ala Ala Ala Ala Ala Ala Ala Gly Gly Tyr Gly Pro
65                  70                  75                  80

Ala Gln Gln Gly Pro Ser Gly Pro Gly Ile Ala Ala Ser Ala Ala Ser
                85                  90                  95

Ala Gly Pro Gly Gly Tyr Gly Pro Ala Gln Gln Gly Pro Ala Gly Tyr
            100                 105                 110

Gly Pro Gly Ser Ala Val Ala Ala Ser Ala Gly Ala Gly Ser Ala Gly
        115                 120                 125

Tyr Gly Pro Gly Ser Gln Ala Ser Ala Ala Ala Ser Arg Leu Ala Ser
    130                 135                 140

Pro Asp Ser Gly Ala Arg Val Ala Ser Ala Val Ser Asn Leu Val Ser
145                 150                 155                 160

Ser Gly Pro Thr Ser Ser Ala Ala Leu Ser Ser Val Ile Ser Asn Ala
                165                 170                 175

Val Ser Gln Ile Gly Ala Ser Asn Pro Gly Leu Ser Gly Cys Asp Val
            180                 185                 190

Leu Ile Gln Ala Leu Leu Glu Ile Val Ser Ala Cys Val Thr Ile Leu
        195                 200                 205

Ser Ser Ser Ser Ile Gly Gln Val Asn Tyr Gly Ala Ala Ser Gln Phe
    210                 215                 220

Ala Gln Val Val Gly Gln Ser Val Leu Ser Ala Phe
225                 230                 235

<210> SEQ ID NO 66
<211> LENGTH: 296
<212> TYPE: PRT
<213> ORGANISM: Nephila clavipes (MaSp II)

<400> SEQUENCE: 66

```
Pro Gly Gly Tyr Gly Pro Gly Gln Gln Gly Pro Ser Gly Ala Gly Ser
1               5                   10                  15

Ala Ala Ala Ala Ala Ala Ala Gly Pro Gly Gln Gln Gly Leu Gly Gly
            20                  25                  30

Tyr Gly Pro Gly Gln Gln Gly Pro Gly Gly Tyr Gly Pro Gly Gln Gln
        35                  40                  45

Gly Pro Gly Gly Tyr Gly Pro Gly Ser Ala Ser Ala Ala Ala Ala Ala
    50                  55                  60

Ala Gly Pro Gly Gln Gln Gly Pro Gly Gly Tyr Gly Pro Gly Gln Gln
65                  70                  75                  80

Gly Pro Ser Gly Pro Gly Ser Ala Ser Ala Ala Ala Ala Ala Ala Ala
            85                  90                  95

Ala Gly Pro Gly Gly Tyr Gly Pro Gly Gln Gln Gly Pro Gly Gly Tyr
            100                 105                 110

Ala Pro Gly Gln Gln Gly Pro Ser Gly Pro Gly Ser Ala Ala Ala Ala
            115                 120                 125

Ala Ala Ala Ala Ala Gly Pro Gly Gly Tyr Gly Pro Ala Gln Gln Gly
    130                 135                 140

Pro Ser Gly Pro Gly Ile Ala Ala Ser Ala Ser Ala Gly Pro Gly Gly
145                 150                 155                 160

Gly Tyr Gly Pro Ala Gln Gln Gly Pro Ala Gly Tyr Gly Pro Gly Ser
                165                 170                 175

Ala Val Ala Ala Ser Ala Gly Ala Gly Ser Ala Gly Tyr Gly Pro Gly
            180                 185                 190

Ser Gln Ala Ser Ala Ala Ala Ser Arg Leu Ala Ser Pro Asp Ser Gly
            195                 200                 205

Ala Arg Val Ala Ser Ala Val Ser Asn Leu Val Ser Ser Gly Pro Thr
            210                 215                 220

Ser Ser Ala Ala Leu Ser Ser Val Ile Ser Asn Ala Val Ser Gln Ile
225                 230                 235                 240

Gly Ala Ser Asn Pro Gly Leu Ser Gly Cys Asp Val Leu Ile Gln Ala
            245                 250                 255

Leu Leu Glu Ile Val Ser Ala Cys Val Thr Ile Leu Ser Ser Ser Ser
            260                 265                 270

Ile Gly Gln Val Asn Tyr Gly Ala Ala Ser Gln Phe Ala Gln Val Val
            275                 280                 285

Gly Gln Ser Val Leu Ser Ala Phe
            290                 295

<210> SEQ ID NO 67
<211> LENGTH: 332
<212> TYPE: PRT
<213> ORGANISM: Nephila clavipes (MaSp II)

<400> SEQUENCE: 67

Gly Pro Gly Gly Tyr Arg Pro Gly Gln Gln Gly Pro Ser Gly Pro Gly
1               5                   10                  15

Ser Ala Ala Ala Ala Ala Ala Ala Ala Gly Pro Gly Gly Tyr Gly
            20                  25                  30

Pro Gly Gln Gln Gly Pro Gly Gly Tyr Gly Pro Gly Gln Gln Gly Pro
        35                  40                  45

Ser Gly Ala Gly Ser Ala Ala Ala Ala Ala Ala Gly Pro Gly Gln
    50                  55                  60
```

```
Gln Gly Leu Gly Gly Tyr Gly Pro Gly Gln Gln Pro Gly Gly Tyr
 65                  70                  75                  80

Gly Pro Gly Gln Gln Gly Pro Gly Tyr Gly Pro Gly Ser Ala Ser
                 85                  90                  95

Ala Ala Ala Ala Ala Ala Gly Pro Gly Gln Gln Gly Pro Gly Gly Tyr
            100                 105                 110

Gly Pro Gly Gln Gln Gly Pro Ser Gly Pro Gly Ser Ala Ser Ala Ala
            115                 120                 125

Ala Ala Ala Ala Gly Pro Gly Tyr Gly Pro Gly Gln Gln Gly Pro
            130                 135                 140

Gly Gly Tyr Ala Pro Gly Gln Gln Gly Pro Ser Gly Pro Gly Ser Ala
145                 150                 155                 160

Ala Ala Ala Ala Ala Ala Arg Ala Gly Pro Gly Gly Tyr Gly Pro
                165                 170                 175

Ala Gln Gln Gly Pro Ser Gly Pro Gly Ile Ala Ala Ser Ala Ala Ser
                180                 185                 190

Ala Gly Pro Gly Gly Tyr Gly Pro Ala Gln Gln Gly Pro Ala Gly Tyr
            195                 200                 205

Gly Pro Gly Ser Ala Val Ala Ala Ser Ala Gly Ala Gly Ser Ala Gly
            210                 215                 220

Tyr Gly Pro Gly Ser Gln Ala Ser Ala Ala Ala Ser Arg Leu Ala Ser
225                 230                 235                 240

Pro Asp Ser Gly Ala Arg Val Ala Ser Ala Val Ser Asn Leu Val Ser
                245                 250                 255

Ser Gly Pro Thr Ser Ser Ala Ala Leu Ser Ser Val Ile Ser Asn Ala
                260                 265                 270

Val Ser Gln Ile Gly Ala Ser Asn Pro Gly Leu Ser Gly Cys Asp Val
                275                 280                 285

Leu Ile Gln Ala Leu Leu Glu Ile Val Ser Ala Cys Val Thr Ile Leu
            290                 295                 300

Ser Ser Ser Ser Ile Gly Gln Val Asn Tyr Gly Ala Ala Ser Gln Phe
305                 310                 315                 320

Ala Gln Val Val Gly Gln Ser Val Leu Ser Ala Phe
                325                 330

<210> SEQ ID NO 68
<211> LENGTH: 313
<212> TYPE: PRT
<213> ORGANISM: Nephila clavipes (MaSp II)

<400> SEQUENCE: 68

Gly Arg Gly Ala Gly Gln Gln Gly Pro Gly Gly Tyr Gly Pro Gly Gln
1               5                   10                  15

Gln Gly Pro Gly Gly Tyr Gly Pro Gly Gln Gln Gly Pro Ser Gly Pro
                20                  25                  30

Gly Ser Ala Ala Ala Ala Ala Ala Ala Ser Gly Pro Gly Gln Gln
            35                  40                  45

Gly Pro Gly Gly Tyr Gly Pro Gly Gln Gln Gly Pro Gly Gly Tyr Gly
            50                  55                  60

Pro Gly Gln Gln Ser Pro Ser Gly Pro Gly Ser Ala Ala Ala Ala
65                  70                  75                  80

Ala Ala Ala Ala Gly Pro Gly Gln Gln Gly Pro Gly Gly Tyr Gly Pro
                85                  90                  95

Gly Gln Gln Gly Pro Ser Gly Pro Gly Ser Ala Ser Ala Ala Ala Ala
```

```
                100                 105                 110
Ala Ala Gly Pro Gly Gly Tyr Gly Pro Gly Gln Gln Gly Pro Gly Gly
            115                 120                 125

Tyr Ala Pro Gly Gln Gln Gly Pro Ser Gly Pro Gly Ser Ala Ala Ala
            130                 135                 140

Ala Ala Ala Arg Ala Gly Pro Gly Gly Tyr Gly Pro Ala Gln Gln
145                 150                 155                 160

Gly Pro Ser Gly Pro Gly Ile Ala Ala Ser Ala Ala Ser Ala Gly Pro
                165                 170                 175

Gly Gly Tyr Gly Pro Ala Gln Gln Gly Pro Ala Gly Tyr Gly Pro Gly
            180                 185                 190

Ser Ala Val Ala Ala Ser Ala Gly Ala Gly Ser Ala Gly Tyr Gly Pro
            195                 200                 205

Gly Ser Gln Ala Ser Ala Ala Ser Arg Leu Ala Ser Pro Asp Ser
            210                 215                 220

Gly Ala Arg Val Ala Ser Ala Val Ser Asn Leu Val Ser Ser Gly Pro
225                 230                 235                 240

Thr Ser Ser Ala Ala Leu Ser Ser Val Ile Ser Asn Ala Val Ser Gln
                245                 250                 255

Ile Gly Ala Ser Asn Pro Gly Leu Ser Gly Cys Asp Val Leu Ile Gln
                260                 265                 270

Ala Leu Leu Glu Ile Val Ser Ala Cys Val Thr Ile Leu Ser Ser Ser
            275                 280                 285

Ser Ile Gly Gln Val Asn Tyr Gly Ala Ala Ser Gln Phe Ala Gln Val
            290                 295                 300

Val Gly Gln Ser Val Leu Ser Ala Phe
305                 310

<210> SEQ ID NO 69
<211> LENGTH: 313
<212> TYPE: PRT
<213> ORGANISM: Nephila clavipes (MaSp II)

<400> SEQUENCE: 69

Ser Ala Ala Ala Ala Ala Ala Ala Ala Gly Pro Gly Gly Tyr Gly
1               5                   10                  15

Pro Gly Gln Gln Gly Pro Gly Gly Tyr Gly Pro Gly Gln Gln Gly Pro
                20                  25                  30

Ser Gly Ala Gly Ser Ala Ala Ala Ala Gly Pro Gly Gln Gln Gly
            35                  40                  45

Leu Gly Gly Tyr Gly Pro Gly Gln Gln Gly Pro Gly Gly Tyr Gly Pro
    50                  55                  60

Gly Gln Gln Gly Pro Gly Gly Tyr Gly Pro Gly Ser Ala Ser Ala Ala
65                  70                  75                  80

Ala Ala Ala Ala Gly Pro Gly Gln Gln Gly Pro Gly Gly Tyr Gly Pro
                85                  90                  95

Gly Gln Gln Gly Pro Ser Gly Pro Gly Ser Ala Ser Ala Ala Ala
            100                 105                 110

Ala Ala Gly Pro Gly Gly Tyr Gly Pro Gly Gln Gln Gly Pro Gly Gly
            115                 120                 125

Tyr Ala Pro Gly Gln Gln Gly Pro Ser Gly Pro Gly Ser Ala Ala Ala
            130                 135                 140

Ala Ala Ala Ala Ala Ala Gly Pro Gly Gly Tyr Gly Pro Ala Gln Gln
145                 150                 155                 160
```

-continued

```
Gly Pro Ser Gly Pro Gly Ile Ala Ala Ser Ala Ala Ser Ala Gly Pro
                165                 170                 175
Gly Gly Tyr Gly Pro Ala Gln Gln Gly Pro Ala Gly Tyr Gly Pro Gly
            180                 185                 190
Ser Ala Val Ala Ala Ser Ala Gly Ala Gly Ser Ala Gly Tyr Gly Pro
            195                 200                 205
Gly Ser Gln Ala Ser Ala Ala Ala Ser Arg Leu Ala Ser Pro Asp Ser
        210                 215                 220
Gly Ala Arg Val Ala Ser Ala Val Ser Asn Leu Val Ser Ser Gly Pro
225                 230                 235                 240
Thr Ser Ser Ala Ala Leu Ser Ser Val Ile Ser Asn Ala Val Ser Gln
                245                 250                 255
Ile Gly Ala Ser Asn Pro Gly Leu Ser Gly Cys Asp Val Leu Ile Gln
            260                 265                 270
Ala Leu Leu Glu Ile Val Ser Ala Cys Val Thr Ile Leu Ser Ser Ser
        275                 280                 285
Ser Ile Gly Gln Val Asn Tyr Gly Ala Ala Ser Gln Phe Ala Gln Val
    290                 295                 300
Val Gly Gln Ser Val Leu Ser Ala Phe
305                 310
```

<210> SEQ ID NO 70
<211> LENGTH: 230
<212> TYPE: PRT
<213> ORGANISM: Nephila senegalensis (MaSp II)
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid

<400> SEQUENCE: 70

```
Gln Gly Pro Gly Gly Tyr Gly Pro Ser Gly Pro Gly Ser Ala Ala Ala
1               5                   10                  15
Ala Ser Ala Ala Ala Gly Pro Gly Gln Gln Gly Pro Gly Ala Tyr Gly
            20                  25                  30
Pro Ser Gly Pro Gly Ser Ala Ala Ala Ala Gly Pro Gly Xaa Tyr
            35                  40                  45
Gly Pro Gly Gln Gln Gly Pro Ser Gly Pro Gly Ala Ala Ala Ala
    50                  55                  60
Ala Gly Pro Gly Gln Gln Gly Pro Gly Tyr Gly Pro Gly Ala Ala
65                  70                  75                  80
Ala Ala Ala Ala Ala Ala Gly Pro Gly Gln Gln Gly Pro Val Ala
                85                  90                  95
Tyr Gly Pro Ser Gly Pro Gly Ser Ala Ala Ser Ala Ala Gly Pro Gly
            100                 105                 110
Gly Tyr Gly Pro Ala Arg Tyr Gly Pro Ser Gly Ser Ala Ala Ala Ala
        115                 120                 125
Ala Ala Ala Gly Ala Gly Ser Ala Gly Tyr Gly Pro Gly Pro Gln Ala
    130                 135                 140
Ser Ala Ala Ala Ser Arg Leu Ala Ser Pro Asp Ser Gly Ala Arg Val
145                 150                 155                 160
```

-continued

```
Ala Ser Ala Val Ser Asn Leu Val Ser Ser Gly Pro Thr Ser Ser Ala
            165                 170                 175

Ala Leu Ser Ser Val Ile Xaa Asn Ala Val Ser Gln Ile Gly Ala Ser
        180                 185                 190

Asn Pro Gly Leu Ser Gly Cys Asp Val Leu Ile Xaa Ala Leu Leu Glu
        195                 200                 205

Ile Val Ser Ala Cys Val Thr Ile Leu Ser Ser Ser Ile Gly Gln
210                 215                 220

Val Asn Tyr Gly Ala Ala
225                 230

<210> SEQ ID NO 71
<211> LENGTH: 563
<212> TYPE: PRT
<213> ORGANISM: Nephila madagascariensis (MaSp II)

<400> SEQUENCE: 71

Gln Gly Pro Ser Gly Pro Gly Ser Ala Ala Ala Ala Ala Ala Ala Gly
1               5                   10                  15

Pro Gly Gln Gln Gly Pro Gly Gly Tyr Gly Pro Gly Gln Gln Gly Pro
            20                  25                  30

Gly Gly Tyr Gly Pro Gly Gln Gln Gly Pro Ser Gly Pro Gly Ser Ala
        35                  40                  45

Ala Ala Ala Ala Ala Ala Ala Gly Pro Gly Gln Gln Gly Pro
    50                  55                  60

Gly Gly Tyr Gly Pro Gly Pro Gln Gly Pro Gly Gly Tyr Gly Pro Gly
65                  70                  75                  80

Gln Gln Gly Pro Ser Gly Tyr Gly Pro Gly Gln Gln Gly Pro Ser Gly
            85                  90                  95

Pro Gly Ser Ala Ala Ser Ala Ala Ala Ala Gly Ser Gly Gln Gln
        100                 105                 110

Gly Pro Gly Gly Tyr Gly Pro Gly Gln Gln Gly Pro Gly Gly Tyr Gly
        115                 120                 125

Pro Gly Gln Gln Gly Pro Ser Gly Pro Gly Ser Ala Ala Ala Ala Ala
    130                 135                 140

Ala Ala Gly Pro Gly Gln Gln Gly Pro Gly Gly Tyr Gly Pro Gly Gln
145                 150                 155                 160

Gln Gly Pro Gly Gly Tyr Gly Pro Gly Gln Gln Gly Pro Ser Gly Pro
            165                 170                 175

Gly Ser Ala Ala Ala Ala Ala Ala Ala Gly Pro Gly Gln Gln Gly
        180                 185                 190

Pro Gly Gly Tyr Gly Pro Gly Gln Gln Gly Pro Gly Gly Tyr Gly Pro
        195                 200                 205

Gly Gln Gln Gly Pro Ser Gly Pro Gly Ser Ala Ala Ala Ala Ala
    210                 215                 220

Ala Gly Pro Gly Gln Gln Gly Pro Gly Gly Tyr Gly Pro Gly Gln Gln
225                 230                 235                 240

Gly Pro Gly Gly Tyr Gly Pro Gly Gln Gln Gly Pro Ser Gly Pro Gly
            245                 250                 255

Ser Ala Ala Ala Ala Ala Ala Ala Gly Pro Gly Gln Gln Gly
        260                 265                 270

Pro Gly Gly Tyr Gly Pro Gly Gln Gln Gly Pro Gly Gln Gln Gly Pro
        275                 280                 285

Ser Gly Pro Gly Ser Ala Ala Ala Ala Ala Ala Ala Gly Pro Gly Pro
```

```
        290                 295                 300
Gln Gly Pro Gly Gly Tyr Pro Gly Gln Gln Gly Pro Gly Tyr
305                 310                 315                 320

Gly Pro Ser Gly Pro Gly Ser Ala Ala Ala Ala Ala Ala Gly
                325                 330                 335

Pro Gly Gln Gln Gly Pro Gly Gly Tyr Gly Pro Gly Gln Arg Pro
                340                 345                 350

Ser Gly Tyr Gly Pro Gly Gln Gln Gly Pro Ser Gly Pro Gly Ser Ala
                355                 360                 365

Ala Ala Ala Ala Ala Ala Gly Pro Gly Gln Gln Gly Pro Gly Ala Tyr
370                 375                 380

Gly Pro Ser Gly Pro Gly Ser Ala Ala Ala Ala Gly Leu Gly Gly
385                 390                 395                 400

Tyr Gly Pro Ala Gln Gln Gly Pro Ser Gly Ala Gly Ser Ala Ala Ala
                405                 410                 415

Ala Ala Ala Ala Gly Pro Gly Gly Tyr Gly Pro Val Gln Gln Gly Pro
                420                 425                 430

Ser Gly Pro Gly Ser Ala Ala Gly Pro Gly Gly Tyr Gly Pro Ala Gln
                435                 440                 445

Gln Gly Pro Ala Arg Tyr Gly Pro Gly Ser Ala Ala Ala Ala Ala
                450                 455                 460

Ala Ala Gly Ser Ala Gly Tyr Gly Pro Gly Pro Gln Ala Ser Ala Ala
465                 470                 475                 480

Ala Ser Arg Leu Ala Ser Pro Asp Ser Gly Ala Arg Val Ala Ser Ala
                485                 490                 495

Val Ser Asn Leu Val Ser Ser Gly Pro Thr Ser Ser Ala Ala Leu Ser
                500                 505                 510

Ser Val Ile Ser Asn Ala Val Ser Gln Ile Gly Ala Ser Asn Pro Gly
                515                 520                 525

Leu Ser Gly Cys Asp Val Leu Ile Gln Ala Leu Leu Glu Ile Val Ser
                530                 535                 540

Ala Cys Val Thr Ile Leu Ser Ser Ser Ile Gly Gln Val Asn Tyr
545                 550                 555                 560

Gly Ala Ala

<210> SEQ ID NO 72
<211> LENGTH: 399
<212> TYPE: PRT
<213> ORGANISM: Latrodectus geometricus (MaSp II)
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid

<400> SEQUENCE: 72
```

```
Ala Gly Pro Gly Ser Tyr Gly Pro Ser Gly Pro Gly Gly Ser Gly Ala
1               5                  10                 15

Ala Ala Ala Ala Ala Ala Ser Gly Pro Gly Gly Gln Gln Gly Tyr
            20                  25                  30

Gly Pro Gly Gly Pro Gly Ala Ser Ala Ala Ala Ala Ala Ala Gly
        35                  40                  45

Gly Ser Gly Pro Gly Gly Tyr Gly Gln Gly Pro Ser Gly Tyr Gly Pro
        50                  55                  60

Ser Gly Pro Gly Ala Gln Gln Gly Tyr Gly Pro Gly Gly Gln Gly Gly
65                  70                  75                  80

Ser Gly Ala Ala Ala Ala Ala Ala Ala Gly Ser Gly Pro Gly
                85                  90                  95

Gly Tyr Gly Pro Gly Ala Ala Gly Pro Gly Asn Tyr Gly Pro Ser Gly
            100                 105                 110

Pro Gly Gly Ser Gly Ala Ala Ser Ala Ala Ala Ser Gly Pro
        115                 120                 125

Gly Gly Gln Gln Gly Tyr Gly Pro Gly Gly Ser Gly Ala Ala Ala
    130                 135                 140

Ala Ala Ser Gly Gly Ala Gly Pro Gly Arg Gln Gln Gly Tyr Gly Pro
145                 150                 155                 160

Gly Gly Ser Gly Ala Ala Ala Ala Ala Ala Xaa Gly Gly Ser
            165                 170                 175

Gly Pro Gly Gly Tyr Gly Gln Gly Pro Xaa Gly Tyr Gly Pro Gly Gly
            180                 185                 190

Gln Gly Gly Ser Gly Gly Ala Ala Ala Ala Ala Ala Ser Ser
        195                 200                 205

Gly Pro Xaa Gly Tyr Gly Pro Gly Ala Ala Gly Pro Gly Asn Tyr Gly
    210                 215                 220

Pro Ser Gly Pro Gly Gly Ser Gly Ala Ala Ala Ala Ala Ala
225                 230                 235                 240

Ser Gly Pro Gly Gly Gln Gln Gly Tyr Gly Pro Gly Gly Ser Gly Ala
            245                 250                 255

Ser Ala Ala Ala Ala Gly Gly Ala Gly Xaa Gly Arg Gln Gln Ala
        260                 265                 270

Tyr Gly Pro Gly Gly Ser Gly Ala Ala Ala Ala Ala Ser Gly Ser
    275                 280                 285

Gly Gly Tyr Gly Pro Ala Gln Tyr Gly Xaa Ser Ser Val Ala Ser Ser
    290                 295                 300

Ala Ala Ser Ala Ala Ser Ala Leu Ser Ser Pro Thr Thr His Ala Arg
305                 310                 315                 320

Ile Ser Ser His Ala Ser Thr Leu Leu Ser Ser Gly Pro Thr Asn Ser
            325                 330                 335

Ala Ala Ile Ser Asn Val Ile Ser Asn Ala Val Ser Gln Val Ser Ala
            340                 345                 350

Ser Asn Pro Gly Ser Ser Ser Cys Asp Val Leu Val Gln Ala Leu Leu
            355                 360                 365

Glu Leu Ile Thr Ala Leu Ile Ser Ile Val Asp Ser Ser Asn Ile Gly
            370                 375                 380

Gln Val Asn Tyr Gly Ser Ser Gly Gln Tyr Ala Gln Met Val Gly
385                 390                 395

<210> SEQ ID NO 73
<211> LENGTH: 444
```

<212> TYPE: PRT
<213> ORGANISM: Argiope trifasciata (MaSp II)

<400> SEQUENCE: 73

```
Ala Gly Pro Gly Tyr Gly Pro Gly Ala Gly Gln Gln Gly Pro Gly Ser
1               5                   10                  15

Gln Gly Pro Gly Ser Gly Gln Gln Gly Pro Gly Gly Gln Gly Pro
            20                  25                  30

Tyr Gly Pro Ser Ala Ala Ala Ala Ala Ala Gly Pro Gly Tyr
            35                  40                  45

Gly Pro Gly Ala Gly Gln Gln Gly Pro Gly Ser Gly Gln Gln Gly
50                  55                  60

Gly Gln Gly Ser Gly Gln Gln Gly Pro Gly Gly Ala Gly Gln Gly Gly
65                  70                  75                  80

Pro Arg Gly Gln Gly Pro Tyr Gly Pro Gly Ala Ala Ala Ala Ala
                85                  90                  95

Ala Ala Gly Gly Tyr Gly Pro Gly Ala Gly Gln Gln Gly Pro Gly Ser
                100                 105                 110

Gln Gly Pro Gly Ser Gly Gln Gln Gly Pro Gly Ser Gln Gly Pro
            115                 120                 125

Tyr Gly Pro Ser Ala Ala Ala Ala Ala Ala Gly Pro Gly Tyr
            130                 135                 140

Gly Pro Gly Ala Gly Gln Gln Gly Pro Gly Ser Gln Gly Pro Gly Ser
145                 150                 155                 160

Gly Gly Gln Gln Gly Pro Gly Gly Pro Tyr Gly Pro Ser Asp
                165                 170                 175

Ala Ala Ala Ala Ala Ala Gly Pro Gly Tyr Gly Pro Gly Ala Gly
            180                 185                 190

Gln Gln Gly Pro Gly Ser Gly Gln Gln Gly Gln Gly Ser Gly
            195                 200                 205

Gln Gln Gly Pro Gly Gly Ala Gly Gln Gly Gly Pro Arg Gly Gln Gly
210                 215                 220

Pro Tyr Gly Pro Gly Ala Ala Ala Ala Ala Ala Ala Gly Gly Tyr
225                 230                 235                 240

Gly Pro Gly Ala Gly Gln Gln Gly Pro Gly Ser Gln Gly Pro Gly Ser
            245                 250                 255

Gly Gly Gln Gln Gly Pro Gly Ser Gln Gly Pro Tyr Gly Pro Ser Ala
            260                 265                 270

Ala Ala Ala Ala Ala Ala Gly Pro Gly Tyr Gly Pro Gly Ala Gly
            275                 280                 285

Gln Gln Gly Pro Gly Ser Gln Gly Pro Gly Ser Gly Gln Gln Gly
            290                 295                 300

Pro Gly Ser Gln Gly Pro Tyr Gly Pro Ser Ala Ala Ala Ala Ala
305                 310                 315                 320

Ala Ala Gly Pro Gly Tyr Gly Pro Gly Ala Gly Gln Gln Gly Pro Gly
                325                 330                 335

Ser Gln Ala Pro Val Ala Ser Ala Ala Ala Ser Arg Leu Ser Ser Pro
            340                 345                 350

Gln Ala Ser Ser Arg Val Ser Ser Ala Val Ser Thr Leu Val Ser Ser
            355                 360                 365

Gly Pro Thr Asn Pro Ala Ser Leu Ser Asn Ala Ile Ser Ser Val Val
            370                 375                 380

Ser Gln Val Ser Ser Asn Pro Gly Leu Ser Gly Cys Asp Val Leu
385                 390                 395                 400
```

-continued

Val Gln Ala Leu Leu Glu Ile Val Ser Ala Leu Val His Ile Leu Gly
                405                 410                 415

Ser Ser Ser Ile Gly Gln Ile Asn Tyr Ala Ala Ser Ser Gln Tyr Ala
                420                 425                 430

Gln Leu Val Gly Gln Ser Leu Thr Gln Ala Leu Gly
            435                 440

<210> SEQ ID NO 74
<211> LENGTH: 349
<212> TYPE: PRT
<213> ORGANISM: Argiope aurantia (MaSp II)
<220> FEATURE:
<221> NAME/KEY: misc_feature
<222> LOCATION: (39)..(39)
<223> OTHER INFORMATION: Xaa can be any naturally occurring amino acid

<400> SEQUENCE: 74

Pro Gly Gly Ala Gly Gln Gln Gly Pro Gly Gln Gly Pro Tyr Gly
1               5                   10                  15

Pro Gly Ala Ala Ala Ala Ala Ala Ala Gly Gly Tyr Gly Pro Gly
                20                  25                  30

Ala Gly Gln Gln Gly Pro Xaa Gly Ala Gly Gln Gln Gly Pro Gly Ser
                35                  40                  45

Gln Gly Pro Gly Gly Ala Gly Gln Gln Gly Pro Gly Gly Gln Gly Pro
            50                  55                  60

Tyr Gly Pro Gly Ala Ala Ala Ala Ala Ala Val Gly Gly Tyr Gly
65                  70                  75                  80

Pro Gly Ala Gly Gln Gln Gly Pro Gly Ser Gln Gly Pro Gly Ser Gly
                85                  90                  95

Gly Gln Gln Gly Pro Gly Gly Gln Gly Pro Tyr Gly Pro Ser Ala Ala
                100                 105                 110

Ala Ala Ala Ala Ala Gly Gly Tyr Gly Pro Gly Ala Gly Gln Gln
            115                 120                 125

Gly Pro Gly Ser Gln Gly Pro Gly Ser Gly Gly Gln Gln Gly Pro Gly
            130                 135                 140

Gly Leu Gly Pro Tyr Gly Pro Ser Ala Ala Ala Ala Ala Ala Ala Ala
145                 150                 155                 160

Gly Gly Tyr Gly Pro Gly Ala Gly Gln Gln Gly Pro Gly Ser Gln Gly
                165                 170                 175

Pro Gly Ser Gly Gly Gln Gln Arg Pro Gly Gly Leu Gly Pro Tyr Gly
            180                 185                 190

Pro Ser Ala Ala Ala Ala Ala Ala Ala Gly Gly Tyr Gly Pro Gly
            195                 200                 205

Ala Gly Gln Gln Gly Pro Gly Ser Gln Gly Pro Gly Ser Gly Gly Gln
            210                 215                 220

Gln Arg Pro Gly Gly Leu Gly Pro Tyr Gly Pro Ser Ala Ala Ala Ala
225                 230                 235                 240

Ala Ala Ala Ala Gly Gly Tyr Gly Pro Gly Ala Gly Gln Gln Gly Pro
                245                 250                 255

Gly Ser Gln Ala Pro Val Ala Ser Ala Ala Ala Ser Arg Leu Ser Ser
            260                 265                 270

Pro Gln Ala Ser Ser Arg Val Ser Ser Ala Val Ser Thr Leu Val Ser
            275                 280                 285

Ser Gly Pro Thr Asn Pro Ala Ala Leu Ser Asn Ala Ile Ser Ser Val
            290                 295                 300

```
Val Ser Gln Val Ser Ala Ser Asn Pro Gly Leu Ser Gly Cys Asp Val
305                 310                 315                 320

Leu Val Gln Ala Leu Leu Glu Leu Val Ser Ala Leu Val His Ile Leu
                325                 330                 335

Gly Ser Ser Ser Ile Gly Gln Ile Asn Tyr Ala Ala Ser
            340                 345
```

<210> SEQ ID NO 75
<211> LENGTH: 231
<212> TYPE: PRT
<213> ORGANISM: Argiope trifasciata (MaSp II)

<400> SEQUENCE: 75

```
Gly Gln Gly Ser Gly Gln Arg Pro Gly Ala Gly Gln Gly Gly
1               5                   10                  15

Leu Gly Pro Tyr Gly Pro Gly Ala Ala Ala Ala Ala Ala Ala
                20                  25                  30

Gly Gly Tyr Gly Pro Gly Ala Gly Gln Gln Pro Gly Ser Gln Gly
            35                  40                  45

Pro Gly Ser Gly Gly Gln Gln Gly Pro Gly Ser Arg Gly Pro Tyr Gly
50                  55                  60

Pro Ser Ala Ala Ala Ala Ala Ala Ala Gly Pro Gly Tyr Gly Pro
65                  70                  75                  80

Gly Ala Gly Gln Arg Gly Pro Arg Ser Gln Gly Pro Gly Ser Gly Gly
                85                  90                  95

Gln Gln Gly Pro Gly Gly Gln Gly Pro Tyr Gly Pro Ser Ala Ala Ala
                100                 105                 110

Ala Ala Ala Ala Gly Pro Gly Tyr Gly Pro Gly Ala Gly Gln Gln
            115                 120                 125

Gly Pro Gly Ser Gln Ala Pro Val Ala Ser Ala Ala Ser Arg Leu
    130                 135                 140

Ser Ser Pro Gln Ala Ser Ser Arg Val Ser Ser Ala Val Ser Thr Leu
145                 150                 155                 160

Val Ser Ser Gly Pro Thr Asn Pro Ala Ser Leu Ser Asn Ala Ile Ser
                165                 170                 175

Ser Val Val Ser Gln Val Ser Ala Ser Asn Pro Gly Leu Ser Gly Cys
            180                 185                 190

Asp Val Leu Val Gln Ala Leu Leu Glu Ile Val Ser Ala Leu Val His
        195                 200                 205

Ile Leu Gly Ser Ser Ser Ile Gly Gln Ile Asn Tyr Ala Ala Ser Ser
    210                 215                 220

Gln Tyr Ala Gln Met Val Gly
225                 230
```

<210> SEQ ID NO 76
<211> LENGTH: 661
<212> TYPE: PRT
<213> ORGANISM: Argiope trifasciata (MaSp II)

<400> SEQUENCE: 76

```
Met Asn Trp Ser Ile Arg Leu Ala Leu Leu Gly Phe Val Val Leu Ser
1               5                   10                  15

Thr Gln Thr Val Phe Ser Ala Gly Gln Gly Ala Thr Pro Trp Glu Asn
                20                  25                  30

Ser Gln Leu Ala Glu Ser Phe Ile Ser Arg Phe Leu Arg Phe Ile Gly
            35                  40                  45
```

-continued

```
Gln Ser Gly Ala Phe Ser Pro Asn Gln Leu Asp Asp Met Ser Ser Ile
     50                  55                  60

Gly Asp Thr Leu Lys Thr Ala Ile Glu Lys Met Ala Gln Ser Arg Lys
 65                  70                  75                  80

Ser Ser Lys Ser Lys Leu Gln Ala Leu Asn Met Ala Phe Ala Ser Ser
                 85                  90                  95

Met Ala Glu Ile Ala Val Ala Glu Gln Gly Leu Ser Leu Glu Ala
            100                 105                 110

Lys Thr Asn Ala Ile Ala Ser Ala Leu Ser Ala Ala Phe Leu Glu Thr
                115                 120                 125

Thr Gly Tyr Val Asn Gln Gln Phe Val Asn Glu Ile Lys Thr Leu Ile
130                 135                 140

Phe Met Ile Ala Gln Ala Ser Ser Asn Glu Ile Ser Gly Ser Ala Ala
145                 150                 155                 160

Ala Ala Gly Gly Ser Ser Gly Gly Gly Gly Ser Gly Gln Gly Gly
                165                 170                 175

Tyr Gly Gln Gly Ala Tyr Ala Ser Ala Ala Ala Ala Tyr Gly
                180                 185                 190

Ser Ala Pro Gln Gly Thr Gly Gly Pro Ala Ser Gln Gly Pro Ser Gln
                195                 200                 205

Gln Gly Pro Val Ser Gln Pro Ser Tyr Gly Pro Ser Ala Thr Val Ala
            210                 215                 220

Val Thr Ala Val Gly Gly Arg Pro Gln Gly Pro Ser Ala Pro Arg Gln
225                 230                 235                 240

Gln Gly Pro Ser Gln Gln Gly Pro Gly Gln Gln Gly Pro Gly Gly Arg
                245                 250                 255

Gly Pro Tyr Gly Pro Ser Ala Ala Ala Ala Ala Ala Ala Gly Gly
            260                 265                 270

Tyr Gly Pro Gly Ala Gly Gln Gln Gly Gln Gln Ala Gly Gln Gly Ser
            275                 280                 285

Gly Gln Gln Gly Pro Gly Gly Ala Gly Gln Gly Gly Pro Arg Gly Gln
            290                 295                 300

Gly Pro Tyr Gly Pro Gly Ala Ala Thr Ala Ala Ala Ala Ala Gly
305                 310                 315                 320

Pro Gly Tyr Gly Pro Gly Ala Gly Gln Gln Gly Pro Gly Ser Gln Gly
                325                 330                 335

Pro Gly Ser Gly Gly Gln Gly Gly Pro Gly Ser Gln Gly Pro Tyr Gly
            340                 345                 350

Pro Ser Ala Ala Ala Ala Ala Ala Ala Gly Pro Gly Tyr Gly Pro
            355                 360                 365

Gly Ala Gly Gln Gln Gly Pro Gly Ser Gln Gly Pro Arg Ser Gly Gly
            370                 375                 380

Gln Gln Gly Pro Gly Gly Gln Gly Pro Tyr Gly Pro Ser Ala Ala Ala
385                 390                 395                 400

Ala Ala Ala Ala Ala Gly Pro Gly Tyr Gly Pro Gly Ala Gly Gln Gln
                405                 410                 415

Gly Pro Gly Ser Gly Gly Gln Gln Gly Pro Gly Ser Gly Gln Gln
            420                 425                 430

Gly Pro Gly Gly Ala Gly Gln Gly Gly Pro Arg Gly Gly Pro Tyr
                435                 440                 445

Gly Pro Gly Ala Ala Ala Ala Ala Ala Ala Gly Gly Tyr Gly
450                 455                 460

Pro Gly Ala Gly Gln Gln Gly Pro Gly Ser Gln Gly Pro Gly Ser Gly
```

```
             465                 470                 475                 480
Gly Gln Gln Gly Pro Gly Ser Gln Gly Pro Tyr Gly Pro Ser Ala Ala
                485                 490                 495
Ala Ala Ala Ala Ala Ala Gly Pro Gly Tyr Gly Pro Gly Ala Gly Gln
                500                 505                 510
Gln Gly Pro Gly Ser Gln Gly Pro Gly Ser Gly Gln Gln Gly Pro
            515                 520                 525
Gly Gly Gln Gly Pro Tyr Gly Pro Ser Ala Ala Ala Ala Ala Ala
            530                 535                 540
Ala Gly Pro Gly Tyr Gly Pro Gly Ala Gly Gln Gln Gly Pro Gly Ser
545                 550                 555                 560
Gly Gly Gln Gln Gly Gly Gln Gly Ser Gly Gln Gln Gly Pro Gly Gly
                565                 570                 575
Ala Gly Gln Gly Gly Pro Arg Gly Gln Gly Pro Tyr Gly Pro Gly Ala
                580                 585                 590
Ala Ala Ala Ala Ala Ala Ala Gly Gly Tyr Gly Pro Gly Ala Gly
                595                 600                 605
Gln Gln Gly Pro Gly Ser Gln Gly Pro Gly Ser Gly Gly Gln Gln Gly
            610                 615                 620
Pro Gly Ser Gln Gly Pro Tyr Gly Pro Ser Ala Ala Ala Ala Ala
625                 630                 635                 640
Ala Ala Gly Pro Gly Tyr Gly Pro Gly Ala Gly Gln Gln Gly Pro Gly
                645                 650                 655
Ser Gly Gly Gln Gln
            660

<210> SEQ ID NO 77
<211> LENGTH: 388
<212> TYPE: PRT
<213> ORGANISM: Latrodectus geometricus (MaSp II)

<400> SEQUENCE: 77

Leu Arg Trp Ser Ser Lys Asp Asn Ala Asp Arg Phe Ile Asn Ala Phe
1               5                   10                  15
Leu Gln Ala Ala Ser Asn Ser Gly Ala Phe Ser Ser Asp Gln Val Asp
                20                  25                  30
Asp Met Ser Val Ile Gly Asn Thr Leu Met Thr Ala Met Asp Asn Met
            35                  40                  45
Gly Gly Arg Ile Thr Pro Ser Lys Leu Gln Ala Leu Asp Met Ala Phe
        50                  55                  60
Ala Ser Ser Val Ala Glu Ile Ala Val Ala Asp Gly Gln Asn Val Gly
65                  70                  75                  80
Gly Ala Thr Asn Ala Ile Ser Asn Ala Leu Arg Ser Ala Phe Tyr Gln
                85                  90                  95
Thr Thr Gly Val Val Asn Asn Gln Phe Ile Ser Glu Ile Ser Asn Leu
                100                 105                 110
Ile Asn Met Phe Ala Gln Val Ser Ala Asn Glu Val Ser Tyr Ala Ser
            115                 120                 125
Gly Gly Ser Ser Ser Ala Ala Ala Ser Ala Ala Ala Ser Ala Gly Pro
        130                 135                 140
Ala Ala Gln Gln Val Tyr Ala Pro Ser Ala Gly Ala Pro Ala Ala Ala
145                 150                 155                 160
Thr Ala Ser Ser Gly Pro Gly Ala Tyr Gly Pro Ser Ala Pro Gly Gly
                165                 170                 175
```

```
Pro Ser Ala Ala Ala Ala Ala Ser Gly Ala Gly Pro Gly
            180                 185                 190

Arg Gln Gln Ser Tyr Gly Pro Gly Gly Ser Gly Ala Ala Ala Ala
        195                 200                 205

Ala Ala Thr Gly Gly Ser Gly Pro Gly Gly Tyr Gly Gln Gly Pro Ala
        210                 215                 220

Ser Tyr Ala Pro Ser Gly Pro Gly Gln Gln Gly Tyr Gly Pro Gly
225                 230                 235                 240

Gly Ser Gly Ala Ala Ser Ala Ala Ala Ala Ala Ser Ser Gly Pro
                245                 250                 255

Gly Gly Tyr Gly Pro Gly Ala Ser Gly Pro Gly Ser Tyr Gly Pro Ser
            260                 265                 270

Gly Pro Gly Gly Ser Gly Ala Ala Ala Ala Ala Ala Ala Ser Ala
            275                 280                 285

Pro Gly Gly Gln Gln Gly Tyr Gly Pro Gly Ser Gly Ala Ala Ala
            290                 295                 300

Ala Ala Ala Ala Gly Gly Ala Gly Pro Gly Ser Gln Gln Ala Tyr Gly
305                 310                 315                 320

Pro Gly Gly Ser Gly Ala Ala Ala Ala Ala Ala Gly Pro Gly Ser
            325                 330                 335

Gly Gly Gln Gln Gly Tyr Gly Pro Gly Gly Ser Ala Ala Ala Ala
            340                 345                 350

Ala Ala Ala Ala Gly Gly Ser Gly Pro Gly Gly Tyr Gly Gln Gly Pro
            355                 360                 365

Ala Gly Tyr Gly Pro Ser Gly Pro Gly Ala Gln Gln Gly Tyr Gly Pro
            370                 375                 380

Gly Gly Pro Gly
385

<210> SEQ ID NO 78
<211> LENGTH: 342
<212> TYPE: PRT
<213> ORGANISM: Gasteracantha mammosa (MaSp II)

<400> SEQUENCE: 78

Gly Gln Gln Gly Pro Gly Ser Gln Gly Pro Tyr Gly Pro Gly Ala Ala
1               5                   10                  15

Ala Ala Ala Ala Ala Ala Gly Gly Tyr Arg Pro Val Ser Gly Gln
            20                  25                  30

Gln Gly Pro Gly Gln Gln Gly Pro Gly Ser Gly Gln Gln Gly Pro
        35                  40                  45

Gly Gly Gln Arg Pro Tyr Gly Pro Gly Ala Ala Ala Ala Ala Ala
    50                  55                  60

Ala Gly Gly Tyr Gly Pro Gly Ser Gly Gln Gln Gly Pro Gly Gln Gln
65                  70                  75                  80

Gly Pro Gly Ser Gly Gln Gln Gly Pro Gly Gln Gly Pro Tyr
            85                  90                  95

Gly Pro Gly Ala Ala Ala Ala Ala Ala Ala Ala Gly Gly Tyr Gly
            100                 105                 110

Pro Gly Ser Gly Gln Gly Gln Gln Gly Pro Gly Ser Gln Gly Pro
        115                 120                 125

Gly Ser Gly Gly Gln Gln Gly Pro Gly Gln Gly Pro Tyr Gly Pro
    130                 135                 140

Ser Ala Ala Ala Ala Ala Ala Ala Val Gly Gly Tyr Gly Pro Gly Ala
145                 150                 155                 160
```

```
Gly Gln Gln Gly Pro Gly Gln Gly Pro Gly Ser Gly Gly Gln Arg
                165                 170                 175

Gly Pro Gly Gly Gln Gly Pro Tyr Gly Pro Gly Ala Ala Ala Ala
            180                 185                 190

Ala Ala Ala Ala Gly Gly Tyr Gly Pro Ala Ser Gly Gln Gln Gly Pro
        195                 200                 205

Gly Gln Gln Gly Pro Gly Ser Gly Gly Gln Arg Gly Pro Gly Gly Gln
    210                 215                 220

Gly Pro Tyr Gly Pro Gly Ala Ala Ala Ala Ser Ala Gly Gly Tyr
225                 230                 235                 240

Gly Pro Gly Ser Gly Ser Pro Ala Ser Gly Ala Ala Ser Arg Leu
            245                 250                 255

Ser Ser Pro Gln Ala Gly Ala Arg Val Ser Ser Ala Val Ser Ala Leu
        260                 265                 270

Val Ala Ser Gly Pro Thr Ser Pro Ala Ala Val Ser Ser Ala Ile Ser
    275                 280                 285

Asn Val Ala Ser Gln Ile Ser Ala Ser Asn Pro Gly Leu Ser Gly Cys
    290                 295                 300

Asp Val Leu Val Gln Ala Leu Leu Glu Ile Val Ser Ala Leu Val Ser
305                 310                 315                 320

Ile Leu Ser Ser Ala Ser Ile Gly Gln Ile Asn Tyr Gly Ala Ser Gly
                325                 330                 335

Gln Tyr Ala Ala Met Ile
            340

<210> SEQ ID NO 79
<211> LENGTH: 251
<212> TYPE: PRT
<213> ORGANISM: Nephila clavipes (MiSp)

<400> SEQUENCE: 79

Gly Ala Gly Gly Tyr Gly Arg Gly Ala Gly Ala Gly Ala Ala Val
1               5                   10                  15

Ala Gly Ala Asp Ala Gly Gly Tyr Gly Arg Asn Tyr Gly Ala Gly Thr
            20                  25                  30

Thr Ala Tyr Ala Gly Ala Arg Ala Gly Gly Ala Gly Gly Tyr Gly Gly
        35                  40                  45

Gln Gly Gly Tyr Ser Ser Gly Ala Gly Ala Ala Ala Ala Ser Gly Ala
    50                  55                  60

Gly Ala Asp Ile Thr Ser Gly Tyr Gly Arg Gly Val Gly Ala Gly Ala
65                  70                  75                  80

Gly Ala Glu Thr Ile Gly Ala Gly Gly Tyr Gly Gly Gly Ala Gly Ser
                85                  90                  95

Gly Ala Arg Ala Ala Ser Ala Ser Gly Ala Gly Thr Gly Tyr Gly Ser
            100                 105                 110

Ser Gly Gly Tyr Asn Val Gly Thr Gly Ile Ser Thr Ser Ser Gly Ala
        115                 120                 125

Ala Ser Ser Tyr Ser Val Ser Ala Gly Tyr Ala Ser Thr Gly Val
    130                 135                 140

Gly Ile Gly Ser Thr Val Thr Ser Thr Thr Ser Arg Leu Ser Ser Ala
145                 150                 155                 160

Glu Ala Cys Ser Arg Ile Ser Ala Ala Ala Ser Thr Leu Val Ser Gly
                165                 170                 175

Ser Leu Asn Thr Ala Ala Leu Pro Ser Val Ile Ser Asp Leu Phe Ala
```

```
                180               185                190
Gln Val Ser Ala Ser Ser Pro Gly Val Ser Gly Asn Glu Val Leu Ile
            195                 200                 205

Gln Val Leu Leu Glu Ile Val Ser Ser Leu Ile His Ile Leu Ser Ser
    210                 215                 220

Ser Ser Val Gly Gln Val Asp Phe Ser Ser Val Gly Ser Ser Ala Ala
225                 230                 235                 240

Ala Val Gly Gln Ser Met Gln Val Val Met Gly
            245                 250

<210> SEQ ID NO 80
<211> LENGTH: 157
<212> TYPE: PRT
<213> ORGANISM: Nephila clavipes (MiSp II)

<400> SEQUENCE: 80

Ser Tyr Gly Pro Ser Val Phe Tyr Thr Pro Thr Ser Ala Gly Ser Tyr
1               5                   10                  15

Gly Ala Gly Ala Gly Gly Phe Gly Ala Gly Ala Ser Ala Gly Val Gly
            20                  25                  30

Ala Gly Ala Gly Thr Val Ala Gly Tyr Gly Gly Gln Gly Gly Tyr Gly
        35                  40                  45

Ala Gly Ser Ala Gly Gly Tyr Gly Arg Gly Thr Gly Ala Gly Ala Ala
    50                  55                  60

Ala Gly Ala Gly Ala Gly Ala Thr Ala Gly Gly Ala Gly Ala Gly Ala
65                  70                  75                  80

Ala Gly Ala Gly Ala Gly Ala Gly Asn Ser Gly Gly Tyr Ser Ala Gly
            85                  90                  95

Val Gly Val Gly Ala Ala Ala Ala Ala Gly Gly Ala Gly Ala Gly Thr
            100                 105                 110

Val Gly Gly Tyr Gly Arg Gly Ala Gly Val Gly Ala Gly Ala Ala Ala
        115                 120                 125

Gly Phe Ala Ala Gly Ala Gly Gly Ala Gly Gly Tyr Arg Arg Asp Gly
    130                 135                 140

Gly Tyr Gly Ala Gly Ala Gly Ala Gly Ala Ala Ala
145                 150                 155

<210> SEQ ID NO 81
<211> LENGTH: 988
<212> TYPE: PRT
<213> ORGANISM: Nephila clavipes (MiSp I)

<400> SEQUENCE: 81

Arg Gly Ala Ala Ser Gly Ala Gly Ala Ala Gly Ala Gly Ala Gly Gly
1               5                   10                  15

Ala Gly Gly Ala Gly Tyr Gly Gly Gln Ile Gly Tyr Gly Ala Gly Ala
            20                  25                  30

Gly Ala Gly Ala Ala Ala Ala Gly Ala Gly Ala Gly Gly Ala Gly Ala
        35                  40                  45

Gly Tyr Gly Arg Gly Ala Gly Ala Gly Ser Gly Ala Ala Ala Gly Ala
    50                  55                  60

Gly Ser Gly Ala Gly Ala Gly Gly Tyr Gly Gly Gln Ala Gly Tyr Gly
65                  70                  75                  80

Ala Gly Ala Gly Ala Gly Ser Ser Ala Gly Asn Ala Phe Ala Gln Ser
            85                  90                  95

Leu Ser Ser Asn Leu Leu Ser Ser Gly Asp Phe Val Gln Met Ile Ser
```

```
                100                 105                 110
Ser Thr Thr Ser Thr Asp His Ala Val Ser Val Ala Thr Ser Val Ala
            115                 120                 125

Gln Asn Val Gly Ser Gln Leu Gly Leu Asp Ala Asn Ala Met Asn Asn
130                 135                 140

Leu Leu Gly Ala Val Ser Gly Tyr Val Ser Thr Leu Gly Asn Ala Ile
145                 150                 155                 160

Ser Asp Ala Ser Ala Tyr Ala Asn Ala Leu Ser Ser Ala Ile Gly Asn
            165                 170                 175

Val Leu Ala Asn Ser Gly Ser Ile Ser Glu Ser Thr Ala Ser Ser Ala
            180                 185                 190

Ala Ser Ser Ala Ala Ser Ser Val Thr Thr Thr Leu Thr Ser Tyr Gly
            195                 200                 205

Pro Ala Val Phe Tyr Ala Pro Ser Ala Ser Ser Gly Gly Tyr Gly Ala
            210                 215                 220

Gly Ala Gly Ala Val Ala Ala Gly Ala Ala Gly Ala Gly Gly Tyr
225                 230                 235                 240

Gly Arg Gly Ala Gly Gly Tyr Gly Gly Gln Gly Gly Tyr Gly Ala Gly
            245                 250                 255

Ala Gly Ala Gly Ala Ala Ala Ala Gly Ala Gly Ala Gly Gly Ala
            260                 265                 270

Gly Gly Tyr Gly Arg Gly Ala Gly Ala Gly Ala Gly Ala Ala Ala Gly
            275                 280                 285

Ala Gly Ala Gly Ala Gly Gly Ala Gly Tyr Gly Gly Gln Gly Gly Tyr
            290                 295                 300

Gly Ala Gly Ala Gly Ala Gly Ala Ala Ala Ala Gly Ala Gly Ala
305                 310                 315                 320

Gly Gly Ala Gly Gly Tyr Gly Arg Gly Ala Gly Ala Gly Ala Gly Ala
            325                 330                 335

Ala Ala Gly Ala Gly Ala Gly Gly Tyr Gly Gly Gln Gly Gly Tyr Gly
            340                 345                 350

Ala Gly Ala Gly Ala Gly Ala Ala Ala Ala Gly Ala Gly Ala Gly Ser
            355                 360                 365

Gly Gly Ala Gly Gly Tyr Gly Arg Gly Ala Gly Ala Gly Ala Gly Ala
            370                 375                 380

Ala Ala Gly Ala Gly Ala Gly Ala Gly Ser Tyr Gly Gly Gln Gly Gly
385                 390                 395                 400

Tyr Gly Ala Gly Ala Gly Ala Gly Ala Ala Ala Ala Gly Ala Gly
            405                 410                 415

Ala Gly Ala Gly Gly Tyr Gly Arg Gly Ala Gly Ala Gly Ala Gly Ala
            420                 425                 430

Gly Ala Gly Ala Ala Ala Arg Ala Gly Ala Gly Ala Gly Ala Gly
            435                 440                 445

Tyr Gly Gly Gln Gly Gly Tyr Gly Ala Gly Ala Gly Ala Gly Ala Ala
            450                 455                 460

Ala Ala Ala Gly Ala Gly Ala Gly Gly Ala Gly Tyr Gly Arg Gly
465                 470                 475                 480

Ala Gly Ala Gly Ala Gly Ala Ala Gly Ala Gly Ala Gly Ala Gly
            485                 490                 495

Gly Tyr Gly Gly Gln Ser Gly Tyr Gly Ala Gly Ala Gly Ala Ala Ala
            500                 505                 510

Ala Ala Gly Ala Gly Ala Gly Gly Ala Gly Gly Tyr Gly Arg Gly Ala
            515                 520                 525
```

```
Gly Ala Gly Ala Gly Ala Ala Gly Ala Gly Ala Gly Ala Ala
        530                 535                 540
Gly Ala Gly Ala Gly Gly Tyr Gly Gly Gln Gly Gly Tyr Gly Ala Gly
545                 550                 555                 560
Ala Gly Ala Gly Ala Ala Ala Ala Gly Ala Gly Ala Gly Ala
                565                 570                 575
Gly Gly Tyr Gly Arg Gly Ala Gly Ala Gly Val Ala Ala Gly
            580                 585                 590
Ala Gly Ala Gly Gly Tyr Gly Gly Gln Gly Gly Tyr Gly Ala Gly Ala
                595                 600                 605
Gly Ala Gly Ala Ala Ala Ala Ala Thr Gly Ala Gly Gly Ala Gly
        610                 615                 620
Gly Tyr Gly Arg Gly Ala Gly Ala Gly Ala Ala Ala Gly Ala
625                 630                 635                 640
Gly Ala Gly Thr Gly Gly Ala Gly Tyr Gly Gly Gln Gly Gly Tyr Gly
                645                 650                 655
Ala Gly Ala Gly Ala Gly Ala Ala Ala Ala Gly Ala Gly Ala Gly
            660                 665                 670
Gly Ala Gly Tyr Gly Arg Gly Ala Gly Ala Gly Ala Ala Ala
        675                 680                 685
Gly Ala Gly Ala Gly Ala Ala Gly Ala Gly Ala Gly Ala Gly Gly
        690                 695                 700
Tyr Gly Gly Gln Gly Gly Tyr Gly Ala Gly Ala Gly Ala Gly Ala Ala
705                 710                 715                 720
Ala Ala Ala Gly Ala Gly Ala Gly Gly Ala Gly Tyr Ser Arg Gly
            725                 730                 735
Gly Arg Ala Gly Ala Ala Gly Ala Gly Ala Gly Ala Ala Gly Ala
            740                 745                 750
Gly Ala Gly Ala Gly Gly Tyr Gly Gly Gln Gly Gly Tyr Gly Ala Gly
                755                 760                 765
Ala Gly Ala Gly Ala Ala Ala Ala Gly Ala Gly Ser Gly Gly Ala
        770                 775                 780
Gly Gly Tyr Gly Arg Gly Ala Gly Ala Gly Ala Ala Ala Gly Ala Gly
785                 790                 795                 800
Ala Ala Ala Gly Ala Gly Ala Gly Gly Tyr Gly Gly Gln Gly
            805                 810                 815
Gly Tyr Gly Ala Gly Ala Gly Ala Ala Ala Ala Gly Ala Gly Ala
        820                 825                 830
Gly Arg Gly Gly Tyr Gly Arg Gly Ala Gly Ala Gly Tyr Gly Gly
        835                 840                 845
Gln Gly Gly Tyr Gly Ala Gly Ala Gly Ala Gly Ala Ala Ala Ala
        850                 855                 860
Gly Ala Gly Ala Gly Gly Tyr Gly Asp Lys Glu Ile Ala Cys Trp Ser
865                 870                 875                 880
Arg Cys Arg Tyr Thr Val Ala Ser Thr Thr Ser Arg Leu Ser Ser Ala
                885                 890                 895
Glu Ala Ser Ser Arg Ile Ser Ser Ala Ala Ser Thr Leu Val Ser Gly
            900                 905                 910
Gly Tyr Leu Asn Thr Ala Ala Leu Pro Ser Val Ile Ser Asp Leu Phe
        915                 920                 925
Ala Gln Val Gly Ala Ser Ser Pro Gly Val Ser Asp Ser Glu Val Leu
    930                 935                 940
```

```
Ile Gln Val Leu Leu Glu Ile Val Ser Ser Leu Ile His Ile Leu Ser
945                 950                 955                 960

Ser Ser Ser Val Gly Gln Val Asp Phe Ser Ser Val Gly Ser Ser Ala
                965                 970                 975

Ala Ala Val Gly Gln Ser Met Gln Val Val Met Gly
            980                 985

<210> SEQ ID NO 82
<211> LENGTH: 907
<212> TYPE: PRT
<213> ORGANISM: Nephila clavipes
<220> FEATURE:
<223> OTHER INFORMATION: flagelliform silk protein

<400> SEQUENCE: 82

Gly Pro Gly Gly Val Gly Pro Gly Gly Ser Gly Pro Gly Gly Tyr Gly
1               5                   10                  15

Pro Gly Gly Ala Gly Pro Gly Gly Tyr Gly Pro Gly Gly Ser Gly Pro
                20                  25                  30

Gly Gly Tyr Gly Pro Gly Gly Ser Gly Pro Gly Gly Tyr Gly Pro Gly
            35                  40                  45

Gly Ser Gly Pro Gly Gly Tyr Gly Pro Gly Gly Ser Gly Pro Gly Gly
        50                  55                  60

Tyr Gly Pro Gly Gly Ser Gly Pro Gly Gly Tyr Gly Pro Gly Gly Tyr
65                  70                  75                  80

Gly Pro Gly Gly Ser Gly Pro Gly Gly Tyr Gly Pro Gly Gly Thr Gly
                85                  90                  95

Pro Gly Gly Ser Gly Pro Gly Gly Tyr Gly Pro Gly Gly Ser Gly Pro
            100                 105                 110

Gly Gly Ser Gly Pro Gly Gly Tyr Gly Pro Gly Gly Ser Gly Pro Gly
        115                 120                 125

Gly Phe Gly Pro Gly Gly Ser Gly Pro Gly Gly Tyr Gly Pro Gly Gly
    130                 135                 140

Ser Gly Pro Gly Gly Ala Gly Pro Gly Gly Val Gly Pro Gly Gly Phe
145                 150                 155                 160

Gly Pro Gly Gly Ala Gly Pro Gly Gly Ala Gly Pro Gly Gly Ala Gly
                165                 170                 175

Pro Gly Gly Ala Gly Pro Gly Gly Ala Gly Pro Gly Gly Ala Gly Pro
            180                 185                 190

Gly Gly Ala Gly Pro Gly Gly Ala Gly Pro Gly Gly Ala Gly Pro Gly
        195                 200                 205

Gly Ala Gly Pro Gly Gly Ala Gly Ala Gly Ala Gly Gly Ala Gly Ala
    210                 215                 220

Gly Gly Ser Gly Gly Ala Gly Ser Gly Gly Thr Thr Ile Ile Glu
225                 230                 235                 240

Asp Leu Asp Ile Thr Ile Asp Gly Ala Asp Gly Pro Ile Thr Ile Ser
                245                 250                 255

Glu Glu Leu Thr Ile Ser Gly Ala Gly Gly Ser Gly Pro Gly Gly Ala
            260                 265                 270

Gly Pro Gly Gly Val Gly Pro Gly Gly Ser Gly Pro Gly Gly Val Gly
        275                 280                 285

Pro Gly Gly Ser Gly Pro Gly Gly Val Gly Pro Gly Gly Ser Gly Pro
    290                 295                 300

Gly Gly Val Gly Pro Gly Gly Ala Gly Gly Pro Tyr Gly Pro Gly Gly
305                 310                 315                 320
```

-continued

```
Ser Gly Pro Gly Gly Ala Gly Gly Ala Gly Pro Gly Gly Ala Tyr
            325                 330                 335
Gly Pro Gly Gly Ser Tyr Gly Pro Gly Gly Ser Gly Gly Pro Gly Gly
            340                 345                 350
Ala Gly Gly Pro Tyr Gly Pro Gly Gly Glu Gly Pro Gly Gly Ala Gly
            355                 360                 365
Gly Pro Tyr Gly Pro Gly Gly Ala Gly Gly Pro Tyr Gly Pro Gly Gly
            370                 375                 380
Ala Gly Gly Pro Tyr Pro Gly Gly Glu Gly Pro Tyr Gly Pro
385                 390                 395                 400
Gly Gly Ser Tyr Gly Pro Gly Gly Ala Gly Pro Tyr Gly Pro Gly
            405                 410                 415
Gly Pro Tyr Gly Pro Gly Gly Glu Gly Pro Gly Gly Ala Gly Gly Pro
            420                 425                 430
Tyr Gly Pro Gly Gly Val Gly Gly Ser Gly Pro Gly Gly Tyr
            435                 440                 445
Gly Pro Gly Gly Ser Gly Pro Gly Gly Tyr Gly Pro Gly Gly Ala Gly
            450                 455                 460
Pro Gly Gly Tyr Gly Pro Gly Gly Ser Gly Pro Gly Gly Tyr Gly Pro
465                 470                 475                 480
Gly Gly Ser Gly Pro Gly Gly Tyr Gly Pro Gly Gly Ser Gly Pro Gly
            485                 490                 495
Gly Tyr Gly Pro Gly Gly Ser Gly Pro Gly Gly Tyr Gly Ser Gly Gly
            500                 505                 510
Ala Gly Pro Gly Gly Tyr Gly Pro Gly Gly Ser Gly Pro Gly Gly Tyr
            515                 520                 525
Gly Pro Gly Gly Ser Gly Pro Gly Gly Tyr Gly Pro Gly Gly Thr Gly
            530                 535                 540
Pro Gly Gly Thr Gly Pro Gly Gly Ser Gly Pro Gly Gly Tyr Gly Pro
545                 550                 555                 560
Gly Gly Ser Gly Pro Gly Gly Ser Gly Pro Gly Gly Ser Gly Pro Gly
            565                 570                 575
Gly Tyr Gly Pro Ser Gly Ser Gly Pro Gly Gly Tyr Gly Pro Ser Gly
            580                 585                 590
Ser Gly Pro Gly Gly Tyr Gly Pro Gly Gly Ser Gly Pro Gly Gly Tyr
            595                 600                 605
Gly Pro Gly Gly Ser Gly Ala Gly Gly Thr Gly Pro Gly Gly Ala Gly
            610                 615                 620
Gly Ala Gly Gly Ala Gly Gly Ser Gly Gly Ala Gly Gly Ser Gly Gly
625                 630                 635                 640
Ala Gly Gly Ser Gly Gly Ala Gly Gly Ser Gly Gly Val Gly Gly Ser
            645                 650                 655
Gly Gly Thr Thr Ile Thr Glu Asp Leu Asp Ile Thr Ile Asp Gly Ala
            660                 665                 670
Asp Gly Pro Ile Thr Ile Ser Glu Glu Leu Thr Ile Ser Gly Ala Gly
            675                 680                 685
Gly Ser Gly Pro Gly Gly Ala Gly Pro Gly Gly Val Gly Pro Gly Gly
            690                 695                 700
Ser Gly Pro Gly Gly Val Gly Pro Gly Val Ser Gly Pro Gly Gly Val
705                 710                 715                 720
Gly Pro Gly Gly Ser Gly Pro Gly Gly Val Gly Ser Gly Gly Ser Gly
            725                 730                 735
Pro Gly Gly Val Gly Pro Gly Gly Tyr Gly Pro Gly Gly Ser Gly Ser
```

```
            740                 745                 750
Gly Gly Val Gly Pro Gly Gly Tyr Gly Pro Gly Gly Ser Gly Gly Phe
            755                 760                 765

Tyr Gly Pro Gly Gly Ser Glu Gly Pro Tyr Gly Pro Ser Gly Thr Tyr
        770                 775                 780

Gly Ser Gly Gly Gly Tyr Gly Pro Gly Gly Ala Gly Gly Pro Tyr Gly
785                 790                 795                 800

Pro Gly Ser Pro Gly Gly Ala Tyr Gly Pro Gly Ser Pro Gly Gly Ala
                805                 810                 815

Tyr Tyr Pro Ser Ser Arg Val Pro Asp Met Val Asn Gly Ile Met Ser
            820                 825                 830

Ala Met Gln Gly Ser Gly Phe Asn Tyr Gln Met Phe Gly Asn Met Leu
        835                 840                 845

Ser Gln Tyr Ser Ser Gly Ser Gly Thr Cys Asn Pro Asn Asn Val Asn
    850                 855                 860

Val Leu Met Asp Ala Leu Leu Ala Ala Leu His Cys Leu Ser Asn His
865                 870                 875                 880

Gly Ser Ser Ser Phe Ala Pro Ser Pro Thr Pro Ala Ala Met Ser Ala
                885                 890                 895

Tyr Ser Asn Ser Val Gly Arg Met Phe Ala Tyr
            900                 905
```

<210> SEQ ID NO 83
<211> LENGTH: 871
<212> TYPE: PRT
<213> ORGANISM: Nephila clavipes
<220> FEATURE:
<223> OTHER INFORMATION: flagelliform silk protein

<400> SEQUENCE: 83

```
Met Gly Lys Gly Arg His Asp Thr Lys Ala Lys Ala Lys Ala Met Gln
1               5                   10                  15

Val Ala Leu Ala Ser Ser Ile Ala Glu Leu Val Ile Ala Glu Ser Ser
            20                  25                  30

Gly Gly Asp Val Gln Arg Lys Thr Asn Val Ile Ser Asn Ala Leu Arg
        35                  40                  45

Asn Ala Leu Met Ser Thr Thr Gly Ser Pro Asn Glu Glu Phe Val His
    50                  55                  60

Glu Val Gln Asp Leu Ile Gln Met Leu Ser Gln Gln Ile Asn Glu
65                  70                  75                  80

Val Asp Thr Ser Gly Pro Gly Gln Tyr Tyr Arg Ser Ser Ser Ser Gly
                85                  90                  95

Gly Gly Gly Gly Gly Gln Gly Gly Pro Val Val Thr Glu Thr Leu Thr
            100                 105                 110

Val Thr Val Gly Gly Ser Gly Gly Gln Pro Ser Gly Ala Gly Pro
        115                 120                 125

Ser Gly Thr Gly Gly Tyr Ala Pro Thr Gly Tyr Ala Pro Ser Gly Ser
    130                 135                 140

Gly Ala Gly Gly Val Arg Pro Ser Ala Ser Gly Pro Ser Gly Ser Gly
145                 150                 155                 160

Pro Ser Gly Gly Ser Arg Pro Ser Ser Ser Gly Pro Ser Gly Thr Arg
                165                 170                 175

Pro Ser Pro Asn Gly Ala Ser Gly Ser Ser Pro Gly Gly Ile Ala Pro
            180                 185                 190

Gly Gly Ser Asn Ser Gly Gly Ala Gly Val Ser Gly Ala Thr Gly Gly
```

```
            195                 200                 205
Pro Ala Ser Ser Gly Ser Tyr Gly Pro Gly Ser Thr Gly Gly Thr Tyr
210                 215                 220

Gly Pro Ser Gly Gly Ser Glu Pro Phe Gly Pro Gly Val Ala Gly Gly
225                 230                 235                 240

Pro Tyr Ser Pro Gly Gly Ala Gly Pro Gly Gly Ala Gly Gly Ala Tyr
            245                 250                 255

Gly Pro Gly Gly Val Gly Thr Gly Gly Ala Gly Pro Gly Gly Tyr Gly
            260                 265                 270

Pro Gly Gly Ala Gly Pro Gly Gly Tyr Gly Pro Gly Gly Ala Gly Pro
            275                 280                 285

Gly Gly Tyr Gly Pro Gly Gly Ala Gly Pro Gly Gly Tyr Gly Pro Gly
            290                 295                 300

Gly Ala Gly Pro Gly Gly Tyr Gly Pro Gly Gly Ala Gly Pro Gly Gly
305                 310                 315                 320

Tyr Gly Pro Gly Gly Ala Gly Pro Gly Gly Tyr Gly Pro Gly Gly Thr
            325                 330                 335

Gly Pro Gly Gly Tyr Gly Pro Gly Gly Thr Gly Pro Gly Gly Val Gly
            340                 345                 350

Pro Gly Gly Ala Gly Pro Gly Gly Tyr Gly Pro Gly Gly Ala Gly Pro
            355                 360                 365

Gly Gly Ala Gly Pro Gly Gly Ala Gly Pro Gly Gly Ala Gly Pro Gly
            370                 375                 380

Gly Ala Gly Pro Gly Gly Ala Gly Pro Gly Gly Tyr Gly Pro Gly Gly
385                 390                 395                 400

Ser Gly Pro Gly Gly Ala Gly Pro Ser Gly Ala Gly Leu Gly Gly Ala
            405                 410                 415

Gly Pro Gly Gly Ala Gly Leu Gly Ala Gly Pro Gly Gly Ala Gly
            420                 425                 430

Thr Ser Gly Ala Gly Pro Gly Gly Ala Gly Pro Gly Gly Ala Gly Gln
            435                 440                 445

Gly Asp Ala Gly Pro Gly Gly Ala Gly Arg Gly Gly Ala Gly Arg Gly
            450                 455                 460

Gly Val Gly Arg Gly Gly Ala Gly Arg Gly Gly Ala Gly Arg Gly Gly
465                 470                 475                 480

Ala Arg Gly Ala Gly Ala Gly Ala Gly Ala Gly Ala Gly Gly Ser
            485                 490                 495

Gly Gly Thr Thr Ile Val Glu Asp Leu Asp Ile Thr Ile Asp Gly Ala
            500                 505                 510

Asp Gly Pro Ile Thr Ile Ser Glu Glu Leu Thr Ile Gly Ala Gly
            515                 520                 525

Ala Gly Gly Ser Gly Pro Gly Gly Ala Gly Pro Gly Asn Val Gly Pro
            530                 535                 540

Gly Arg Ser Gly Pro Gly Gly Val Gly Pro Gly Gly Ser Gly Pro Gly
545                 550                 555                 560

Gly Val Gly Pro Gly Ser Phe Gly Pro Gly Gly Val Gly Pro Gly Gly
            565                 570                 575

Ser Gly Pro Gly Gly Val Gly Ser Gly Gly Ser Gly Gln Gly Gly Val
            580                 585                 590

Arg Pro Ser Gly Ser Gly Pro Gly Gly Val Gly Thr Gly Gly Val Gly
            595                 600                 605

Pro Gly Gly Ala Gly Gly Pro Tyr Gly Pro Gly Gly Ser Gly Pro Gly
            610                 615                 620
```

-continued

Ser Ala Gly Ser Ala Gly Thr Tyr Gly Pro Gly Phe Gly Gly
625                 630                 635                 640

Pro Gly Gly Phe Gly Gly Pro Gly Gly Ala Gly Pro Tyr Gly Pro
            645                 650                 655

Gly Gly Ala Gly Gly Pro Tyr Gly Pro Gly Gly Ala Gly Gly Pro Tyr
        660                 665                 670

Gly Pro Gly Gly Ala Gly Gly Pro Tyr Gly Pro Gly Gly Ala Gly Gly
            675                 680                 685

Pro Tyr Gly Pro Gly Gly Ala Gly Gly Ser Tyr Gly Leu Gly Gly Ala
        690                 695                 700

Gly Gly Ser Gly Gly Val Gly Pro Gly Gly Ser Gly Pro Gly Gly Tyr
705                 710                 715                 720

Gly Pro Gly Gly Ala Gly Pro Gly Gly Tyr Gly Pro Gly Gly Ser Gly
            725                 730                 735

Pro Gly Gly Tyr Gly Pro Gly Gly Ser Gly Ser Gly Tyr Gly Pro
            740                 745                 750

Gly Gly Ser Gly Pro Gly Gly Ser Gly Pro Gly Gly Tyr Gly Pro Gly
        755                 760                 765

Gly Thr Gly Pro Gly Gly Ser Glu Ser Gly Gly Tyr Gly Pro Gly Gly
    770                 775                 780

Ser Gly Pro Gly Gly Ser Gly Pro Gly Gly Ser Gly Pro Gly Gly Ser
785                 790                 795                 800

Gly Pro Gly Gly Tyr Gly Pro Gly Gly Ser Gly Pro Ser Ser Phe Val
            805                 810                 815

Pro Gly Gly Ser Gly Pro Gly Gly Ser Gly Pro Gly Gly Ala Gly Pro
            820                 825                 830

Gly Gly Ala Gly Pro Gly Gly Val Gly Leu Gly Gly Ala Gly Arg Gly
            835                 840                 845

Gly Ala Gly Arg Gly Gly Ala Gly Ser Val Gly Ala Gly Arg Gly Gly
        850                 855                 860

Ala Gly Arg Gly Gly Thr Gly
865                 870

<210> SEQ ID NO 84
<211> LENGTH: 1002
<212> TYPE: PRT
<213> ORGANISM: Nephila clavipes
<220> FEATURE:
<223> OTHER INFORMATION: flagelliform silk protein

<400> SEQUENCE: 84

Gly Ala Pro Gly Gly Pro Gly Gly Ala Gly Pro Gly Gly Ala Gly
1               5                   10                  15

Phe Gly Pro Gly Gly Gly Ala Gly Phe Gly Pro Gly Gly Ala Gly
                20                  25                  30

Phe Gly Pro Gly Gly Ala Ala Gly Gly Pro Gly Gly Pro Gly Pro
            35                  40                  45

Gly Gly Pro Gly Gly Ala Gly Gly Tyr Gly Pro Gly Gly Ala Gly Gly
        50                  55                  60

Tyr Gly Pro Gly Gly Val Gly Pro Gly Gly Ala Gly Tyr Gly Pro
65                  70                  75                  80

Gly Gly Ala Gly Gly Tyr Gly Pro Gly Gly Ser Gly Pro Gly Gly Ala
            85                  90                  95

Gly Pro Gly Gly Ala Gly Gly Glu Gly Pro Val Thr Val Asp Val Asp
            100                 105                 110

-continued

```
Val Thr Val Gly Pro Glu Val Gly Gly Pro Gly Gly Ala Gly
        115                 120                 125
Pro Gly Gly Ala Gly Phe Gly Pro Gly Gly Ala Gly Phe Gly Pro
    130                 135                 140
Gly Gly Ala Pro Gly Ala Pro Gly Gly Pro Gly Gly Pro Gly Pro
145                 150                 155                 160
Gly Gly Pro Gly Gly Pro Gly Gly Val Gly Pro Gly Gly Ala Gly Gly
            165                 170                 175
Tyr Gly Pro Gly Gly Ala Gly Val Gly Pro Ala Gly Thr Gly Gly
                180                 185                 190
Phe Gly Pro Gly Gly Ala Gly Gly Phe Gly Pro Gly Gly Ala Gly Gly
                195                 200                 205
Phe Gly Pro Gly Gly Ala Gly Gly Phe Gly Pro Gly Gly Ala Gly Gly
    210                 215                 220
Tyr Gly Pro Gly Gly Val Gly Pro Gly Gly Ala Gly Gly Phe Gly Pro
225                 230                 235                 240
Gly Gly Val Gly Pro Gly Gly Ser Gly Pro Gly Gly Ala Gly Gly Glu
                245                 250                 255
Gly Pro Val Thr Val Asp Val Asp Val Ser Val Gly Gly Ala Pro Gly
            260                 265                 270
Gly Gly Pro Gly Gly Ala Gly Pro Gly Gly Ala Gly Phe Gly Pro Gly
        275                 280                 285
Gly Gly Ala Gly Phe Gly Pro Gly Gly Ala Gly Phe Gly Pro Gly
    290                 295                 300
Gly Ala Ala Gly Gly Pro Gly Gly Pro Gly Pro Gly Gly Pro Gly
305                 310                 315                 320
Gly Ala Gly Gly Tyr Gly Pro Gly Gly Ala Gly Gly Tyr Gly Pro Gly
                325                 330                 335
Gly Val Gly Pro Gly Gly Ala Gly Gly Tyr Gly Pro Gly Gly Ala Gly
            340                 345                 350
Gly Tyr Gly Pro Gly Gly Ser Gly Pro Gly Gly Ala Gly Pro Gly Gly
        355                 360                 365
Ala Gly Gly Glu Gly Pro Val Thr Val Asp Val Asp Val Thr Val Gly
    370                 375                 380
Pro Glu Gly Val Gly Gly Pro Gly Gly Ala Gly Pro Gly Gly Ala
385                 390                 395                 400
Gly Phe Gly Pro Gly Gly Gly Ala Gly Phe Gly Pro Gly Gly Ala Pro
                405                 410                 415
Gly Ala Pro Gly Gly Pro Gly Gly Pro Gly Pro Gly Gly Pro Gly
            420                 425                 430
Gly Pro Gly Gly Val Gly Pro Gly Gly Ala Gly Tyr Gly Pro Gly
        435                 440                 445
Gly Ala Gly Gly Val Gly Pro Ala Gly Thr Gly Gly Phe Gly Pro Gly
    450                 455                 460
Gly Ala Gly Gly Phe Gly Pro Gly Gly Ala Gly Phe Gly Pro Gly
465                 470                 475                 480
Gly Ala Gly Gly Phe Gly Pro Ala Gly Ala Gly Gly Tyr Gly Pro Gly
                485                 490                 495
Gly Val Gly Pro Gly Gly Ala Gly Gly Phe Gly Pro Gly Gly Val Gly
            500                 505                 510
Pro Gly Gly Ser Gly Pro Gly Gly Ala Gly Gly Glu Gly Pro Val Thr
        515                 520                 525
```

-continued

```
Val Asp Val Asp Val Ser Val Gly Gly Ala Pro Gly Gly Pro Gly
    530                 535                 540

Gly Ala Gly Pro Gly Gly Ala Gly Phe Gly Pro Gly Gly Gly Ala Gly
545                 550                 555                 560

Phe Gly Pro Gly Gly Ala Gly Phe Gly Pro Gly Gly Ala Ala Gly
                565                 570                 575

Gly Pro Gly Gly Pro Gly Gly Pro Gly Gly Pro Gly Gly Ala Gly Gly
                580                 585                 590

Tyr Gly Pro Gly Gly Ala Gly Tyr Gly Pro Gly Gly Val Gly Pro
            595                 600                 605

Gly Gly Ala Gly Gly Tyr Gly Pro Gly Gly Ala Gly Gly Tyr Gly Pro
    610                 615                 620

Gly Gly Ser Gly Pro Gly Gly Ala Gly Pro Gly Gly Ala Gly Gly Glu
625                 630                 635                 640

Gly Pro Val Thr Val Asp Val Asp Val Thr Val Gly Pro Glu Gly Val
                645                 650                 655

Gly Gly Gly Pro Gly Gly Ala Gly Pro Gly Gly Ala Gly Phe Gly Pro
                660                 665                 670

Gly Gly Gly Ala Gly Phe Gly Pro Gly Gly Ala Pro Gly Ala Pro Gly
            675                 680                 685

Gly Pro Gly Gly Pro Gly Gly Pro Gly Gly Pro Gly Gly Pro Gly Gly
    690                 695                 700

Val Gly Pro Gly Gly Ala Gly Gly Tyr Gly Pro Gly Gly Ala Gly Gly
705                 710                 715                 720

Phe Gly Pro Gly Gly Thr Gly Phe Gly Pro Gly Gly Ala Gly Gly
            725                 730                 735

Phe Gly Pro Gly Gly Ala Gly Gly Phe Gly Pro Gly Gly Ala Gly Gly
                740                 745                 750

Phe Gly Pro Gly Gly Ala Gly Tyr Gly Pro Gly Gly Val Gly Pro
            755                 760                 765

Gly Gly Ala Gly Gly Phe Gly Pro Gly Gly Val Gly Pro Gly Gly Ser
    770                 775                 780

Gly Pro Gly Gly Ala Gly Gly Glu Gly Pro Val Thr Val Asp Val Asp
785                 790                 795                 800

Val Ser Val Gly Gly Ala Pro Gly Gly Pro Gly Gly Ala Gly Pro
            805                 810                 815

Gly Gly Ala Gly Phe Gly Pro Gly Gly Ala Gly Phe Gly Pro Gly
                820                 825                 830

Gly Gly Ala Gly Phe Gly Pro Gly Gly Ala Ala Gly Pro Ser Gly
                835                 840                 845

Pro Gly Gly Pro Gly Gly Pro Gly Gly Ala Gly Gly Tyr Gly Pro Gly
    850                 855                 860

Gly Ala Gly Gly Tyr Gly Pro Gly Gly Val Gly Pro Gly Gly Ala Gly
865                 870                 875                 880

Gly Tyr Gly Pro Gly Gly Ala Gly Gly Tyr Gly Pro Gly Gly Ser Gly
                885                 890                 895

Pro Gly Gly Ala Gly Pro Gly Gly Ala Gly Gly Glu Gly Pro Val Thr
                900                 905                 910

Val Asp Val Asp Val Thr Val Gly Pro Glu Gly Val Gly Gly Pro
            915                 920                 925

Gly Gly Ala Gly Pro Gly Gly Ala Gly Phe Gly Pro Gly Gly Gly Ala
    930                 935                 940

Gly Phe Gly Pro Gly Gly Ala Pro Gly Ala Pro Gly Gly Pro Gly Gly
```

```
                945                 950                 955                 960
Pro Gly Gly Pro Gly Gly Pro Gly Gly Pro Gly Gly Val Pro Gly
                    965                 970                 975

Gly Ala Gly Gly Tyr Gly Pro Gly Gly Ala Gly Gly Val Gly Pro Ala
                    980                 985                 990

Gly Thr Gly Gly Phe Gly Pro Gly  Gly Ala
            995                1000

<210> SEQ ID NO 85
<211> LENGTH: 626
<212> TYPE: PRT
<213> ORGANISM: Nephila clavipes
<220> FEATURE:
<223> OTHER INFORMATION: flagelliform silk protein

<400> SEQUENCE: 85

Ser Gly Gly Ser Gly Gly Thr Thr Val Ile Glu Asp Leu Asp Ile Thr
1               5                   10                  15

Ile Asp Gly Ala Asp Gly Pro Ile Thr Ile Ser Glu Glu Leu Thr Ile
            20                  25                  30

Ser Gly Ala Gly Ala Gly Gly Ser Gly Pro Gly Gly Ala Gly Pro Gly
        35                  40                  45

Gly Val Gly Pro Gly Gly Ser Gly Pro Gly Gly Val Gly Pro Gly Gly
    50                  55                  60

Ser Gly Pro Gly Gly Val Gly Pro Gly Gly Ala Gly Pro Tyr Gly
65                  70                  75                  80

Pro Gly Gly Ser Gly Pro Gly Ala Gly Gly Ala Gly Gly Pro Gly
                85                  90                  95

Gly Ala Tyr Gly Pro Gly Gly Ser Gly Gly Pro Gly Gly Ala Gly Gly
            100                 105                 110

Pro Tyr Gly Pro Gly Gly Glu Gly Pro Gly Gly Ala Gly Gly Pro Tyr
        115                 120                 125

Gly Pro Gly Gly Glu Gly Pro Gly Gly Ala Gly Gly Pro Tyr Gly Pro
    130                 135                 140

Gly Gly Ala Gly Gly Pro Tyr Gly Pro Gly Gly Ala Gly Gly Pro Tyr
145                 150                 155                 160

Gly Pro Gly Gly Ala Gly Gly Pro Tyr Gly Pro Gly Gly Ala Gly Gly
                165                 170                 175

Pro Tyr Gly Pro Gly Gly Val Gly Pro Gly Gly Thr Gly Pro Gly Gly
            180                 185                 190

Tyr Gly Pro Gly Gly Ala Gly Pro Gly Gly Tyr Gly Pro Gly Gly Ser
        195                 200                 205

Gly Pro Gly Gly Tyr Gly Pro Gly Gly Ser Gly Pro Gly Gly Tyr Gly
    210                 215                 220

Pro Gly Gly Ser Gly Pro Gly Gly Phe Gly Pro Gly Gly Ser Gly Pro
225                 230                 235                 240

Gly Gly Ser Gly Pro Gly Gly Ser Gly Pro Gly Gly Tyr Gly Pro Gly
                245                 250                 255

Gly Ser Gly Pro Gly Gly Tyr Gly Pro Gly Gly Ser Gly Pro Gly Gly
            260                 265                 270

Tyr Gly Pro Gly Gly Ser Gly Pro Gly Gly Tyr Gly Pro Gly Gly Ser
        275                 280                 285

Gly Pro Gly Gly Ser Gly Pro Gly Gly Tyr Gly Pro Gly Gly Ser Gly
    290                 295                 300

Pro Gly Gly Tyr Gly Pro Gly Gly Ser Gly Pro Gly Gly Ala Gly Pro
```

```
                305                 310                 315                 320
Gly Gly Ala Gly Pro Gly Gly Val Gly Pro Gly Gly Ala Gly Pro Gly
                325                 330                 335
Gly Ala Gly Pro Gly Gly Val Gly Pro Gly Gly Ala Gly Pro Gly Gly
                340                 345                 350
Ala Gly Pro Gly Gly Ala Gly Pro Gly Gly Ala Gly Arg Gly Gly Ala
                355                 360                 365
Gly Pro Gly Gly Ala Gly Ala Gly Gly Ala Gly Gly Ser Gly Gly
                370                 375                 380
Ala Gly Gly Ser Gly Gly Thr Thr Val Ile Glu Asp Leu Asp Ile Thr
385                 390                 395                 400
Ile Asp Gly Ala Asp Gly Pro Ile Thr Ile Ser Glu Glu Leu Thr Ile
                405                 410                 415
Gly Gly Ala Gly Gly Ser Gly Pro Gly Gly Ala Gly Gly Ser Gly Pro
                420                 425                 430
Gly Gly Ala Gly Pro Gly Gly Val Gly Pro Gly Gly Ser Gly Pro Gly
                435                 440                 445
Gly Leu Gly Ser Gly Gly Ser Gly Pro Gly Gly Val Gly Pro Gly Gly
                450                 455                 460
Ser Gly Pro Gly Gly Val Gly Pro Gly Gly Tyr Gly Pro Gly Gly Ser
465                 470                 475                 480
Gly Gly Leu Tyr Gly Pro Gly Ser Tyr Gly Pro Gly Gly Ser Gly Val
                485                 490                 495
Pro Tyr Gly Ser Ser Gly Thr Tyr Gly Ser Gly Gly Tyr Gly Pro
                500                 505                 510
Gly Gly Ala Gly Gly Ala Tyr Gly Pro Gly Ser Pro Gly Gly Ala Tyr
                515                 520                 525
Gly Pro Gly Ser Gly Gly Ser Tyr Tyr Pro Ser Ser Arg Val Pro Asp
                530                 535                 540
Met Val Asn Gly Ile Met Ser Ala Met Gln Gly Ser Gly Phe Asn Tyr
545                 550                 555                 560
Gln Met Phe Gly Asn Met Leu Ser Gln Tyr Ser Ser Gly Ser Gly Ser
                565                 570                 575
Cys Asn Pro Asn Asn Val Asn Val Leu Met Asp Ala Leu Leu Ala Ala
                580                 585                 590
Leu His Cys Leu Ser Asn His Gly Ser Ser Phe Ala Pro Ser Pro
                595                 600                 605
Thr Pro Ala Ala Met Ser Ala Tyr Ser Asn Ser Val Gly Arg Met Phe
610                 615                 620
Ala Tyr
625

<210> SEQ ID NO 86
<211> LENGTH: 651
<212> TYPE: PRT
<213> ORGANISM: Argiope trifasciata
<220> FEATURE:
<223> OTHER INFORMATION: flagelliform silk protein

<400> SEQUENCE: 86

Ala Gly Gly Pro Gly Ala Gly Gly Ala Gly Ala Gly Gly Val Gly Pro
1               5                   10                  15
Gly Gly Phe Gly Gly Pro Gly Gly Phe Gly Gly Ala Gly Gly Pro Gly
                20                  25                  30
Gly Pro Gly Gly Pro Gly Gly Ala Gly Gly Ala Gly Gly Ala Gly
```

```
                   35                  40                  45
Gly Leu Tyr Gly Pro Gly Gly Ala Gly Gly Leu Tyr Gly Pro Gly Gly
 50                  55                  60

Leu Tyr Gly Pro Gly Gly Ala Gly Val Pro Gly Ala Pro Gly Ala Ser
 65                  70                  75                  80

Gly Arg Ala Gly Gly Ile Gly Ala Ala Gly Ala Gly Ala Gly
                 85                  90                  95

Gly Val Gly Pro Gly Gly Val Ser Gly Ala Gly Ala Gly
                100                 105                 110

Ser Gly Val Thr Val Val Glu Ser Val Ser Val Gly Gly Ala Gly Gly
                115                 120                 125

Pro Gly Ala Gly Gly Val Gly Pro Gly Gly Val Gly Pro Gly Gly Val
                130                 135                 140

Gly Pro Gly Gly Ile Tyr Gly Pro Gly Gly Ala Gly Gly Leu Tyr Gly
145                 150                 155                 160

Pro Gly Ala Gly Gly Ala Phe Gly Pro Gly Gly Ala Gly Ala Pro
                165                 170                 175

Gly Gly Pro Gly Gly Pro Gly Gly Pro Gly Gly Pro Gly Gly Leu Gly
                180                 185                 190

Gly Gly Val Gly Gly Ala Gly Thr Gly Gly Val Gly Pro Gly Ala
                195                 200                 205

Gly Gly Val Gly Pro Ser Gly Ala Gly Gly Thr Gly Pro Val Ser
                210                 215                 220

Val Ser Ser Thr Val Ser Val Gly Gly Ala Gly Gly Pro Gly Ala Gly
225                 230                 235                 240

Gly Pro Gly Ala Gly Gly Ala Gly Ala Gly Gly Val Gly Pro Gly Gly
                245                 250                 255

Phe Gly Gly Pro Gly Gly Phe Gly Gly Ala Gly Gly Pro Gly Gly Pro
                260                 265                 270

Gly Gly Pro Gly Gly Ala Gly Gly Ala Gly Ala Gly Gly Leu
                275                 280                 285

Tyr Gly Pro Gly Gly Ala Gly Gly Leu Tyr Gly Pro Gly Gly Leu Tyr
                290                 295                 300

Gly Pro Gly Gly Ala Gly Val Pro Gly Ala Pro Gly Ala Ser Gly Arg
305                 310                 315                 320

Ala Gly Gly Ile Gly Gly Ala Ala Gly Ala Gly Val Gly Pro Gly
                325                 330                 335

Gly Val Ser Gly Gly Ala Gly Gly Ser Gly Val Ser Val Thr Glu Ser
                340                 345                 350

Val Thr Val Gly Gly Ala Gly Gly Ala Gly Ala Gly Ile Gly Gly
                355                 360                 365

Pro Ser Gly Leu Gly Gly Ala Gly Ala Thr Gly Gly Phe Gly Gly Arg
                370                 375                 380

Gly Gly Pro Gly Gly Pro Gly Gly Pro Gly Gly Pro Gly Arg Phe Gly
385                 390                 395                 400

Gly Ala Ala Gly Gly Ala Gly Ala Gly Val Gly Pro Gly Gly Val
                405                 410                 415

Ser Gly Gly Ala Gly Gly Ala Gly Gly Ser Gly Val Thr Val Val Glu
                420                 425                 430

Ser Val Ser Val Gly Gly Ala Gly Gly Pro Gly Ala Gly Gly Val Gly
                435                 440                 445

Pro Gly Gly Val Gly Pro Gly Gly Val Gly Pro Gly Gly Ile Tyr Gly
                450                 455                 460
```

Pro Gly Gly Ala Gly Gly Leu Tyr Gly Pro Gly Ala Gly Ala Phe
465                 470                 475                 480

Gly Ser Gly Gly Gly Ala Gly Ala Pro Gly Gly Pro Gly Gly Pro Gly
                485                 490                 495

Gly Pro Gly Gly Pro Gly Gly Leu Gly Gly Val Gly Gly Ala Gly
            500                 505                 510

Thr Gly Gly Gly Val Gly Pro Gly Val Gly Val Gly Pro Ser Gly
                515                 520                 525

Gly Ala Gly Gly Thr Gly Pro Val Ser Val Ser Thr Ile Thr Val
530                 535                 540

Gly Gly Gly Gln Ser Ser Gly Gly Val Leu Pro Ser Thr Ser Tyr Ala
545                 550                 555                 560

Pro Thr Thr Ser Gly Tyr Glu Arg Leu Pro Asn Leu Ile Asn Gly Ile
                565                 570                 575

Lys Ser Ser Met Gln Gly Gly Phe Asn Tyr Gln Asn Phe Gly Asn
                580                 585                 590

Ile Leu Ser Gln Tyr Ala Thr Gly Ser Gly Thr Cys Asn Tyr Tyr Asp
            595                 600                 605

Ile Asn Leu Leu Met Asp Ala Leu Leu Ala Ala Leu His Thr Leu Asn
            610                 615                 620

Tyr Gln Gly Ala Ser Tyr Val Pro Ser Tyr Pro Ser Pro Ser Glu Met
625                 630                 635                 640

Leu Ser Tyr Thr Glu Asn Val Arg Arg Tyr Phe
                645                 650

<210> SEQ ID NO 87
<211> LENGTH: 1884
<212> TYPE: PRT
<213> ORGANISM: Nephila madagascariensis
<220> FEATURE:
<223> OTHER INFORMATION: flagelliform silk protein
<220> FEATURE:
<221> NAME/KEY: misc_feature
<222> LOCATION: (1652)..(1652)
<223> OTHER INFORMATION: Xaa can be any naturally occurring amino acid

<400> SEQUENCE: 87

Met Gly Lys Gly Arg His Asp Thr Lys Ala Lys Ala Lys Ala Met Gln
1               5                   10                  15

Val Ala Leu Ala Ser Ser Ile Ala Glu Leu Val Ile Ala Glu Ser Ser
                20                  25                  30

Gly Gly Asp Val Gln Arg Lys Thr Asn Val Ile Ser Asn Ala Leu Arg
            35                  40                  45

Asn Ala Leu Met Ser Thr Thr Gly Ser Pro Asn Glu Glu Phe Val His
        50                  55                  60

Glu Val Gln Asp Leu Ile Gln Met Leu Ser Gln Gln Ile Asn Glu
65                  70                  75                  80

Val Asp Thr Ser Gly Pro Gly Gln Tyr Tyr Arg Ser Ser Ser Ser Gly
                85                  90                  95

Gly Gly Gly Gly Gly Gly Gly Pro Val Ile Thr Glu Thr Leu Thr
            100                 105                 110

Val Thr Val Gly Gly Ser Gly Ala Gly Gln Pro Ser Gly Ala Gly Pro
        115                 120                 125

Ser Gly Thr Gly Gly Tyr Ala Pro Thr Gly Tyr Ala Pro Ser Gly Ser
    130                 135                 140

Gly Pro Gly Gly Val Arg Pro Ser Ala Ser Gly Pro Ser Gly Ser Gly

-continued

```
            145                 150                 155                 160
        Pro Ser Gly Ser Arg Pro Ser Ser Gly Ser Ser Gly Thr Arg Pro
                        165                 170                 175
        Ser Ala Asn Ala Ala Gly Gly Ser Ser Pro Gly Gly Ile Ala Pro Gly
                            180                 185                 190
        Gly Ser Ser Pro Gly Gly Ala Gly Val Ser Gly Ala Thr Gly Gly Pro
                        195                 200                 205
        Ala Ser Ser Gly Ser Tyr Gly Ser Gly Thr Thr Gly Gly Ala Tyr Gly
                    210                 215                 220
        Pro Gly Gly Gly Ser Glu Pro Phe Gly Pro Gly Ala Ala Gly Gly Gln
        225                 230                 235                 240
        Tyr Gly Pro Gly Gly Ala Gly Pro Gly Gly Ala Gly Ala Tyr Gly Pro
                        245                 250                 255
        Gly Gly Val Gly Pro Gly Gly Ala Gly Pro Gly Gly Tyr Gly Pro Gly
                        260                 265                 270
        Gly Ala Gly Pro Gly Gly Tyr Gly Pro Gly Gly Ala Gly Pro Gly Gly
                    275                 280                 285
        Tyr Gly Pro Gly Gly Ala Gly Pro Gly Gly Tyr Gly Pro Gly Gly Ala
                290                 295                 300
        Gly Pro Gly Gly Tyr Gly Pro Gly Gly Ala Gly Pro Gly Gly Tyr Gly
        305                 310                 315                 320
        Pro Gly Gly Ala Gly Pro Gly Gly Tyr Gly Pro Gly Gly Ser Gly Thr
                        325                 330                 335
        Gly Gly Ala Gly Pro Gly Gly Tyr Thr Pro Gly Gly Ala Gly Pro Gly
                        340                 345                 350
        Gly Tyr Gly Pro Gly Gly Tyr Gly Pro Gly Gly Ser Gly Pro Gly Gly
                    355                 360                 365
        Ala Gly Ser Gly Gly Val Gly Pro Gly Gly Tyr Gly Pro Gly Gly Ala
                370                 375                 380
        Gly Pro Gly Gly Ala Gly Pro Gly Gly Ala Gly Pro Gly Gly Ala Gly
        385                 390                 395                 400
        Pro Ser Gly Ala Gly Pro Gly Gly Ala Gly Thr Gly Gly Ala Gly Thr
                        405                 410                 415
        Gly Gly Ala Gly Pro Gly Gly Ala Gly Pro Gly Gly Ala Gly Pro Gly
                        420                 425                 430
        Gly Ala Gly Pro Gly Gly Ala Gly Arg Gly Gly Ala Gly Arg Gly Gly
                    435                 440                 445
        Ala Gly Arg Gly Gly Ala Gly Arg Gly Gly Ala Gly Arg Gly Gly Ala
                450                 455                 460
        Gly Arg Gly Gly Ala Gly Gly Ala Gly Ala Gly Gly Ala Gly Gly Gly
        465                 470                 475                 480
        Ala Gly Gly Ala Gly Ala Gly Gly Ser Gly Ser Thr Thr Ile Ile
                        485                 490                 495
        Glu Asp Leu Asp Ile Thr Ile Asp Gly Ala Asp Gly Pro Ile Thr Ile
                        500                 505                 510
        Ser Glu Glu Leu Thr Ile Gly Gly Ala Gly Ala Gly Ser Gly Pro
                    515                 520                 525
        Gly Gly Ala Gly Pro Gly Gly Val Gly Pro Gly Arg Ser Gly Pro Gly
                    530                 535                 540
        Gly Val Gly Pro Gly Gly Ser Gly Pro Gly Ser Val Gly Pro Gly Gly
        545                 550                 555                 560
        Ser Gly Gln Gly Gly Leu Gly Ile Gly Arg Ser Gly Pro Gly Gly Val
                        565                 570                 575
```

-continued

```
Gly Pro Gly Gly Ser Gly Pro Gly Ser Ile Gly Pro Gly Gly Ser Gly
            580                 585                 590
Gln Gly Gly Leu Gly Pro Gly Ser Gly Gln Gly Gly Leu Gly Pro
        595                 600                 605
Gly Gly Ser Gly Pro Gly Val Gly Ser Gly Val Gly Gly Pro
    610                 615                 620
Tyr Gly Pro Gly Gly Ser Gly Pro Gly Val Gly Gly Ala Gly Gly
625                 630                 635                 640
Pro Tyr Gly Pro Gly Gly Ser Gly Gly Pro Gly Gly Ala Gly Gly Pro
                645                 650                 655
Tyr Gly Pro Gly Gly Pro Tyr Gly Pro Gly Gly Ala Gly Gly Pro Tyr
            660                 665                 670
Gly Pro Gly Gly Ala Gly Gly Pro Tyr Gly Pro Gly Gly Pro Tyr Gly
        675                 680                 685
Pro Gly Gly Ala Gly Gly Pro Gly Gly Gly Pro Gly Gly Ala Gly
    690                 695                 700
Gly Pro Tyr Gly Pro Gly Gly Pro Gly Gly Ala Gly Pro Gly Gly Tyr
705                 710                 715                 720
Gly Pro Gly Gly Tyr Gly Pro Gly Gly Ala Gly Pro Gly Gly Ala Gly
                725                 730                 735
Pro Gly Gly Tyr Gly Pro Gly Gly Ala Gly Pro Gly Gly Tyr Gly Pro
            740                 745                 750
Gly Gly Ala Gly Pro Gly Gly Ser Gly Pro Gly Gly Ile Gly Pro Gly
        755                 760                 765
Gly Ser Gly Pro Gly Gly Tyr Gly Pro Gly Gly Ile Gly Pro Gly Gly
    770                 775                 780
Thr Gly Pro Gly Gly Ala Gly Pro Gly Gly Ala Gly Pro Gly Gly Ala
785                 790                 795                 800
Gly Pro Ser Gly Ala Gly Pro Gly Gly Ala Gly Pro Ser Gly Ala Gly
                805                 810                 815
Arg Gly Gly Ser Gly Arg Gly Ser Val Gly Arg Gly Gly Ala Gly Arg
            820                 825                 830
Gly Gly Ala Gly Arg Gly Gly Ala Gly Gly Ala Gly Gly Ser Gly Gly
        835                 840                 845
Ala Gly Gly Ser Gly Gly Ala Gly Gly Ser Gly Thr Thr Ile Ile
    850                 855                 860
Glu Asp Leu Asp Ile Thr Val Asp Ala Asn Gly Pro Ile Thr Ile
865                 870                 875                 880
Ser Glu Glu Leu Thr Ile Gly Gly Ala Gly Ala Gly Val Gly Pro
                885                 890                 895
Gly Gly Ser Gly Pro Gly Gly Val Gly Pro Gly Gly Ser Gly Pro Gly
            900                 905                 910
Gly Val Gly Pro Gly Gly Ser Gly Pro Gly Gly Val Gly Ser Gly Gly
        915                 920                 925
Ser Gly Pro Gly Gly Val Gly Pro Gly Gly Ser Gly Pro Gly Gly Val
    930                 935                 940
Gly Ser Gly Gly Phe Gly Pro Gly Gly Ile Gly Pro Gly Gly Ser Gly
945                 950                 955                 960
Pro Gly Gly Val Gly Pro Gly Gly Val Gly Pro Tyr Gly Pro Gly
                965                 970                 975
Gly Ser Gly Pro Gly Gly Ala Gly Gly Ala Gly Ser Tyr Gly Pro
            980                 985                 990
```

```
Gly Gly Pro Tyr Gly Pro Gly Gly  Ser Gly Gly Pro Gly  Gly Ala Gly
        995                  1000                 1005

Gly Pro Tyr Gly Pro Gly Gly  Ala Gly Gly Pro Tyr  Gly Pro Gly
    1010             1015                  1020

Gly Pro Tyr Gly Pro Gly Gly  Ala Gly Gly Pro Gly  Gly Glu Gly
    1025             1030                  1035

Pro Gly Gly Ala Gly Gly Pro  Tyr Gly Pro Gly Gly  Pro Gly Gly
    1040             1045                  1050

Ala Gly Pro Gly Gly Tyr Gly  Pro Gly Gly Ala Gly  Pro Gly Gly
    1055             1060                  1065

Tyr Gly Pro Gly Gly Ala Gly  Pro Gly Gly Tyr Gly  Pro Gly Gly
    1070             1075                  1080

Ala Gly Ser Gly Gly Tyr Gly  Pro Gly Gly Ala Gly  Pro Gly Gly
    1085             1090                  1095

Tyr Gly Pro Gly Gly Pro Gly  Pro Gly Gly Tyr Gly  Pro Gly Gly
    1100             1105                  1110

Ala Gly Pro Gly Gly Tyr Gly  Pro Gly Gly Thr Gly  Pro Gly Gly
    1115             1120                  1125

Ser Ala Pro Gly Gly Ala Gly  Pro Gly Gly Ala Gly  Pro Gly Gly
    1130             1135                  1140

Tyr Gly Pro Gly Gly Ser Gly  Pro Gly Gly Tyr Gly  Pro Gly Gly
    1145             1150                  1155

Gly Pro Gly Gly Ala Gly Pro  Gly Gly Ala Gly Pro  Gly Gly Ala
    1160             1165                  1170

Gly Pro Gly Gly Ala Gly Pro  Gly Gly Ala Gly Pro  Gly Gly Ala
    1175             1180                  1185

Gly Pro Gly Gly Ala Gly Pro  Gly Gly Ala Gly Pro  Gly Gly Ala
    1190             1195                  1200

Gly Pro Gly Gly Ala Gly Pro  Gly Gly Val Gly Thr  Gly Gly Leu
    1205             1210                  1215

Gly Arg Gly Gly Ala Gly Arg  Gly Gly Ala Gly Arg  Gly Gly Ala
    1220             1225                  1230

Gly Arg Gly Gly Ala Gly Arg  Gly Gly Ala Gly Arg  Gly Gly Thr
    1235             1240                  1245

Gly Gly Val Gly Gly Ala Gly  Gly Ala Gly Gly Ala  Gly Gly Val
    1250             1255                  1260

Gly Gly Ala Gly Gly Ser Gly  Gly Thr Thr Val Ile  Glu Asp Leu
    1265             1270                  1275

Asp Ile Thr Ile Asp Gly Ala  Asp Gly Pro Ile Thr  Ile Ser Glu
    1280             1285                  1290

Glu Leu Thr Ile Ser Gly Ala  Gly Ala Gly Gly Ser  Gly Pro Gly
    1295             1300                  1305

Gly Ala Gly Pro Gly Gly Val  Gly Pro Gly Gly Ser  Gly Pro Gly
    1310             1315                  1320

Gly Val Gly Pro Gly Gly Ser  Gly Pro Gly Gly Val  Gly Pro Gly
    1325             1330                  1335

Gly Ala Gly Gly Pro Tyr Arg  Pro Gly Gly Ser Gly  Pro Gly Gly
    1340             1345                  1350

Ala Gly Gly Ala Gly Gly Pro  Gly Gly Ala Tyr Gly  Pro Gly Gly
    1355             1360                  1365

Ser Gly Gly Pro Gly Gly Ala  Gly Gly Pro Tyr Gly  Pro Gly Gly
    1370             1375                  1380

Glu Gly Pro Gly Gly Ser Gly  Gly Pro Tyr Gly Pro  Gly Gly Glu
```

```
             1385                1390                1395

Gly Pro Gly Gly Ala Gly Gly Pro Tyr Gly Pro Gly Gly Ala Gly
             1400                1405                1410

Gly Pro Tyr Gly Pro Gly Gly Ala Gly Gly Pro Tyr Gly Pro Gly
             1415                1420                1425

Gly Ala Gly Gly Pro Tyr Gly Pro Gly Gly Ala Gly Gly Pro Tyr
             1430                1435                1440

Gly Pro Gly Gly Ala Gly Gly Pro Tyr Gly Pro Gly Gly Ala Gly
             1445                1450                1455

Gly Pro Tyr Gly Pro Gly Gly Glu Gly Pro Gly Gly Ala Gly Gly
             1460                1465                1470

Pro Tyr Gly Pro Gly Gly Val Gly Pro Gly Gly Thr Gly Pro Gly
             1475                1480                1485

Gly Tyr Gly Pro Gly Gly Ala Gly Pro Gly Gly Tyr Gly Pro Gly
             1490                1495                1500

Gly Ser Gly Pro Gly Gly Tyr Gly Pro Gly Gly Ser Gly Pro Gly
             1505                1510                1515

Gly Phe Gly Pro Gly Gly Ser Gly Pro Gly Gly Tyr Gly Pro Gly
             1520                1525                1530

Gly Ser Gly Pro Gly Gly Tyr Gly Pro Gly Gly Ser Gly Pro Gly
             1535                1540                1545

Gly Ala Gly Pro Gly Gly Tyr Gly Pro Gly Gly Thr Gly Pro Gly
             1550                1555                1560

Gly Ser Gly Pro Gly Gly Tyr Gly Pro Gly Gly Ser Gly Pro Gly
             1565                1570                1575

Gly Tyr Gly Pro Gly Gly Ser Gly Pro Gly Gly Tyr Gly Pro Gly
             1580                1585                1590

Gly Ser Gly Pro Gly Gly Ala Gly Pro Gly Gly Ala Gly Pro Gly
             1595                1600                1605

Gly Ala Gly Pro Gly Gly Ala Gly Pro Gly Gly Val Gly Pro Gly
             1610                1615                1620

Gly Ala Gly Pro Gly Gly Ser Gly Pro Gly Gly Ala Gly Pro Gly
             1625                1630                1635

Gly Ala Gly Arg Gly Gly Ala Gly Arg Gly Gly Ala Gly Xaa Gly
             1640                1645                1650

Gly Ala Gly Pro Gly Gly Ala Gly Gly Ala Gly Gly Ala Gly Gly
             1655                1660                1665

Ser Gly Gly Ala Gly Gly Ser Gly Gly Thr Thr Val Ile Glu Asp
             1670                1675                1680

Leu Asp Ile Thr Ile Asp Gly Ala Asp Gly Pro Ile Thr Ile Ser
             1685                1690                1695

Glu Glu Leu Thr Ile Asn Gly Ala Gly Ala Gly Gly Ser Gly Pro
             1700                1705                1710

Gly Gly Ala Gly Pro Gly Gly Val Gly Pro Gly Gly Ser Gly Pro
             1715                1720                1725

Gly Gly Val Gly Pro Gly Gly Ser Gly Pro Gly Gly Val Gly Pro
             1730                1735                1740

Gly Gly Ala Gly Gly Pro Tyr Gly Pro Gly Gly Ser Gly Pro Gly
             1745                1750                1755

Gly Ala Gly Gly Ala Gly Gly Pro Gly Gly Ala Tyr Gly Pro Gly
             1760                1765                1770

Gly Ser Gly Gly Pro Gly Gly Ala Gly Gly Pro Tyr Gly Pro Gly
             1775                1780                1785
```

```
Gly Glu Gly Pro Gly Gly Ala Gly Gly Pro Tyr Gly Pro Gly Gly
        1790                1795                1800

Glu Gly Pro Gly Gly Ala Gly Gly Pro Tyr Gly Pro Gly Gly Ala
    1805                1810                1815

Gly Gly Pro Tyr Gly Pro Gly Gly Ala Gly Gly Pro Tyr Gly Pro
        1820                1825                1830

Gly Gly Ala Gly Gly Pro Tyr Gly Pro Gly Gly Ala Gly Gly Pro
        1835                1840                1845

Tyr Gly Pro Gly Gly Ala Gly Pro Tyr Gly Pro Gly Gly Ala
    1850                1855                1860

Gly Gly Pro Tyr Gly Pro Gly Gly Glu Pro Gly Gly Ala Gly
        1865                1870                1875

Gly Pro Tyr Gly Pro Gly
        1880

<210> SEQ ID NO 88
<211> LENGTH: 2249
<212> TYPE: PRT
<213> ORGANISM: Nephila clavipes
<220> FEATURE:
<223> OTHER INFORMATION: flagelliform silk protein

<400> SEQUENCE: 88

Ala Gly Pro Ser Gly Thr Gly Gly Tyr Ala Pro Thr Gly Tyr Ala Pro
1               5                   10                  15

Ser Gly Ser Gly Ala Gly Gly Val Arg Pro Ser Ala Ser Gly Pro Ser
            20                  25                  30

Gly Ser Gly Pro Ser Gly Gly Ser Arg Pro Ser Ser Ser Gly Pro Ser
        35                  40                  45

Gly Thr Arg Pro Ser Pro Asn Gly Ala Ser Gly Ser Pro Gly Gly
    50                  55                  60

Ile Ala Pro Gly Gly Ser Asn Ser Gly Gly Ala Gly Val Ser Gly Ala
65                  70                  75                  80

Thr Gly Gly Pro Ala Ser Ser Gly Ser Tyr Gly Pro Gly Ser Thr Gly
                85                  90                  95

Gly Thr Tyr Gly Pro Ser Gly Gly Ser Glu Pro Phe Gly Pro Gly Val
            100                 105                 110

Ala Gly Gly Pro Tyr Ser Pro Gly Gly Ala Pro Gly Gly Ala Gly
        115                 120                 125

Gly Ala Tyr Gly Pro Gly Gly Val Gly Thr Gly Ala Gly Pro Gly
    130                 135                 140

Gly Tyr Gly Pro Gly Gly Ala Gly Pro Gly Gly Tyr Gly Pro Gly Gly
145                 150                 155                 160

Ala Gly Pro Gly Gly Tyr Gly Pro Gly Ala Gly Pro Gly Gly Tyr
                165                 170                 175

Gly Pro Gly Gly Ala Gly Pro Gly Gly Tyr Gly Pro Gly Gly Ala Gly
            180                 185                 190

Pro Gly Gly Tyr Gly Pro Gly Gly Ala Gly Pro Gly Gly Tyr Gly Pro
        195                 200                 205

Gly Gly Thr Gly Pro Gly Gly Tyr Gly Pro Gly Gly Thr Gly Pro Gly
    210                 215                 220

Gly Val Gly Pro Gly Gly Ala Gly Pro Gly Gly Tyr Gly Pro Gly Gly
225                 230                 235                 240

Ala Gly Pro Gly Gly Ala Gly Pro Gly Gly Ala Gly Pro Gly Gly Ala
                245                 250                 255
```

```
Gly Pro Gly Gly Ala Gly Pro Gly Gly Tyr Gly Pro Gly Gly Ser Gly
            260                 265                 270

Pro Gly Gly Ala Gly Pro Ser Gly Ala Gly Leu Gly Gly Ala Gly Pro
            275                 280                 285

Gly Gly Ala Gly Leu Gly Gly Ala Gly Pro Gly Gly Ala Gly Thr Ser
290                 295                 300

Gly Ala Gly Pro Gly Gly Ala Gly Pro Gly Gly Ala Gly Gln Gly Gly
305                 310                 315                 320

Ala Gly Pro Gly Gly Ala Gly Arg Gly Ala Gly Arg Gly Gly Val
            325                 330                 335

Gly Arg Gly Gly Ala Gly Arg Gly Ala Gly Arg Gly Gly Ala Arg
            340                 345                 350

Gly Ala Gly Gly Ala Gly Gly Ala Gly Ala Gly Gly Ser Gly Gly
            355                 360                 365

Thr Thr Ile Val Glu Asp Leu Asp Ile Thr Ile Asp Gly Ala Asp Gly
            370                 375                 380

Pro Ile Thr Ile Ser Glu Glu Leu Thr Ile Gly Gly Ala Gly Ala Gly
385                 390                 395                 400

Gly Ser Gly Pro Gly Gly Ala Gly Pro Gly Asn Val Gly Pro Gly Arg
            405                 410                 415

Ser Gly Pro Gly Gly Val Gly Pro Gly Ser Gly Pro Gly Gly Val
            420                 425                 430

Gly Pro Gly Ser Phe Gly Pro Gly Gly Val Gly Ser Gly Gly Ser Gly
            435                 440                 445

Pro Gly Gly Val Arg Pro Ser Gly Ser Gly Pro Gly Gly Val Gly Thr
450                 455                 460

Gly Gly Val Gly Pro Gly Gly Ala Gly Gly Pro Tyr Gly Pro Gly Gly
465                 470                 475                 480

Ser Gly Pro Gly Gly Ala Gly Ser Ala Gly Gly Thr Tyr Gly Pro Gly
            485                 490                 495

Gly Phe Gly Gly Pro Gly Gly Phe Gly Gly Pro Gly Gly Ala Gly Gly
            500                 505                 510

Pro Tyr Gly Pro Gly Gly Ala Gly Gly Pro Tyr Gly Pro Gly Gly Ala
            515                 520                 525

Gly Gly Pro Tyr Gly Pro Gly Gly Ala Gly Gly Pro Tyr Gly Pro Gly
            530                 535                 540

Gly Ala Gly Gly Pro Tyr Gly Pro Gly Gly Ala Gly Gly Ser Tyr Gly
545                 550                 555                 560

Leu Gly Gly Ala Gly Gly Ser Gly Gly Val Gly Pro Gly Gly Ser Gly
            565                 570                 575

Pro Gly Gly Tyr Gly Pro Gly Gly Ala Gly Pro Gly Gly Tyr Gly Pro
            580                 585                 590

Gly Gly Ser Gly Pro Gly Gly Tyr Gly Pro Gly Gly Ser Gly Ser Gly
            595                 600                 605

Gly Tyr Gly Pro Gly Gly Ser Gly Pro Gly Gly Ser Gly Pro Gly Gly
            610                 615                 620

Tyr Gly Pro Gly Gly Thr Gly Pro Gly Gly Ser Glu Ser Gly Gly Tyr
625                 630                 635                 640

Gly Pro Gly Gly Ser Gly Pro Gly Gly Ser Gly Pro Gly Gly Ser Gly
            645                 650                 655

Pro Gly Gly Ser Gly Pro Gly Gly Tyr Gly Pro Gly Gly Ser Gly Pro
            660                 665                 670
```

-continued

```
Ser Ser Phe Val Pro Gly Gly Ser Gly Pro Gly Gly Ser Pro Gly
            675                 680                 685

Gly Ala Gly Pro Gly Gly Ala Gly Pro Gly Gly Ala Gly Pro Gly Gly
690                 695                 700

Ala Gly Pro Gly Gly Val Gly Leu Gly Gly Ala Gly Arg Gly Ala
705                 710                 715                 720

Gly Arg Gly Gly Ala Gly Ser Val Ala Gly Arg Gly Gly Ala Gly
            725                 730                 735

Arg Gly Gly Ala Gly Arg Gly Gly Ala Gly Arg Gly Gly Ala Gly Arg
            740                 745                 750

Gly Gly Ala Gly Ala Gly Ala Gly Gly Ala Gly Gly Pro Gly
            755                 760                 765

Gly Ala Gly Gly Ser Gly Gly Thr Val Ile Glu Asp Leu Asp Ile
770                 775                 780

Thr Ile Asp Gly Ala Asp Gly Pro Ile Thr Ile Ser Glu Glu Leu Thr
785                 790                 795                 800

Ile Ser Gly Ala Gly Ser Gly Pro Gly Gly Ala Gly Thr Gly Gly
            805                 810                 815

Val Gly Pro Gly Gly Ser Gly Pro Gly Gly Val Gly Pro Gly Gly Phe
            820                 825                 830

Gly Pro Gly Gly Val Gly Pro Gly Gly Ser Gly Pro Gly Gly Val Gly
            835                 840                 845

Pro Gly Gly Ala Gly Arg Pro Tyr Gly Pro Gly Gly Ser Gly Pro Gly
850                 855                 860

Gly Ala Gly Gly Ala Gly Gly Thr Gly Gly Ala Tyr Gly Pro Gly Gly
865                 870                 875                 880

Ala Tyr Gly Pro Gly Gly Ser Gly Gly Pro Gly Gly Ala Gly Pro
            885                 890                 895

Gly Gly Glu Gly Pro Gly Gly Ala Gly Pro Tyr Gly Pro Gly Gly
            900                 905                 910

Ala Gly Gly Pro Tyr Gly Pro Gly Gly Ala Gly Gly Pro Tyr Gly Pro
            915                 920                 925

Gly Gly Glu Gly Pro Tyr Gly Pro Gly Val Ser Tyr Gly Pro Gly
            930                 935                 940

Gly Ala Gly Gly Pro Tyr Gly Pro Gly Gly Pro Tyr Gly Pro Gly Gly
945                 950                 955                 960

Glu Gly Pro Gly Gly Ala Gly Pro Tyr Gly Pro Gly Gly Val Gly
            965                 970                 975

Pro Gly Gly Ser Gly Pro Gly Gly Tyr Gly Pro Gly Gly Ala Gly Pro
            980                 985                 990

Gly Gly Tyr Gly Pro Gly Gly Ser Gly Pro Gly Gly Tyr Gly Pro Gly
            995                 1000                1005

Gly Ser Gly Pro Gly Gly Tyr Gly Pro Gly Gly Ser Gly Pro Gly
            1010                1015                1020

Gly Tyr Gly Pro Gly Gly Ser Gly Pro Gly Gly Tyr Gly Pro Gly
            1025                1030                1035

Gly Tyr Gly Pro Gly Gly Ser Gly Pro Gly Gly Ser Gly Pro Gly
            1040                1045                1050

Gly Ser Gly Pro Gly Gly Tyr Gly Pro Gly Gly Thr Gly Pro Gly
            1055                1060                1065

Gly Ser Gly Pro Gly Gly Tyr Gly Pro Gly Gly Ser Gly Pro Gly
            1070                1075                1080

Gly Ser Gly Pro Gly Gly Tyr Gly Pro Gly Gly Ser Gly Pro Gly
```

-continued

```
            1085                1090                1095
Gly Phe Gly Pro Gly Gly Ser Gly Pro Gly Gly Tyr Gly Pro Gly
        1100                1105                1110
Gly Ser Gly Pro Gly Gly Ala Gly Pro Gly Gly Val Gly Pro Gly
        1115                1120                1125
Gly Phe Gly Pro Gly Gly Ala Gly Pro Gly Gly Ala Ala Pro Gly
        1130                1135                1140
Gly Ala Gly Pro Gly Gly Ala Gly Pro Gly Gly Ala Gly Pro Gly
        1145                1150                1155
Gly Ala Gly Pro Gly Gly Ala Gly Pro Gly Gly Ala Gly Pro Gly
        1160                1165                1170
Gly Ala Gly Gly Ala Gly Gly Ala Gly Gly Ser Gly Gly Ala Gly
        1175                1180                1185
Gly Ser Gly Gly Thr Thr Ile Ile Glu Asp Leu Asp Ile Thr Ile
        1190                1195                1200
Asp Gly Ala Asp Gly Pro Ile Thr Ile Ser Glu Glu Leu Pro Ile
        1205                1210                1215
Ser Gly Ala Gly Gly Ser Gly Pro Gly Gly Ala Gly Pro Gly Gly
        1220                1225                1230
Val Gly Pro Gly Gly Ser Gly Pro Gly Gly Val Gly Pro Gly Gly
        1235                1240                1245
Ser Gly Pro Gly Gly Val Gly Pro Gly Gly Ser Gly Pro Gly Gly
        1250                1255                1260
Val Gly Pro Gly Gly Ala Gly Gly Pro Tyr Gly Pro Gly Gly Ser
        1265                1270                1275
Gly Pro Gly Gly Ala Gly Gly Ala Gly Pro Gly Gly Ala Gly Tyr
        1280                1285                1290
Gly Pro Gly Gly Ser Tyr Gly Pro Gly Gly Ser Gly Gly Pro Gly
        1295                1300                1305
Gly Ala Gly Gly Pro Tyr Gly Pro Gly Gly Glu Gly Pro Gly Gly
        1310                1315                1320
Ala Gly Gly Pro Tyr Gly Pro Gly Gly Ala Gly Pro Tyr Gly
        1325                1330                1335
Pro Gly Gly Ala Gly Gly Pro Tyr Gly Pro Gly Gly Glu Gly Gly
        1340                1345                1350
Pro Tyr Gly Pro Gly Gly Ser Tyr Gly Pro Gly Gly Ala Gly Gly
        1355                1360                1365
Pro Tyr Gly Pro Gly Gly Pro Tyr Gly Pro Gly Gly Glu Gly Pro
        1370                1375                1380
Gly Gly Ala Gly Gly Pro Tyr Gly Pro Gly Gly Val Gly Pro Gly
        1385                1390                1395
Gly Gly Gly Pro Gly Gly Tyr Gly Pro Gly Gly Ala Gly Pro Gly
        1400                1405                1410
Gly Tyr Gly Pro Gly Gly Ser Gly Pro Gly Gly Tyr Gly Pro Gly
        1415                1420                1425
Gly Ser Gly Pro Gly Gly Tyr Gly Pro Gly Gly Ser Gly Pro Gly
        1430                1435                1440
Gly Tyr Gly Pro Gly Gly Ser Gly Pro Gly Gly Tyr Gly Pro Gly
        1445                1450                1455
Gly Ser Gly Pro Gly Gly Ser Gly Pro Gly Gly Tyr Gly Pro Gly
        1460                1465                1470
Gly Ser Gly Pro Gly Gly Ser Gly Pro Gly Gly Tyr Gly Pro Gly
        1475                1480                1485
```

-continued

```
Gly Ser Gly Pro Gly Gly Tyr Gly Pro Gly Gly Ser Gly Pro Gly
    1490                1495                1500

Gly Ser Gly Pro Gly Gly Tyr Gly Pro Gly Gly Ser Gly Pro Gly
    1505                1510                1515

Gly Ser Gly Pro Gly Gly Tyr Gly Pro Gly Gly Ser Gly Pro Gly
    1520                1525                1530

Gly Phe Gly Pro Gly Gly Phe Gly Pro Gly Gly Ser Gly Pro Gly
    1535                1540                1545

Gly Tyr Gly Pro Gly Gly Ser Gly Pro Gly Gly Ala Gly Pro Gly
    1550                1555                1560

Gly Val Gly Pro Gly Gly Phe Gly Pro Gly Gly Ala Gly Pro Gly
    1565                1570                1575

Gly Ala Gly Pro Gly Gly Ala Gly Pro Gly Gly Ala Gly Pro Gly
    1580                1585                1590

Gly Ala Gly Pro Gly Gly Ala Gly Pro Gly Gly Ala Gly Pro Gly
    1595                1600                1605

Gly Ala Gly Pro Gly Gly Ala Gly Gly Ala Gly Gly Ala Gly Gly
    1610                1615                1620

Ala Gly Gly Ser Gly Gly Ala Gly Gly Ser Gly Gly Thr Thr Ile
    1625                1630                1635

Ile Glu Asp Leu Asp Ile Thr Ile Asp Gly Ala Asp Gly Pro Ile
    1640                1645                1650

Thr Ile Ser Glu Glu Leu Thr Ile Ser Gly Ala Gly Gly Ser Gly
    1655                1660                1665

Pro Gly Gly Ala Gly Pro Gly Gly Val Gly Pro Gly Gly Ser Gly
    1670                1675                1680

Pro Gly Gly Val Gly Pro Gly Gly Ser Gly Pro Gly Gly Val Gly
    1685                1690                1695

Pro Gly Gly Ser Gly Pro Gly Gly Val Gly Pro Gly Gly Ala Gly
    1700                1705                1710

Gly Pro Tyr Gly Pro Gly Gly Ser Gly Pro Gly Gly Ala Gly Gly
    1715                1720                1725

Ala Gly Gly Pro Gly Gly Ala Tyr Gly Pro Gly Gly Ser Tyr Gly
    1730                1735                1740

Pro Gly Gly Ser Gly Gly Pro Gly Gly Ala Gly Gly Pro Tyr Gly
    1745                1750                1755

Pro Gly Gly Glu Gly Pro Gly Gly Ala Gly Gly Pro Tyr Gly Pro
    1760                1765                1770

Gly Gly Ala Gly Gly Pro Tyr Gly Pro Gly Gly Ala Gly Gly Pro
    1775                1780                1785

Tyr Gly Pro Gly Gly Glu Gly Gly Pro Tyr Gly Pro Gly Gly Ser
    1790                1795                1800

Tyr Gly Pro Gly Gly Ala Gly Gly Pro Tyr Gly Pro Gly Gly Pro
    1805                1810                1815

Tyr Gly Pro Gly Gly Glu Gly Pro Gly Gly Ala Gly Gly Pro Tyr
    1820                1825                1830

Gly Pro Gly Gly Val Gly Pro Gly Gly Gly Gly Pro Gly Gly Tyr
    1835                1840                1845

Gly Pro Gly Gly Ala Gly Pro Gly Gly Tyr Gly Pro Gly Gly Ser
    1850                1855                1860

Gly Pro Gly Gly Tyr Gly Pro Gly Gly Ser Gly Pro Gly Gly Tyr
    1865                1870                1875
```

Gly Pro Gly Gly Ser Gly Pro Gly Gly Tyr Gly Pro Gly Gly Ser
1880             1885             1890

Gly Pro Gly Gly Tyr Gly Pro Gly Gly Ser Gly Pro Gly Gly Ser
1895             1900             1905

Gly Pro Gly Gly Tyr Gly Pro Gly Gly Ser Gly Pro Gly Gly Tyr
1910             1915             1920

Gly Pro Gly Gly Ser Gly Pro Gly Gly Ser Gly Pro Gly Gly Tyr
1925             1930             1935

Gly Pro Gly Gly Ser Gly Pro Gly Gly Phe Gly Pro Gly Gly Phe
1940             1945             1950

Gly Pro Gly Gly Ser Gly Pro Gly Gly Tyr Gly Pro Gly Gly Ser
1955             1960             1965

Gly Pro Gly Gly Ala Gly Pro Gly Gly Val Gly Pro Gly Gly Phe
1970             1975             1980

Gly Pro Gly Gly Ala Gly Pro Gly Gly Ala Gly Pro Gly Gly Ala
1985             1990             1995

Gly Pro Gly Gly Ala Gly Pro Gly Gly Ala Gly Pro Gly Gly Ala
2000             2005             2010

Gly Pro Gly Gly Ala Gly Pro Gly Gly Ala Gly Pro Gly Gly Ala
2015             2020             2025

Gly Gly Ala Gly Gly Ala Gly Gly Ala Gly Ser Gly Gly Ala
2030             2035             2040

Gly Gly Ser Gly Gly Thr Thr Ile Ile Glu Asp Leu Asp Ile Thr
2045             2050             2055

Ile Asp Gly Ala Asp Gly Pro Ile Thr Ile Ser Glu Glu Leu Thr
2060             2065             2070

Ile Ser Gly Ala Gly Gly Ser Gly Pro Gly Gly Ala Gly Pro Gly
2075             2080             2085

Gly Val Gly Pro Gly Gly Ser Gly Pro Gly Gly Val Gly Pro Gly
2090             2095             2100

Gly Ser Gly Pro Gly Gly Val Gly Pro Gly Gly Ser Gly Ala Gly
2105             2110             2115

Gly Val Gly Pro Gly Gly Ala Gly Gly Pro Tyr Gly Pro Gly Gly
2120             2125             2130

Ser Gly Pro Gly Gly Ala Gly Gly Ala Gly Gly Pro Gly Gly Ala
2135             2140             2145

Tyr Gly Pro Gly Gly Ser Tyr Gly Pro Gly Gly Ser Gly Gly Pro
2150             2155             2160

Gly Gly Ala Gly Gly Pro Tyr Gly Pro Gly Gly Glu Gly Pro Gly
2165             2170             2175

Gly Ala Gly Gly Pro Tyr Gly Pro Gly Gly Ala Gly Gly Pro Tyr
2180             2185             2190

Gly Pro Gly Gly Ala Gly Gly Pro Tyr Gly Pro Gly Gly Glu Gly
2195             2200             2205

Gly Pro Tyr Gly Pro Gly Gly Ser Tyr Gly Pro Gly Gly Ala Gly
2210             2215             2220

Gly Pro Tyr Gly Pro Gly Gly Pro Tyr Gly Pro Gly Gly Glu Gly
2225             2230             2235

Pro Gly Gly Ala Gly Gly Pro Tyr Gly Pro Gly
2240             2245

<210> SEQ ID NO 89
<211> LENGTH: 462
<212> TYPE: PRT

-continued

<213> ORGANISM: Nephila clavipes
<220> FEATURE:
<223> OTHER INFORMATION: flagelliform silk protein

<400> SEQUENCE: 89

```
Val Gly Pro Gly Gly Ser Gly Pro Gly Gly Tyr Gly Pro Gly Gly Ser
1               5                   10                  15
Gly Pro Gly Gly Tyr Gly Pro Gly Gly Ala Gly Pro Gly Gly Tyr Gly
                20                  25                  30
Pro Gly Gly Ser Gly Pro Gly Gly Tyr Gly Pro Gly Gly Ser Gly Pro
            35                  40                  45
Gly Gly Tyr Gly Pro Gly Gly Ser Gly Pro Gly Gly Tyr Gly Pro Gly
        50                  55                  60
Gly Ser Gly Pro Gly Gly Tyr Gly Ser Gly Gly Ala Gly Pro Gly Gly
65                  70                  75                  80
Tyr Gly Pro Gly Gly Ser Gly Pro Gly Gly Tyr Gly Pro Gly Gly Ser
                85                  90                  95
Gly Pro Gly Gly Tyr Gly Pro Gly Gly Thr Gly Pro Gly Gly Thr Gly
            100                 105                 110
Pro Gly Gly Ser Gly Pro Gly Gly Tyr Gly Pro Gly Gly Ser Gly Pro
        115                 120                 125
Gly Gly Ser Gly Pro Gly Gly Ser Gly Pro Gly Gly Tyr Gly Pro Ser
    130                 135                 140
Gly Ser Gly Pro Gly Gly Tyr Gly Pro Ser Gly Ser Gly Pro Gly Gly
145                 150                 155                 160
Tyr Gly Pro Gly Gly Ser Gly Pro Gly Gly Tyr Gly Pro Gly Gly Ser
                165                 170                 175
Gly Ala Gly Gly Thr Gly Pro Gly Gly Ala Gly Gly Ala Gly Gly Ala
            180                 185                 190
Gly Gly Ser Gly Gly Ala Gly Ser Gly Gly Ala Gly Gly Ser Gly Gly
        195                 200                 205
Gly Ala Gly Gly Ser Gly Gly Val Gly Gly Ser Gly Gly Thr Thr Ile
    210                 215                 220
Thr Glu Asp Leu Asp Ile Thr Ile Asp Gly Ala Asp Gly Pro Ile Thr
225                 230                 235                 240
Ile Ser Glu Glu Leu Thr Ile Ser Gly Ala Gly Gly Ser Gly Pro Gly
                245                 250                 255
Gly Ala Gly Pro Gly Gly Val Gly Pro Gly Gly Ser Gly Pro Gly Gly
            260                 265                 270
Val Gly Pro Gly Val Ser Gly Pro Gly Gly Val Gly Pro Gly Gly Ser
        275                 280                 285
Gly Pro Gly Gly Val Gly Ser Gly Gly Ser Gly Pro Gly Gly Val Gly
    290                 295                 300
Pro Gly Gly Tyr Gly Pro Gly Gly Ser Gly Ser Gly Val Gly Pro
305                 310                 315                 320
Gly Gly Tyr Gly Pro Gly Gly Ser Gly Gly Phe Tyr Gly Pro Gly Gly
                325                 330                 335
Ser Glu Gly Pro Tyr Gly Pro Ser Gly Pro Tyr Gly Ser Gly Gly Gly
            340                 345                 350
Tyr Gly Pro Gly Gly Ala Gly Pro Tyr Gly Pro Gly Ser Pro Gly
    355                 360                 365
Gly Ala Tyr Gly Pro Gly Ser Pro Gly Gly Ala Tyr Tyr Pro Ser Ser
    370                 375                 380
Arg Val Pro Asp Met Val Asn Gly Ile Met Ser Ala Met Gln Gly Ser
```

```
385             390             395             400
Gly Phe Asn Tyr Gln Met Phe Gly Asn Met Leu Ser Gln Tyr Ser Ser
                405                 410                 415
Gly Ser Gly Thr Cys Asn Pro Asn Val Asn Val Leu Met Asp Ala
                420                 425                 430
Leu Leu Ala Ala Leu His Cys Leu Ser Asn His Gly Ser Ser Ser Phe
                435                 440                 445
Ala Pro Ser Pro Thr Pro Ala Ala Met Ser Ala Tyr Ser Asn
                450                 455                 460

<210> SEQ ID NO 90
<211> LENGTH: 2834
<212> TYPE: PRT
<213> ORGANISM: Argiope trifasciata
<220> FEATURE:
<223> OTHER INFORMATION: aciniform spidroin 1

<400> SEQUENCE: 90

Ser Ser Ala Leu Phe Asn Ala Gly Val Leu Asn Ala Ser Asn Ile Asp
1               5                   10                  15
Thr Leu Gly Ser Arg Val Leu Ser Ala Leu Leu Asn Gly Val Ser Ser
                20                  25                  30
Ala Ala Gln Gly Leu Gly Ile Asn Val Asp Ser Gly Ser Val Gln Ser
                35                  40                  45
Asp Ile Ser Ser Ser Ser Ser Phe Leu Ser Thr Ser Ser Ser Ser Ala
            50                  55                  60
Ser Tyr Ser Gln Ala Ser Ala Ser Ser Thr Ser Gly Ala Gly Tyr Thr
65                  70                  75                  80
Gly Pro Ser Gly Pro Ser Thr Gly Pro Ser Gly Tyr Pro Gly Pro Leu
                85                  90                  95
Gly Gly Gly Ala Pro Phe Gly Gln Ser Gly Phe Gly Ser Asp Gly
                100                 105                 110
Pro Gln Gly Gly Phe Gly Ala Thr Gly Gly Ala Ser Ala Gly Leu Ile
                115                 120                 125
Ser Arg Val Ala Asn Ala Leu Ala Asn Thr Ser Thr Leu Arg Thr Val
                130                 135                 140
Leu Arg Thr Gly Val Ser Gln Gln Ile Ala Ser Ser Val Val Gln Arg
145                 150                 155                 160
Ala Ala Gln Ser Leu Ala Ser Thr Leu Gly Val Asp Gly Asn Asn Leu
                165                 170                 175
Ala Arg Phe Ala Val Gln Ala Val Ser Arg Leu Pro Ala Gly Ser Asp
                180                 185                 190
Thr Ser Ala Tyr Ala Gln Ala Phe Ser Ser Ala Leu Phe Asn Ala Gly
                195                 200                 205
Val Leu Asn Ala Ser Asn Ile Asp Thr Leu Gly Ser Arg Val Leu Ser
                210                 215                 220
Ala Leu Leu Asn Gly Val Ser Ser Ala Ala Gln Gly Leu Gly Ile Asn
225                 230                 235                 240
Val Asp Ser Gly Ser Val Gln Ser Asp Ile Ser Ser Ser Ser Ser Phe
                245                 250                 255
Leu Ser Thr Ser Ser Ser Ser Ala Ser Tyr Ser Gln Ala Ser Ala Ser
                260                 265                 270
Ser Thr Ser Gly Ala Gly Tyr Thr Gly Pro Ser Gly Pro Ser Thr Gly
                275                 280                 285
Pro Ser Gly Tyr Pro Gly Leu Leu Gly Gly Gly Ala Pro Phe Gly Gln
```

```
            290                 295                 300

Ser Gly Phe Gly Gly Ser Asp Gly Pro Gln Gly Gly Phe Gly Ala Thr
305                 310                 315                 320

Gly Gly Ala Ser Ala Gly Leu Ile Ser Arg Val Ala Asn Ala Leu Ala
                325                 330                 335

Asn Thr Ser Thr Leu Arg Thr Val Leu Arg Thr Gly Val Ser Gln Gln
                340                 345                 350

Ile Ala Ser Ser Val Val Gln Arg Ala Ala Gln Ser Leu Ala Ser Thr
            355                 360                 365

Leu Gly Val Asp Gly Asn Asn Leu Ala Arg Phe Ala Val Gln Ala Val
        370                 375                 380

Ser Arg Leu Pro Ala Gly Ser Asp Thr Ser Ala Tyr Ala Gln Ala Phe
385                 390                 395                 400

Ser Ser Ala Leu Phe Asn Ala Gly Val Leu Asn Ala Ser Asn Ile Asp
                405                 410                 415

Thr Leu Gly Ser Arg Val Leu Ser Ala Leu Leu Asn Gly Val Ser Ser
                420                 425                 430

Ala Ala Gln Gly Leu Gly Ile Asn Val Asp Ser Gly Ser Val Gln Ser
            435                 440                 445

Asp Ile Ser Ser Ser Ser Ser Phe Leu Ser Thr Ser Ser Ser Ser Ala
        450                 455                 460

Ser Tyr Ser Gln Ala Ser Ala Ser Ser Thr Ser Gly Ala Gly Tyr Thr
465                 470                 475                 480

Gly Pro Ser Gly Pro Ser Thr Gly Pro Ser Gly Tyr Pro Gly Pro Leu
                485                 490                 495

Gly Gly Gly Ala Pro Phe Gly Gln Ser Gly Phe Gly Gly Ser Asp Gly
                500                 505                 510

Pro Gln Gly Gly Phe Gly Ala Thr Gly Gly Ala Ser Ala Gly Leu Ile
            515                 520                 525

Ser Arg Val Ala Asn Ala Leu Ala Asn Thr Ser Thr Leu Arg Thr Val
        530                 535                 540

Leu Arg Thr Gly Val Ser Gln Gln Ile Ala Ser Ser Val Val Gln Arg
545                 550                 555                 560

Ala Ala Gln Ser Leu Ala Ser Thr Leu Gly Val Asp Gly Asn Asn Leu
                565                 570                 575

Ala Arg Phe Ala Val Gln Ala Val Ser Arg Leu Pro Ala Gly Ser Asp
                580                 585                 590

Thr Ser Ala Tyr Ala Gln Ala Phe Ser Ser Ala Leu Phe Asn Ala Gly
            595                 600                 605

Val Leu Asn Ala Ser Asn Ile Asp Thr Leu Gly Ser Arg Val Leu Ser
        610                 615                 620

Ala Leu Leu Asn Gly Val Ser Ser Ala Ala Gln Gly Leu Gly Ile Asn
625                 630                 635                 640

Val Asp Ser Gly Ser Val Gln Ser Asp Ile Ser Ser Ser Ser Ser Phe
                645                 650                 655

Leu Ser Thr Ser Ser Ser Ser Ala Ser Tyr Ser Gln Ala Ser Ala Ser
                660                 665                 670

Ser Thr Ser Gly Ala Gly Tyr Thr Gly Pro Ser Gly Pro Ser Thr Gly
            675                 680                 685

Pro Ser Gly Tyr Pro Gly Pro Leu Gly Gly Gly Ala Pro Phe Gly Gln
        690                 695                 700

Ser Gly Phe Gly Gly Ser Ala Gly Pro Gln Gly Gly Phe Gly Ala Thr
705                 710                 715                 720
```

```
Gly Gly Ala Ser Ala Gly Leu Ile Ser Arg Val Ala Asn Ala Leu Ala
                725                 730                 735

Asn Thr Ser Thr Leu Arg Thr Val Leu Arg Thr Gly Val Ser Gln Gln
                740                 745                 750

Ile Ala Ser Ser Val Val Gln Arg Ala Ala Gln Ser Leu Ala Ser Thr
                755                 760                 765

Leu Gly Val Asp Gly Asn Asn Leu Ala Arg Phe Ala Val Gln Ala Val
            770                 775                 780

Ser Arg Leu Pro Ala Gly Ser Asp Thr Ser Ala Tyr Ala Gln Ala Phe
785                 790                 795                 800

Ser Ser Ala Leu Phe Asn Ala Gly Val Leu Asn Ala Ser Asn Ile Asp
                805                 810                 815

Thr Leu Gly Ser Arg Val Leu Ser Ala Leu Leu Asn Gly Val Ser Ser
            820                 825                 830

Ala Ala Gln Gly Leu Gly Ile Asn Val Asp Ser Gly Ser Val Gln Ser
            835                 840                 845

Asp Ile Ser Ser Ser Ser Ser Phe Leu Ser Thr Ser Ser Ser Ser Ala
850                 855                 860

Ser Tyr Ser Gln Ala Ser Ala Ser Ser Thr Ser Gly Ala Gly Tyr Thr
865                 870                 875                 880

Gly Pro Ser Gly Pro Ser Thr Gly Pro Ser Gly Tyr Pro Gly Pro Leu
                885                 890                 895

Gly Gly Gly Ala Pro Phe Gly Gln Ser Gly Phe Gly Gly Ser Ala Gly
                900                 905                 910

Pro Gln Gly Gly Phe Gly Ala Thr Gly Gly Ala Ser Ala Gly Leu Ile
            915                 920                 925

Ser Arg Val Ala Asn Ala Leu Ala Asn Thr Ser Thr Leu Arg Thr Val
930                 935                 940

Leu Arg Thr Gly Val Ser Gln Gln Ile Ala Ser Ser Val Val Gln Arg
945                 950                 955                 960

Ala Ala Gln Ser Leu Ala Ser Thr Leu Gly Val Asp Gly Asn Asn Leu
                965                 970                 975

Ala Arg Phe Ala Val Gln Ala Val Ser Arg Leu Pro Ala Gly Ser Asp
            980                 985                 990

Thr Ser Ala Tyr Ala Gln Ala Phe  Ser Ser Ala Leu Phe  Asn Ala Gly
                995                 1000                1005

Val Leu  Asn Ala Ser Asn Ile  Asp Thr Leu Gly Ser  Arg Val Leu
    1010                1015                1020

Ser Ala  Leu Leu Asn Gly Val  Ser Ser Ala Ala Gln  Gly Leu Gly
    1025                1030                1035

Ile Asn  Val Asp Ser Gly Ser  Val Gln Ser Asp Ile  Ser Ser Ser
    1040                1045                1050

Ser Ser  Phe Leu Ser Thr Ser  Ser Ser Ser Ala Ser  Tyr Ser Gln
    1055                1060                1065

Ala Ser  Ala Ser Ser Thr Ser  Gly Thr Gly Tyr Thr  Gly Pro Ser
    1070                1075                1080

Gly Pro  Ser Thr Gly Pro Ser  Gly Tyr Pro Gly Pro  Leu Gly Gly
    1085                1090                1095

Gly Ala  Pro Phe Gly Gln Ser  Gly Phe Gly Gly Ser  Ala Gly Pro
    1100                1105                1110

Gln Gly  Gly Phe Gly Ala Thr  Gly Gly Ala Ser Ala  Gly Leu Ile
    1115                1120                1125
```

-continued

```
Ser Arg Val Ala Asn Ala Leu Ala Asn Thr Ser Thr Leu Arg Thr
    1130                1135                1140

Val Leu Arg Thr Gly Val Ser Gln Gln Ile Ala Ser Ser Val Val
    1145                1150                1155

Gln Arg Ala Ala Gln Ser Leu Ala Ser Thr Leu Gly Val Asp Gly
    1160                1165                1170

Asn Asn Leu Ala Arg Phe Ala Val Gln Ala Val Ser Arg Leu Pro
    1175                1180                1185

Ala Gly Ser Asp Thr Ser Ala Tyr Ala Gln Ala Phe Ser Ser Ala
    1190                1195                1200

Leu Phe Asn Ala Gly Val Leu Asn Ala Ser Asn Ile Asp Thr Leu
    1205                1210                1215

Gly Ser Arg Val Leu Ser Ala Leu Leu Asn Gly Val Ser Ser Ala
    1220                1225                1230

Ala Gln Gly Leu Gly Ile Asn Val Asp Ser Gly Ser Val Gln Ser
    1235                1240                1245

Asp Ile Ser Ser Ser Ser Ser Phe Leu Ser Thr Ser Ser Ser Ser
    1250                1255                1260

Ala Ser Tyr Ser Gln Ala Ser Ala Ser Ser Thr Ser Gly Ala Gly
    1265                1270                1275

Tyr Thr Gly Pro Ser Gly Pro Ser Thr Gly Pro Ser Gly Tyr Pro
    1280                1285                1290

Gly Pro Leu Gly Gly Gly Ala Pro Phe Gly Gln Ser Gly Phe Gly
    1295                1300                1305

Gly Ser Ala Gly Pro Gln Gly Gly Phe Gly Ala Thr Gly Gly Ala
    1310                1315                1320

Ser Ala Gly Leu Ile Ser Arg Val Ala Asn Ala Leu Ala Asn Thr
    1325                1330                1335

Ser Thr Leu Arg Thr Val Leu Arg Thr Gly Val Ser Gln Gln Ile
    1340                1345                1350

Ala Ser Ser Val Val Gln Arg Ala Ala Gln Ser Leu Ala Ser Thr
    1355                1360                1365

Leu Gly Val Asp Gly Asn Asn Leu Ala Arg Phe Ala Val Gln Ala
    1370                1375                1380

Val Ser Arg Leu Pro Ala Gly Ser Asp Thr Ser Ala Tyr Ala Gln
    1385                1390                1395

Ala Phe Ser Ser Ala Leu Phe Asn Ala Gly Val Leu Asn Ala Ser
    1400                1405                1410

Asn Ile Asp Thr Leu Gly Ser Arg Val Leu Ser Ala Leu Leu Asn
    1415                1420                1425

Gly Val Ser Ser Ala Ala Gln Gly Leu Gly Ile Asn Val Asp Ser
    1430                1435                1440

Gly Ser Val Gln Ser Asp Ile Ser Ser Ser Ser Ser Phe Leu Ser
    1445                1450                1455

Thr Ser Ser Ser Ser Ala Ser Tyr Ser Gln Ala Ser Ala Ser Ser
    1460                1465                1470

Thr Ser Gly Ala Gly Tyr Thr Gly Pro Ser Gly Pro Ser Thr Gly
    1475                1480                1485

Pro Ser Gly Tyr Pro Gly Pro Leu Gly Gly Gly Ala Pro Phe Gly
    1490                1495                1500

Gln Ser Gly Phe Gly Gly Ser Asp Gly Pro Gln Gly Gly Phe Gly
    1505                1510                1515

Ala Thr Gly Gly Ala Ser Ala Gly Leu Ile Ser Arg Val Ala Asn
```

```
            1520                1525                1530

Ala Leu Ala Asn Thr Ser Thr Leu Arg Thr Val Leu Arg Thr Gly
          1535                1540                1545

Val Ser Gln Gln Ile Ala Ser Ser Val Val Gln Arg Ala Ala Gln
          1550                1555                1560

Ser Leu Ala Ser Thr Leu Gly Val Asp Gly Asn Asn Leu Ala Arg
          1565                1570                1575

Phe Ala Val Gln Ala Val Ser Arg Leu Pro Ala Gly Ser Asp Thr
          1580                1585                1590

Ser Ala Tyr Ala Gln Ala Phe Ser Ser Ala Leu Phe Asn Ala Gly
          1595                1600                1605

Val Leu Asn Ala Ser Asn Ile Asp Thr Leu Gly Ser Arg Val Leu
          1610                1615                1620

Ser Ala Leu Leu Asn Gly Val Ser Ser Ala Ala Gln Gly Leu Gly
          1625                1630                1635

Ile Asn Val Asp Ser Gly Ser Val Gln Ser Asp Ile Ser Ser Ser
          1640                1645                1650

Ser Ser Phe Leu Ser Thr Ser Ser Ser Ala Ser Tyr Ser Gln
          1655                1660                1665

Ala Ser Ala Ser Ser Thr Ser Gly Ala Gly Tyr Thr Gly Pro Ser
          1670                1675                1680

Gly Pro Ser Thr Gly Pro Ser Gly Tyr Pro Gly Pro Leu Gly Gly
          1685                1690                1695

Gly Ala Pro Phe Gly Gln Ser Gly Phe Gly Gly Ser Ala Gly Pro
          1700                1705                1710

Gln Gly Gly Phe Gly Ala Thr Gly Gly Ala Ser Ala Gly Leu Ile
          1715                1720                1725

Ser Arg Val Ala Asn Ala Leu Ala Asn Thr Ser Thr Leu Arg Thr
          1730                1735                1740

Val Leu Arg Thr Gly Val Ser Gln Gln Ile Ala Ser Ser Val Val
          1745                1750                1755

Gln Arg Ala Ala Gln Ser Leu Ala Ser Thr Leu Gly Val Asp Gly
          1760                1765                1770

Asn Asn Leu Ala Arg Phe Ala Val Gln Ala Val Ser Arg Leu Pro
          1775                1780                1785

Ala Gly Ser Asp Thr Ser Ala Tyr Ala Gln Ala Phe Ser Ser Ala
          1790                1795                1800

Leu Phe Asn Ala Gly Val Leu Asn Ala Ser Asn Ile Asp Thr Leu
          1805                1810                1815

Gly Ser Arg Val Leu Ser Ala Leu Leu Asn Gly Val Ser Ser Ala
          1820                1825                1830

Ala Gln Gly Leu Gly Ile Asn Val Asp Ser Gly Ser Val Gln Ser
          1835                1840                1845

Asp Ile Ser Ser Ser Ser Ser Phe Leu Ser Thr Ser Ser Ser Ser
          1850                1855                1860

Ala Ser Tyr Ser Gln Ala Ser Ala Ser Ser Thr Ser Gly Ala Gly
          1865                1870                1875

Tyr Thr Gly Pro Ser Gly Pro Ser Thr Gly Pro Ser Gly Tyr Pro
          1880                1885                1890

Gly Pro Leu Gly Gly Gly Ala Pro Phe Gly Gln Ser Gly Phe Gly
          1895                1900                1905

Gly Ser Ala Gly Pro Gln Gly Gly Phe Gly Ala Thr Gly Gly Ala
          1910                1915                1920
```

-continued

Ser Ala Gly Leu Ile Ser Arg Val Ala Asn Ala Leu Ala Asn Thr
1925                1930                1935

Ser Thr Leu Arg Thr Val Leu Arg Thr Gly Val Ser Gln Gln Ile
1940                1945                1950

Ala Ser Ser Val Val Gln Arg Ala Ala Gln Ser Leu Ala Ser Thr
1955                1960                1965

Leu Gly Val Asp Gly Asn Asn Leu Ala Arg Phe Ala Val Gln Ala
1970                1975                1980

Val Ser Arg Leu Pro Ala Gly Ser Asp Thr Ser Ala Tyr Ala Gln
1985                1990                1995

Ala Phe Ser Ser Ala Leu Phe Asn Ala Gly Val Leu Asn Ala Ser
2000                2005                2010

Asn Ile Asp Thr Leu Gly Ser Arg Val Leu Ser Ala Leu Leu Asn
2015                2020                2025

Gly Val Ser Ser Ala Ala Gln Gly Leu Gly Ile Asn Val Asp Ser
2030                2035                2040

Gly Ser Val Gln Ser Asp Ile Ser Ser Ser Ser Phe Leu Ser
2045                2050                2055

Thr Ser Ser Ser Ser Ala Ser Tyr Ser Gln Ala Ser Ala Ser Ser
2060                2065                2070

Thr Ser Gly Ala Gly Tyr Thr Gly Pro Ser Gly Ser Thr Gly
2075                2080                2085

Pro Ser Gly Tyr Pro Gly Pro Leu Gly Gly Ala Pro Phe Gly
2090                2095                2100

Gln Ser Gly Phe Gly Gly Ser Ala Gly Pro Gln Gly Gly Phe Gly
2105                2110                2115

Ala Thr Gly Gly Ala Ser Ala Gly Leu Ile Ser Arg Val Ala Asn
2120                2125                2130

Ala Leu Ala Asn Thr Ser Thr Leu Arg Thr Val Leu Arg Thr Gly
2135                2140                2145

Val Ser Gln Gln Ile Ala Ser Ser Val Val Gln Arg Ala Ala Gln
2150                2155                2160

Ser Leu Ala Ser Thr Leu Gly Val Asp Gly Asn Asn Leu Ala Arg
2165                2170                2175

Phe Ala Val Gln Ala Val Ser Arg Leu Pro Ala Gly Ser Asp Thr
2180                2185                2190

Ser Ala Tyr Ala Gln Ala Phe Ser Ser Ala Leu Phe Asn Ala Gly
2195                2200                2205

Val Leu Asn Ala Ser Asn Ile Asp Thr Leu Gly Ser Arg Val Leu
2210                2215                2220

Ser Ala Leu Leu Asn Gly Val Ser Ser Ala Ala Gln Gly Leu Gly
2225                2230                2235

Ile Asn Val Asp Ser Gly Ser Val Gln Ser Asp Ile Ser Ser Ser
2240                2245                2250

Ser Ser Phe Leu Ser Thr Ser Ser Ser Ser Ala Ser Tyr Ser Gln
2255                2260                2265

Ala Ser Ala Ser Ser Thr Ser Gly Ala Gly Tyr Thr Gly Pro Ser
2270                2275                2280

Gly Pro Ser Thr Gly Pro Ser Gly Tyr Pro Gly Pro Leu Gly Gly
2285                2290                2295

Gly Ala Pro Phe Gly Gln Ser Gly Phe Gly Gly Ser Ala Gly Pro
2300                2305                2310

```
Gln Gly Gly Phe Gly Ala Thr Gly Gly Ala Ser Ala Gly Leu Ile
    2315                2320                2325

Ser Arg Val Ala Asn Ala Leu Ala Asn Thr Ser Thr Leu Arg Thr
    2330                2335                2340

Val Leu Arg Thr Gly Val Ser Gln Gln Ile Ala Ser Ser Val Val
    2345                2350                2355

Gln Arg Ala Ala Gln Ser Leu Ala Ser Thr Leu Gly Val Asp Gly
    2360                2365                2370

Asn Asn Leu Ala Arg Phe Ala Val Gln Ala Val Ser Arg Leu Pro
    2375                2380                2385

Ala Gly Ser Asp Thr Ser Ala Tyr Ala Gln Ala Phe Ser Ser Ala
    2390                2395                2400

Leu Phe Asn Ala Gly Val Leu Asn Ala Ser Asn Ile Asp Thr Leu
    2405                2410                2415

Gly Ser Arg Val Leu Ser Ala Leu Leu Asn Gly Val Ser Ser Ala
    2420                2425                2430

Ala Gln Gly Leu Gly Ile Asn Val Asp Ser Gly Ser Val Gln Ser
    2435                2440                2445

Asp Ile Ser Ser Ser Ser Ser Phe Leu Ser Thr Ser Ser Ser Ser
    2450                2455                2460

Ala Ser Tyr Ser Gln Ala Leu Ala Ser Ser Thr Ser Gly Ala Gly
    2465                2470                2475

Tyr Thr Gly Pro Ser Gly Pro Ser Thr Gly Pro Ser Gly Tyr Pro
    2480                2485                2490

Gly Pro Leu Gly Gly Gly Ala Pro Phe Gly Gln Ser Gly Phe Gly
    2495                2500                2505

Gly Ser Ala Gly Pro Gln Gly Gly Phe Gly Ala Thr Gly Gly Ala
    2510                2515                2520

Ser Ala Gly Leu Ile Ser Arg Val Ala Asn Ala Leu Ala Asn Thr
    2525                2530                2535

Ser Thr Leu Arg Thr Val Leu Arg Thr Gly Val Ser Gln Gln Ile
    2540                2545                2550

Ala Ser Ser Val Val Gln Arg Ala Ala Gln Ser Leu Ala Ser Thr
    2555                2560                2565

Leu Gly Val Asp Gly Asn Asn Leu Ala Arg Phe Ala Val Gln Ala
    2570                2575                2580

Val Ser Arg Leu Pro Ala Gly Ser Asp Thr Ser Ala Tyr Ala Gln
    2585                2590                2595

Ala Phe Ser Ser Ala Leu Phe Asn Ala Gly Val Leu Asn Ala Ser
    2600                2605                2610

Asn Ile Asp Thr Leu Gly Ser Arg Val Leu Ser Ala Leu Leu Asn
    2615                2620                2625

Gly Val Ser Ser Ala Ala Gln Gly Leu Gly Ile Asn Val Asp Ser
    2630                2635                2640

Gly Ser Val Gln Ser Asp Ile Ser Ser Ser Ser Ser Phe Leu Ser
    2645                2650                2655

Thr Ser Ser Ser Ser Ala Ser Tyr Ser Gln Ala Ser Ala Ser Ser
    2660                2665                2670

Thr Ser Gly Ala Gly Tyr Thr Gly Pro Ser Gly Pro Ser Thr Gly
    2675                2680                2685

Pro Ser Gly Tyr Pro Gly Pro Leu Ser Gly Gly Ala Ser Phe Gly
    2690                2695                2700

Ser Gly Gln Ser Ser Phe Gly Gln Thr Ser Ala Phe Ser Ala Ser
```

-continued

```
              2705                2710                2715

Gly Ala Gly Gln Ser Ala Gly Val Ser Val Ile Ser Ser Leu Asn
        2720                2725                2730

Ser Pro Val Gly Leu Arg Ser Ala Ser Ala Ala Ser Arg Leu Ser
    2735                2740                2745

Gln Leu Thr Ser Ser Ile Thr Asn Ala Val Gly Ala Asn Gly Val
2750                2755                2760

Asp Ala Asn Ser Leu Ala Arg Ser Leu Gln Ser Ser Phe Ser Ala
    2765                2770                2775

Leu Arg Ser Ser Gly Met Ser Ser Ser Asp Ala Lys Ile Glu Val
        2780                2785                2790

Leu Leu Glu Thr Ile Val Gly Leu Leu Gln Leu Leu Ser Asn Thr
    2795                2800                2805

Gln Val Arg Gly Val Asn Pro Ala Thr Ala Ser Ser Val Ala Asn
    2810                2815                2820

Ser Ala Ala Arg Ser Phe Glu Leu Val Leu Ala
    2825                2830

<210> SEQ ID NO 91
<211> LENGTH: 131
<212> TYPE: PRT
<213> ORGANISM: Argiope aurantia
<220> FEATURE:
<223> OTHER INFORMATION: tubuliform spidroin 1
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 91

Gly Asn Ala Ala Gly Leu Gly Asn Ala Leu Ser Gln Ala Val Ser Ser
1               5                   10                  15

Val Gly Val Gly Ala Ser Ser Thr Tyr Ala Asn Ala Val Ser Asn
            20                  25                  30

Ala Val Gly Gln Phe Leu Ala Gly Gln Gly Ile Leu Asn Xaa Ala Asn
                35                  40                  45

Ala Gly Ser Leu Ala Ser Ser Phe Ala Ser Ala Leu Ser Ala Ser Ala
50                  55                  60

Ala Ser Val Ala Ser Ser Ala Ala Ala Gln Xaa Ala Ser Gln Ser Gln
65                  70                  75                  80

Ala Ala Ala Ser Ala Phe Ser Arg Ala Ala Ser Gln Ser Ala Ser Gln
                85                  90                  95

Ser Ala Ala Arg Ser Gly Ala Gln Ser Ser Ser Xaa Thr Thr Thr
            100                 105                 110

Ser Thr Ser Gly Ser Gln Ala Ala Ser Gln Ser Ala Ser Ser Ala Ala
        115                 120                 125

Ser Gln Ala
    130

<210> SEQ ID NO 92
<211> LENGTH: 545
<212> TYPE: PRT
```

<213> ORGANISM: Argiope aurantia
<220> FEATURE:
<223> OTHER INFORMATION: tubuliform spidroin

<400> SEQUENCE: 92

```
Thr Thr Thr Ser Thr Ala Gly Ser Gln Ala Ala Ser Gln Phe Ala Ser
1               5                   10                  15

Ser Ala Ala Ser Gln Ala Ser Ala Ser Ser Phe Ala Arg Ala Ser Ser
            20                  25                  30

Ala Ser Leu Ala Ala Ser Ser Phe Ser Ser Ala Phe Ser Ser Ala
        35                  40                  45

Asn Ser Leu Ser Ala Leu Gly Asn Val Gly Tyr Gln Leu Gly Phe Asn
50                  55                  60

Val Ala Asn Asn Leu Gly Ile Gly Asn Ala Ala Gly Leu Gly Asn Ala
65                  70                  75                  80

Leu Ser Gln Ala Val Ser Ser Val Gly Val Gly Ala Ser Ser Ser
            85                  90                  95

Tyr Ala Asn Ala Val Ser Asn Ala Val Gly Gln Leu Leu Ala Gly Gln
                100                 105                 110

Gly Ile Leu Asn Ala Ala Asn Ala Gly Ser Leu Ala Ser Ser Phe Ala
            115                 120                 125

Ser Ala Leu Ser Ala Ser Ala Ala Ser Val Ala Ser Ser Ala Ala Ala
        130                 135                 140

Gln Ala Ala Ser Gln Ser Gln Ala Ala Ser Ala Phe Ser Arg Ala
145                 150                 155                 160

Ala Ser Gln Ser Ala Ser Gln Ser Ala Ala Arg Ser Gly Ala Gln Ser
                165                 170                 175

Ile Ser Thr Thr Thr Thr Thr Ser Thr Ala Gly Ser Gln Ala Ala Ser
            180                 185                 190

Gln Ser Ala Ser Ser Ala Ala Ser Gln Ala Ser Ala Ser Ser Phe Ala
        195                 200                 205

Arg Ala Ser Ser Ala Ser Leu Ala Ala Ser Ser Phe Ser Ser Ala
210                 215                 220

Phe Ser Ser Ala Asn Ser Leu Ser Ala Leu Gly Asn Val Gly Tyr Gln
225                 230                 235                 240

Leu Gly Phe Asn Val Ala Asn Asn Leu Gly Ile Gly Asn Ala Ala Gly
                245                 250                 255

Leu Gly Asn Ala Leu Ser Gln Ala Val Ser Ser Val Gly Val Gly Ala
            260                 265                 270

Ser Ser Ser Thr Tyr Ala Asn Ala Val Ser Asn Ala Val Gly Gln Phe
        275                 280                 285

Leu Ala Gly Gln Gly Ile Leu Asn Ala Ala Asn Ala Gly Ser Leu Ala
290                 295                 300

Ser Ser Phe Ala Ser Ala Leu Ser Ala Ser Ala Ala Ser Val Ala Ser
305                 310                 315                 320

Ser Ala Ala Ala Gln Ala Ala Ser Gln Ser Gln Ala Ala Ser Ala
                325                 330                 335

Phe Ser Arg Ala Ala Ser Gln Ser Ala Ser Gln Ser Ala Ala Arg Ser
            340                 345                 350

Gly Ala Gln Ser Ser Ser Thr Thr Thr Thr Ser Thr Ala Gly Ser
        355                 360                 365

Gln Ala Ala Ser Gln Phe Ala Ser Ser Ala Ala Ser Gln Ala Ser Ala
370                 375                 380

Ser Ser Phe Ala Arg Ala Ser Ser Ala Ser Leu Ala Ala Ser Ser Ser
```

```
                385                 390                 395                 400
        Phe Ser Ser Ala Phe Ser Ala Asn Ser Leu Ser Ala Leu Gly Asn
                            405                 410                 415

Val Gly Tyr Gln Leu Gly Phe Asn Val Ala Asn Asn Leu Gly Ile Ser
                        420                 425                 430

Asn Ala Ala Gly Leu Gly Asn Ala Leu Ser Gln Ala Val Ser Ser Val
                        435                 440                 445

Gly Val Gly Ala Ser Ser Ser Tyr Ala Asn Ala Val Ser Asn Ala
            450                 455                 460

Val Gly Gln Phe Leu Ala Gly Gln Gly Ile Leu Asn Ala Ala Asn Ala
        465                 470                 475                 480

Gly Ser Leu Ala Ser Ser Phe Ala Ser Ala Leu Ser Ala Ser Ala Ala
                        485                 490                 495

Ser Val Ala Ser Ser Ala Ala Gln Ala Ala Ser Gln Ser Gln Ala
                        500                 505                 510

Ala Ala Ser Ala Phe Ser Arg Ala Ala Ser Gln Ser Ala Ser Gln Ser
                        515                 520                 525

Ala Ala Arg Ser Gly Ala Gln Ser Ser Ser Thr Thr Thr Thr Thr Ser
                        530                 535                 540

Thr
        545

<210> SEQ ID NO 93
<211> LENGTH: 376
<212> TYPE: PRT
<213> ORGANISM: Argiope aurantia
<220> FEATURE:
<223> OTHER INFORMATION: tubuliform spidroin

<400> SEQUENCE: 93

Ser Thr Tyr Ala Asn Ala Val Ser Asn Ala Val Gly Gln Phe Leu Ala
        1               5                   10                  15

Gly Gln Gly Ile Leu Asn Ala Ala Asn Ala Gly Ser Leu Ala Ser Ser
                        20                  25                  30

Phe Ala Ser Ala Leu Ser Ala Ser Ala Ala Ser Val Ala Ser Ser Ala
                        35                  40                  45

Ala Ala Gln Ala Ala Ser Gln Ser Gln Ala Ala Ser Ala Phe Ser
                    50                  55                  60

Arg Ala Ala Ser Gln Ser Ala Ser Gln Ser Ala Ala Arg Ser Gly Ala
        65                  70                  75                  80

Gln Ser Phe Ser Thr Thr Thr Thr Ser Thr Ala Gly Ser Gln Ala
                        85                  90                  95

Ala Ser Gln Ser Ala Ser Ser Ala Ala Ser Gln Ala Ser Ala Ser Ser
                        100                 105                 110

Phe Ala Arg Ala Ser Ser Ala Ser Leu Ala Ala Ser Ser Ala Phe Ser
                        115                 120                 125

Ser Ala Phe Ser Ser Ala Asn Ser Leu Ser Ala Leu Gly Asn Val Ala
                        130                 135                 140

Tyr Gln Leu Gly Phe Asn Val Ala Asn Thr Leu Gly Ile Gly Asn Ala
        145                 150                 155                 160

Ala Gly Leu Gly Asn Ala Leu Ser Gln Ala Val Ser Ser Val Gly Val
                        165                 170                 175

Gly Ala Ser Ser Ser Thr Tyr Ala Asn Ala Val Ser Asn Ala Val Gly
                        180                 185                 190

Gln Phe Leu Ala Gly Gln Gly Val Leu Asn Ala Gly Asn Ala Gly Ser
```

```
                195                 200                 205

Leu Ala Ser Ser Phe Ala Asn Ala Leu Ser Asn Ser Ala Leu Ser Val
    210                 215                 220

Gly Ser Arg Val Ser Ser Pro Ser Tyr Gly Ala Leu Ser Pro Ile Ala
225                 230                 235                 240

Ala Gly Pro Asn Phe Ile Ser Thr Gly Leu Asn Val Gly Gly Pro Phe
                245                 250                 255

Thr Thr Leu Ser Gln Ser Leu Pro Thr Ser Leu Gln Thr Ala Leu Ala
            260                 265                 270

Pro Ile Val Ser Ser Ser Gly Leu Gly Ser Ser Ala Ala Thr Ala Arg
            275                 280                 285

Val Arg Ser Leu Ala Asn Ser Ile Ala Ser Ala Ile Ser Ser Ser Gly
        290                 295                 300

Gly Ser Leu Ser Val Pro Ala Phe Leu Asn Leu Leu Ser Val Gly
305                 310                 315                 320

Ala Gln Val Ser Ser Ser Ser Leu Asn Ser Ser Glu Val Thr Asn
                325                 330                 335

Glu Val Leu Leu Glu Ala Ile Ala Ala Leu Leu Gln Val Ile Asn Gly
                340                 345                 350

Gly Ser Ile Thr Ser Val Asp Leu Arg Asn Val Pro Asn Ala Gln Gln
            355                 360                 365

Asp Leu Val Asn Ala Leu Ser Gly
        370                 375

<210> SEQ ID NO 94
<211> LENGTH: 654
<212> TYPE: PRT
<213> ORGANISM: Araneus gemmoides
<220> FEATURE:
<223> OTHER INFORMATION: tubuliform spidroin

<400> SEQUENCE: 94

Ala Ser Gln Ser Gln Ala Ala Ser Gln Ser Gln Ala Ala Ala Ser Ala
1               5                   10                  15

Phe Arg Gln Ala Ala Ser Gln Ser Ala Ser Gln Ser Ala Ser Arg Ala
                20                  25                  30

Gly Ser Gln Ser Ser Thr Lys Thr Thr Ser Thr Ser Thr Ser Gly Ser
            35                  40                  45

Gln Ala Asp Ser Arg Ser Ala Ser Ser Ala Ser Gln Ala Ser Ala
    50                  55                  60

Ser Ala Phe Ala Gln Gln Ser Ser Ala Ser Leu Ser Ser Ser Ser Ser
65                  70                  75                  80

Phe Ser Ser Ala Phe Ser Ser Ala Thr Ser Ile Ser Ala Val Gly Asn
                85                  90                  95

Val Gly Tyr Gln Leu Gly Leu Lys Val Ala Asn Ser Leu Gly Leu Gly
                100                 105                 110

Asn Ala Gln Ala Leu Ala Ser Ser Leu Ser Gln Ala Val Ser Ala Val
            115                 120                 125

Gly Val Gly Ala Ser Ser Asn Ala Tyr Ala Asn Ala Val Ser Asn Ala
        130                 135                 140

Val Gly Gln Val Leu Ala Gly Gln Gly Ile Leu Asn Ala Ala Asn Ala
145                 150                 155                 160

Gly Ser Leu Ala Ser Ser Phe Ala Ser Ala Leu Ser Ser Ser Ala Ala
                165                 170                 175

Ser Val Ala Ser Gln Ser Ala Ser Gln Ser Gln Ala Ala Ser Gln Ser
```

-continued

```
               180                 185                 190
Gln Ala Ala Ser Ala Phe Arg Gln Ala Ser Gln Ser Ala Ser
            195                 200                 205
Gln Ser Ala Ser Arg Ala Gly Ser Gln Ser Ser Thr Lys Thr Thr Ser
        210                 215                 220
Thr Ser Thr Ser Gly Ser Gln Ala Asp Ser Arg Ser Ala Ser Ser Ser
225                 230                 235                 240
Ala Ser Gln Ala Ser Ala Ser Ala Phe Ala Gln Gln Ser Ser Ala Ser
                245                 250                 255
Leu Ser Ser Ser Ser Ser Phe Ser Ser Ala Phe Ser Ser Ala Thr Ser
            260                 265                 270
Ile Ser Ala Val Gly Asn Val Gly Tyr Gln Leu Gly Leu Lys Val Ala
        275                 280                 285
Asn Ser Leu Gly Leu Gly Asn Ala Gln Ala Leu Ala Ser Ser Leu Ser
        290                 295                 300
Gln Ala Val Ser Ala Val Gly Val Gly Ala Ser Ser Asn Ala Tyr Ala
305                 310                 315                 320
Asn Ala Val Ser Asn Ala Val Gly Gln Val Leu Ala Gly Gln Gly Ile
                325                 330                 335
Leu Asn Ala Ala Asn Ala Gly Ser Leu Ala Ser Ser Phe Ala Ser Ala
                340                 345                 350
Leu Ser Ser Ser Ala Ala Ser Val Ala Ser Gln Ser Ala Ser Gln Ser
            355                 360                 365
Gln Ala Ala Ser Gln Ser Gln Ala Ala Ser Ala Phe Arg Gln Ala
        370                 375                 380
Ala Ser Gln Ser Ala Ser Gln Ser Asp Ser Arg Ala Gly Ser Gln Ser
385                 390                 395                 400
Ser Thr Lys Thr Thr Ser Thr Ser Thr Ser Gly Ser Gln Ala Asp Ser
                405                 410                 415
Arg Ser Ala Ser Ser Ser Ala Ser Gln Ala Ser Ala Ser Ala Phe Ala
                420                 425                 430
Gln Gln Ser Ser Ala Ser Leu Ser Ser Ser Ser Ser Phe Ser Ser Ala
        435                 440                 445
Phe Ser Ser Ala Thr Ser Ile Ser Ala Val Gly Asn Val Gly Tyr Gln
    450                 455                 460
Leu Gly Leu Lys Val Ala Asn Ser Leu Gly Leu Gly Asn Ala Gln Ala
465                 470                 475                 480
Leu Ala Ser Ser Leu Ser Gln Ala Val Ser Ala Val Gly Val Gly Ala
                485                 490                 495
Ser Ser Asn Ala Tyr Ala Asn Ala Val Ser Asn Ala Val Gly Gln Val
            500                 505                 510
Leu Ala Gly Gln Gly Ile Leu Asn Ala Ala Asn Ala Gly Ser Leu Ala
        515                 520                 525
Ser Ser Phe Ala Ser Ala Leu Ser Ser Ser Ala Ala Ser Val Ala Ser
        530                 535                 540
Gln Ser Ala Ser Gln Ser Gln Ala Ala Ser Gln Ser Gln Ala Ala Ala
545                 550                 555                 560
Ser Ala Phe Arg Gln Ala Ala Ser Gln Ser Ala Ser Gln Ser Ala Ser
                565                 570                 575
Arg Ala Gly Ser Gln Ser Ser Thr Lys Thr Thr Ser Thr Ser Thr Ser
            580                 585                 590
Gly Ser Gln Ala Asp Ser Arg Ser Ala Ser Ser Ser Ala Ser Gln Ala
        595                 600                 605
```

-continued

```
Ser Ala Ser Ala Phe Ala Gln Gln Ser Ser Ala Ser Leu Ser Ser Ser
    610                 615                 620
Ser Ser Phe Ser Ser Ala Phe Ser Ser Ala Thr Ser Ile Ser Ala Val
625                 630                 635                 640
Gly Asn Val Gly Tyr Gln Leu Gly Leu Lys Val Ala Asn Ser
                645                 650

<210> SEQ ID NO 95
<211> LENGTH: 294
<212> TYPE: PRT
<213> ORGANISM: Araneus gemmoides
<220> FEATURE:
<223> OTHER INFORMATION: tubuliform spidroin

<400> SEQUENCE: 95

Ser Ala Ser Gln Ser Gln Ala Ala Ala Ser Ala Phe Arg Gln Ala Ala
1               5                   10                  15
Ser Gln Ser Ala Ser Gln Ser Ala Ser Arg Ala Gly Ser Gln Ser Ser
            20                  25                  30
Ser Lys Thr Thr Ser Thr Ser Thr Ser Gly Ser Gln Ala Asp Ser Arg
        35                  40                  45
Ser Ala Ser Ser Ala Ser Gln Ala Ser Ala Ser Ala Ile Ala Gln
    50                  55                  60
Gln Ser Ala Ser Leu Ser Ser Ser Ser Phe Ser Ser Ala Phe
65                  70                  75                  80
Ser Ser Ala Thr Ser Leu Ser Ala Val Gly Asn Val Gly Tyr Gln Leu
                85                  90                  95
Gly Leu Lys Val Ala Asn Ser Leu Gly Leu Gly Asn Ala Gln Ala Leu
                100                 105                 110
Ala Ser Gln Gly Ile Leu Asn Ala Ala Asn Ala Gly Ser Leu Ala Ser
            115                 120                 125
Ser Phe Ala Ser Ala Leu Ser Ala Ser Ala Gly Ser Val Gly Asn Arg
        130                 135                 140
Ser Ser Ala Gly Pro Ser Ala Val Gly Leu Gly Gly Val Ser Ala Val
145                 150                 155                 160
Pro Gly Phe Ile Ser Ala Thr Pro Val Val Gly Pro Val Thr Val
                165                 170                 175
Asn Gly Gln Val Leu Pro Ala Ala Leu Gln Thr Ala Leu Ala Pro Val
            180                 185                 190
Val Thr Ser Ser Gly Leu Ala Ser Ser Ala Ala Ser Ala Arg Val Ser
        195                 200                 205
Ser Leu Ala Gln Ser Ile Ala Ser Ala Ile Ser Ser Gly Gly Thr
    210                 215                 220
Leu Ser Val Pro Ile Phe Leu Asn Leu Leu Ser Ser Ala Gly Ala Gln
225                 230                 235                 240
Ala Thr Ala Ser Ser Leu Ser Ser Ser Gln Val Thr Ser Gln Val
                245                 250                 255
Leu Leu Glu Gly Ile Ala Ala Leu Leu Gln Val Ile Asn Gly Ala Gln
            260                 265                 270
Ile Arg Ser Val Asn Leu Ala Asn Val Pro Asn Val Gln Gln Ala Leu
        275                 280                 285
Val Ser Ala Leu Ser Gly
    290

<210> SEQ ID NO 96
```

<211> LENGTH: 592
<212> TYPE: PRT
<213> ORGANISM: Nephila clavipes
<220> FEATURE:
<223> OTHER INFORMATION: tubuliform spidroin

<400> SEQUENCE: 96

```
Ala Ser Ala Ala Ser Leu Ala Tyr Ser Ile Gly Ile Ser Ala Ala
 1               5                  10                  15

Arg Ser Leu Gly Ile Ala Asp Ala Ala Gly Leu Ala Gly Ala Leu Ala
            20                  25                  30

Arg Ala Ala Gly Ala Leu Gly Gln Gly Asp Thr Ala Ala Ser Tyr Gly
            35                  40                  45

Asn Ala Leu Ser Thr Ala Ala Gly Gln Phe Phe Ala Thr Ala Gly Leu
 50                  55                  60

Leu Asn Ala Gly Asn Ala Ser Ala Leu Ala Ser Ser Phe Ala Arg Ala
 65                  70                  75                  80

Phe Ser Ala Ser Ala Glu Ser Gln Ser Phe Ala Gln Ser Gln Ala Phe
                85                  90                  95

Gln Gln Ala Ser Ala Phe Gln Gln Ala Ala Ser Arg Ser Ala Ser Gln
                100                 105                 110

Ser Ala Ala Glu Ala Asp Ser Thr Ser Ser Ser Thr Thr Thr Thr Thr
                115                 120                 125

Ser Ala Ala Arg Ser Gln Ala Ala Ser Gln Ser Ala Ser Ser Ser Tyr
130                 135                 140

Ser Ser Ala Phe Ala Gln Ala Ala Ser Ser Phe Ala Ile Ser Ser
145                 150                 155                 160

Ala Leu Ser Arg Ala Phe Ser Ser Val Ser Ser Ala Ser Ala Ala Ser
                165                 170                 175

Ser Leu Ala Tyr Ser Ile Gly Leu Ser Ala Ala Arg Ser Leu Gly Ile
                180                 185                 190

Ala Asp Ala Thr Gly Leu Ala Gly Ala Leu Ala Arg Ala Val Gly Ala
                195                 200                 205

Leu Gly Gln Gly Ala Thr Ala Ala Ser Tyr Gly Asn Ala Leu Ser Thr
210                 215                 220

Ala Ala Ala Gln Phe Phe Ala Thr Ala Gly Leu Leu Asn Ala Gly Asn
225                 230                 235                 240

Ala Ser Ala Leu Ala Ser Ser Phe Ala Arg Ala Phe Ser Ala Ser Ala
                245                 250                 255

Glu Ser Gln Ser Phe Ala Gln Ser Gln Ala Phe Gln Gln Ala Ser Ala
                260                 265                 270

Phe Gln Gln Ala Ala Ser Arg Ser Ala Ser Gln Ser Ala Ala Glu Ala
                275                 280                 285

Gly Ser Thr Ser Ser Ser Thr Thr Thr Thr Ser Ala Ala Arg Ser
290                 295                 300

Gln Ala Ala Ser Gln Ser Ala Ser Ser Ser Tyr Ser Ser Ala Phe Ala
305                 310                 315                 320

Gln Ala Ala Ser Ser Leu Ala Thr Ser Ser Ala Leu Ser Arg Ala
                325                 330                 335

Phe Ser Ser Val Ser Ser Ala Ser Ala Ala Ser Ser Leu Ala Tyr Ser
                340                 345                 350

Ile Gly Leu Ser Ala Ala Arg Ser Leu Gly Ile Ala Asp Ala Ala Gly
                355                 360                 365

Leu Ala Gly Val Leu Ala Arg Ala Ala Gly Ala Leu Gly Gln Gly Ala
370                 375                 380
```

-continued

```
Thr Ala Ala Ser Tyr Gly Asn Ala Leu Ser Thr Ala Ala Gly Gln Phe
385                 390                 395                 400

Phe Ala Ala Gln Gly Leu Leu Asn Ala Gly Asn Val Ser Ser Leu Ala
                405                 410                 415

Ser Ala Leu Ala Asn Ala Leu Ser Tyr Ser Ala Ala Asn Ser Ala Ala
                420                 425                 430

Ser Gly Asn Tyr Ile Gly Val Ser Gln Asn Phe Gly Ser Ile Ala Pro
            435                 440                 445

Val Ala Gly Thr Ala Gly Ile Ser Val Gly Val Pro Gly Leu Leu Pro
        450                 455                 460

Thr Ser Ala Gly Thr Val Leu Ala Pro Ala Asn Ala Gln Ile Ile Ala
465                 470                 475                 480

Pro Gly Leu Gln Thr Thr Leu Ala Pro Val Phe Ser Ser Ser Gly Leu
                485                 490                 495

Ser Ser Ala Ser Ala Asn Ala Arg Val Ser Ser Leu Ala Gln Ser Phe
                500                 505                 510

Ala Ser Ala Leu Ser Ala Ser Arg Gly Thr Leu Ser Val Ser Thr Phe
            515                 520                 525

Leu Thr Leu Leu Ser Pro Ile Ser Ser Gln Ile Arg Ala Asn Thr Ser
        530                 535                 540

Leu Asp Gly Thr Gln Ala Thr Val Gln Val Leu Leu Glu Ala Leu Ala
545                 550                 555                 560

Ala Leu Leu Gln Val Ile Asn Ala Ala Gln Ile Thr Glu Val Asn Val
                565                 570                 575

Ser Asn Val Ser Ser Ala Asn Ala Ala Leu Val Ser Ala Leu Ala Gly
            580                 585                 590
```